US008080642B2

(12) United States Patent
Vilalta et al.

(10) Patent No.: US 8,080,642 B2
(45) Date of Patent: Dec. 20, 2011

(54) SEVERE ACUTE RESPIRATORY SYNDROME DNA COMPOSITIONS AND METHODS OF USE

(75) Inventors: Adrian Vilalta, San Diego, CA (US); Thomas G. Evans, Cambridge, MA (US); Melanie W. Quong, San Diego, CA (US); Marston Manthorpe, San Diego, CA (US)

(73) Assignee: Vical Incorporated, San Diego, CA (US)

( * ) Notice: Subject to any disclaimer, the term of this patent is extended or adjusted under 35 U.S.C. 154(b) by 675 days.

(21) Appl. No.: 10/843,656

(22) Filed: May 12, 2004

(65) Prior Publication Data

US 2007/0105193 A1 May 10, 2007

Related U.S. Application Data

(60) Provisional application No. 60/482,505, filed on Jun. 26, 2003, provisional application No. 60/470,820, filed on May 16, 2003.

(51) Int. Cl.
*C07H 21/02* (2006.01)
*C12N 15/00* (2006.01)
*C12Q 1/68* (2006.01)

(52) U.S. Cl. ........................ 536/23.1; 435/320.1; 435/6

(58) Field of Classification Search ........................ None
See application file for complete search history.

(56) References Cited

U.S. PATENT DOCUMENTS

| | | | |
|---|---|---|---|
| 4,597,966 | A | 7/1986 | Zolton et al. |
| 4,683,195 | A | 7/1987 | Mullis et al. |
| 4,816,567 | A | 3/1989 | Cabilly et al. |
| 5,032,520 | A | 7/1991 | Binns et al. |
| 5,143,726 | A | 9/1992 | Thornton et al. |
| 5,264,618 | A | 11/1993 | Felgner et al. |
| 5,369,026 | A | 11/1994 | Parker et al. |
| 5,389,540 | A | 2/1995 | Makoff et al. |
| 5,459,127 | A | 10/1995 | Felgner et al. |
| 5,580,859 | A | 12/1996 | Felgner et al. |
| 5,589,466 | A | 12/1996 | Felgner et al. |
| 5,643,578 | A | 7/1997 | Robinson et al. |
| 5,656,611 | A | 8/1997 | Kabanov et al. |
| 5,661,006 | A | 8/1997 | Brown et al. |
| 5,703,055 | A | 12/1997 | Felgner et al. |
| 5,807,551 | A | 9/1998 | Reynolds |
| 5,837,693 | A | 11/1998 | German et al. |
| 5,861,397 | A | 1/1999 | Wheeler |
| 5,994,317 | A | 11/1999 | Wheeler |
| 6,004,944 | A | 12/1999 | Rothman et al. |
| 6,022,874 | A | 2/2000 | Wheeler |
| 6,080,850 | A | 6/2000 | Darteil et al. |
| 6,096,535 | A | 8/2000 | Darteil et al. |
| 6,171,586 | B1 | 1/2001 | Lam et al. |
| 6,207,646 | B1 | 3/2001 | Krieg et al. |
| 6,214,804 | B1 | 4/2001 | Felgner et al. |
| 6,224,870 | B1 | 5/2001 | Segal |
| 6,231,864 | B1 | 5/2001 | Birkett |
| 6,358,512 | B1 | 3/2002 | Darteil et al. |
| 6,379,966 | B2 | 4/2002 | Monahan et al. |
| 6,406,705 | B1 | 6/2002 | Davis et al. |
| 6,429,199 | B1 | 8/2002 | Krieg et al. |
| 6,500,432 | B1 | 12/2002 | Dalemans et al. |
| 6,586,409 | B1 | 7/2003 | Wheeler |
| 6,632,436 | B2 | 10/2003 | Segal |
| 6,670,332 | B1 | 12/2003 | Wheeler |
| 6,696,424 | B1 | 2/2004 | Wheeler |
| 6,710,035 | B2 | 3/2004 | Felgner et al. |
| 6,867,195 | B1 | 3/2005 | Felgner et al. |
| 6,875,748 | B2 | 4/2005 | Manthorpe et al. |
| 2001/0031264 | A1 | 10/2001 | Segal |
| 2002/0045594 | A1 | 4/2002 | Volkin et al. |
| 2002/0165172 | A1 | 11/2002 | Sallberg et al. |
| 2003/0032615 | A1 | 2/2003 | Felgner et al. |
| 2003/0191082 | A1 | 10/2003 | Wheeler |
| 2004/0023911 | A1 | 2/2004 | Felgner et al. |
| 2004/0157244 | A1 | 8/2004 | Budahazi et al. |
| 2004/0157789 | A1 | 8/2004 | Geall |
| 2004/0162256 | A1 | 8/2004 | Geall et al. |

(Continued)

FOREIGN PATENT DOCUMENTS

| | | |
|---|---|---|
| CN | 1548452 A | 11/2004 |

(Continued)

OTHER PUBLICATIONS

Azevedo V et al. "Main features of DNA-based immunization vectors" Braz J Med Biol Res, Feb. 1999, vol. 32(2) 147-153.*

Navas-Martin S et al. "Coronavirus replication and pathogenesis: Implications for the recent outbreak of severe acute respiratory syndrome (SARS), and the challenge for vaccine development". J Neurovirol. Apr. 2004;10(2):75-85.*

Stockman L. et al "SARS: systematic review of treatment effects". PLoS Med. Sep. 2006;3(9):e343. Review.*

Kostopoulou E. et al. "A Rev-independent human immunodeficiency virus type 1 (HIV-1)-based vector that exploits a codon-optimized HIV-1 gag-pol gene". J Virol. May 2000;74(10):4839-52.*

(Continued)

*Primary Examiner* — Bo Peng
(74) *Attorney, Agent, or Firm* — Sughrue Mion, PLLC

(57) ABSTRACT

The present invention is directed to raising a detectable immune response in a vertebrate by administering in vivo, into a tissue of the vertebrate, at least one polynucleotide comprising one or more regions of nucleic acid encoding a SARS-CoV protein or a fragment, a variant, or a derivative thereof. The present invention is further directed to raising a detectable immune response in a vertebrate by administering, in vivo, into a tissue of the vertebrate, at least one SARS-CoV protein or a fragment, a variant, or derivative thereof. The SARS-CoV protein can be, for example, in purified form. The polynucleotide is incorporated into the cells of the vertebrate in vivo, and an immunologically effective amount of an immunogenic epitope of a SARS-CoV polypeptide, fragment, variant, or derivative thereof is produced in vivo. The SARS-CoV protein is also administered in an immunologically effective amount.

16 Claims, 3 Drawing Sheets

U.S. PATENT DOCUMENTS

| | | | | |
|---|---|---|---|---|
| 2004/0171572 A1 | 9/2004 | Wheeler | | |
| 2005/0002953 A1* | 1/2005 | Herold | ..................... | 424/186.1 |
| 2005/0181357 A1* | 8/2005 | Peiris et al. | ..................... | 435/5 |
| 2006/0257852 A1* | 11/2006 | Rappuoli et al. | ................. | 435/5 |

FOREIGN PATENT DOCUMENTS

| | | | |
|---|---|---|---|
| EP | 0 173 494 | A2 | 3/1986 |
| EP | 0 171 496 | B1 | 5/1993 |
| EP | 0 385 610 | B1 | 3/1994 |
| EP | 1 314 437 | A1 | 5/2003 |
| EP | 0 907 378 | B1 | 2/2006 |
| JP | 2000-302692 | A | 10/2000 |
| WO | WO 86/01533 | A1 | 3/1986 |
| WO | WO 87/02671 | A1 | 5/1987 |
| WO | WO 90/06764 | A1 | 6/1990 |
| WO | WO 00/02591 | A1 | 1/2000 |
| WO | WO 00/56282 | A1 | 9/2000 |
| WO | WO 00/57917 | A2 | 10/2000 |
| WO | WO 01/34801 | A2 | 5/2001 |
| WO | WO 02/00844 | A2 | 1/2002 |
| WO | WO 03/025003 | A2 | 3/2003 |
| WO | WO 2004/085650 | A1 | 10/2004 |
| WO | WO 2004/091524 | A2 | 10/2004 |
| WO | WO 2004/092208 | A2 | 10/2004 |
| WO | WO 2004/092360 | A2 | 10/2004 |
| WO | WO 2004/096842 | A2 | 11/2004 |
| WO | W02004/111187 | A2 | 12/2004 |
| WO | WO 2005/016238 | A2 | 2/2005 |

OTHER PUBLICATIONS

Nakamura Y et al. "Codon usage tabulated from international DNA sequence databases: status for the year 2000". Nucleic Acids Res. Jan. 1, 2000;28(1):292.*

Klavinskis et al. "Intranasal Immunization with Plasmid DNA—Lipid Complexes Elicits Mucosal Immunity in the Female Genital and Rectal Tracts" (1999, The Journal of Immunology,162: 254-262).*

Anand, K., et al., "Coronavirus Main Proteinase (3CL$^{pro}$) Structure: Basis for Design of anti-SARS Drugs," *Science 300*:1763-1767, Originally published in *Sciencexpress* pp. 1-10, American Association for the Advancement of Science (published online May 2003).

Donnelly, C.A., et al., "Epidemiological determinants of spread of causal agent of severe acute respiratory syndrome in Hong Kong," *Lancet 361*:1761-1766, The Lancet Publishing Group (May 2003).

Drazen, M.D., J.M., "Case Clusters of the Severe Acute Respiratory Syndrome," *N. Engl. J. Med. 348*:e6-7, Massachusetts Medical Society (published online Mar. 2003).

Drosten, C., et al., "Identification of a Novel Coronavirus in Patients with Severe Acute Respiratory Syndrome," *New Engl. J. Med. 348*:1967-1976, Massachusetts Medical Society (published online Apr. 2003).

Glansbeek, H.L., et al., "Adverse effects of feline IL-12 during DNA vaccination against feline infectious peritonitis virus," *J. Gen. Virol. 83*:1-10, Society for General Microbiology (Jan. 2002).

He, J.-F., et al., "Molecular Evolution of the SARS Coronavirus During the Course of the SARS Epidemic in China," with supplementary text, *Science 303*:1666-1669, Originally published in *Sciencexpress* pp. 1-32, American Association for the Advancement of Science (published online Jan. 2004).

Holmes, K.V., "SARS coronvirus: a new challenge for prevention and therapy," *J. Clin. Invest. 111*:1605-1609, American Society for Clinical Investigation (Jun. 2003).

Holmes, K.V. and Enjuanes, L., "The SARS Coronavirus: A Postgenomic Era," *Science 300*:1377-1364, American Association for the Advancement of Science (May 2003).

Kida, K., et al., "Selection of Antigenic Variants of the S Glycoprotein of Feline Infectious Peritonitis Virus and Analysis of Anitgenic Sites Involved in Neutralization," *J. Vet. Med. Sci. 61*:935-938, Japanese Society of Veterinary Science (1999).

Ksiazek, T.G., et al., "A Novel Coronavirus Associated with Severe Acute Respiratory Syndrome," *N. Engl. J. Med. 348*:1953-1966, Massachusetts Medical Society (May 2003).

Little, S.F., et al., "Defining a serological correlate of protection in rabbits for a recombinant anthrax vaccine," *Vaccine 22*:422-430, Elsevier Ltd. (Jan. 2004).

Peiris, J.S.M., et al., "Coronavirus as a possible cause of severe acute respiratory syndrome," *Lancet 361*:1319-1325, The Lancet Publishing Group (published online Apr. 2003).

Poutanen, S.M., et al., "Identification of Severe Acute Respiratory Syndrome in Canada," *N. Engl. J. Med. 348*:1995-2005, Massachusetts Medical Society (published online Mar. 2003).

Ruan, Y., et al., "Comparative full-length genome sequence analysis of 14 SARS coronavirus isolates and common mutations associated with putative origins of infection," *Lancet. 361*:1779-1785, The Lancet Publishing Group (May 2003).

Scott, F.W., "Evaluation of Risks and Benefits Associated with Vaccination against Coronavirus Infections in Cats," *Adv. Vet. Med. 41*:347-358, Academic Press (1999).

Walgate, R., "Human SARS virus not identical to civet virus," *The Scientist 4*: 20030527-03, Institute For Scientific Information (May 2003).

Vogel, G., "Flood of Sequence Data Yields Clues But Few Answers," *Science 300*:1062-1063, American Association for the Advancement of Science (May 2003).

Vilalta, A., et al., "Plasmid DNA Constructs Expressing SARS-CoV Antigens Are Immunogenic in Mice and Rabbits," *Mol. Ther. 9* (*Suppl. 1*):S184, Abstract No. 486, Elsevier Inc. (May 2004).

Spaan, W, et al., "Review Article—Coronaviruses and Genome Expression," *J. gen. Virol*, 69:2939-2952, The Society for General Microbiology (1988).

Qin, E'de et al., "A Complete sequence and comparative analysis of a SARS-associated virus (Isolate BJ01)," *Chinese Science Bulletin 2003*, vol. 48, No. 10:941-948, Science in China Press (May 2003).

Cavanagh, Dave, "Review Article—Severe Acute Respiratory Syndrome Vaccine Development: Experiences of Vaccination Against Avian Infectious Bronchitis Coronavirus," *Avian Pathology*, 32:6, 567-582, Taylor & Francis (Dec. 2003).

Australian Patent Office Search Report for International Application No. SG 200507477-8, mailed Mar. 15, 2006, 5 pages.

Aihara, H. and Miyazaki J.-I., "Gene transfer into muscle by electroporation in vivo," *Nat. Biotechnol. 16*:867-870, Nature America, Inc. (1998).

Banchereau, J., et al., "Long-term human B cell lines dependent on interleukin-4 and antibody to CD40," *Science 251*:70-72, American Association for the Advancement of Science (1991).

Bende, M., et al., "Changes in human nasal mucosa during experimental coronavirus common colds," *Acta Otolaryngol. 107*:262-269, Taylor & Francis (1989).

Berendt, R.F. and Hall, W.C., "Reaction of Squirrel Monkeys to Intratracheal Inoculation with Influenza/A/New Jersey/76 (Swine) Virus," *Infect. Immun. 16*:476-479, American Society for Microbiology (1977).

Billaut-Mulot, O., et al., "Interleukin-18 modulates immune responses induced by HIV-1 Nef DNA prime/protein boost vaccine," *Vaccine 19*:95-102, Elsevier Science Ltd. (2001).

Bonavia, A., et al., "Identification of a receptor-binding domain of the spike glycoprotein of human coronavirus HCoV-229E," *J. Virol. 77*:2530-2538, American Society for Microbiology (2003).

Bos, E.C.W., et al., "The function of the spike protein of mouse hepatitis virus strain A59 can be studied on virus-like particles: cleavage is not required for infectivity," *J. Virol. 71*:9427-9233, American Society for Microbiology (1997).

Boulianne, G.L., et al., "Production of functional chimaeric mouse/human antibody," *Nature 312*:643-646, Macmillan Journals Ltd: (1984).

Breslin, J.J., et al., "Human coronavirus 229E: receptor binding domain and neutralization by soluble receptor at 37 degrees C," *J. Virol. 77*:4435-4438, American Society for Microbiology (2003).

Britton, P., et al., "The cloning and sequencing of the virion protein genes from a British isolate of porcine respiratory coronavirus: comparison with transmissible gastroenteritis virus genes," *Virus Res. 21*:181-198, Elsevier Science Publishers B.V. (1991).

Brutlag, D.L., et al., "Improved sensitivity of biological sequence database searches," *Comp. App. Biosci. 6*:237-245, Oxford University Press (1990).

Callow, K.A., et al., "The time course of the immune response to experimental coronavirus infection of man," *Epidemiol. Infect. 105*:435-446, Cambridge University Press (1990).
Casadevall, A., "Passive antibody administration (immediate immunity) as a specific defense against biological weapons," *Emerging Infectious Diseases 8*:833-841, Centers for Disease Control and Prevention (2002).
Chaudhuri, T. R., et al., "Human monoclonal antibody developed against ovarian cancer cell surface antigen," *Cancer 73*(Supplement 3):1098-1104, American Cancer Society (1994).
Chen, Z.-Y., et al., "Linear DNAs concatemerize in vivo and result in sustained transgene expression in mouse liver." *Mol. Ther. 3*:403-410, Academic Press (2001).
Cherng, J.-Y., et al., "Effect of DNA topology on the transfection efficiency of poly((2-dimethylamino)ethyl methacrylate)-plasmid complexes," *J. Control. Release 60*:343-353, Elsevier Science B.V. (1999).
Cohen, J., "Naked DNA points way to vaccines," *Science 259*:1691-1692, American Association for the Advancement of Science (1993).
Collisson, E.W., et al., "Cytotoxic T lymphocytes are critical in the control of infectious bronchitis virus in poultry," *Dev. Comp. Immunol. 24*:187-200, Elsevier Science Ltd. (2000).
Darquet, A.-M., et al., "A new DNA vehicle for nonviral gene delivery: supercoiled minicircle," *Gene Therapy 4*:1341-1349, Stockton Press (1997).
Davis, H.L., et al., "Direct gene transfer in skeletal muscle: plasmid DNA-based immunization against the hepatitis B virus surface antigen," *Vaccine 12*:1503-1509, Butterworth-Heinemann Ltd. (1994).
De Haan, C.A.M., et al., "Coronavirus particle assembly: primary structure requirements of the membrane protein," *J. Virol. 72*:6838-6850, American Society for Microbiology (1998).
Duchosal, M.A., et al., "Immunization of hu-PBL-SCID mice and the rescue of human monoclonal Fab fragments through combinatorial libraries," *Nature 355*:258-262, Macmillan Magazines Ltd. (1992).
Enjuanes, L., et al., "Development of protection against coronavirus induced diseases. A review," *Adv. Exp. Med. Biol. 380*:197-211, Plenum Press (1995).
Felgner, P.L., et al., "Lipofection: A highly efficient, lipid-mediated DNA-transfection procedure," *Proc. Natl. Acad. Sci. USA 84*:7413-7417, The National Academy of Sciences (1987).
Felgner, P.L., "Nonviral strategies for gene therapy," *Scientific American 276*:102-106, Scientific American, Inc. (1997).
Ferrarro, A.S. and Newkirk, M.M., "In vitro stimulation of human peripheral blood B cells from normal individuals by activated T cells increases the efficiency of hybridoma generation," *Hum. Antibod. Hybridomas 4*:80-85, Butterworth-Heinemann (1993).
Fouchier, R.A.M., et al., "Aetiology: Koch's postulates fulfilled for SARS virus," *Nature 423*:240, Nature Publishing Group (2003).
Gallagher, T.M. and Buchmeier, M.J., "Coronavirus spike proteins in viral entry and pathogenesis," *Virology 279*:371-374, Academic Press (2001).
Gao, X. and Huang, L., "Potentiation of Cationic Liposome-Mediated Gene Delivery by Polycations," *Biochemistry 35*:1027-1036, American Chemical Society (1996).
Gilbert, S.C., et al., "Enhanced CD8 T cell immunogenicity and protective efficacy in a mouse malaria model using a recombinant adenoviral vaccine in heterologous prime-boost immunisation regimes," Vaccine 20:1039-1045, Elsevier Science Ltd. (2002).
Gonzalo, R.M., et al., "A heterologous prime-boost regime using DNA and recombinant vaccinia virus expressing the *Leishmania infantum* P36/LACK antigen protects BALB/c mice from cutaneous leishmaniasis," *Vaccine 20*:1226-1231, Elsevier Science Ltd. (2002).
Gramzinski, R.A., et al., "Immune Response to a Hepatitis B DNA Vaccine in *Aotus* Monkeys: A Comparison of Vaccine Formulation, Route, and Method of Administration," *Mol. Med. 4*:109-118, The Picower Institute Press (1998).
Haijema, B.J., et al., "Switching species tropism: an effective way to manipulate the feline coronavirus genome," *J. Virol. 77*:4528-4538, American Society for Microbiology (2003).
"Codon Usage Database" maintained by Kazusa DNA Research Institute, 1 page, available at http://www.kazusa.or.jp/codon/ (visited Jul. 9, 2002).
Hartikka, J., et al., "Vaxfectin enhances the humoral immune response to plasmid DNA-encoded antigens," *Vaccine 19*:1911-1923, Elsevier Science Ltd. (2001).
Hartikka, J., et al., "An Improved Plasmid DNA Expression Vector for Direct Injection into Skeletal Muscle," *Hum. Gene Ther. 7*:1205-1217, Mary Ann Liebert, Inc. (1996).
Hartikka, J., et al., "Electroporation-Facilitated Delivery of Plasmid DNA in Skeletal Muscle: Plasmid Dependence of Muscle Damage and Effect of Poloxamer 188," *Mol Ther 4*:407-415, Academic Press (2001).
Hayashi, M., et al., "Intramuscular injection of plasmid DNA expressing mRNA7 coding the nucleocapsid protein of JHMV partially protected mice against acute infection with JHMV," *Adv. Exp. Med. Biol. 440*:693-699, Plenum Press (1998).
Hays, J.P. and Myint, S.H., "PCR sequencing of the spike genes of geographically and chronologically distinct human coronaviruses 229E," *J. Virol. Methods 75*:179-193, Elsevier Science B.V. (1998).
Hendley, J.O., et al., "Coronavirus infections in working adults. Eight-year study with 229 E and OC 43," *Am. Rev. Respir. Dis. 105*:805-811, The National Tuberculosis and Respiratory Disease Association (1972).
Holmes, K.V., "SARS-associated coronavirus," *N. Eng. J. Med. 348*:1948-1951, Massachusetts Medical Society (2003).
Holste, D., et al., "Optimization of coding potentials using positional dependence of nucleotide frequencies," *J. Theor. Biol. 206*:525-537, Academic Press (2000).
Horn, N.A., et al., "Cancer Gene Therapy Using Plasmid DNA: Purification of DNA for Human Clinical Trials," *Hum. Gene Ther. 6*:565-573, Mary Ann Liebert, Inc. (1995).
Irie, R.F. and Morton, D.L., "Regression of cutaneous metastatic melanoma by intralesional injection with human monoclonal antibody to ganglioside GD2," *Proc. Natl. Acad. Sci. USA 83*:8694-8698, The National Academy of Sciences (1986).
Jang, S.K., et al., "Cap-independent translation of picornavirus RNAs: structure and function of the internal ribosomal entry site," *Enzyme 44*:292-309, S. Karger Medical and Scientific Publishers (1990).
Jang, S.K., et al., "A segment of the 5' nontranslated region of encephalomyocarditis virus RNA directs internal entry of ribosomes during in vitro translation," *J. Virol. 62*:2636-2643, American Society for Microbiology (1988).
Jung, J., et al., "Distinct Response of Human B cell Subpopulations in Recognition of an Innate Immune Signal, CpG DNA," *J. Immunol. 169*:2368-2373, The American Association of Immunologists, Inc. (2002).
Klinman, D.M., et al., "CpG motifs present in bacterial DNA rapidly induce lymphocytes to secrete interleukin 6, interleukin 12, and interferon γ," *Proc. Natl Acad. Sci. USA 93*:2879-2883, The National Academy of Sciences (1996).
Kodihalli, S., et al., "Strategies for inducing protection against avian influenza A virus subtypes with DNA vaccines," *Vaccine 18*:2592-2599, Elsevier Science Ltd. (2000).
Köhler, G., et al., "Fusion between immunoglobulin-secreting and nonsecreting myeloma cell lines," *Eur. J. Immunol. 6*:292-295, Verlag Chemie, GmbH and Academic Press Inc. (1976).
Köhler, G. and Milstein, C., "Derivation of specific antibody-producing tissue culture and tumor lines by cell fusion," *Eur. J. Immunol. 6*:511-519, Verlag Chemie, GmbH and Academic Press Inc. (1976).
Köhler, G. and Milstein, C., "Continuous cultures of fused cells secreting antibody of predefined specificity," *Nature 256*:495-497, Macmillan Journals Ltd. (1975).
Kunkel, F. and Herrler, G., "Structural and functional analysis of the S proteins of two human coronavirus OC43 strains adapted to growth in different cells," *Arch. Virol. 141*:1123-1131, Springer-Verlag (1996).
Kwekkeboom, J., et al., "An efficient procedure for the generation of human monoclonal antibodies based on activation of human B lymphocytes by a murine thymoma cell line," *J. Immunol. Methods 160*:117-127, Elsevier Science Publishers B.V. (1993).
Lin, X.Q., et al., "Antibody responses to respiratory coronavirus infections of cattle during shipping fever pathogenesis," *Arch. Virol. 145*:2335-2349, Springer-Verlag (2000).

Lindmayer, I., et al., "Development of New Jet Injector for Insulin Therapy," *Diabetes Care 9*:294-297, American Diabetes Association, Inc. (1986).
Manickan, E., et al., "DNA Vaccines—A Modern Gimmick or a Boon to Vaccinology?" *Crit. Rev. Immunol. 17*:139-154, Begell House, Inc. (1997).
Marra, M.A., et al., "The Genome sequence of the SARS-associated coronavirus," *Science 300*:1399-1404, American Association for the Advancement of Science (2003).
Martins, J.K. and Roedl, E.A., "Medijector—A New Method of Corticosteroid-Anesthetic Delivery," *J. Occup. Med. 21*:821-824, Oxford University Press (1979).
Mathiesen, I., "Electropermeabilization of skeletal muscle enhances gene transfer in vivo," *Gene Ther. 6*:508-514, Stockton Press (1999).
McCune, J.M., et al., "The SCID-hu mouse: murine model for the analysis of human hematolymphoid differentiation and function," *Science 241*:1632-1639, American Association for the Advancement of Science (1988).
McShane, H., "Prime-boost immunization strategies for infectious diseases," *Curr. Opin. Molec. Ther. 4*:23-27, PharmaPress Ltd. (2002).
Mir, L.M., et al., "High-efficiency gene transfer into skeletal muscle mediated by electric pulses," *Proc. Natl Acad. Sci. USA 96*:4262-4267, The National Academy of Sciences (1999).
Mondal, S.P., et al., "Isolation and characterization of a novel antigenic subtype of infectious bronchitis virus serotype DE072," *Avian. Dis. 45*:1054-1059, The American Association of Avian Pathologists (2001).
Morrison, S.L., "Transfectomas provide novel chimeric antibodies," *Science 229*:1202-1207, American Association for the Advancement of Science (1985).
Mosier, D.E., et al., "Transfer of a functional human immune system to mice with severe combined immunodeficiency," *Nature* 335:256-259, Macmillan Magazines Ltd. (1988).
Nagata, T., et al., "Codon optimization effect on translational efficiency of DNA vaccine in mammalian cells: analysis of plasmid DNA encoding a CTL epitope derived from microorganisms," *Biochem. Biophys. Res. Commun. 261*:445-451, Academic Press (1999).
Nakamura, Y., et al., "Codon usage tabulated from international DNA sequence databases: status for the year 2000," *Nucl. Acids Res. 28*:292, Oxford University Press (2000).
Narum, D.L., et al., "Codon optimization of gene fragments encoding Plasmodium falciparum merzoite proteins enhances DNA vaccine protein expression and immunogenicity in mice," *Infection and Immunity 69*:7250-7253, American Society for Microbioogy (2001).
Neuberger, M.S., et al., "A hapten-specific chimaeric IgE antibody with human physiological effector function," *Nature 314*:268-270, Macmillan Journals Ltd. (1985).
Nossal, G., "Living up to the legacy," *Nat. Med. 4*(Vaccine Suppl. ):475-476, Nature America, Inc. (1998).
Oi, V.T. and Morrison, S.L., "Chimeric Antibodies," *Bio Techniques 4*:214-221, Eaton Publishing Co. (1986).
Osorio, J.E., et al., "Immunization of dogs and cats with a DNA vaccine against rabies virus," *Vaccine 17*:1109-1116, Elsevier Science Ltd. (1999).
Page, K.W., et al., "Sequence comparison of the 5' end of mRNA 3 from transmissible gastroenteritis virus and porcine respiratory coronavirus," *J. Gen. Virol. 72*:579-587, Society for General Microbiology (1991).
Pewe, L. and Perlman, S., "Immune response to the immunodominant epitope of mouse hepatitis virus is polyclonal, but functionally monospecific in C57Bl/6 mice," *Virology 255*:106-116, Academic Press (1999).
Pewe, L. et al., "Cytotoxic T-cell-resistant variants arise at early times after infection in C57BL/6 but not in SCID mice infected with a neurotropic coronavirus," *J. Virol. 71*:7640-7647, American Society for Microbiology (1997).
Qin, Y.-J., et al., "Gene suture—a novel method for intramuscular gene transfer and its application in hypertension therapy," *Life Sciences 65*: 2193-2203, Elsevier Science Inc. (1999).
Ramsay, A.J., et al., "Genetic vaccination strategies for enhanced cellular, humoral and mucosal immunity," *Immunol. Rev. 171*:27-44, Munksgaard International Publishers Ltd. (1999).
Ramshaw, I.A. and Ramsay, A.J., "The prime-boost strategy: exciting prospects for improved vaccination," *Immunol. Today 21*:163-165, Elsevier Science Ltd. (2000).
Reed, S.E., "The behaviour of recent isolates of human respiratory coronavirus in vitro and in volunteers: evidence of heterogeneity among 229E-related strains," *J. Med. Virol. 13*:179-192, Alan R. Liss, Inc. (1984).
Reilley, B., et al., "SARS and Carlo Urbani," *N. Eng. J. Med. 348*:1951-1952, Massachusetts Medical Society (2003).
Ritz, J., et al., "Serotherapy of acute lymphoblastic leukemia with monoclonal antibody," *Blood 58*:141-152, Grune & Stratton, Inc. (1981).
Rizzuto G., et al., "Gene electrotransfer results in a high-level transduction of rat skeletal muscle and corrects anemia of renal failure," *Hum. Gen. Ther. 11*:1891-1900, Mary Ann Liebert, Inc. (2000).
Robinson, H.L., "New hope for an AIDS vaccine," *Nat. Rev. Immunol. 2*:239-250, Nature Publishing Group (2002).
Rota, P.A., et al., "Characterization of a novel coronavirus associated with severe acute respiratory syndrome," *Science 300*:1394-1399, American Association for the Advancement of Science (2003).
Sanchez, C.M., et al., "Targeted recombination demonstrates that the spike gene of transmissible gastroenteritis coronavirus is a determinant of its enteric tropism and virulence," *J. Virol. 73*:7607-7618, American Society for Microbiology (1999).
Schaffer, C., et al., "Prokaryotic glycosylation," *Proteomics 1*:248-261, Wiley-VCH Verlag GmbH (2001).
Schneider, J., et al., "Induction of CD8+ T cells using heterologous prime-boost immunisation strategies," *Immunol. Rev. 170*:29-38, Munksgaard Inetrnational Publishers Ltd. (1999).
Schrijver, R.S., et al., "Immunization of cattle with a BHV1 vector vaccine or a DNA vaccine both coding for the G protein of BRSV," *Vaccine 15*:1908-1916, Elsevier Science Ltd. (1997).
Schulz, G., et al., "Detection of ganglioside $G_{D2}$ in tumor tissues and sera of neuroblastoma patients," *Cancer Res. 44*:5914-5920, Cancer Research, Inc. (1984).
Scott, F.W., "Evaluation of risks and benefits associated with vaccination against coronavirus infections in cats," *Adv. Vet. Med. 41*:347-358, Academic Press (1999).
Seo, S.H., et al., "The carboxyl-terminal 120-residue polypeptide of infectious bronchitis virus nucleocapsid induces cytotoxic T lymphocytes and protects chickens from acute infection," *J. Virol. 71*:7889-7894, American Society for Microbiology (1997).
Sestak, K., et al., "Active immunity and T-cell populations in pigs intraperitoneally inoculated with baculovirus-expressed transmissible gastroenteritis virus structural proteins," *Vet. Immunol. Immunopathol. 70*:203-221, Elsevier Science B.V. (1999).
Shiver, J.W., et al., "Replication-incompetent adenoviral vaccine vector elicits effective anti-immunodeficiency-virus immunity," *Nature 415*:331-335, Nature Publishing Group (2002).
Shoup, D.I., et al., "Active and passive immune responses to transmissible gastroenteritis virus (TGEV) in swine inoculated with recombinant baculovirus-expressed TGEV spike glycoprotein vaccines," *Am. J. Vet. Res. 58*:242-250, American Veterinary Medical Association (1997).
Sin, J.I., et al., "DNA priming-protein boosting enhances both antigen-specific antibody and Th1-type cellular immune responses in a murine herpes simplex virus-2 gD vaccine model," *DNA Cell Biol. 18*:771-779, Mary Ann Liebert, Inc. (1999).
Sonnhammer, E.L.L., et al., "A hidden Markov model for predicting transmembrane helices in protein sequences," *Proc. Int. Conf. Intell. Syst. Mol. Biol. 6*:175-82, American Association for Artificial Intelligence Press (1998).
Spaan, W.J.M., "Background paper. Progress towards a coronavirus recombinant DNA vaccine," *Adv. Exp. Med. Biol. 276*:201-203, Plenum Press (1990).
Spencer, J.S., et al., "Characterization of human T cell clones specific for coronavirus 229E," *Adv. Exp. Med. Biol. 380*:121-129, Plenum Press (1995).

Steenbakkers, P.G.A., et al., "Efficient generation of human anti-cytomegalovirus IgG monoclonal antibodies from preselected antigen-specific B cells," *Hum. Antibod. Hybridomas 4*:166-173, Butterworth-Heinemann (1993).
Stohlman, S.A., et al., "Mouse hepatitis virus nucleocapsid protein-specific cytotoxic T lymphocytes are $L^d$ restricted and specific for the carboxy terminus," *Virology 189*:217-224, Academic Press, Inc. (1992).
Sutcliffe, J.G., et al., "Antibodies that react with predetermined sites on proteins," *Science 219*:660-666, American Association for the Advancement of Science (1983).
Tanghe, A., "Improved immunogenicity and protective efficacy of a tuberculosis DNA vaccine encoding Ag85 by protein boosting," *Infect. Immun. 69*:3041-3047, American Society for Microbiology (2001).
Tohma, S. and Lipsky, P.E., "Analysis of the mechanisms of T cell-dependent polyclonal activation of human B cells. Induction of human B cell responses by fixed activated T cells," *J. Immunol. 146*:2544-2552, The American Association of Immunologists (1991).
Toncheva, V., et al., "Novel vectors for gene delivery formed by self-assembly of DNA with poly(L-lysine) grafted with hydrophilic polymers," *Biochim. Biophys. Acta 1380*:354-368, Elsevier Science B.V. (1998).
Trubetskoy, V.S., et al., "Cationic liposomes enhance targeted delivery and expression of exogenous DNA mediated by N-terminal modified poly(L-lysine)-antibody conjugate in mouse lung endothelial cells," *Biochem. Biophys. Acta 1131*:311-313, Elsevier Science Publishers B.V. (1992).
Tsang, K.W., et al., "A cluster of cases of severe acute respiratory syndrome in Hong Kong," *N. Engl. J. Med. 348*:1977-1985, Massachusetts Medical Society (May 2003).
Tuboly, T., et al., "Immunogenicity of the S protein of transmissible gastroenteritis virus expressed in baculovirus," *Arch. Virol. 137*:55-67, Springer-Verlag (1994).
Tuboly, T., et al., "Immunogenicity of porcine transmissible gastroenteritis virus spike protein expressed in plants," *Vaccine 18*: 2023-2028, Elsevier Science Ltd. (2000).
Uchijima, M., et al., "Optimization of codon usage of plasmid DNA vaccine is required for the effective MHC class I-restricted T cell responses against an intracellular bacterium," *J. Immunol. 161*:5594-5599, The American Association of Immunologists (1998).
Ulmer, J.B., et al., "Protective $CD4_{30}$ and $CD8^+$T cells against influenza virus induced by vaccination with nucleoprotein DNA," *J Virol. 72*:5648-5653, American Society for Microbiology (1998).
Ulmer, J.B., et al., "Heterologous protection against influenza by injection of DNA encoding a viral protein," *Science 259*:1745-1749, American Association for the Advancement of Science (1993).
Vahlsing, H.L., et al., "Immunization with plasmid DNA using a pneumatic gun," *J. Immunol. Methods 175*:11-22, Elsevier Science B.V. (1994).
Van Drunen Littel-Van Den Hurk, S., et al., "Intradermal immunization with a bovine herpesvirus-1 DNA vaccine induces protective immunity in cattle," *J. Gen. Virol. 79*:831-839, Society for General Microbiology (1998).
Vlasak, R., et al., "Human and bovine coronaviruses recognize sialic acid-containing receptors similar to those of influenza C viruses," *Proc. Natl. Acad. Sci. USA 85*:4526-4529, The National Academy of Sciences (1988).
Wagner, H., "Interactions between bacterial CpG-DNA and TLR9 bridge innate and adaptive immunity," *Curr. Opin. Microbiol. 5*:62-69, Elsevier Science Ltd. (2002).
Walgate, R., "Human SARS virus not identical to civet virus," *The Scientist* 4:20030527-03, Institute for Scientific Information (2003).
Wands, J.R. and Zurawski, Jr., V.R., "High Affinity Monoclonal Antibodies to Hepatitis B Surface Antigen (HBsAg) Produced by Somatic Cell Hybrids," *Gastroenterology 80*:225-232, Elsevier North-Holland, Inc. (1981).
Wheeler, C.J., et al., "Converting an alcohol to an amine in a cationic lipid dramatically alters the co-lipid requirement, cellular transfection activity and the ultrastructure of DNA-cytofectin complexes," *Biochim. Biophys. Acta 1280*:1-11, Elsevier Science B.V. (1996).
Wheeler, C.J., et al., "A novel cationic lipid greatly enhances plasmid DNA delivery and expression in mouse lung," *Proc. Natl. Acad. Sci. USA 93*:11454-11459, The National Academy of Sciences (1996).
Widera, G., et al, "Increased DNA Vaccine Delivery and Immunogenicity by Electroporation In Vivo," *J. Immunol. 164*:4635-4640, The American Association of Immunologists (2000).
Yang, Z.-Y., et al. "Overcoming Immunity to a Viral Vaccine by DNA Priming before Vector Boosting," *J. Virol. 77*:799-803, American Society for Microbiology (2003).
Yanisch-Perron, C., et al. "Improved M13 phage cloning vectors and host strains: nucleotide sequences of the M13mp18 and pUC19 vectors," *Gene 33*:103-119, Elsevier Science Publishers (1985).
Yeager, C.L., et al., "Human aminopeptidase N is a receptor for human coronavirus 229E," *Nature 357*:420-422, Macmillan Magazines Ltd. (1992).
Yoo, D., et al., "The S2 subunit of the spike glycoprotein of bovine coronavirus mediates membrane fusion in insect cells," *Virology 180*:395-399, Academic Press (1991).
Yoo, D., et al., "Structural analysis of the conformational domains involved in neutralization of bovine coronavirus using deletion mutants of the spike glycoprotein S1 subunit expressed by recombinant baculoviruses," *Virology 183*:91-98, Academic Press (1991).
Zelphati, O., et al., "Stable and monodisperse lipoplex formulations for gene delivery," *Gene Ther. 5*:1272-1282, Stockton Press (1998).
Zhang, X., et al., "Soluble factor-independent stimulation of human B cell response by mouse thymoma cells. Cyclosporine A-resistant and -sensitive cell contact signals," *J. Immunol. 144*:2955-2960, The American Association of Immunologists (1990).
NCBI Entrez, GenBank Report, Accession No. NC_004781 (Entry date 2003).
NCBI Entrez, GenBank Report, Accession No. AY274119 (Entry date 2003).
NCBI Entrez, GenBank Report, Accession No. AY278491 (Entry date 2003).
NCBI Entrez, GenBank Report, Accession No. AY278488 (Entry date 2003).
NCBI Entrez, GenBank Report, Accession No. AY278554 (Entry date 2003).
NCBI Entrez, GenBank Report, Accession No. AY278741 (Entry date 2003).
NCBI Entrez, GenBank Report, Accession No. AY282752 (Entry date 2003).
Japan Patent Office, Patent Abstracts of Japan, English language abstract for JP 2000-302692, document FP9, 2 pages, available at http://www19.ipdl.ncipi.go.jp/PA1/result/detail/main/wAAAoCaaDCDA412302692P1.htm (Copyright 2003).
Co-pending U.S. Appl. No. 60/681,975, inventors Hermanson, G., et al., filed May 18, 2005 (Not Published).
André, S. et al., "Increased Immune Response Elicited by DNA Vaccination with a Synthetic gp120 Sequence with Optimized Codon Usage," *J. of Virology* 72(9):1497-1503, American Society for Microbology (1998).
Boisgérault, F. et al., "Virus-Like Particles: A New Family of Delivery Systems," *Expert Rev. Vaccines* 1(1):101-109, Future Drugs Ltd. (2002).
Enserink, M. "Calling All Coronavirologists," *Science* 300:413-414, American Association for the Advancement of Science (2003).
Navas-Martin, S.and Weiss, S., "Coronavirus Replication and Pathogenesis: Implications for the Recent Outbreak of Severe Acute Respiratory Syndrome (SARS), and the Challenge for Vaccine Development," *J. of NeuroVirology* 10:75-85, Taylor & Francis (2004).
Schultz, J. et al., "Update on Antiviral DNA Vaccine Research (1998-2000)", *Intervirology* 43:197-217, S. Karger AG, Basel (2000).
Vennema, H. et al., "Nucleocapsid-Independent Assembly of Coronovirus-Like Particles by Co-Expression of Viral Envelope Protein Genes", *EMBO J.* 15(8):2020-2028, Oxford University Press (1996).
Weeratna, R.D. et al., "Optimization Strategies for DNA Vaccines" *Intervirology* 43:218-226, S. Karger AG, Basel (2000).
Buchholz, U.J., et al., "Contributions of the structural proteins of severe acute respiratory syndrome coronavirus to protective immunity," *Proc. Natl. Acad. Sci. USA 101*:9804-9809, National Academy of Sciences (Jun. 2004).

Krokhin, O., et al., "Mass Spectrometric Characterization of Proteins from the SARS Virus," *Mol. Cell. Proteomics 2*:346-356, The American Society for Biochemistry and Molecular Biology, Inc. (May 2003).
Qin, E., et al., "A complete sequence and comparative analysis of a SARS-associated virus (Isolate BJ01)," *Chinese Sci. Bull. 48*:941-948, Science in China Press (May 2003).
Australian Patent Office Supplementary Search Report for Austrailian Patent Application No. SG 200507477-8, Australian Patent Office, Woden, Australia, mailed on Oct. 9, 2006.
Stephensen, C.B., et al., "Phylogenetic analysis of a highly conserved region of the polymerase gene from 11 coronaviruses and development of a consensus polymerase chain reaction assay," *Virus Research 60*:181-189, Elsevier Science B.V. (1999).
Australian Patent Office, Written Opinion for Australian Patent Office No. SG 200507477-8, Australian Patent Office, Woden, Australia, mailed on Apr. 21, 2008.
Australian Patent Office, Examiner's First Report on Patent Application No. 2003251592, Australian Patent Office, Woden, Australia, mailed on Sep. 16, 2008.
Supplementary European Search Report for European Application No. EP 04 77 6029, mailed on Aug. 22, 2008, European Patent Office, The Hague, Netherlands.

* cited by examiner

SEVERE ACUTE RESPIRATORY SYNDROME DNA COMPOSITIONS AND METHODS OF USE

CROSS-REFERENCE TO RELATED APPLICATIONS

The present application claims the benefit of the filing date of U.S. Provisional Application Ser. No. 60/470,820, filed May 16, 2003, and U.S. Provisional Application Ser. No. 60/482,505, filed Jun. 26, 2003, which are both incorporated herein by reference in their entirety.

BACKGROUND OF THE INVENTION

The present invention relates to a novel coronavirus (referred to herein as SARS-CoV) and to SARS-CoV vaccine compositions and methods of treating or preventing SARS-CoV infection and disease in mammals. SARS-CoV was discovered in March of 2003, in association with Severe Acute Respiratory Syndrome (SARS), a newly emerging infectious disease of global importance.

The recognition of SARS has led to activation of a global response network, with resultant travel restrictions, major quarantine, and closure of health care facilities. As of May 14, 2003, 7628 cases and 587 deaths from SARS have been reported from 29 countries. Initial reports of an atypical pneumonia began to surface in November of 2002 from the Guangdong province of China. This early outbreak reportedly involved 305 people, many of whom were healthcare workers. On Feb. 21, 2003, a healthcare worker from Guangdong traveled to Hong Kong, where his pre-existing cold symptoms escalated and he was hospitalized for acute respiratory distress. From Hong Kong, the illness spread rapidly throughout Southeast Asia and to Canada from this one index case. Seven individuals can be linked to the index case through a stay on the ninth floor of the hotel he occupied during his first night in Hong Kong. Infected persons from three hospitals in the Hong Kong metropolitan area are traceable to this index case as well. The primary mode of transmission has been either person-to-person contact or droplet transmission. Two notable exceptions to this are the hotel in Hong Kong, where direct human contact cannot be established for all those infected, and the Amoy Garden apartment buildings where more than 221 residents have been infected. In the outbreak at the Amoy Garden apartments, an unknown environmental factor is suspected of playing a role in transmission.

The incubation period ranges on average between two and seven days. Onset of symptoms begins with a high fever associated with chills and rigors. Additional symptoms at onset may include headache, malaise, myalgia, mild respiratory symptoms and more rarely common cold symptoms such as sore throat and runny nose. After this initial three to seven day period, additional lower respiratory symptoms appear including dry, non-productive cough and dyspnea. Initial chest x-rays reveal small, unilateral, patchy shadowings that progress quickly to bilateral, diffuse infiltrates. Preliminary. Outbreak news: severe acute respiratory syndrome (SARS). *Wkly. Epidemiol. Rec.,* 2003: 81-88 (2003). The median duration of symptoms in a small epidemiologic study was 25.5 days. Tsang, K.W., et al. *A cluster of cases of severe acute respiratory syndrome in Hong Kong, N. Engl. J. Med.* (2003). The severity of illness can range widely from a mild illness to acute respiratory failure resulting in death. Patients with a significant co-morbidity, such as diabetes, or who are older, are more likely to suffer from a severe form of the disease. Questions remain as to why some patients become infected, while others who have intimate contact with infected individuals are spared. It does appear that patients are very contagious at the onset of symptoms. Studies from hospitals in Hong Kong and Hanoi have shown attack rates >56% among healthcare workers caring for SARS patients. It is unclear at this time whether individuals are contagious during the incubation phase.

Important Features of Coronaviruses

Coronaviruses are large, enveloped, positive-stranded RNA viruses, and they are known to elicit coincident diseases in animals and humans. Mature human coronavirus (HCoV) virions are approximately 100 nm-diameter enveloped particles exposing prominent spike (S), hemagglutinin-esterase (HE) (in some types of coronaviruses), envelope (E) and membrane (M) glycoproteins. Each particle contains an approximately 30 kilobase (kB) RNA genome complexed with an approximately 60 kilodalton (kD) nucleoprotein (N). Fields, B.N. VIROLOGY New York: Lippincott, Williams & Wilkins, (Fields, B.N., ed. 2001). All of the above references are herein incorporated by reference in their entireties.

The S proteins of HCoV's have two large domains, the variable S1 domain responsible for host cell binding, Breslin, J.J. et al. *J Virol.* 77: 4435-8 (2003), and the S2 domain containing a heptad coiled-coiled structure reminiscent of those involved in fusion in HIV and influenza. Yoo, D.W. et al. *Virology* 183: 91-8 (1991). The HCoV-229E, group I S protein appears to bind to the human aminopeptidase N glycoprotein, Yeager, C.L., et al. *Nature* 357: 420-2 (1992); Bonavia, A. et al. *J. Virol.* 77: 2530-8 (2003), whereas the HCoV-OC43 strain (HCoV-OC43, group II) may bind via sialic acid moieties. Vlasak, R. et al. *Proc. Natl. Acad. Sci. USA* 85:4526-9 (1988). The genetic variability between strains of coronavirus has not been thoroughly evaluated, although only minor variability has been observed in the S protein in the small number of strains sequenced. Hays, J.P. and Myint, S.H. *J. Virol. Methods* 75: 179-93 (1998); Kunkel, F. and Herrler, *G. Arch. Virol.* 141: 1123-31 (1996). Most coronaviruses are not only species specific, but also somewhat tissue tropic. This tropism is mostly related to changes in the S protein. Sanchez, C.M. et al. *J Virol.* 73: 7607-18 (1999). Examples of such coronavirus tropism changes are the in vitro demonstration that tropism can be experimentally manipulated by genetically replacing a feline S protein with a mouse S protein, and the natural emergence of the porcine respiratory coronavirus (PRCoV) from the transmissible gastroenteritis virus of swine (TGEV) strain merely through a deletion of a region in the S protein. Haijema, B.J. et al. *J. Virol.* 77:4528-38 (2003); Page, K.W. et al. *J. Gen. Virol.* 72:579-87 (1991); Britton, P. et al. *Virus Res.* 21:181-98 (1991). All of the above references are herein incorporated by reference in their entireties.

The recently discovered novel coronavirus, SARS-CoV, appears to be a new member of the order Nidovirales. Concerted efforts by many laboratories worldwide has led to the rapid sequencing of various strains of SARS-CoV, including CUKH-Su10 (GenBank Accession No. AY282752), TOR2 (GenBank Accession No. AY274119 and NC.sub.-004781), BJ01 (GenBank Accession No. AY278488), CUHK-W1 (GenBank Accession No. AY278554), Urbani (GenBank Accession No. AY278741) and HKU-39849 (GenBank Accession No. AY278491). The Urbani strain of SARS-CoV, sequenced by the Centers for Disease Control in Atlanta, Ga., is a 29,727-nucleotide, polyadenylated RNA with a genomic organization that is typical of coronaviruses: 5'-replicase, spike (S), envelope (E), membrane (M)-3'. Rota et al., Science 300:1394-1399 (2003), (hereinafter "Rota et al."). In addition, there are short untranslated regions at both termini, and open reading frames (ORFs) encoding non-structural proteins located between S and E, between M and N, or downstream of N. Rota et al. The hemagglutinin-esterase (HE) gene found in group 2 and some group 3 coronaviruses was not found in SARS-CoV. Rota et al. Sequencing of the Tor2 SARS-CoV strain by a collaboration of researchers in British Columbia, Canada, yielded a genomic sequence that differed from the Urbani SARS-CoV strain by eight nucleotide bases. Marra et al., Science 300:1399-1404 (2003), (hereinafter "Marra et al."). A comparison of the HKU-39849 and CUHK-W1 SARS-CoV strains also differed from the Urbani sequence by 10 or fewer nucleotide bases. Rota et al. All of the above references are herein incorporated by reference in their entireties.

Phylogenetic analyses indicate that, based on the genetic distance between SARS-CoV and other known coronaviruses in all of their genetic regions, no large region of the SARS-CoV genome was derived from other known viruses, and that SARS forms a distinct group within the genus *Cornavirus*. Rota et al.; Marra et al. The analyses also showed greater sequence conservation among enzymatic proteins of SARS-CoV than among the S, N, M, and E structural proteins; and, while there were regions of amino acid conservation within each protein as between SARS-CoV and other coronaviruses, the overall similarity was low. Rota et al. All of the above references are herein incorporated by reference in their entireties.

A virus, almost identical to the human SARS-CoV virus, has been isolated from rare Chinese masked palm civet cats. This virus is believed to be identical to human SARS-CoV except for a 29 nucleotide deletion in the region encoding the N protein of the virus. Walgate, R. "Human SARS virus not identical to civet virus" The Scientist, May 27, 2003, incorporated herein by reference in its entirety.

Coronavirus Vaccine Candidates

Because SARS-CoV was so recently discovered, there are no vaccines against the virus. The approach to vaccine development can, however, be partially guided by the results of past studies in animals, of which three diseases have received the greatest attention. These are transmissible gastroenteritis virus (TGEV) in swine, feline infectious peritonitis virus (FIPV), and avian infectious bronchitis virus (IBV). Of note, none of the vaccines, most of which have been attenuated vaccines, have proven to be highly efficacious except for inactivated IBV. Enjuanes, L. et al., *Adv. Exp. Med. Biol.* 380: 197-211 (1995). The FIPV vaccine is a live attenuated virus that has provided minimal efficacy in field trials, and the TGEV vaccine has also been problematic. Scott, F. W., *Adv. Vet. Med.* 41:347-58 (1999); Sestak, K. et al., *Vet. Immunol. Immunopathol.* 70:203-21 (1999). All of the above references are herein incorporated by reference in their entireties.

In the TGEV model, the major focus has been on neutralizing antibody directed at the S glycoprotein. Sestak, K. et al., *Vet. Immunol. Immunopathol.* 70: 203-21 (1999); Tuboly, T. et al. *Vaccine* 18: 2023-8 (2000); Shoup, D.I. et al. *Am. J. Vet. Res.* 58: 242-50 (1997). Protection has also been associated with antibodies in IBV and bovine coronavirus. Mondal, S. P. et al. *Avian. Dis.* 45:1054-9 (2001); Yoo, D.W. et al. *Virology* 180: 395-9 (1991). In fact, in most of the animal models, control of coronavirus infection can be due to antibodies reactive to the N-terminal region of the S protein. Gallagher, T.M. and Buchmeier, M.J. *Virology* 279: 371-4 (2001); Tuboly, T. et al. *Arch. Virol.* 137: 55-67 (1994). In one study of respiratory bovine coronavirus, antibody appearance to the S and N proteins was correlated with recovery. Lin, X.Q. et al. *Arch. Virol.* 145: 2335-49 (2000); Passive transfer studies have also been successful and demonstrated the value of humoral immune responses. Enjuanes, L. et al., *Adv. Exp. Med. Biol.* 380: 197-211 (1995); Spaan, W.J. *Adv. Exp. Med. Biol.* 276: 201-3 (1990). All of the above references are herein incorporated by reference in their entireties.

Cell-mediated immune responses have been most clearly detected in coronaviruses against the S, M and N proteins. Spencer, J.S. et al. *Adv. Exp. Med. Biol.* 380: 121-9 (1995); Collisson, E.W. et al. *Dev. Comp. Immunol.* 24: 187-200 (2000); Stohlman, S.A. et al. *Virology* 189: 217-24 (1992). In one study, the use of a DNA vaccine encoding the carboxyl terminus of the N gene of IBV, which induced cytotoxic T cell (CTL) activity, was able to decrease virus titers by 7 logs in target organs. Seo, S.H. et al. *J. Virol.* 71: 7889-94 (1997). Some protection was also noted in a DNA vaccine encoding the N protein in the Mouse Hepatitis Virus (MHV) model. Hayashi, M. et al. *Adv. Exp. Med. Biol.* 440:693-9 (1998). There is also some evidence that CTL may be involved in the control of MHV, and prevent the development of persistent infection and neuropathology. Pewe, L. and Perlman, S. *Virology* 255: 106-16 (1999); Pewe, L. et al. *J. Virol.* 71: 7640-7 (1997). All of the above references are herein incorporated by reference in their entireties.

A large number of coronavirus challenge studies have been conducted in humans by Tyrrell and colleagues, in which the subjects were inoculated intranasally and followed. Callow, K.A. et al. *Epidemiol. Infect.* 105: 435-46 (1990); Bende, M. et al. *Acta Otolaryngol.* 107: 262-9 (1989). Such challenge studies will clearly be impossible for the much more serious SARS-CoV virus. The presence of antibodies to the challenge strain did not prevent infection or disease, even in the face of rising neutralizing antibody titers. However, a second infection with similar strains led to decreased symptoms, revealing persistence of immunity against homologous challenge. Reed, S.E. *J. Med. Virol.* 13: 179-92 (1984). Also, the 2-4 year cyclical nature of the disease points to some persistence of immune response over time. Reed, S.E. *J. Med. Virol.* 13: 179-92 (1984); Hendley, J.O. et al. *Am. Rev. Respir. Dis.* 105: 805-11 (1972); Evans, A.S. and Kaslow, R.A. VIRAL INFECTIONS OF HUMANS. 4th ed. New York and London: Plenum Medical Book Company, (Evans, A.S. and Kaslow, R.A., eds., 1997). All of the above references are herein incorporated by reference in their entireties.

Heterologous "prime boost" strategies have been effective for enhancing immune responses and protection against numerous pathogens. Schneider et al., *Immunol. Rev.* 170:29-38 (1999); Robinson, H.L., *Nat. Rev. Immunol.* 2:239-50 (2002); Gonzalo, R.M. et al., Vaccine 20:1226-31 (2002); Tanghe, A., *Infect. Immun.* 69: 3041-7 (2001). Providing antigen in different forms in the prime and the boost injections appears to maximize the immune response to the antigen. DNA vaccine priming followed by boosting with protein in adjuvant or by viral vector delivery of DNA encoding antigen appears to be the most effective way of improving antigen specific antibody and CD4+ T-cell responses or CD8+ T-cell responses respectively. Shiver J.W. et al., *Nature* 415: 331-5 (2002); Gilbert, S.C. et al., *Vaccine* 20:1039-45 (2002); Billaut-Mulot, O. et al., *Vaccine* 19:95-102 (2000); Sin, J.I. et al., DNA Cell Biol. 18:771-9 (1999). Recent data from monkey vaccination studies suggests that adding CRL1005 poloxamer to DNA encoding the HIV gag antigen enhances T-cell responses when monkeys are vaccinated with an HIV gag DNA prime followed by a boost with an adenoviral vector expressing HIV gag (Ad5-gag). The cellular immune responses for a DNA/poloxamer prime followed by an Ad5-gag boost were greater than the responses induced with a DNA (without poloxamer) prime followed by Ad5-gag boost or for Ad5-gag only. Shiver, J.W. et al. *Nature* 415:331-5

(2002). U.S. Patent Appl. Publication No. US 2002/0165172 A1describes simultaneous administration of a vector construct encoding an immunogenic portion of an antigen and a protein comprising the said immunogenic portion of an antigen such that an immune response is generated. The document is limited to hepatitis B antigens and HIV antigens. Moreover, U.S. Pat. No. 6,500,432 is directed to methods of enhancing an immune response of nucleic acid vaccination by simultaneous administration of a polynucleotide and polypeptide of interest. According to the patent, simultaneous administration means administration of the polynucleotide and the polypeptide during the same immune response, preferably within 0-10 or 3-7 days of each other. The antigens contemplated by the patent include, among others, those of Hepatitis (all forms), HSV, HIV, CMV, EBV, RSV, VZV, HPV, polio, influenza, parasites (e.g., from the genus *Plasmodium*), pathogenic bacteria (including but not limited to *M tuberculosis, M leprae, Chlamydia, Shigella, B. burgdorferi, enterotoxigenic E. coli, S. typhosa, H. pylori, V. cholerae, B. pertussis*, etc.). All of the above references are herein incorporated by reference in their entireties.

SUMMARY OF THE INVENTION

The present invention is directed to compositions and methods for raising a detectable immune response in a vertebrate against the infectious agent transmitting Severe Acute Respiratory Syndrome (SARS), by administering in vivo, into a tissue of a vertebrate, at least one polynucleotide comprising one or more nucleic acid fragments, wherein each nucleic acid fragment is a fragment of a coding region operably encoding a polypeptide, or a fragment, variant, or derivative thereof, or a fragment of a codon-optimized coding region operably encoding a polypeptide, or a fragment, variant, or derivative thereof, from a coronavirus which causes SARS (SARS-CoV). The present invention is also directed to administering in vivo, into a tissue of the vertebrate the above-described polynucleotide and at least one isolated SARS-CoV polypeptide, or a fragment, variant, or derivative thereof. The isolated SARS-CoV polypeptide or fragment, variant, or derivative thereof can be, for example, a recombinant protein, a purified subunit protein, a protein expressed and carried by a heterologous live or inactivated or attenuated viral vector expressing the protein. According to either method, the polynucleotide is incorporated into the cells of the vertebrate in vivo, and an amount of the SARS-CoV protein, or fragment or variant encoded by the polynucleotide sufficient to raise a detectable immune response is produced in vivo. The isolated protein or fragment, variant, or derivative thereof is also administered in an amount sufficient to raise a detectable immune response. The polynucleotide may be administered to the vertebrate either prior to, at the same time (simultaneously), or subsequent to the administration of the isolated SARS-CoV polypeptide or fragment, variant, or derivative thereof.

Also within the scope of the present invention are combinations of SARS-CoV polypeptides and polynucleotides that encode SARS-CoV polypeptides that assemble into virus-like particles (VLP). One such combination is, but is not limited to a combination of SARS-CoV S, M, and E polypeptides or fragments, variants, or derivatives thereof, and polynucleotides encoding SARS-CoV S, M, and E polypeptides or fragments, variants, or derivatives thereof.

In a specific embodiment, the invention provides polynucleotide (e.g., DNA) vaccines in which the single formulation comprises a SARS-CoV polypeptide-encoding polynucleotide vaccine as described herein. An alternative embodiment of the invention provides for a multivalent formulation comprising several (e.g., two, three, four, or more) SARS-CoV polypeptide-encoding polynucleotides, as described herein, within a single vaccine composition. The SARS-CoV polypeptide-encoding polynucleotides, fragments or variants thereof may be contained within a single expression vector (e.g., plasmid or viral vector) or may be contained within multiple expression vectors.

In a specific embodiment, the invention provides combinatorial polynucleotide (e.g., DNA) vaccines which combine both a polynucleotide vaccine and polypeptide (e.g., either a recombinant protein, a purified subunit protein, a viral vector expressing an isolated SARS-CoV polypeptide) vaccine in a single formulation. , The single formulation comprises a SARS-CoV polypeptide-encoding polynucleotide vaccine as described herein, and optionally, an effective amount of a desired isolated SARS-CoV polypeptide or fragment, variant, or derivative thereof. The polypeptide may exist in any form, for example, a recombinant protein, a purified subunit protein, or a viral vector expressing an isolated SARS-CoV polypeptide. The SARS-CoV polypeptide or fragment, variant, or derivative thereof encoded by the polynucleotide vaccine may be identical to the isolated SARS-CoV polypeptide or fragment, variant, or derivative thereof. Alternatively, the SARS-CoV polypeptide or fragment, variant, or derivative thereof encoded by the polynucleotide may be different from the isolated SARS-CoV polypeptide or fragment, variant, or derivative thereof.

The present invention further provides a method for generating, enhancing, or modulating a protective and/or therapeutic immune response to SARS-CoV in a vertebrate, comprising administering to a vertebrate in need of therapeutic and/or preventative immunity one or more of the compositions described herein.

The invention also provides for antibodies specifically reactive with SARS Co-V polypeptides which have been produced from an immune response elicited by the administration, to a vertebrate, of polynucleotide and polypeptides of the present invention.

In one embodiment, purified monoclonal antibodies or polyclonal antibodies containing the variable heavy and light sequences are used as therapeutic and prophylactic agents to treat or prevent SARS-CoV infection by passive antibody therapy. In general, this will comprise administering a therapeutically or prophylactically effective amount of the monoclonal antibodies to a susceptible vertebrate or one exhibiting SARS Co-V infection.

BRIEF DESCRIPTION OF THE DRAWINGS/FIGURES

DETAILED DESCRIPTION OF THE INVENTION

Figure 1:
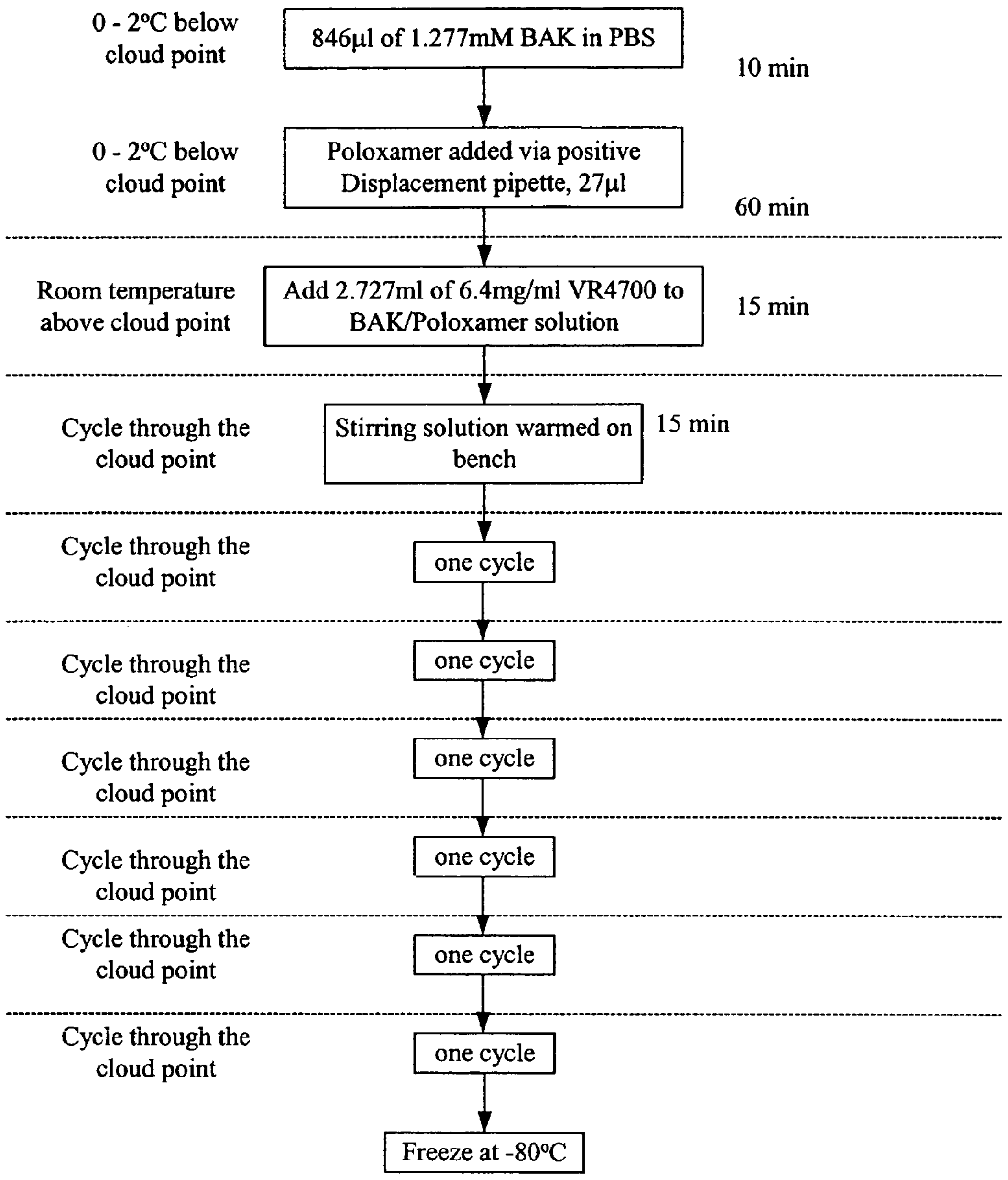
FIG. 1 shows the protocol for the preparation of a formulation comprising 0.3 mM BAK, 7.5 mg/ml CRL 1005, and 5 mg/ml of DNA in a final volume of 3.6 ml, through the use of thermal cycling.

The present invention is directed to compositions and methods for raising a detectable immune response in a vertebrate against the infectious agent transmitting Severe Acute Respiratory Syndrome (SARS), by administering in vivo, into a tissue of a vertebrate, at least one polynucleotide comprising one or more nucleic acid fragments, wherein each nucleic acid fragment is a fragment of a coding region operably encoding a polypeptide, or a fragment, variant, or derivative thereof, or a fragment of a codon-optimized coding region operably encoding a polypeptide, or a fragment, variant, or derivative thereof, from a coronavirus which causes SARS (SARS-CoV). The present invention is also directed to administering in vivo, into a tissue of the vertebrate the above-described polynucleotide and at least one isolated SARS-CoV polypeptide, or a fragment, variant, or derivative thereof. The isolated SARS-CoV polypeptide or fragment, variant, or derivative thereof can be, for example, a recombinant protein, a purified subunit protein, a protein expressed and carried by a heterologous live or inactivated or attenuated viral vector expressing the protein. According to either method, the polynucleotide is incorporated into the cells of the vertebrate in vivo, and an amount of the SARS-CoV protein, or fragment or variant encoded by the polynucleotide sufficient to raise a detectable immune response is produced in vivo. The isolated protein or fragment, variant, or derivative thereof is also administered in an amount sufficient to raise a detectable immune response. The polynucleotide may be administered to the vertebrate either prior to, at the same time (simultaneously), or subsequent to the administration of the isolated SARS-CoV polypeptide or fragment, variant, or derivative thereof.

In certain embodiments, the present invention provides for methods for raising a detectable immune response to polypeptides from a SARS-CoV virus, comprising administering to a vertebrate a polynucleotide which operably encodes a SARS-CoV polypeptide, wherein said polynucleotide is administered in an amount sufficient to elicit a detectable immune response to the encoded polypeptide.

The nucleotide and amino acid sequences of several SARS-CoV polypeptides have recently been determined. Several strains of human SARS-CoV (hSARS-CoV) have been sequenced. Sequences available on GenBank include the complete genomic sequences for SARS coronavirus strains CUKH-Su1, TOR2, BJ01, CUHK-W1, Urbani, and HKU-39849. SARS-CoV polypeptides from any of these strains are within the scope of the invention. Non-limiting examples of SARS-CoV polypeptides within the scope of the invention include the Spike (S), Nucleocapsid (N), Envelope (E), and Membrane glycoprotein (M) polypeptides, fragments, derivatives, (e.g., a TPA-S fusion), and variants thereof. As shown in Table 1 below, adapted from Rota et al., the various SARS-CoV strains that have been sequenced differ in various nucleotide base positions, some of which, as shown in Table 2 below, adapted from Marra et al., may result in a different amino acid residue. Thus, also within the scope of the invention are polypeptides that have different amino acids at those positions. The SARS-CoV polypeptide examples described below are from the Urbani strain of SARS-CoV, and are not meant to be limiting in terms of the scope of the invention.

TABLE 1

Comparison of Genomic Sequences of SARS-CoV Strains

| Nucleotide Position[d] | Consensus | HKU-39849 | CUHK-W1 | Urbani | TOR2 |
|---|---|---|---|---|---|
| 2,601 | T | C | * | * | * |
| 7,746 | G | * | T | * | * |
| 7,919 | C | * | * | T | * |

TABLE 1-continued

Comparison of Genomic Sequences of SARS-CoV Strains

| Nucleotide Position[d] | Consensus | HKU-39849 | CUHK-W1 | Urbani | TOR2 |
|---|---|---|---|---|---|
| 7,930 | G | A | * | * | * |
| 8,387 | G | C | * | * | * |
| 8,417 | G | C | * | * | * |
| 9,404 | T | * | C | * | * |
| 9,479 | T | * | C | * | * |
| 13,494 | G | A | * | * | * |
| 13,495 | T | G | * | * | * |
| 16,622 | C | * | * | T | * |
| 17,564 | T | * | G | * | * |
| 17,846 | C | * | T | * | * |
| 18,065 | G | A | * | * | * |
| 19,064 | R | A | G | G | A |
| 21,721 | G | * | A | * | * |
| 22,222 | T | * | C | * | * |
| 23,220 | T | * | * | * | G |
| 24,872 | T | * | * | C | * |
| 25,298 | G | * | * | * | A |
| 25,569 | T | A | * | * | * |
| 26,600 | C | T | * | * | * |
| 26,857 | T | * | * | C | * |
| 27,827 | T | * | C | * | * |

TABLE 2

Comparison of Tor2 and Urbani Strains of SARS-CoV and Corresponding Amino Acid Substitutions

| Nucleotide Position | Tor2 Base | Corresponding Amino Acid | Urbani Base | Corresponding Amino Acid | Protein |
|---|---|---|---|---|---|
| 7,919 | C | A | T | V | Rep1A |
| 16,622 | C | A | T | A | Rep1B |
| 19,064 | A | E | G | E | Rep1B |
| 19,183 | T | V | C | A | Rep1B |
| 23,220 | G | A | T | S* | Spike (S) |
| 24,872 | T | L | C | L | Spike (S) |
| 25,298 | A | R | G | G* | ORF 3 |
| 26,857 | T | S | C | P* | M |

*Non-conservative Amino Acid Substitution

From about nucleotide 21492 to about 25259 of the Urbani strain of the SARS-CoV genome encode the Spike (S) protein. (Bellini et al. SARS Coronavirus Urbani, complete genome. GenBank Accession No. AY278741.) The complete S protein is about 1255 amino acids in length (139.12 kDa) and is predicted, by analogy to other coronaviruses, to be a surface projection glycoprotein precursor. The S protein has several important biologic functions. Monoclonal antibodies against S can neutralize virus infectivity, consistent with the observation that S protein binds to cellular receptors. The S glycoprotein has several important biologic functions. Monoclonal antibodies against S can neutralize virus infectivity, consistent with the observation that S protein binds to cellular receptors. The S protein is encoded by the following polynucleotide sequence in the Urbani strain and is referred to herein as SEQ ID NO:22.

ATGTTTATTTTCTTATTATTTCTTACTCTCACTAGTGGTAGTGACCTTGA

CCGGTGCACCACTTTTGATGATGTTCAAGCTCCTAATTACACTCAACATA

CTTCATCTATGAGGGCGGTTTACTATCCTGATGAAATTTTTAGATCAGAC

ACTCTTTATTTAACTCAGGATTTATTTCTTCCATTTTATTCTAATGTTAC

AGGGTTTCATACTATTAATCATACGTTTGGCAACCCTGTCATACCTTTTA

-continued

AGGATGGTATTTATTTTGCTGCCACAGAGAAATCAAATGTTGTCCGTGGT
TGGGTTTTTGGTTCTACCATGAACAACAAGTCACAGTCGGTGATTATTAT
TAACAATTCTACTAATGTTGTTATACGAGCATGTAACTTTGAATTGTGTG
ACAACCCTTTCTTTGCTGTTTCTAAACCCATGGGTACACAGACACATACT
ATGATATTCGATAATGCATTTAATTGCACTTTCGAGTACATATCTGATGC
CTTTTCGCTTGATGTTTCAGAAAAGTCAGGTAATTTTAAACACTTACGAG
AGTTTGTGTTTAAAAATAAAGATGGGTTTCTCTATGTTTATAAGGGCTAT
CAACCTATAGATGTAGTTCGTGATCTACCTTCTGGTTTTAACACTTTGAA
ACCTATTTTTAAGTTGCCTCTTGGTATTAACATTACAAATTTTAGAGCCA
TTCTTACAGCCTTTTCACCTGCTCAAGACATTTGGGGCACGTCAGCTGCA
GCCTATTTTGTTGGCTATTTAAAGCCAACTACATTTATGCTCAAGTATGA
TGAAAATGGTACAATCACAGATGCTGTTGATTGTTCTCAAAATCCACTTG
CTGAACTCAAATGCTCTGTTAAGAGCTTTGAGATTGACAAAGGAATTTAC
CAGACCTCTAATTTCAGGGTTGTTCCCTCAGGAGATGTTGTGAGATTCCC
TAATATTACAAACTTGTGTCCTTTTGGAGAGGTTTTTAATGCTACTAAAT
TCCCTTCTGTCTATGCATGGGAGAGAAAAAAAATTTCTAATTGTGTTGCT
GATTACTCTGTGCTCTACAACTCAACATTTTTTTCAACCTTTAAGTGCTA
TGGCGTTTCTGCCACTAAGTTGAATGATCTTTGCTTCTCCAATGTCTATG
CAGATTCTTTTGTAGTCAAGGGAGATGATGTAAGACAAATAGCGCCAGGA
CAAACTGGTGTTATTGCTGATTATAATTATAAATTGCCAGATGATTTCAT
GGGTTGTGTCCTTGCTTGGAATACTAGGAACATTGATGCTACTTCAACTG
GTAATTATAATTATAAATATAGGTATCTTAGACATGGCAAGCTTAGGCCC
TTTGAGAGAGACATATCTAATGTGCCTTTCTCCCCTGATGGCAAACCTTG
CACCCCACCTGCTCTTAATTGTTATTGGCCATTAAATGATTATGGTTTTT
ACACCACTACTGGCATTGGCTACCAACCTTACAGAGTTGTAGTACTTTCT
TTTGAACTTTTAAATGCACCGGCCACGGTTTGTGGACCAAAATTATCCAC
TGACCTTATTAGAACCAGTGTGTCAATTTTAATTTTAATGGACTCACTGG
TACTGGTGTGTTAACTCCTTCTTCAAAGAGATTTCAACCATTTCAACAAT
TTGGCCGTGATGTTTCTGATTTCACTGATTCCGTTCGAGATCCTAAAACA
TCTGAAATATTAGACATTTCACCTTGCTCTTTTGGGGGTGTAAGTGTAAT
TACACCTGGAACAAATGCTTCATCTGAAGTTGCTGTTCTATATCAAGATG
TTAACTGCACTGATGTTTCTACAGCAATTCATGCAGATCAACTCACACCA
GCTTGGCGCATATATTCTACTGGAAACAATGTATTCCAGACTCAAGCAGG
CTGTCTTATAGGAGCTGAGCATGTCGACACTTCTTATGAGTGCGACATTC
CTATTGGAGCTGGCATTTGTGCTAGTTACCATACAGTTTCTTTATTACGT
AGTACTAGCCAAAAATCTATTGTGGCTTATACTATGTCTTTAGGTGCTGA
TAGTTCAATTGCTTACTCTAATAACACCATTGCTATACCTACTAACTTTT
CAATTAGCATTACTACAGAAGTAATGCCTGTTTCTATGGCTAAAACCTCC
GTAGATTGTAATATGTACATCTGCGGAGATTCTACTGAATGTGCTAATTT
GCTTCTCCAATATGGTAGCTTTTGCACACAACTAAATCGTGCACTCTCAG
GTATTGCTGCTGAACAGGATCGCAACACACGTGAAGTGTTCGCTCAAGTC
AAACAAATGTACAAAACCCCAACTTTGAAATATTTTGGTGGTTTTAATTT
TTCACAAATATTACCTGACCCTCTAAAGCCAACTAAGAGGTCTTTTATTG
AGGACTTGCTCTTTAATAAGGTGACACTCGCTGATGCTGGCTTCATGAAG
CAATATGGCGAATGCCTAGGTGATATTAATGCTAGAGATCTCATTTGTGC
GCAGAAGTTCAATGGACTTACAGTGTTGCCACCTCTGCTCACTGATGATA
TGATTGCTGCCTACACTGCTGCTCTAGTTAGTGGTACTGCCACTGCTGGA
TGGACATTTGGTGCTGGCGCTGCTCTTCAAATACCTTTTGCTATGCAAAT
GGCATATAGGTTCAATGGCATTGGAGTTACCCAAAATGTTCTCTATGAGA
ACCAAAAACAAATCGCCAACCAATTTAACAAGGCGATTAGTCAAATTCAA
GAATCACTTACAACAACATCAACTGCATTGGGCAAGCTGCAAGACGTTGT
TAACCAGAATGCTCAAGCATTAAACACACTTGTTAAACAACTTAGCTCTA
ATTTTGGTGCAATTTCAAGTGTGCTAAATGATATCCTTTCGCGACTTGAT
AAAGTCGAGGCGGAGGTACAAATTGACAGGTTAATTACAGGCAGACTTCA
AAGCCTTCAAACCTATGTAACACAACAACTAATCAGGGCTGCTGAAATCA
GGGCTTCTGCTAATCTTGCTGCTACTAAAATGTCTGAGTGTGTTCTTGGA
CAATCAAAAAGAGTTGACTTTTGTGGAAAGGGCTACCACCTTATGTCCTT
CCCACAAGCAGCCCCGCATGGTGTTGTCTTCCTACATGTCACGTATGTGC
CATCCCAGGAGAGGAACTTCACCACAGCGCCAGCAATTTGTCATGAAGGC
AAAGCATACTTCCCTCGTGAAGGTGTTTTTGTGTTTAATGGCACTTCTTG
GTTTATTACACAGAGGAACTTCTTTTCTCCACAAATAATTACTACAGACA
ATACATTTGTCTCAGGAAATTGTGATGTCGTTATTGGCATCATTAACAAC
ACAGTTTATGATCCTCTGCAACCTGAGCTCGACTCATTCAAAGAAGAGCT
GGACAAGTACTTCAAAAATCATACATCACCAGATGTTGATCTTGGCGACA
TTTCAGGCATTAACGCTTCTGTCGTCAACATTCAAAAAGAAATTGACCGC
CTCAATGAGGTCGCTAAAAATTTAAATGAATCACTCATTGACCTTCAAGA
ATTGGGAAAATATGAGCAATATATTAAATGGCCTTGGTATGTTTGGCTCG
GCTTCATTGCTGGACTAATTGCCATCGTCATGGTTACAATCTTGCTTTGT
TGCATGACTAGTTGTTGCAGTTGCCTCAAGGGTGCATGCTCTTGTGGTTC
TTGCTGCAAGTTTGATGAGGATGACTCTGAGCCAGTTCTCAAGGGTGTCAA
ATTACATTACACATAA

The S protein has the following amino acid sequence and is referred to herein as SEQ ID NO:23.

MFIFLLFLTLTSGSDLDRCTTFDDVQAPNYTQHTSSMRGVYYPDEIFRSD
TLYLTQDLFLPFYSNVTGFHTINHTFGNPVIPFKDGIYFAATEKSNVVRG
WVFGSTMNNKSQSVIIINNSTNVVIRACNFELCDNPFFAVSKPMGTQTHT
MIFDNAFNCTFEYISDAFSLDVSEKSGNFKHLREFVFKNKDGFLYVYKGY
QPIDVVRDLPSGFNTLKPIFKLPLGINITNFRAILTAFSPAQDIWGTSAA
AYFVGYLKPTTFMLKYDENGTITDAVDCSQNPLAELKCSVKSFEIDKGIY
QTSNFRVVPSGDVVRFPNITNLCPFGEVFNATKFPSVYAWERKKISNCVA

-continued

```
DYSVLYNSTFFSTFKCYGVSATKLNDLCFSNVYADSFVVKGDDVRQIAPG

QTGVIADYNYKLPDDFMGCVLAWNTRNIDATSTGNYNYKYRYLRHGKLRP

FERDISNVPFSPDGKPCTPPALNCYWPLNDYGFYTTTGIGYQPYRVVVLS

FELLNAPATVCGPKLSTDLIKNQCVNFNFNGLTGTGVLTPSSKRFQPFQQ

FGRDVSDFTDSVRDPKTSEILDISPCSFGGVSVITPGTNASSEVAVLYQD

VNCTDVSTAIHADQLTPAWRIYSTGNNVFQTQAGCLIGAEHVDTSYECDI

PIGAGICASYHTVSLLRSTSQKSIVAYTMSLGADSSIAYSNNTIAIPTNF

SISITTEVMPVSMAKTSVDCNMYICGDSTECANLLLQYGSFCTQLNRALS

GIAAEQDRNTREVFAQVKQMYKTPTLKYFGGFNFSQILPDPLKPTKRSFI

EDLLFNKVTLADAGFMKQYGECLGDINARDLICAQKFNGLTVLPPLLTDD

MIAAYTAALVSGTATAGWTFGAGAALQIPFAMQMAYRFNGIGVTQNVLYE

NQKQIANQFNKAISQIQESLTTTSTALGKLQDVVNQNAQALNTLVKQLSS

NFGAISSVLNDILSRLDKVEAEVQIDRLITGRLQSLQTYVTQQLIRAAEI

RASANLAATKMSECVLGQSKRVDFCGKGYHLMSFPQAAPHGVVFLHVTYV

PSQERNFTTAPAICHEGKAYFPREGVFVFNGTSWFITQRNFFSPQIITTD

NTFVSGNCDVVIGIINNTVYDPLQPELDSFKEELDKYFKNHTSPDVDLGD

ISGINASVVNIQKEIDRLNEVAKNLNESLIDLQELGKYEQYIKWPWYVWL

GFIAGLIAIVMVTILLCCMTSCCSCLKGACSCGSCCKFDEDDSEPVLKGV

KLHYT
```

The S protein can be divided into three structural domains: a large external domain at the N-terminus, a transmembrane domain and a short carboxyterminal cytoplasmic domain. These domains within the S protein of SARS-CoV Urbani strain have been identified using the program TMHMM2.0. (Sonnhammer et al. *Proc. Of 6$^{th}$ Int. Conf On Intelligent Systems for Molecular Biology*. AAAI Press: 175-182 (1998). Based on this algorithm, amino acids about 1 to about 1195 comprise an extracellular domain; amino acids about 1196 to about 1218 are part of a transmembrane domain; and amino acids about 1219 to about 1240 comprise the cytoplasmic domain. Removal of residues comprising the transmembrane domain and optionally, the cytoplasmic domain, results in a soluble protein that can be used in the compositions of the invention.

The large external domain of the S protein is further divided into two sub-domains, S1 and S2. The S1 sub-domain (amino acids about 1 to about 683) includes the N-terminal half of the molecule and forms the globular portion of the spikes. This region contains sequences that are responsible for binding to specific receptors on the membranes of susceptible cells. S1 sequences are variable, containing various degrees of deletion and substitutions in different coronavirus strains or isolates. Mutations in S1 sequences have been associated with altered antigenicity and pathogenicity of the virus. The receptor-binding domain of the S protein of murine hepatitis virus (MHV) is localized within the N-terminal 330 amino acids of the S1 domain. Consequently, the amino acid sequences of the S1 domain may determine the target cell specificity of coronaviruses in animals.

The S2 sub-domain comprises amino acids about 684 to about 1210 of the S protein. In coronaviruses, the S2 sub-domain of the S protein is usually acylated and contains two heptad repeat motifs. The motifs suggest that this portion of the S protein may assume a coiled-coil structure. The mature S protein forms an oligomer, which is most likely a trimer based on the spike proteins of other coronaviruses. Thus, the S2 subdomain probably constitutes the stalk of the viral spike.

Non limiting examples of nucleotide sequences encoding the S protein are as follows. It should be noted that S sequences vary between SARS-CoV strains. Virtually any nucleotide sequence encoding a SARS-CoV S protein is suitable for the present invention. In fact, S polynucleotide sequences included in vaccines and therapeutic formulations of the current invention may change from year to year, depending on the prevalent strain or strains of SARS-CoV.

From about nucleotide 21492 to about 25080 of the Urbani strain of the SARS-CoV genome encode a soluble extracellular portion of the S protein (Bellini et al. SARS Coronavirus Urbani, compete genome, Genbank accession number AY278741) and has the following sequence, referred to herein as SEQ ID NO: 1:

```
ATGTTTATTTTCTTATTATTTCTTACTCTCACTAGTGGTAGTGACCTTGA

CCGGTGCACCACTTTTGATGATGTTCAAGCTCCTAATTACACTCAACATA

CTTCATCTATGAGGGGGGTTTACTATCCTGATGAAATTTTTAGATCAGAC

ACTCTTTATTTAACTCAGGATTTATTTCTTCCATTTTATTCTAATGTTAC

AGGGTTTCATACTATTAATCATACGTTTGGCAACCCTGTCATACCTTTTA

AGGATGGTATTTATTTTGCTGCCACAGAGAAATCAAATGTTGTCCGTGGT

TGGGTTTTTGGTTCTACCATGAACAACAAGTCACAGTCGGTGATTATTAT

TAACAATTCTACTAATGTTGTTATACGAGCATGTAACTTTGAATTGTGTG

ACAACCCTTTCTTTGCTGTTTCTAAACCCATGGGTACACAGACACATACT

ATGATATTCGATAATGCATTTAATTGCACTTTCGAGTACATATCTGATGC

CTTTTCGCTTGATGTTTCAGAAAAGTCAGGTAATTTTAAACACTTACGAG

AGTTTGTGTTTAAAAATAAAGATGGGTTTCTCTATGTTTATAAGGGCTAT

CAACCTATAGATGTAGTTCGTGATCTACCTTCTGGTTTTAACACTTTGAA

ACCTATTTTTAAGTTGCCTCTTGGTATTAACATTACAAATTTTAGAGCCA

TTCTTACAGCCTTTTCACCTGCTCAAGACATTTGGGGCACGTCAGCTGCA

GCCTATTTTGTTGGCTATTTAAAGCCAACTACATTTATGCTCAAGTATGA

TGAAAATGGTACAATCACAGATGCTGTTGATTGTTCTCAAAATCCACTTG

CTGAACTCAAATGCTCTGTTAAGAGCTTTGAGATTGACAAAGGAATTTAC

CAGACCTCTAATTTCAGGGTTGTTCCCTCAGGAGATGTTGTGAGATTCCC

TAATATTACAAACTTGTGTCCTTTTGGAGAGGTTTTTAATGCTACTAAAT

TCCCTTCTGTCTATGCATGGGAGAGAAAAAAAATTTCTAATTGTGTTGCT

GATTACTCTGTGCTCTACAACTCAACATTTTTTTCAACCTTTAAGTGCTA

TGGCGTTTCTGCCACTAAGTTGAATGATCTTTGCTTCTCCAATGTCTATG

CAGATTCTTTTGTAGTCAAGGGAGATGATGTAAGACAAATAGCGCCAGGA

CAAACTGGTGTTATTGCTGATTATAATTATAAATTGCCAGATGATTTCAT

GGGTTGTGTCCTTGCTTGGAATACTAGGAACATTGATGCTACTTCAACTG

GTAATTATAATTATAAATATAGGTATCTTAGACATGGCAAGCTTAGGCCC

TTTGAGAGAGACATATCTAATGTGCCTTTCTCCCCTGATGGCAAACCTTG

CACCCCACCTGCTCTTAATTGTTATTGGCCATTAAATGATTATGGTTTTT
```

-continued

ACACCACTACTGGCATTGGCTACCAACCTTACAGAGTTGTAGTACTTTCT

TTTGAACTTTTAAATGCACCGGCCACGGTTTGTGGACCAAAATTATCCAC

TGACCTTATTAAGAACCAGTGTGTCAATTTTAATTTTAATGGACTCACTG

GTACTGGTGTGTTAACTCCTTCTTCAAAGAGATTTCAACCATTTCAACAA

TTTGGCCGTGATGTTTCTGATTTCACTGATTCCGTTCGAGATCCTAAAAC

ATCTGAAATATTAGACATTTCACCTTGCTCTTTTGGGGGTGTAAGTGTAA

TTACACCTGGAACAAATGCTTCATCTGAAGTTGCTGTTCTATATCAAGAT

GTTAACTGCACTGATGTTTCTACAGCAATTCATGCAGATCAACTCACACC

AGCTTGGCGCATATATTCTACTGGAAACAATGTATTCCAGACTCAAGCAG

GCTGTCTTATAGGAGCTGAGCATGTCGACACTTCTTATGAGTGCGACATT

CCTATTGGAGCTGGCATTTGTGCTAGTTACCATACAGTTTCTTTATTACG

TAGTACTAGCCAAAAATCTATTGTGGCTTATACTATGTCTTTAGGTGCTG

ATAGTTCAATTGCTTACTCTAATAACACCATTGCTATACCTACTAACTTT

TCAATTAGCATTACTACAGAAGTAATGCCTGTTTCTATGGCTAAAACCTC

CGTAGATTGTAATATGTACATCTGCGGAGATTCTACTGAATGTGCTAATT

TGCTTCTCCAATATGGTAGCTTTTGCACACAACTAAATCGTGCACTCTCA

GGTATTGCTGCTGAACAGGATCGCAACACACGTGAAGTGTTCGCTCAAGT

CAAACAAATGTACAAAACCCCAACTTTGAAATATTTTGGTGGTTTTAATT

TTTCACAAATATTACCTGACCCTCTAAAGCCAACTAAGAGGTCTTTTATT

GAGGACTTGCTCTTTAATAAGGTGACACTCGCTGATGCTGGCTTCATGAA

GCAATATGGCGAATGCCTAGGTGATATTAATGCTAGAGATCTCATTTGTG

CGCAGAAGTTCAATGGACTTACAGTGTTGCCACCTCTGCTCACTGATGAT

ATGATTGCTGCCTACACTGCTGCTCTAGTTAGTGGTACTGCCACTGCTGG

ATGGACATTTGGTGCTGGCGCTGCTCTTCAAATACCTTTTGCTATGCAAA

TGGCATATAGGTTCAATGGCATTGGAGTTACCCAAAATGTTCTCTATGAG

AACCAAAAACAAATCGCCAACCAATTTAACAAGGCGATTAGTCAAATTCA

AGAATCACTTACAACAACATCAACTGCATTGGGCAAGCTGCAAGACGTTG

TTAACCAGAATGCTCAAGCATTAAACACACTTGTTAAACAACTTAGCTCT

AATTTTGGTGCAATTTCAAGTGTGCTAAATGATATCCTTTCGCGACTTGA

TAAAGTCGAGGCGGAGGTACAAATTGACAGGTTAATTACAGGCAGACTTC

AAAGCCTTCAAACCTATGTAACACAACAACTAATCAGGGCTGCTGAAATC

AGGGCTTCTGCTAATCTTGCTGCTACTAAAATGTCTGAGTGTGTTCTTGG

ACAATCAAAAAGAGTTGACTTTTGTGGAAAGGGCTACCACCTTATGTCCT

TCCCACAAGCAGCCCCGCATGGTGTTGTCTTCCTACATGTCACGTATGTG

CCATCCCAGGAGAGGAACTTCACCACAGCGCCAGCAATTTGTCATGAAGG

CAAAGCATACTTCCCTCGTGAAGGTGTTTTTGTGTTTAATGGCACTTCTT

GGTTTATTACACAGAGGAACTTCTTTTCTCCACAAATAATTACTACAGAC

AATACATTTGTCTCAGGAAATTGTGATGTCGTTATTGGCATCATTAACAA

CACAGTTTATGATCCTCTGCAACCTGAGCTCGACTCATTCAAAGAAGAGC

TGGACAAGTACTTCAAAAATCATACATCACCAGATGTTGATCTTGGCGAC

ATTTCAGGCATTAACGCTTCTGTCGTCAACATTCAAAAAGAAATTGACCG

-continued

CCTCAATGAGGTCGCTAAAAATTTAAATGAATCACTCATTGACCTTCAAG

AATTGGGAAAATATGAGCAATATATTAAATGGCCTTGG

In a further embodiment the methods of the present invention provide for administering a polynucleotide which operably encodes a SARS-CoV S polypeptide, wherein said polynucleotide is 60%, 70%, 80%, 90%, 95%, 96%, 97%, 98%, 99% or 100% identical to SEQ ID NO:1, or a codon-optimized version as described below, and wherein said polynucleotide encodes a polypeptide that elicits a detectable immune response. The present invention is also directed to raising a detectable immune response with or without a wild-type or other secretory leader sequence as described below.

The amino acid sequence of the soluble S protein encoded by SEQ ID NO:1 has the following sequence shown below and is referred to herein as SEQ ID NO:2:

MFIFLLFLTLTSGSDLDRCTTFDDVQAPNYTQHTSSMRGVYYPDEIFRSD

TLYLTQDLFLPFYSNVTGFHTINHTFGNPVIPFKDGIYFAATEKSNVVRG

WVFGSTMNNKSQSVIIINNSTNVVIRACNFELCDNPFFAVSKPMGTQTHT

MIFDNAFNCTFEYISDAFSLDVSEKSGNFKHLREFVFKNKDGFLYVYKGY

QPIDVVRDLPSGFNTLKPIFKLPLGINITNFRAILTAFSPAQDIWGTSAA

AYFVGYLKPTTFMLKYDENGTITDAVDCSQNPLAELKCSVKSFEIDKGIY

QTSNFRVVPSGDVVRFPNITNLCPFGEVFNATKFPSVYAWERKKISNCVA

DYSVLYNSTFFSTFKCYGVSATKLNDLCFSNVYADSFVVKGDDVRQIAPG

QTGVIADYNYKLPDDFMGCVLAWNTRNIDATSTGNYNYKYRYLRHGKLRP

FERDISNVPFSPDGKPCTPPALNCYWPLNDYGFYTTTGIGYQPYRVVVLS

FELLNAPATVCGPKLSTDLIKNQCVNFNFNGLTGTGVLTPSSKRFQPFQQ

FGRDVSDFTDSVRDPKTSEILDISPCSFGGVSVITPGTNASSEVAVLYQD

VNCTDVSTAIHADQLTPAWRIYSTGNNVFQTQAGCLIGAEHVDTSYECDI

PIGAGICASYHTVSLLRSTSQKSIVAYTMSLGADSSIAYSNNTIAIPTNF

SISITTEVMPVSMAKTSVDCNMYICGDSTECANLLLQYGSFCTQLNRALS

GIAAEQDRNTREVFAQVKQMYKTPTLKYFGGFNFSQILPDPLKPTKRSFI

EDLLFNKVTLADAGFMKQYGECLGDINARDLICAQKFNGLTVLPPLLTDD

MIAAYTAALVSGTATAGWTFGAGAALQIPFAMQMAYRFNGIGVTQNVLYE

NQKQIANQFNKAISQIQESLTTTSTALGKLQDVVNQNAQALNTLVKQLSS

NFGAISSVLNDILSRLDKVEAEVQIDRLITGRLQSLQTYVTQQLIRAAEI

RASANLAATKMSECVLGQSKRVDFCGKGYHLMSFPQAAPHGVVFLHVTYV

PSQERNFTTAPAICHEGKAYFPREGVFVFNGTSWFITQRNFFSPQIITTD

NTFVSGNCDVVIGIINNTVYDPLQPELDSFKEELDKYFKNHTSPDVDLGD

ISGINASVVNIQKEIDRLNEVAKNLNESLIDLQELGKYEQYIKWPW

In a further embodiment the methods of the present invention provide for administering a polynucleotide which operably encodes a SARS-CoV S polypeptide comprising an amino acid sequence at least 60%, 70%, 80%, 90%, 95%, 96%, 97%, 98%, 99% or 100% identical to SEQ ID NO:2, wherein said polypeptide raises a detectable immune response. The present invention is also directed to raising a detectable immune response with or without a wildtype or other secretory leader sequence as described below.

A conserved protein domain program on the National Center for Biotechnology Information's web site (www.ncbi.nlm.nih.gov) was used to predict domains within the SARS-CoV S protein. Two domains, S1 and S2, were predicted within the soluble portion of the S protein. The S1 domain spans from amino acids about 1 to about 683 of the S protein. The nucleotide sequence encoding the soluble S1 domain from SARS-CoV Urbani strain has the following sequence and is referred to herein as SEQ ID NO:3: TABLE-US-00007

```
ATGTTTATTTTCTTATTATTTCTTACTCTCACTAGTGGTAGTGACCTTGA
CCGGTGCACCACTTTTGATGATGTTCAAGCTCCTAATTACACTCAACATA
CTTCATCTATGAGGGGGGTTTACTATCCTGATGAAATTTTTAGATCAGAC
ACTCTTTATTTAACTCAGGATTTATTTCTTCCATTTTATTCTAATGTTAC
AGGGTTTCATACTATTAATCATACGTTTGGCAACCCTGTCATACCTTTTA
AGGATGGTATTTATTTTGCTGCCACAGAGAAATCAAATGTTGTCCGTGGT
TGGGTTTTTGGTTCTACCATGAACAACAAGTCACAGTCGGTGATTATTAT
TAACAATTCTACTAATGTTGTTATACGAGCATGTAACTTTGAATTGTGTG
ACAACCCTTTCTTTGCTGTTTCTAAACCCATGGGTACACAGACACATACT
ATGATATTCGATAATGCATTTAATTGCACTTTCGAGTACATATCTGATGC
CTTTTCGCTTGATGTTTCAGAAAAGTCAGGTAATTTTAAACACTTACGAG
AGTTTGTGTTTAAAAATAAAGATGGGTTTCTCTATGTTTATAAGGGCTAT
CAACCTATAGATGTAGTTCGTGATCTACCTTCTGGTTTTAACACTTTGAA
ACCTATTTTTAAGTTGCCTCTTGGTATTAACATTACAAATTTTAGAGCCA
TTCTTACAGCCTTTTCACCTGCTCAAGACATTTGGGGCACGTCAGCTGCA
GCCTATTTTGTTGGCTATTTAAAGCCAACTACATTTATGCTCAAGTATGA
TGAAAATGGTACAATCACAGATGCTGTTGATTGTTCTCAAAATCCACTTG
CTGAACTCAAATGCTCTGTTAAGAGCTTTGAGATTGACAAAGGAATTTAC
CAGACCTCTAATTTCAGGGTTGTTCCCTCAGGAGATGTTGTGAGATTCCC
TAATATTACAAACTTGTGTCCTTTTGGAGAGGTTTTTAATGCTACTAAAT
TCCCTTCTGTCTATGCATGGGAGAGAAAAAAAATTTCTAATTGTGTTGCT
GATTACTCTGTGCTCTACAACTCAACATTTTTTTCAACCTTTAAGTGCTA
TGGCGTTTCTGCCACTAAGTTGAATGATCTTTGCTTCTCCAATGTCTATG
CAGATTCTTTTGTAGTCAAGGGAGATGATGTAAGACAAATAGCGCCAGGA
CAAACTGGTGTTATTGCTGATTATAATTATAAATTGCCAGATGATTTCAT
GGGTTGTGTCCTTGCTTGGAATACTAGGAACATTGATGCTACTTCAACTG
GTAATTATAATTATAAATATAGGTATCTTAGACATGGCAAGCTTAGGCCC
TTTGAGAGAGACATATCTAATGTGCCTTTCTCCCCTGATGGCAAACCTTG
CACCCCACCTGCTCTTAATTGTTATTGGCCATTAAATGATTATGGTTTTT
ACACCACTACTGGCATTGGCTACCAACCTTACAGAGTTGTAGTACTTTCT
TTTGAACTTTTAAATGCACCGGCCACGGTTTGTGGACCAAAATTATCCAC
TGACCTTATTAAGAACCAGTGTGTCAATTTTAATTTTAATGGACTCACTG
GTACTGGTGTGTTAACTCCTTCTTCAAAGAGATTTCAACCATTTCAACAA
TTTGGCCGTGATGTTTCTGATTTCACTGATTCCGTTCGAGATCCTAAAAC
```

-continued

```
ATCTGAAATATTAGACATTTCACCTTGCTCTTTTGGGGGTGTAAGTGTAA
TTACACCTGGAACAAATGCTTCATCTGAAGTTGCTGTTCTATATCAAGAT
GTTAACTGCACTGATGTTTCTACAGCAATTCATGCAGATCAACTCACACC
AGCTTGGCGCATATATTCTACTGGAAACAATGTATTCCAGACTCAAGCAG
GCTGTCTTATAGGAGCTGAGCATGTCGACACTTCTTATGAGTGCGACATT
CCTATTGGAGCTGGCATTTGTGCTAGTTACCATACAGTTTCTTTATTACG
TAGTACTAGCCAAAAATCTATTGTGGCTTATACTATGTCTTTAGGTGCT
```

In a further embodiment the methods of the present invention provide for administering a polynucleotide which operably encodes a SARS-CoV S1 polypeptide, wherein said polynucleotide is 60%, 70%, 80%, 90%, 95%, 96%, 97%, 98%, 99% or 100% identical to SEQ ID NO:3, or a codon-optimized version as described below, and wherein said polynucleotide encodes a polypeptide that elicits a detectable immune response. The present invention is also directed to raising a detectable immune response with or without a wild-type or other secretory leader sequence as described below.

The amino acid sequence of the soluble S1 protein encoded by SEQ ID NO:3 has the following sequence shown below and is referred to herein as SEQ ID NO:4:

```
MFIFLLFLTLTSGSDLDRCTTFDDVQAPNYTQHTSSMRGVYYPDEIFRSD
TLYLTQDLFLPFYSNVTGFHTINHTFGNPVIPFKDGIYFAATEKSNVVRG
WVFGSTMNNKSQSVIIINNSTNVVIRACNFELCDNPFFAVSKPMGTQTHT
MIFDNAFNCTFEYISDAFSLDVSEKSGNFKHLREFVFKNKDGFLYVYKGY
QPIDVVRDLPSGFNTLKPIFKLPLGINITNFRAILTAFSPAQDIWGTSAA
AYFVGYLKPTTFMLKYDENGTITDAVDCSQNPLAELKCSVKSFEIDKGIY
QTSNFRVVPSGDVVRFPNITNLCPFGEVFNATKFPSVYAWERKKISNCVA
DYSVLYNSTFFSTFKCYGVSATKLNDLCFSNVYADSFVVKGDDVRQIAPG
QTGVIADYNYKLPDDFMGCVLAWNTRNIDATSTGNYNYKYRYLRHGKLRP
FERDISNVPFSPDGKPCTPPALNCYWPLNDYGFYTTTGIGYQPYRVVVLS
FELLNAPATVCGPKLSTDLIKNQCVNFNFNGLTGTGVLTPSSKRFQPFQQ
FGRDVSDFTDSVRDPKTSEILDISPCSFGGVSVITPGTNASSEVAVLYQD
VNCTDVSTAIHADQLTPAWRIYSTGNNVFQTQAGCLIGAEHVDTSYECDI
PIGAGICASYHTVSLLRSTSQKSIVAYTMSLGA
```

In a further embodiment the methods of the present invention provide for administering a polynucleotide which operably encodes a SARS-CoV S1 polypeptide comprising an amino acid sequence at least 60%, 70%, 80%, 90%, 95%, 96%, 97%, 98%, 99%, or 100% identical to SEQ ID NO:4, wherein said polypeptide raises a detectable immune response. The present invention is also directed to raising a detectable immune response with or without a wildtype or other secretory leader sequence as described below.

The S2 domain spans from amino acids about 684 to about 1210 of the S protein. The nucleotide sequence encoding the soluble S2 domain from SARS-CoV Urbani strain has the following sequence and is referred to herein as SEQ ID NO:5:

GATAGTTCAATTGCTTACTCTAATAACACCATTGCTATACCTACTAACTT
TTCAATTAGCATTACTACAGAAGTAATGCCTGTTTCTATGGCTAAAACCT
CCGTAGATTGTAATATGTACATCTGCGGAGATTCTACTGAATGTGCTAAT
TTGCTTCTCCAATATGGTAGCTTTTGCACACAACTAAATCGTGCACTCTC
AGGTATTGCTGCTGAACAGGATCGCAACACACGTGAAGTGTTCGCTCAAG
TCAAACAAATGTACAAAACCCCAACTTTGAAATATTTTGGTGGTTTTAAT
TTTTCACAAATATTACCTGACCCTCTAAAGCCAACTAAGAGGTCTTTTAT
TGAGGACTTGCTCTTTAATAAGGTGACACTCGCTGATGCTGGCTTCATGA
AGCAATATGGCGAATGCCTAGGTGATATTAATGCTAGAGATCTCATTTGT
GCGCAGAAGTTCAATGGACTTACAGTGTTGCCACCTCTGCTCACTGATGA
TATGATTGCTGCCTACACTGCTGCTCTAGTTAGTGGTACTGCCACTGCTG
GATGGACATTTGGTGCTGGCGCTGCTCTTCAAATACCTTTTGCTATGCAA
ATGGCATATAGGTTCAATGGCATTGGAGTTACCCAAAATGTTCTCTATGA
GAACCAAAAACAAATCGCCAACCAATTTAACAAGGCGATTAGTCAAATTC
AAGAATCACTTACAACAACATCAACTGCATTGGGCAAGCTGCAAGACGTT
GTTAACCAGAATGCTCAAGCATTAAACACACTTGTTAAACAACTTAGCTC
TAATTTTGGTGCAATTTCAAGTGTGCTAAATGATATCCTTTCGCGACTTG
ATAAAGTCGAGGCGGAGGTACAAATTGACAGGTTAATTACAGGCAGACTT
CAAAGCCTTCAAACCTATGTAACACAACAACTAATCAGGGCTGCTGAAAT
CAGGGCTTCTGCTAATCTTGCTGCTACTAAAATGTCTGAGTGTGTTCTTG
GACAATCAAAAAGAGTTGACTTTTGTGGAAAGGGCTACCACCTTATGTCC
TTCCCACAAGCAGCCCCGCATGGTGTTGTCTTCCTACATGTCACGTATGT
GCCATCCCAGGAGAGGAACTTCACCACAGCGCCAGCAATTTGTCATGAAG
GCAAAGCATACTTCCCTCGTGAAGGTGTTTTTGTGTTTAATGGCACTTCT
TGGTTTATTACACAGAGGAACTTCTTTTCTCCACAAATAATTACTACAGA
CAATACATTTGTCTCAGGAAATTGTGATGTCGTTATTGGCATCATTAACA
ACACAGTTTATGATCCTCTGCAACCTGAGCTCGACTCATTCAAAGAAGAG
CTGGACAAGTACTTCAAAAATCATACATCACCAGATGTTGATCTTGGCGA
CATTTCAGGCATTAACGCTTCTGTCGTCAACATTCAAAAAGAAATTGACC
GCCTCAATGAGGTCGCTAAAAATTTAAATGAATCACTCATTGACCTTCAA
GAATTGGGAAAATATGAGCAATATATTAAATGGCCTTGG

In a further embodiment the methods of the present invention provide for administering a polynucleotide which operably encodes a SARS-CoV S2 polypeptide, wherein said polynucleotide is 60%, 70%, 80%, 90%, 95%, 96%, 97%, 98%, 99% or 100% identical to SEQ ID NO:5, or a codon-optimized version as described below, and wherein said polynucleotide encodes a polypeptide that elicits a detectable immune response. It should be noted that in order to achieve a polynucleotide "operably encoding" a SARS-CoV S2 polypeptide, at least a methionine codon (ATG) would need to be included, in frame, upstream of the polynucleotide presented herein as SEQ ID NO:5. An example of such a polynucleotide includes, but is not limited to the following, presented herein as SEQ ID NO:54.

ATGGATAGTTCAATTGCTTACTCTAATAACACCATTGCTATACCTACTAA
CTTTTCAATTAGCATTACTACAGAAGTAATGCCTGTTTCTATGGCTAAAA
CCTCCGTAGATTGTAATATGTACATCTGCGGAGATTCTACTGAATGTGCT
AATTTGCTTCTCCAATATGGTAGCTTTTGCACACAACTAAATCGTGCACT
CTCAGGTATTGCTGCTGAACAGGATCGCAACACACGTGAAGTGTTCGCTC
AAGTCAAACAAATGTACAAAACCCCAACTTTGAAATATTTTGGTGGTTTT
AATTTTTCACAAATATTACCTGACCCTCTAAAGCCAACTAAGAGGTCTTT
TATTGAGGACTTGCTCTTTAATAAGGTGACACTCGCTGATGCTGGCTTCA
TGAAGCAATATGGCGAATGCCTAGGTGATATTAATGCTAGAGATCTCATT
TGTGCGCAGAAGTTCAATGGACTTACAGTGTTGCCACCTCTGCTCACTGA
TGATATGATTGCTGCCTACACTGCTGCTCTAGTTAGTGGTACTGCCACTG
CTGGATGGACATTTGGTGCTGGCGCTGCTCTTCAAATACCTTTTGCTATG
CAAATGGCATATAGGTTCAATGGCATTGGAGTTACCCAAAATGTTCTCTA
TGAGAACCAAAAACAAATCGCCAACCAATTTAACAAGGCGATTAGTCAAA
TTCAAGAATCACTTACAACAACATCAACTGCATTGGGCAAGCTGCAAGAC
GTTGTTAACCAGAATGCTCAAGCATTAAACACACTTGTTAAACAACTTAG
CTCTAATTTTGGTGCAATTTCAAGTGTGCTAAATGATATCCTTTCGCGAC
TTGATAAAGTCGAGGCGGAGGTACAAATTGACAGGTTAATTACAGGCAGA
CTTCAAAGCCTTCAAACCTATGTAACACAACAACTAATCAGGGCTGCTGA
AATCAGGGCTTCTGCTAATCTTGCTGCTACTAAAATGTCTGAGTGTGTTC
TTGGACAATCAAAAAGAGTTGACTTTTGTGGAAAGGGCTACCACCTTATG
TCCTTCCCACAAGCAGCCCCGCATGGTGTTGTCTTCCTACATGTCACGTA
TGTGCCATCCCAGGAGAGGAACTTCACCACAGCGCCAGCAATTTGTCATG
AAGGCAAAGCATACTTCCCTCGTGAAGGTGTTTTTGTGTTTAATGGCACT
TCTTGGTTTATTACACAGAGGAACTTCTTTTCTCCACAAATAATTACTAC
AGACAATACATTTGTCTCAGGAAATTGTGATGTCGTTATTGGCATCATTA
ACAACACAGTTTATGATCCTCTGCAACCTGAGCTCGACTCATTCAAAGAA
GAGCTGGACAAGTACTTCAAAAATCATACATCACCAGATGTTGATCTTGG
CGACATTTCAGGCATTAACGCTTCTGTCGTCAACATTCAAAAAGAAATTG
ACCGCCTCAATGAGGTCGCTAAAAATTTAAATGAATCACTCATTGACCTT
CAAGAATTGGGAAAATATGAGCAATATATTAAATGGCCTTGG

The present invention is also directed to raising a detectable immune response with or without a wildtype or other secretory leader sequence as described below.

The amino acid sequence of the soluble S2 protein encoded by SEQ ID NO:5 has the following sequence shown below and is referred to herein as SEQ ID NO:6

DSSIAYSNNTIAIPTNFSISITTEVMPVSMAKTSVDCNMYICGDSTECAN
LLLQYGSFCTQLNRALSGIAAEQDRNTREVFAQVKQMYKTPTLKYFGGFN
FSQILPDPLKPTKRSFIEDLLFNKVTLADAGFMKQYGECLGDINARDLIC
AQKFNGLTVLPPLLTDDMIAAYTAALVSGTATAGWTFGAGAALQIPFAMQ
MAYRFNGIGVTQNVLYENQKQIANQFNKAISQIQESLTTTSTALGKLQDV

-continued

```
VNQNAQALNTLVKQLSSNFGAISSVLNDILSRLDKVEAEVQIDRLITGRL

QSLQTYVTQQLIRAAEIRASANLAATKMSECVLGQSKRVDFCGKGYHLMS

FPQAAPHGVVFLHVTYVPSQERNFTTAPAICHEGKAYFPREGVFVFNGTS

WFITQRNFFSPQIITTDNTFVSGNCDVVIGIINNTVYDPLQPELDSFKEE

LDKYFKNHTSPDVDLGDISGINASVVNIQKEIDRLNEVAKNLNESLIDLQ

ELGKYEQYIKWPW
```

The amino acid sequence of the soluble S2 protein encoded by SEQ ID NO:54 has the following sequence shown below and is referred to herein as SEQ ID NO:56

```
MDSSIAYSNNTIAIPTNFSISITTEVMPVSMAKTSVDCNMYICGDSTECA

NLLLQYGSFCTQLNRALSGIAAEQDRNTREVFAQVKQMYKTPTLKYFGGF

NFSQILPDPLKPTKRSFIEDLLFNKVTLADAGFMKQYGECLGDINARDLI

CAQKFNGLTVLPPLLTDDMIAAYTAALVSGTATAGWTFGAGAALQIPFAM

QMAYRFNGIGVTQNVLYENQKQIANQFNKAISQIQESLTTTSTALGKLQD

VVNQNAQALNTLVKQLSSNFGAISSVLNDILSRLDKVEAEVQIDRLITGR

LQSLQTYVTQQLIRAAEIRASANLAATKMSECVLGOSKRVDFCGKGYHLM

SFPQAAPHGVVFLHVTYVPSQERNFTTAPAICHEGKAYFPREGVFVFNGT

SWFITQRNFFSPQIITTDNTFVSGNCDVVIGIINNTVYDPLQPELDSFKE

ELDKYFKNHTSPDVDLGDISGINASVVNIQKEIDRLNEVAKNLNESLIDL

QELGKYEQYIKWPW
```

In a further embodiment the methods of the present invention provide for administering a polynucleotide which operably encodes a SARS-CoV S2 polypeptide comprising an amino acid sequence at least 60%, 70%, 80%, 90%, 95%, 96%, 97%, 98%, 99% or 100% identical to SEQ ID NO:6, wherein said polypeptide raises a detectable immune response. The present invention is also directed to raising a detectable immune response with or without a wildtype or other secretory leader sequence as described below.

In one embodiment, soluble S, soluble S1 and soluble S2, described herein, are encoded by a polynucleotide which contains the wild-type S secretory leader peptide sequence. The secretory leader peptide of the S protein in SARS-CoV Urbani strain comprises about the first 13 residues of the protein. Marra et al. The present invention is also directed to raising a detectable immune response with or without amino acids about 1 to about 10, about 1 to about 11, about 1 to about 12, about 1 to about 13, about 1 to about 14, about 1 to about 15, about 1 to about 16, about 1 to about 17, about 1 to about 18, about 1 to about 19, about 1 to about 20, about 1 to about 21, about 1 to about 22, about 1 to about 23, about 1 to about 24, and about 1 to about 25 of the secretory leader peptide sequence.

In an alternative embodiment, the secretory leader peptide of soluble S, soluble S1 and soluble S2 can be replaced by the secretory leader peptide of human Tissue Plasminogen Activator (TPA). The polynucleotide sequences encoding the various S polypeptides with the TPA secretory leader peptide are shown below.

```
Soluble TPA-S
                                          (SEQ ID NO: 7)
ATGGATGCAATGAAGAGAGGGCTCTGCTGTGTGCTGCTGCTGTGTGGAGC

AGTCTTCGTTTCGCCCAGCGCTAGAGGATCGGGAAGTGACCTTGACCGGT

GCACCACTTTTGATGATGTTCAAGCTCCTAATTACACTCAACATACTTCA

TCTATGAGGGGGGTTTACTATCCTGATGAAATTTTTAGATCAGACACTCT

TTATTTAACTCAGGATTTATTTCTTCCATTTTATTCTAATGTTACAGGGT

TTCATACTATTAATCATACGTTTGGCAACCCTGTCATACCTTTTAAGGAT

GGTATTTATTTTGCTGCCACAGAGAAATCAAATGTTGTCCGTGGTTGGGT

TTTTGGTTCTACCATGAACAACAAGTCACAGTCGGTGATTATTATTAACA

ATTCTACTAATGTTGTTATACGAGCATGTAACTTTGAATTGTGTGACAAC

CCTTTCTTTGCTGTTTCTAAACCCATGGGTACACAGACACATACTATGAT

ATTCGATAATGCATTTAATTGCACTTTCGAGTACATATCTGATGCCTTTT

CGCTTGATGTTTCAGAAAAGTCAGGTAATTTTAAACACTTACGAGAGTTT

GTGTTTAAAAATAAAGATGGGTTTCTCTATGTTTATAAGGGCTATCAACC

TATAGATGTAGTTCGTGATCTACCTTCTGGTTTTAACACTTTGAAACCTA

TTTTTAAGTTGCCTCTTGGTATTAACATTACAAATTTTAGAGCCATTCTT

ACAGCCTTTTCACCTGCTCAAGACATTTGGGGCACGTCAGCTGCAGCCTA

TTTTGTTGGCTATTTAAAGCCAACTACATTTATGCTCAAGTATGATGAAA

ATGGTACAATCACAGATGCTGTTGATTGTTCTCAAAATCCACTTGCTGAA

CTCAAATGCTCTGTTAAGAGCTTTGAGATTGACAAAGGAATTTACCAGAC

CTCTAATTTCAGGGTTGTTCCCTCAGGAGATGTTGTGAGATTCCCTAATA

TTACAAACTTGTGTCCTTTTGGAGAGGTTTTTAATGCTACTAAATTCCCT

TCTGTCTATGCATGGGAGAGAAAAAAAATTTCTAATTGTGTTGCTGATTA

CTCTGTGCTCTACAACTCAACATTTTTTTCAACCTTTAAGTGCTATGGCG

TTTCTGCCACTAAGTTGAATGATCTTTGCTTCTCCAATGTCTATGCAGAT

TCTTTTGTAGTCAAGGGAGATGATGTAAGACAAATAGCGCCAGGACAAAC

TGGTGTTATTGCTGATTATAATTATAAATTGCCAGATGATTTCATGGGTT

GTGTCCTTGCTTGGAATACTAGGAACATTGATGCTACTTCAACTGGTAAT

TATAATTATAAATATAGGTATCTTAGACATGGCAAGCTTAGGCCCTTTGA

GAGAGACATATCTAATGTGCCTTTCTCCCCTGATGGCAAACCTTGCACCC

CACCTGCTCTTAATTGTTATTGGCCATTAAATGATTATGGTTTTTACACC

ACTACTGGCATTGGCTACCAACCTTACAGAGTTGTAGTACTTTCTTTTGA

ACTTTTAAATGCACCGGCCACGGTTTGTGGACCAAAATTATCCACTGACC

TTATTAAGAACCAGTGTGTCAATTTTAATTTTAATGGACTCACTGGTACT

GGTGTGTTAACTCCTTCTTCAAAGAGATTTCAACCATTTCAACAATTTGG

CCGTGATGTTTCTGATTTCACTGATTCCGTTCGAGATCCTAAAACATCTG

AAATATTAGACATTTCACCTTGCTCTTTTGGGGGTGTAAGTGTAATTACA

CCTGGAACAAATGCTTCATCTGAAGTTGCTGTTCTATATCAAGATGTTAA

CTGCACTGATGTTTCTACAGCAATTCATGCAGATCAACTCACACCAGCTT

GGCGCATATATTCTACTGGAAACAATGTATTCCAGACTCAAGCAGGCTGT

CTTATAGGAGCTGAGCATGTCGACACTTCTTATGAGTGCGACATTCCTAT
```

-continued

TGGAGCTGGCATTTGTGCTAGTTACCATACAGTTTCTTTATTACGTAGTA

CTAGCCAAAAATCTATTGTGGCTTATACTATGTCTTTAGGTGCTGATAGT

TCAATTGCTTACTCTAATAACACCATTGCTATACCTACTAACTTTTCAAT

TAGCATTACTACAGAAGTAATGCCTGTTTCTATGGCTAAAACCTCCGTAG

ATTGTAATATGTACATCTGCGGAGATTCTACTGAATGTGCTAATTTGCTT

CTCCAATATGGTAGCTTTTGCACACAACTAAATCGTGCACTCTCAGGTAT

TGCTGCTGAACAGGATCGCAACACACGTGAAGTGTTCGCTCAAGTCAAAC

AAATGTACAAAACCCCAACTTTGAAATATTTTGGTGGTTTTAATTTTTCA

CAAATATTACCTGACCCTCTAAAGCCAACTAAGAGGTCTTTTATTGAGGA

CTTGCTCTTTAATAAGGTGACACTCGCTGATGCTGGCTTCATGAAGCAAT

ATGGCGAATGCCTAGGTGATATTAATGCTAGAGATCTCATTTGTGCGCAG

AAGTTCAATGGACTTACAGTGTTGCCACCTCTGCTCACTGATGATATGAT

TGCTGCCTACACTGCTGCTCTAGTTAGTGGTACTGCCACTGCTGGATGGA

CATTTGGTGCTGGCGCTGCTCTTCAAATACCTTTTGCTATGCAAATGGCA

TATAGGTTCAATGGCATTGGAGTTACCCAAAATGTTCTCTATGAGAACCA

AAAACAAATCGCCAACCAATTTAACAAGGCGATTAGTCAAATTCAAGAAT

CACTTACAACAACATCAACTGCATTGGGCAAGCTGCAAGACGTTGTTAAC

CAGAATGCTCAAGCATTAAACACACTTGTTAAACAACTTAGCTCTAATTT

TGGTGCAATTTCAAGTGTGCTAAATGATATCCTTTCGCGACTTGATAAAG

TCGAGGCGGAGGTACAAATTGACAGGTTAATTACAGGCAGACTTCAAAGC

CTTCAAACCTATGTAACACAACAACTAATCAGGGCTGCTGAAATCAGGGC

TTCTGCTAATCTTGCTGCTACTAAAATGTCTGAGTGTGTTCTTGGACAAT

CAAAAAGAGTTGACTTTTGTGGAAAGGGCTACCACCTTATGTCCTTCCCA

CAAGCAGCCCCGCATGGTGTTGTCTTCCTACATGTCACGTATGTGCCATC

CCAGGAGAGGAACTTCACCACAGCGCCAGCAATTTGTCATGAAGGCAAAG

CATACTTCCCTCGTGAAGGTGTTTTTGTGTTTAATGGCACTTCTTGGTTT

ATTACACAGAGGAACTTCTTTTCTCCACAAATAATTACTACAGACAATAC

ATTTGTCTCAGGAAATTGTGATGTCGTTATTGGCATCATTAACAACACAG

TTTATGATCCTCTGCAACCTGAGCTCGACTCATTCAAAGAAGAGCTGGAC

AAGTACTTCAAAAATCATACATCACCAGATGTTGATCTTGGCGACATTTC

AGGCATTAACGCTTCTGTCGTCAACATTCAAAAAGAAATTGACCGCCTCA

ATGAGGTCGCTAAAAATTTAAATGAATCACTCATTGACCTTCAAGAATTG

GGAAAATATGAGCAATATATTAAATGGCCTTGG

Soluble TPA-S1

(SEQ ID NO: 9)

ATGGATGCAATGAAGAGAGGGCTCTGCTGTGTGCTGCTGCTGTGTGGAGC

AGTCTTCGTTTCGCCCAGCGCTAGAGGATCGGGAAGTGACCTTGACCGGT

GCACCACTTTTGATGATGTTCAAGCTCCTAATTACACTCAACATACTTCA

TCTATGAGGGGGGTTTACTATCCTGATGAAATTTTTAGATCAGACACTCT

TTATTTAACTCAGGATTTATTTCTTCCATTTTATTCTAATGTTACAGGGT

TTCATACTATTAATCATACGTTTGGCAACCCTGTCATACCTTTTAAGGAT

GGTATTTATTTTGCTGCCACAGAGAAATCAAATGTTGTCCGTGGTTGGGT

TTTTGGTTCTACCATGAACAACAAGTCACAGTCGGTGATTATTATTAACA

ATTCTACTAATGTTGTTATACGAGCATGTAACTTTGAATTGTGTGACAAC

CCTTTCTTTGCTGTTTCTAAACCCATGGGTACACAGACACATACTATGAT

ATTCGATAATGCATTTAATTGCACTTTCGAGTACATATCTGATGCCTTTT

CGCTTGATGTTTCAGAAAAGTCAGGTAATTTTAAACACTTACGAGAGTTT

GTGTTTAAAAATAAAGATGGGTTTCTCTATGTTTATAAGGGCTATCAACC

TATAGATGTAGTTCGTGATCTACCTTCTGGTTTTAACACTTTGAAACCTA

TTTTTAAGTTGCCTCTTGGTATTAACATTACAAATTTTAGAGCCATTCTT

ACAGCCTTTTCACCTGCTCAAGACATTTGGGGCACGTCAGCTGCAGCCTA

TTTTGTTGGCTATTTAAAGCCAACTACATTTATGCTCAAGTATGATGAAA

ATGGTACAATCACAGATGCTGTTGATTGTTCTCAAAATCCACTTGCTGAA

CTCAAATGCTCTGTTAAGAGCTTTGAGATTGACAAAGGAATTTACCAGAC

CTCTAATTTCAGGGTTGTTCCCTCAGGAGATGTTGTGAGATTCCCTAATA

TTACAAACTTGTGTCCTTTTGGAGAGGTTTTTAATGCTACTAAATTCCCT

TCTGTCTATGCATGGGAGAGAAAAAAAATTTCTAATTGTGTTGCTGATTA

CTCTGTGCTCTACAACTCAACATTTTTTTCAACCTTTAAGTGCTATGGCG

TTTCTGCCACTAAGTTGAATGATCTTTGCTTCTCCAATGTCTATGCAGAT

TCTTTTGTAGTCAAGGGAGATGATGTAAGACAAATAGCGCCAGGACAAAC

TGGTGTTATTGCTGATTATAATTATAAATTGCCAGATGATTTCATGGGTT

GTGTCCTTGCTTGGAATACTAGGAACATTGATGCTACTTCAACTGGTAAT

TATAATTATAAATATAGGTATCTTAGACATGGCAAGCTTAGGCCCTTTGA

GAGAGACATATCTAATGTGCCTTTCTCCCCTGATGGCAAACCTTGCACCC

CACCTGCTCTTAATTGTTATTGGCCATTAAATGATTATGGTTTTTACACC

ACTACTGGCATTGGCTACCAACCTTACAGAGTTGTAGTACTTTCTTTTGA

ACTTTTAAATGCACCGGCCACGGTTTGTGGACCAAAATTATCCACTGACC

TTATTAAGAACCAGTGTGTCAATTTTAATTTTAATGGACTCACTGGTACT

GGTGTGTTAACTCCTTCTTCAAAGAGATTTCAACCATTTCAACAATTTGG

CCGTGATGTTTCTGATTTCACTGATTCCGTTCGAGATCCTAAAACATCTG

AAATATTAGACATTTCACCTTGCTCTTTTGGGGGTGTAAGTGTAATTACA

CCTGGAACAAATGCTTCATCTGAAGTTGCTGTTCTATATCAAGATGTTAA

CTGCACTGATGTTTCTACAGCAATTCATGCAGATCAACTCACACCAGCTT

GGCGCATATATTCTACTGGAAACAATGTATTCCAGACTCAAGCAGGCTGT

CTTATAGGAGCTGAGCATGTCGACACTTCTTATGAGTGCGACATTCCTAT

TGGAGCTGGCATTTGTGCTAGTTACCATACAGTTTCTTTATTACGTAGTA

CTAGCCAAAAATCTATTGTGGCTTATACTATGTCTTTAGGTGC

Soluble TPA-S2

(SEQ ID NO: 11)

ATGGATGCAATGAAGAGAGGGCTCTGCTGTGTGCTGCTGCTGTGTGGAGC

AGTCTTCGTTTCGCCCAGCGCTAGAGGATCGGGAGATAGTTCAATTGCTT

ACTCTAATAACACCATTGCTATACCTACTAACTTTTCAATTAGCATTACT

ACAGAAGTAATGCCTGTTTCTATGGCTAAAACCTCCGTAGATTGTAATAT

-continued

GTACATCTGCGGAGATTCTACTGAATGTGCTAATTTGCTTCTCCAATATG

GTAGCTTTTGCACACAACTAAATCGTGCACTCTCAGGTATTGCTGCTGAA

CAGGATCGCAACACACGTGAAGTGTTCGCTCAAGTCAAACAAATGTACAA

AACCCCAACTTTGAAATATTTTGGTGGTTTTAATTTTTCACAAATATTAC

CTGACCCTCTAAAGCCAACTAAGAGGTCTTTTATTGAGGACTTGCTCTTT

AATAAGGTGACACTCGCTGATGCTGGCTTCATGAAGCAATATGGCGAATG

CCTAGGTGATATTAATGCTAGAGATCTCATTTGTGCGCAGAAGTTCAATG

GACTTACAGTGTTGCCACCTCTGCTCACTGATGATATGATTGCTGCCTAC

ACTGCTGCTCTAGTTAGTGGTACTGCCACTGCTGGATGGACATTTGGTGC

TGGCGCTGCTCTTCAAATACCTTTTGCTATGCAAATGGCATATAGGTTCA

ATGGCATTGGAGTTACCCAAAATGTTCTCTATGAGAACCAAAAACAAATC

GCCAACCAATTTAACAAGGCGATTAGTCAAATTCAAGAATCACTTACAAC

AACATCAACTGCATTGGGCAAGCTGCAAGACGTTGTTAACCAGAATGCTC

AAGCATTAAACACACTTGTTAAACAACTTAGCTCTAATTTTGGTGCAATT

TCAAGTGTGCTAAATGATATCCTTTCGCGACTTGATAAAGTCGAGGCGGA

GGTACAAATTGACAGGTTAATTACAGGCAGACTTCAAAGCCTTCAAACCT

ATGTAACACAACAACTAATCAGGGCTGCTGAAATCAGGGCTTCTGCTAAT

CTTGCTGCTACTAAAATGTCTGAGTGTGTTCTTGGACAATCAAAAAGAGT

TGACTTTTGTGGAAAGGGCTACCACCTTATGTCCTTCCCACAAGCAGCCC

CGCATGGTGTTGTCTTCCTACATGTCACGTATGTGCCATCCCAGGAGAGG

AACTTCACCACAGCGCCAGCAATTTGTCATGAAGGCAAAGCATACTTCCC

TCGTGAAGGTGTTTTTGTGTTTAATGGCACTTCTTGGTTTATTACACAGA

GGAACTTCTTTTCTCCACAAATAATTACTACAGACAATACATTTGTCTCA

GGAAATTGTGATGTCGTTATTGGCATCATTAACAACACAGTTTATGATCC

TCTGCAACCTGAGCTCGACTCATTCAAAGAAGAGCTGGACAAGTACTTCA

AAAATCATACATCACCAGATGTTGATCTTGGCGACATTTCAGGCATTAAC

GCTTCTGTCGTCAACATTCAAAAAGAAATTGACCGCCTCAATGAGGTCGC

TAAAAATTTAAATGAATCACTCATTGACCTTCAAGAATTGGGAAAATATG

AGCAATATATTAAATGGCCTTGG

In a further embodiment the methods of the present invention provide for administering a polynucleotide which operably encodes a SARS-CoV S, S1, or S2 polypeptide, wherein said polynucleotide is 60%, 70%, 80%, 90%, 95%, 96%, 97%, 98%, 99% or 100% identical to SEQ ID NOs:7, 9, or 11, or a codon-optimized version as described below, and wherein said polynucleotide encodes a polypeptide that elicits a detectable immune response.

The amino acid sequences of the soluble S protein, S1 and S2 proteins with the TPA secretory leader peptide are shown below.

Soluble TPA-S (SEQ ID NO: 8)

MDAMKRGLCCVLLLCGAVFVSPSARGSGSDLDRCTTFDDVQAPNYTQHTS

SMRGVYYPDEIFRSDTLYLTQDLFLPFYSNVTGFHTINHTFGNPVIPFKD

-continued

GIYFAATEKSNVVRGWVFGSTMNNKSQSVIIINNSTNVVIRACNFELCDN

PFFAVSKPMGTQTHTMIFDNAFNCTFEYISDAFSLDVSEKSGNFKHLREF

VFKNKDGFLYVYKGYQPIDVVRDLPSGFNTLKPIFKLPLGINITNFRAIL

TAFSPAQDIWGTSAAAYFVGYLKPTTFMLKYDENGTITDAVDCSQNPLAE

LKCSVKSFEIDKGIYQTSNFRVVPSGDVVRFPNITNLCPFGEVFNATKFP

SVYAWERKKISNCVADYSVLYNSTFFSTFKCYGVSATKLNDLCFSNVYAD

SFVVKGDDVRQIAPGQTGVIADYNYKLPDDFMGCVLAWNTRNIDATSTGN

YNYKYRYLRHGKLRPFERDISNVPFSPDGKPCTPPALNCYWPLNDYGFYT

TTGIGYQPYRVVVLSFELLNAPATVCGPKLSTDLIKMQCVNFNFNGLTGT

GVLTPSSKRFQPFQQFGRDVSDFTDSVRDPKTSEILDISPCSFGGVSVIT

PGTNASSEVAVLYQDVNCTDVSTAIHADQLTPAWRIYSTGNNVFQTQAGC

LIGAEHVDTSYECDIPIGAGICASYHTVSLLRSTSQKSIVAYTMSLGADS

SIAYSNNTIAIPTNFSISITTEVMPVSMAKTSVDCNMYICGDSTECANLL

LQYGSFCTQLNRALSGIAAEQDRNTREVFAQVKQMYKTPTLKYFGGFNFS

QILPDPLKPTKRSFIEDLLFNKVTLADAGFMKQYGECLGDINARDLICAQ

KFNGLTVLPPLLTDDMIAAYTAALVSGTATAGWTFGAGAALQIPFAMQMA

YRFNGIGVTQNVLYENQKQIANQFNKAISQIQESLTTTSTALGKLQDVVN

QNAQALNTLVKQLSSNFGAISSVLNDILSRLDKVEAEVQIDRLITGRLQS

LQTYVTQQLIRAAEIRASANLAATKMSECVLGQSKRVDFCGKGYHLMSFP

QAAPHGVVFLHVTYVPSQERNFTTAPAICHEGKAYFPREGVFVFNGTSWF

ITQRNFFSPQIITTDNTFVSGNCDVVIGIINNTVYDPLQPELDSFKEELD

KYFKNHTSPDVDLGDISGINASVVNIQKEIDRLNEVAKNLNESLIDLQEL

GKYEQYIKWPW

Soluble TPA-S1 protein (SEQ ID NO: 10)

MDAMKRGLCCVLLLCGAVFVSPSARGSGSDLDRCTTFDDVQAPNYTQHTS

SMRGVYYPDEIFRSDTLYLTQDLFLPFYSNVTGFHTINHTFGNPVIPFKD

GIYFAATEKSNVVRGWVFGSTMNNKSQSVIIINNSTNVVIRACNFELCDN

PFFAVSKPMGTQTHTMIFDNAFNCTFEYISDAFSLDVSEKSGNFKMLREF

VFKNKDGFLYVYKGYQPIDVVRDLPSGFNTLKPIFKLPLGINITNFRAIL

TAFSPAQDIWGTSAAAYFVGYLKPTTFMLKYDENGTITDAVDCSQNPLAE

LKCSVKSFEIDKGIYQTSNFRVVPSGDVVRFPNITNLCPFGEVFNATKFP

SVYAWERKKISNCVADYSVLYNSTFFSTFKCYGVSATKLNDLCFSNVYAD

SFVVKGDDVRQIAPGQTGVIADYNYKLPDDFMGCVLAWNTRNIDATSTGN

YNYKYRYLRHGKLRPFERDISNVPFSPDGKPCTPPALNCYWPLNDYGFYT

TTGIGYQPYRVVVLSFELLNAPATVCGPKLSTDLIKNQCVNFNFNGLTGT

GVLTPSSKRFQPFQQFGRDVSDFTDSVRDPKTSEILDISPCSFGGVSVIT

PGTNASSEVAVLYQDVNCTDVSTAIHADQLTPAWRIYSTGNNVFQTQAGC

LIGAEHVDTSYECDIPIGAGICASYHTVSLLRSTSQKSIVAYTMSLGA

Soluble TPA-S2 protein (SEQ ID NO: 12)

MDAMKRGLCCVLLLCGAVFVSPSARGSGDSSIAYSNNTIAIPTNFSISIT

TEVMPVSMAKTSVDCNMYICGDSTECANLLLQYGSFCTQLNRALSGIAAE

-continued

QDRNTREVFAQVKQMYKTPTLKYFGGFNFSQILPDPLKPTKRSFIEDLLF

NKVTLADAGFMKQYGECLGDINARDLICAQKFNGLTVLPPLLTDDMIAAY

TAALVSGTATAGWTFGAGAALQIPFAMQMAYRFNGIGVTQNVLYENQKQI

ANQFNKAISQIQESLTTTSTALGKLQDVVNQNAQALNTLVKQLSSNFGAI

SSVLNDILSRLDKVEAEVQIDRLITGRLQSLQTYVTQQLIRAAEIRASAN

LAATKMSECVLGQSKRVDFCGKGYHLMSFPQAAPHGVVFLHVTYVPSQER

NFTTAPAICHEGKAYFPREGVFVFNGTSWFITQRNFFSPQIITTDNTFVS

GNCDVVIGIINNTVYDPLQPELDSFKEELDKYFKNHTSPDVDLGDISGIN

ASVVNIQKEIDRLNEVAKNLNESLIDLQELGKYEQYIKWPW

In a further embodiment the methods of the present invention provide for administering a polynucleotide which operably encodes a SARS-CoV S, S1, or S2 polypeptide comprising an amino acid sequence at least 60%, 70%, 80%, 90%, 95%, 96%, 97%, 98%, 99% or 100% identical to SEQ ID NOs:8, 10, or 12, wherein said polypeptide raises a detectable immune response.

In a further embodiment, the present invention provides for methods for raising a a detectable immune response to the SARS-CoV polypeptides, comprising administering to a vertebrate a polynucleotide which operably encodes polypeptides, fragments, variants, or derivatives thereof as described above.

The S protein of some coronaviruses contain an Fcγ-like domain that binds immunoglobulin. Data from the FIPV immunization suggests that high levels of potentially neutralizing antibody may be bound by the Fc-mimicking region of the S protein. Scott, F. W. *Adv. Vet. Med.* 41: 347-58 (1999). Thus, modification or deletion of an Fcγ region of the SARS-CoV S protein may be useful in the compositions of the present invention.

The nucleocapsid protein (N) is encoded by about nucleotides 28120 through about 29388 of the Urbani strain of SARS-CoV. (Bellini et al. SARS Coronavirus Urbani, complete genome. GenBank Accession No. AY278741).

The protein is a phosphoprotein of 50 to 60 kd that interacts with viral genomic RNA to form the viral nucleocapsid. N has three relatively conserved structural domains, including an RNA-binding domain in the middle that binds to the leader sequence of viral RNA. N protein in the viral nucleocapsid further interacts with the membrane protein (M), leading to the formation of virus particles. N is also suggested to play a role in viral RNA synthesis, by a study in which an antibody directed against N inhibited an in vitro coronavirus RNA polymerase reaction. Marra et al. N protein also binds to cellular membranes and phospholipids, a property that may help to facilitate both virus assembly and formation of RNA replication complexes.

From about nucelotides 28120 to about 29388 of the Urbani strain of the SARS-CoV genome encode the N protein. (Bellini et al. SARS Coronavirus Urbani, complete genome. GenBank Accession No. AY278741) and has the following sequence, referred to herein as SEQ ID NO:13:

ATGTCTGATAATGGACCCCAATCAAACCAACGTAGTGCCCCCCGCATTAC

ATTTGGTGGACCCACAGATTCAACTGACAATAACCAGAATGGAGGACGCA

ATGGGGCAAGGCCAAAACAGCGCCGACCCCAAGGTTTACCCAATAATACT

-continued

GCGTCTTGGTTCACAGCTCTCACTCAGCATGGCAAGGAGGAACTTAGATT

CCCTCGAGGCCAGGGCGTTCCAATCAACACCAATAGTGGTCCAGATGACC

AAATTGGCTACTACCGAAGAGCTACCCGACGAGTTCGTGGTGGTGACGGC

AAAATGAAAGAGCTCAGCCCCAGATGGTACTTCTATTACCTAGGAACTGG

CCCAGAAGCTTCACTTCCCTACGGCGCTAACAAAGAAGGCATCGTATGGG

TTGCAACTGAGGGAGCCTTGAATACACCCAAAGACCACATTGGCACCCGC

AATCCTAATAACAATGCTGCCACCGTGCTACAACTTCCTCAAGGAACAAC

ATTGCCAAAAGGCTTCTACGCAGAGGGAAGCAGAGGCGGCAGTCAAGCCT

CTTCTCGCTCCTCATCACGTAGTCGCGGTAATTCAAGAAATTCAACTCCT

GGCAGCAGTAGGGGAAATTCTCCTGCTCGAATGGCTAGCGGAGGTGGTGA

AACTGCCCTCGCGCTATTGCTGCTAGACAGATTGAACCAGCTTGAGAGCA

AAGTTTCTGGTAAAGGCCAACAACAACAAGGCCAAACTGTCACTAAGAAA

TCTGCTGCTGAGGCATCTAAAAAGCCTCGCCAAAAACGTACTGCCACAAA

ACAGTACAACGTCACTCAAGCATTTGGGAGACGTGGTCCAGAACAAACCC

AAGGAAATTTCGGGGACCAAGACCTAATCAGACAAGGAACTGATTACAAA

CATTGGCCGCAAATTGCACAATTTGCTCCAAGTGCCTCTGCATTCTTTGG

AATGTCACGCATTGGCATGGAAGTCACACCTTCGGOAACATGGCTGACTT

ATCATGGAGCCATTAAATTGGATGACAAAGATCCACAATTCAAAGACAAC

GTCATACTGCTGAACAAGCACATTGACGCATACAAAACATTCCCACCAAC

AGAGCCTAAAAAGGACAAAAAGAAAAAGACTGATGAAGCTCAGCCTTTGC

CGCAGAGACAAAAGAAGCAGCCCACTGTGACTCTTCTTCCTGCGGCTGAC

ATGGATGATTTCTCCAGACAACTTCAAAATTCCATGAGTGGAGCTTCTGC

TGATTCAACTCAGGCATAA

In a further embodiment the methods of the present invention provide for administering a polynucleotide which operably encodes a SARS-CoV N, polypeptide, wherein said polynucleotide is 60%, 70%, 80%, 90%, 95%, 96%, 97%, 98%, 99% or 100% identical to SEQ ID NO:13, or a codon-optimized version as described below, and wherein said polynucleotide encodes a polypeptide that elicits a detectable immune response.

The amino acid sequence of the N protein encoded by SEQ ID NO:13 has the following sequence shown below and is referred to herein as SEQ ID NO:14

MSDNGPQSNQRSAPRITFGGPTDSTDNNQNGGRNGARPKQRRPQGLPNNT

ASWFTALTQHGKEELRFPRGQGVPINTNSGPDDQIGYYRRATRRVRGGDG

KMKELSPRWYFYYLGTGPEASLPYGANKEGIVWVATEGALNTPKDHIGTR

NPNNNAATVLQLPQGTTLPKGFYAEGSRGGSQASSRSSSRSRGNSRNSTP

GSSRGNSPARMASGGGETALALLLLDRLNQLESKVSGKGQQQQGQTVTKK

SAAEASKKPRQKRTATKQYNVTQAFGRRGPEQTQGNFGDQDLIRQGTDYK

HWPQIAQFAPSASAFFGMSRIGMEVTPSGTWLTYHGAIKLDDKDPQFKDN

VILLNKHIDAYKTFPPTEPKKDKKKKTDEAQPLPQRQKKQPTVTLLPAAD

MDDFSRQLQNSMSGASADSTQA

In a further embodiment the methods of the present invention provide for administering a polynucleotide which operably encodes a SARS-CoV N polypeptide comprising an amino acid sequence at least 60%, 70%, 80%, 90%, 95%, 96%, 97%, 98%, 99% or 100% identical to SEQ ID NO:14, wherein said polypeptide raises a detectable immune response.

The N protein contains a nuclear localization sequence (NLS) which directs the protein to the nucleus infected cells or cells in which the protein is expressed. The sequence of the NLS is KTFPPTEPKKDKKKKTDEAQ (underlined above) and is referred to herein as SEQ ID NO:17. For purposes of the invention, the NLS may be deleted from the protein to obtain a non-nuclear localized version of the protein. The nucleotide sequence of an N protein lacking the NLS is referred to herein as SEQ ID NO:15 and is shown below.

```
ATGTCTGATAATGGACCCCAATCAAACCAACGTAGTGCCCCCCGCATTAC
ATTTGGTGGACCCACAGATTCAACTGACAATAACCAGAATGGAGGACGCA
ATGGGGCAAGGCCAAAACAGCGCCGACCCCAAGGTTTACCCAATAATACT
GCGTCTTGGTTCACAGCTCTCACTCAGCATGGCAAGGAGGAACTTAGATT
CCCTCGAGGCCAGGGCGTTCCAATCAACACCAATAGTGGTCCAGATGACC
AAATTGGCTACTACCGAAGAGCTACCCGACGAGTTCGTGGTGGTGACGGC
AAAATGAAAGAGCTCAGCCCCAGATGGTACTTCTATTACCTAGGAACTGG
CCCAGAAGCTTCACTTCCCTACGGCGCTAACAAAGAAGGCATCGTATGGG
TTGCAACTGAGGGAGCCTTGAATACACCCAAAGACCACATTGGCACCCGC
AATCCTAATAACAATGCTGCCACCGTGCTACAACTTCCTCAAGGAACAAC
ATTGCCAAAAGGCTTCTACGCAGAGGGAAGCAGAGGCGGCAGTCAAGCCT
CTTCTCGCTCCTCATCACGTAGTCGCGGTAATTCAAGAAATTCAACTCCT
GGCAGCAGTAGGGGAAATTCTCCTGCTCGAATGGCTAGCGGAGGTGGTGA
AACTGCCCTCGCGCTATTGCTGCTAGACAGATTGAACCAGCTTGAGAGCA
AAGTTTCTGGTAAAGGCCAACAACAACAAGGCCAAACTGTCACTAAGAAA
TCTGCTGCTGAGGCATCTAAAAAGCCTCGCCAAAAACGTACTGCCACAAA
ACAGTACAACGTCACTCAAGCATTTGGGAGACGTGGTCCAGAACAAACCC
AAGGAAATTTCGGGGACCAAGACCTAATCAGACAAGGAACTGATTACAAA
CATTGGCCGCAAATTGCACAATTTGCTCCAAGTGCCTCTGCATTCTTTGG
AATGTCACGCATTGGCATGGAAGTCACACCTTCGGGAACATGGCTGACTT
ATCATGGAGCCATTAAATTGGATGACAAAGATCCACAATTCAAAGACAAC
GTCATACTGCTGAACAAGCACATTGACGCATACCCTTTGCCGCAGAGACA
AAAGAAGCAGCCCACTGTGACTCTTCTTCCTGCGGCTGACATGGATGATT
TCTCCAGACAACTTCAAAATTCCATGAGTGGAGCTTCTGCTGATTCAACT
CAGGCATAA
```

In a further embodiment the methods of the present invention provide for administering a polynucleotide which operably encodes a SARS-CoV N, polypeptide, wherein said polynucleotide is 60%, 70%, 80%, 90%, 95%, 96%, 97%, 98%, 99% or 100% identical to SEQ ID NO:15, or a codon-optimized version as described below, and wherein said polynucleotide encodes a polypeptide that elicits a detectable immune response.

The amino acid sequence of the N protein without the NLS sequence is encoded by SEQ ID NO:15 has the following sequence shown below and is referred to herein as SEQ ID NO:16:

```
MSDNGPQSNQRSAPRITFGGPTDSTDNNQNGGRNGARPKQRRPQGLPNNT
ASWFTALTQHGKEELRFPRGQGVPINTNSGPDDQIGYYRRATRRVRGGDG
KMKELSPRWYFYYLGTGPEASLPYGANKEGIVWVATEGALNTPKDHIGTR
NPNNNAATVLQLPQGTTLPKGFYAEGSRGGSQASSRSSSRSRGNSRNSTP
GSSRGNSPARMASGGGETALALLLLDRLNQLESKVSGKGQQQQGQTVTKK
SAAEASKKPRQKRTATKQYNVTQAFGRRGPEQTQGNFGDQDLIRQGTDYK
HWPQIAQFAPSASAFFGMSRIGMEVTPSGTWLTYHGAIKLDDKDPQFKDN
VILLNKHIDAYPLPQRQKKQPTVTLLPAADMDDFSRQLQNSMSGASADST
QA
```

In a further embodiment the methods of the present invention provide for administering a polynucleotide which operably encodes a SARS-CoV N polypeptide comprising an amino acid sequence at least 60%, 70%, 80%, 90%, 95%, 96%, 97%, 98%, 99% or 100% identical to SEQ ID NO:16, wherein said polypeptide raises a detectable immune response.

The membrane glycoprotein (M) is encoded by about nucleotides 26398 to about 27063 of the Urbani strain of SARS-CoV. (Bellini et al. SARS Coronavirus Urbani, complete genome. GenBank Accession No. AY278741). The M protein differs from other coronavirus glycoproteins in that only a short amino terminal domain of M is exposed on the exterior of the viral envelope. This domain is followed by a triple-membrane-spanning domain, an α-helical domain, and a large carboxylterminal domain inside the viral envelope. In some coronaviruses, such as transmissible gastroenteritis coronavirus (TGEV), the carboxylterminus of the M protein is exposed on the virion surface. Glycosylation of the amino-terminal domain is O-linked for MHV and N-linked for infectious bronchitis virus (IBV) and TGEV. Monoclonal antibodies against the external domain of M neutralize viral infectivity, but only in the presence of complement. M proteins of some coronaviruses can induce interferon-α. The M proteins are targeted to the Golgi apparatus and not transported to the plasma membrane. In TGEV and MHV virions, the M glycoprotein is present not only in the viral envelope but also in the internal core structure. (*Field's Virology*, B. N. Fields, D. M. Knipe, P. M. Howley, R. M. Chanock, J. L. Melnick, T. P. Monath, B. Roizman, and S. E. Straus, eds., 4th Edition. Lippincott-Raven, Philadelphia, Pa.).

From about nucelotides 26398 to about 27063 of the Urbani strain of the SARS-CoV genome encode the M protein, Bellini et al. SARS Coronavirus Urbani, complete genome, GenBank Accession No. AY27874, and has the following sequence, referred to herein as SEQ ID NO:18:

```
ATGGCAGACAACGGTACTATTACCGTTGAGGAGCTTAAACAACTCCTGGA
ACAATGGAACCTAGTAATAGGTTTCCTATTCCTAGCCTGGATTATGTTAC
TACAATTTGCCTATTCTAATCGGAACAGGTTTTTGTACATAATAAAGCTT
GTTTTCCTCTGGCTCTTGTGGCCAGTAACACTTGCTTGTTTTGTGCTTGC
TGCTGTCTACAGAATTAATTGGGTGACTGGCGGGATTGCGATTGCAATGG
CTTGTATTGTAGGCTTGATGTGGCTTAGCTACTTCGTTGCTTCCTTCAGG
CTGTTTGCTCGTACCCGCTCAATGTGGTCATTCAACCCAGAAACAAACAT
TCTTCTCAATGTGCCTCTCCGGGGGACAATTGTGACCAGACCGCTCATGG
```

-continued

AAAGTGAACTTGTCATTGGTGCTGTGATCATTCGTGGTCACTTGCGAATG

GCCGGACACCCCCTAGGGCGCTGTGACATTAAGGACCTGCCAAAAGAGAT

CACTGTGGCTACATCACGAACGCTTTCTTATTACAAATTAGGAGCGTCGC

AGCGTGTAGGCACTGATTCAGGTTTTGCTGCATACAACCGCTACCGTATT

GGAAACTATAAATTAAATACAGACCACGCCGGTAGCAACGACAATATTGC

TTTGCTAGTACAGTAA

In a further embodiment the methods of the present invention provide for administering a polynucleotide which operably encodes a SARS-CoV M, polypeptide, wherein said polynucleotide is 60%, 70%, 80%, 90%, 95%, 96%, 97%, 98%, 99% or 100% identical to SEQ ID NO:18, or a codon-optimized version as described below, and wherein said polynucleotide encodes a polypeptide that elicits a detectable immune response.

The amino acid sequence of the M protein encoded by SEQ ID NO:18 has the following sequence shown below and is referred to herein as SEQ ID NO:19:

MADNGTITVEELKQLLEQWNLVIGFLFLAWIMLLQFAYSNRNRFLYIIKL

VFLWLLWPVTLACFVLAAVYRINWVTGGIAIAMACIVGLMWLSYFVASFR

LFARTRSMWSFNPETNILLNVPLRGTIVTRPLMESELVIGAVIIRGHLRM

AGHPLGRCDIKDLPKEITVATSRTLSYYKLGASQRVGTDSGFAAYNRYRI

GNYKLNTDHAGSNDNIALLVQ

In a further embodiment the methods of the present invention provide for administering a polynucleotide which operably encodes a SARS-CoV M polypeptide comprising an amino acid sequence at least 60%, 70%, 80%, 90%, 95%, 96%, 97%, 98%, 99% or 100% identical to SEQ ID NO:19 wherein said polypeptide raises a detectable immune response.

The small envelope protein (E) is encoded by about nucleotide 26117 to about 26347 of the Urbani strain of SARS-CoV (Bellini et al. SARS Coronavirus Urbani, complete genome, GenBank Accession No. AY278741), and has the following sequence, referred to herein as SEQ ID NO: 20:

ATGTACTCATTCGTTTCGGAAGAAACAGGTACGTTAATAGTTAATAGCGT

ACTTCTTTTTCTTGCTTTCGTGGTATTCTTGCTAGTCACACTAGCCATCC

TTACTGCGCTTCGATTGTGTGCGTACTGCTGCAATATTGTTAACGTGAGT

TTAGTAAAACCAACGGTTTACGTCTACTCGCGTGTTAAAAATCTGAACTC

TTCTGAAGGAGTTCCTGATCTTCTGGTCTAA

In a further embodiment the methods of the present invention provide for administering a polynucleotide which operably encodes a SARS-CoV E, polypeptide, wherein said polynucleotide is 60%, 70%, 80%, 90%, 95%, 96%, 97%, 98%,. 99% or 100% identical to SEQ ID NO:20, or a codon-optimized version as described below, and wherein said polynucleotide encodes a polypeptide that elicits a detectable immune response Based on protein comparisons with other coronaviruses, the SARS-CoV E protein shares conserved sequences with TGEV and MHV. For some coronaviruses, such as TGEV, the E protein is necessary for replication of the virus, while for others, such as MHV, loss of the E protein merely reduces virus replication without eliminating it completely. Marra et al. The protein sequence is shown below and referred to, herein as SEQ ID NO:21.

MYSFVSEETGTLIVNSVLLFLAFVVFLLVTLAILTALRLCAYCCNIVNVS

LVKPTVYVYSRVKNLNSSEGVPDLLV

In a further embodiment the methods of the present invention provide for administering a polynucleotide which operably encodes a SARS-CoV E polypeptide comprising an amino acid sequence at least 60%, 70%, 80%, 90%, 95%, 96%, 97%, 98%, 99% or 100% identical to SEQ ID NO:21 wherein said polypeptide raises a detectable immune response.

It should be noted that nucleotide sequences encoding various SARS-CoV polypeptides may vary between SARS-CoV strains. Virtually any nucleotide sequence encoding a SARS-CoV protein is suitable for the present invention. In fact, polynucleotide sequences included in vaccines and therapeutic formulations of the current invention may change from year to year, depending on the prevalent strain or strains of SARS-CoV.

Further examples of SARS-CoV polypeptides within the scope of the invention are multimerized fragments of SARS-CoV polypeptides and polynucleotides that encode multimerized fragments of SARS-CoV polypeptides. The polypeptide fragments of the invention contain at least one antigenic region. The SARS-CoV polypeptide fragments are fused to small assembly polypeptides. Non-limiting examples within the scope of the invention include coiled-coiled structures such as: an amphipathic helix, the yeast CGN4 leucine zipper, the human p53 tetramerization domain, and synthetic coil polypeptides. The SARS-CoV and assembly peptide fusion proteins self-assemble into stable multimers forming dimers, trimers, tetramers, and higher order multimers depending on the interacting amino acid residues. These multimerized SARS-CoV polypeptide fragments have increased local epitope valency which functions to more efficiently activate B lymphocytes, thereby producing a more robust immune response. Also within the scope of the invention are multimerized SARS-CoV polypeptide fragments that maintain conformational neutralizing epitopes.

Also within the scope of the present invention are combinations of SARS-CoV polypeptides and polynucleotides that encode SARS-CoV polypeptides, where the polypeptides assemble into virus-like particles (VLP). One such combination is, but is not limited to a combination of SARS-CoV S, M, and E polypeptides or fragments, variants, or derivatives thereof, and polynucleotides encoding SARS-CoV S, M, and E polypeptides or fragments, variants, or derivatives thereof. Combinations of SARS-CoV polypeptides that form VLPs may be useful in enhancing immunogenicity of SARS-CoV polypeptides and in eliciting a detectable immune response to the SARS-CoV virus. Also within the scope of the present invention are methods of producing SARS-CoV VLPs in vitro by using protocols that are well known in the art. The production of VLPs may be performed in any tissue culture cell line that can tolerate expression of SARS-CoV polypeptide. Examples of cell lines include, but are not limited to, fungal cells, including yeast cells such as *Saccharomyces* spp. cells; insect cells such as *Drosophila* S2, *Spodoptera* Sf9 or Sf21 cells and *Trichoplusa* High-Five cells; other animal cells (particularly mammalian cells and human cells) such as Vero, MDCK, CV1, 3T3, CPAE, A10, Sp2/0-Ag14, PC12, CHO, COS, HeLa, Bowes melanoma cells, SW-13, NCI-H295, RT4, HT-1376, UM-UC-3, IM-9, KG-1, R54;11, A-172, U-87MG, BT-20, MCF-7, SK-BR-3, ChaGo K-1, CCD-14Br, CaSki, ME-180, FHC, HT-29, Caco-2, SW480, HuTu80, Tera 1, NTERA-2, AN3 CA, KLE, RL95-2, Caki-1, ACHN, 769 P, CCRF-CEM, Hut 78, MOLT 4, HL-60, Hep-3B, HepG2, SK-HEP1, A-549, NCI-H146, NCI-H82, NCI-H82, SK-LU-1, WI-38, MRC-5, HLF-a, CCD-19Lu, C39, Hs294T, SK-MEL5, COLO 829, U266B1, RPMI 2650, BeWo, JEG-3, JAR, SW 1353, MeKam, and SCC-4; and higher plant cells. Appropriate culture media and conditions for the above-described host cells are known in the art.

De Haan et al., *J. Virol.* 72: 6838-50 (1998), describe the assembly of coronavirus VLPs from the coexpression of mouse hepatitis virus M and E genes in eukaryotic cells. Bos et al., *J. Virol.* 71: 9427-33 describe the role of the S protein in infectivity of coronavirus VLPs produced by coexpression of mouse hepatitis virus S, M, and E proteins. These references are hereby incorporated by reference in their entireties.

In another embodiment, the VLP comprising SARS-CoV polypeptides S, M, and E provides a method for mimicking a SARS-CoV infection without the use of the actual infectious agent. In addtion, the VLP provides a method for eliciting a detectable immune response to multiple antigens in a confirmation similar to the actual virus particle thereby enhancing the immunogenicity of the SARS-CoV polypeptides.

The VLP's of the invention can be produced in vivo by delivery of S, M or E polynucleotides or polypeptides, described herein, to a vertebrate wherein assembly of the VLPs occurs with the cells of the vertebrate. In an alternative embodiment, VLPs of the invention can be produced in vitro in cells that have received the S, M, and E polynucleotides described herein and express said proteins. VLPs are then purified from the cells using techniques known in the art for coronavirus particle purification. These purified particles can then be administered to a vertebrate to elicit a detectable immune response or to study the pathogenesis of the SARS-CoV infection without the need of the actual infectious agent.

The combination of S, M and E to create virus like particles in the previous examples is not meant to be limiting. Other SARS-CoV polypeptides, which assemble into, or are engineered to assemble into virus like particles, may be used as well.

The present invention also provides vaccine compositions and methods for delivery of SARS-CoV coding sequences to a vertebrate. In other embodiments, the present invention provides vaccine compositions and methods for delivery of SARS-CoV coding sequences to a vertebrate with optimal expression and safety conferred through codon optimization and/or other manipulations. These vaccine compositions are prepared and administered in such a manner that the encoded gene products are optimally expressed in the vertebrate of interest. As a result, these compositions and methods are useful in stimulating an immune response against SARS-CoV infection. Also included in the invention are expression systems, delivery systems, and codon-optimized SARS-CoV coding regions.

In a specific embodiment, the invention provides polynucleotide (e.g., DNA) vaccines in which the single formulation comprises a SARS-CoV polypeptide-encoding polynucleotide vaccine as described herein. An alternative embodiment of the invention provides for a multivalent formulation comprising several (e.g., two, three, four, or more) SARS-CoV polypeptide-encoding polynucleotides, as described herein, within a single vaccine composition. The SARS-CoV polypeptide-encoding polynucleotides, fragments, or variants thereof may be contained within a single expression vector (e.g., plasmid or viral vector) or may be contained within multiple expression vectors.

In a specific embodiment, the invention provides combinatorial polynucleotide (e.g., DNA) vaccines which combine both a polynucleotide vaccine and polypeptide (e.g., either a recombinant protein, a purified subunit protein, a viral vector expressing an isolated SARS-CoV polypeptide) vaccine in a single formulation. The single formulation comprises a SARS-CoV polypeptide-encoding polynucleotide vaccine as described herein, and optionally, an effective amount of a desired isolated SARS-CoV polypeptide or fragment, variant, or derivative thereof. The polypeptide may exist in any form, for example, a recombinant protein, a purified subunit protein, or a viral vector expressing an isolated SARS-CoV polypeptide. The SARS-CoV polypeptide or fragment, variant, or derivative thereof encoded by the polynucleotide vaccine may be identical to the isolated SARS-CoV polypeptide or fragment, variant, or derivative thereof. Alternatively, the SARS-CoV polypeptide or fragment, variant, or derivative thereof encoded by the polynucleotide may be different from the isolated SARS-CoV polypeptide or fragment, variant, or derivative thereof.

It is to be noted that the term "a" or "an" entity refers to one or more of that entity; for example, "a polynucleotide," is understood to represent one or more polynucleotides. As such, the terms "a" (or "an"), "one or more," and "at least one" can be used interchangeably herein.

It is to be noted that the term "about" when referring to a polynucleotide, coding region or any nucleotide sequence, for example, is understood to represent plus or minus 1 to 30 nucleotides on either end of the defined coding region, polynucleotide or nucleotide sequence. It is to be noted that when referring to a polypeptide, or polypeptide sequence, that the term "about" is understood to represent plus or minus 1 to 10 amino acids on either end of the defined polypeptide or polypeptide sequence. It should be further noted that the term "about," when referring to the quantity of a specific codon in a given codon-optimized coding region has a specific meaning, described in more detail below.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in Darquet, A-M et al., *Gene Therapy* 4:1341-1349 (1997)) comprising a polynucleotide. A nucleic acid or fragment thereof may be provided in linear (e.g., mRNA), circular (e.g., plasmid), or branched form as well as double-stranded or single-stranded forms. A polynucleotide may comprise a conventional phosphodiester bond or a non-conventional bond (e.g., an amide bond, such as found in peptide nucleic acids (PNA)).

The terms "nucleic acid" or "nucleic acid fragment" refer to any one or more nucleic acid segments, e.g., DNA or RNA fragments, present in a polynucleotide or construct.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, and the like, are not part of a coding region. Two or more nucleic acids or nucleic acid fragments of the present invention can be present in a single polynucleotide construct, e.g., on a single plasmid, or in separate polynucleotide constructs, e.g., on separate (different) plasmids. Furthermore, any nucleic acid or nucleic acid fragment may encode a single SARS-CoV polypeptide or fragment, derivative, or variant thereof, e.g., or may encode more than one polypeptide, e.g., a nucleic acid may encode two or more polypeptides. In addition, a nucleic acid may include a regulatory element such as a promoter, ribosome binding site, or a transcription terminator, or may encode heterologous coding regions fused to the SARS-CoV coding region, e.g., specialized elements or motifs, such as a secretory signal peptide or a heterologous functional domain.

The terms "fragment," "variant," "derivative," and "analog," when referring to SARS-CoV polypeptides of the present invention, include any polypeptides which retain at least some of the immunogenicity or antigenicity of the corresponding native polypeptide. Fragments of SARS-CoV polypeptides of the present invention include proteolytic fragments, deletion fragments, and in particular, fragments of SARS-CoV polypeptides which exhibit increased secretion from the cell or higher immunogenicity or reduced pathogenicity when delivered to an animal. Polypeptide fragments further include any portion of the polypeptide which comprises an antigenic or immunogenic epitope of the native polypeptide, including linear as well as three-dimensional epitopes. Variants of SARS-CoV polypeptides of the present invention include fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome or genome of an organism or virus. *Genes II*, Lewin, B., ed., John Wiley & Sons, New York (1985), which is incorporated herein by reference. Naturally or non-naturally occurring variations such as amino acid deletions, insertions or substitutions may occur. Non-naturally occurring variants may be produced using art-known mutagenesis techniques. Variant polypeptides may comprise conservative or non-conservative amino acid substitutions, deletions or additions. Derivatives of SARS-CoV polypeptides of the present invention, are polypeptides which have been altered so as to exhibit additional features not found on the native polypeptide. Examples include fusion proteins. An analog is another form of a SARS-CoV polypeptide of the present invention. An example is a proprotein which can be activated by cleavage of the proprotein to produce an active mature polypeptide.

The terms "infectious polynucleotide" or "infectious nucleic acid" are intended to encompass isolated viral polynucleotides and/or nucleic acids which are solely sufficient to mediate the synthesis of complete infectious virus particles upon uptake by permissive cells. Thus, "infectious nucleic acids" do not require pre-synthesized copies of any of the polypeptides it encodes, e.g., viral replicases, in order to initiate its replication cycle in a permissive host cell.

The terms "non-infectious polynucleotide" or "non-infectious nucleic acid" as defined herein are polynucleotides or nucleic acids which cannot, without additional added materials, e.g, polypeptides, mediate the synthesis of complete infectious virus particles upon uptake by permissive cells. An infectious polynucleotide or nucleic acid is not made "non-infectious" simply because it is taken up by a non-permissive cell. For example, an infectious viral polynucleotide from a virus with limited host range is infectious if it is capable of mediating the synthesis of complete infectious virus particles when taken up by cells derived from a permissive host (i.e., a host permissive for the virus itself). The fact that uptake by cells derived from a non-permissive host does not result in the synthesis of complete infectious virus particles does not make the nucleic acid "non-infectious." In other words, the term is not qualified by the nature of the host cell, the tissue type, or the species taking up the polynucleotide or nucleic acid fragment.

In some cases, an isolated infectious polynucleotide or nucleic acid may produce fully-infectious virus particles in a host cell population which lacks receptors for the virus particles, i.e., is non-permissive for virus entry.

Thus viruses produced will not infect surrounding cells. However, if the supernatant containing the virus particles is transferred to cells which are permissive for the virus, infection will take place.

The terms "replicating polynucleotide" or "replicating nucleic acid" are meant to encompass those polynucleotides and/or nucleic acids which, upon being taken up by a permissive host cell, are capable of producing multiple, e.g., one or more copies of the same polynucleotide or nucleic acid. Infectious polynucleotides and nucleic acids are a subset of replicating polynucleotides and nucleic acids; the terms are not synonymous. For example, a defective virus genome lacking the genes for virus coat proteins may replicate, e.g., produce multiple copies of itself, but is NOT infectious because it is incapable of mediating the synthesis of complete infectious virus particles unless the coat proteins, or another nucleic acid encoding the coat proteins, are exogenously provided.

In certain embodiments, the polynucleotide, nucleic acid, or nucleic acid fragment is DNA. In the case of DNA, a polynucleotide comprising a nucleic acid which encodes a polypeptide normally also comprises a promoter and/or other transcription or translation control elements operably associated with the polypeptide-encoding nucleic acid fragment. An operable association is when a nucleic acid fragment encoding a gene product, e.g., a polypeptide, is associated with one or more regulatory sequences in such a way as to place expression of the gene product under the influence or control of the regulatory sequence(s). Two DNA fragments (such as a polypeptide-encoding nucleic acid fragment and a promoter associated with the 5' end of the nucleic acid fragment) are "operably associated" if induction of promoter function results in the transcription of mRNA encoding the desired gene product and if the nature of the linkage between the two DNA fragments does not (1) result in the introduction of a frame-shift mutation, (2) interfere with the ability of the expression regulatory sequences to direct the expression of the gene product, or (3) interfere with the ability of the DNA template to be transcribed. Thus, a promoter region would be operably associated with a nucleic acid fragment encoding a polypeptide if the promoter were capable of effecting transcription of that nucleic acid fragment. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g. promoters inducible by interferons or interleukins).

Similarly, a variety of translation control elements are known to those of ordinary skill in the art. These include, but are not limited to ribosome binding sites, translation initiation and termination codons, elements from picomaviruses (particularly an internal ribosome entry site, or IRES, also referred to as a CITE sequence).

A DNA polynucleotide of the present invention may be a circular or linearized plasmid, or other linear DNA which may also be non-infectious and nonintegrating (i.e., does not integrate into the genome of vertebrate cells). A linearized plasmid is a plasmid that was previously circular but has been linearized, for example, by digestion with a restriction endonuclease. Linear DNA may be advantageous in certain situations as discussed, e.g., in Cherng, J. Y., et al., *J. Control. Release* 60:343-53 (1999), and Chen, Z. Y., et al. *Mol. Ther.* 3:403-10 (2001), both of which are incorporated herein by reference.

Alternatively, DNA virus genomes may be used to administer DNA polynucleotides into vertebrate cells. In certain embodiments, a DNA virus genome of the present invention is nonreplicative, noninfectious, and/or nonintegrating. Suitable DNA virus genomes include without limitation, herpesvirus genomes, adenovirus genomes, adeno-associated virus genomes, and poxvirus genomes. References citing methods for the in vivo introduction of non-infectious virus genomes to vertebrate tissues are well known to those of ordinary skill in the art, and are cited supra.

In other embodiments, a polynucleotide of the present invention is RNA, for example, in the form of messenger RNA (mRNA). Methods for introducing RNA sequences into vertebrate cells are described in U.S. Pat. No. 5,580,859, the disclosure of which is incorporated herein by reference in its entirety.

Polynucleotides, nucleic acids, and nucleic acid fragments of the present invention may be associated with additional nucleic acids which encode secretory or signal peptides, which direct the secretion of a polypeptide encoded by a nucleic acid fragment or polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native leader sequence is used, or a functional derivative of that sequence that retains the ability to direct the secretion of the polypeptide that is operably associated with it. Alternatively, a heterologous mammalian leader sequence, or a functional derivative thereof, may be used. For example, the wild-type leader sequence may be substituted with the leader sequence of human tissue plasminogen activator (TPA) or mouse β-glucuronidase.

In accordance with one aspect of the present invention, there is provided a polynucleotide construct, for example, a plasmid, comprising a nucleic acid fragment, where the nucleic acid fragment is a fragment of a coding region operably encoding an SARS-CoV-derived polypeptide. In accordance with another aspect of the present invention, there is provided a polynucleotide construct, for example, a plasmid, comprising a nucleic acid fragment, where the nucleic acid fragment is a fragment of a codon-optimized coding region operably encoding an SARS-CoV-derived polypeptide, where the coding region is optimized for expression in vertebrate cells, of a desired vertebrate species, e.g., humans, to be delivered to a vertebrate to be treated or immunized. Suitable SARS-CoV polypeptides, or fragments, variants, or derivatives thereof may be derived from, but are not limited to, the SARS-CoV S, Soluble S1, Soluble S2, N, E or M proteins. Additional SARS-CoV-derived coding sequences, e.g., coding for S, Soluble S1, Soluble S2, N, E or M, may also be included on the plasmid, or on a separate plasmid, and expressed, either using native SARS-CoV codons or one or more codons optimized for expression in the vertebrate to be treated or immunized. When such a plasmid encoding one or more optimized SARS-CoV sequences and/or one or more optimized SARS-CoV sequences is delivered, in vivo to a tissue of the vertebrate to be treated or immunized, one or more of the encoded gene products will be expressed, i.e., transcribed and translated. The level of expression of the gene product(s) will depend to a significant extent on the strength of the associated promoter and the presence and activation of an associated enhancer element, as well as the degree of optimization of the coding region.

As used herein, the term "plasmid" refers to a construct made up of genetic material (i.e., nucleic acids). Typically a plasmid contains an origin of replication which is functional in bacterial host cells, e.g., *Escherichia coli*, and selectable markers for detecting bacterial host cells comprising the plasmid. Plasmids of the present invention may include genetic elements as described herein arranged such that an inserted coding sequence can be transcribed and translated in eukaryotic cells. Also, the plasmid may include a sequence from a viral nucleic acid. However, such viral sequences normally are not sufficient to direct or allow the incorporation of the plasmid into a viral particle, and the plasmid is therefore a non-viral vector. In certain embodiments described herein, a plasmid is a closed circular DNA molecule.

The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product.

As used herein, the term "polypeptide" is intended to encompass a singular "polypeptide" as well as plural "polypeptides," and comprises any chain or chains of two or more amino acids. Thus, as used herein, terms including, but not limited to "peptide," "dipeptide," "tripeptide," "protein," "amino acid chain," or any other term used to refer to a chain or chains of two or more amino acids, are included in the definition of a "polypeptide," and the term "polypeptide" may be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

Also included as polypeptides of the present invention are fragments, derivatives, analogs, or variants of the foregoing polypeptides, and any combination thereof. Polypeptides, and fragments, derivatives, analogs, or variants thereof of the present invention can be antigenic and immunogenic polypeptides related to SARS-CoV polypeptides, which are used to prevent or treat, i.e., cure, ameliorate, lessen the severity of, or prevent or reduce contagion of infectious disease caused by the SARS-CoV.

As used herein, an antigenic polypeptide or an immunogenic polypeptide is a polypeptide which, when introduced into a vertebrate, reacts with the vertebrate's immune system molecules, i.e., is antigenic, and/or induces an immune response in the vertebrate, i.e., is immunogenic. It is quite likely that an immunogenic polypeptide will also be antigenic, but an antigenic polypeptide, because of its size or conformation, may not necessarily be immunogenic. Examples of antigenic and immunogenic polypeptides of the present invention include, but are not limited to, e.g., S or fragments, derivatives, or variants thereof; N or fragments, derivatives, or variants thereof; E or fragments, derivatives, or variants thereof; M or fragments, derivatives, or variants thereof; other predicted ORF's within the sequence of the SARS-CoV viruses which may posses antigenic properties, for example, an ORF which may encode for the hemagglutinin-esterase or fragments, derivatives, or variants thereof; or any of the foregoing polypeptides or fragments, derivatives, or variants thereof fused to a heterologous polypeptide, for example, a hepatitis B core antigen. Isolated antigenic and immunogenic polypeptides of the present invention in addition to those encoded by polynucleotides of the invention, may be provided as a recombinant protein, a purified subunit, a viral vector expressing the protein, or may be provided in the form of an inactivated SARS-CoV vaccine, e.g., a live-attenuated virus vaccine, a heat-killed virus vaccine, etc.

By an "isolated" SARS-CoV polypeptide or a fragment, variant, or derivative thereof is intended a SARS-CoV polypeptide or protein that is not in its natural environment. No particular level of purification is required. For example, an isolated SARS-CoV polypeptide can be removed from its native or natural environment. Recombinantly produced SARS-CoV polypeptides and proteins expressed in host cells are considered isolated for purposed of the invention, as are native or recombinant SARS-CoV polypeptides which have been separated, fractionated, or partially or substantially purified by any suitable technique, including the separation of SARS-CoV virions from tissue samples or culture cells in which they have been propagated. In addition, an isolated. Thus, isolated SARS-CoV polypeptides and proteins can be provided as, for example, recombinant SARS-CoV polypeptides, a purified subunit of SARS-CoV, or a viral vector expressing an isolated SARS-CoV polypeptide.

The term "epitopes," as used herein, refers to portions of a polypeptide having antigenic or immunogenic activity in a vertebrate, for example a human. An "immunogenic epitope," as used herein, is defined as a portion of a protein that elicits an immune response in an animal, as determined by any method known in the art. The term "antigenic epitope," as used herein, is defined as a portion of a protein to which an antibody or T-cell receptor can immunospecifically bind as determined by any method well known in the art. Immunospecific binding excludes non-specific binding but does not exclude cross-reactivity with other antigens. Where all immunogenic epitopes are antigenic, antigenic epitopes need not be immunogenic.

The term "immunogenic carrier" as used herein refers to a first polypeptide or fragment, variant, or derivative thereof which enhances the immunogenicity of a second polypeptide or fragment, variant, or derivative thereof. Typically, an "immunogenic carrier" is fused to or conjugated to the desired polypeptide or fragment thereof. An example of an "immunogenic carrier" is a recombinant hepatitis B core antigen expressing, as a surface epitope, an immunogenic epitope of interest. See, e.g., European Patent No. EP 0385610 B 1, which is incorporated herein by reference in its entirety.

In the present invention, antigenic epitopes preferably contain a sequence of at least 4, at least 5, at least 6, at least 7, at least 8, at least 9, at least 10, at least 15, at least 20, at least 25, or between about 8 to about 30 amino acids contained within the amino acid sequence of a SARS-CoV polypeptide of the invention, e.g., an S polypeptide, an N polypeptide, an E polypeptide or an M polypeptide. Certain polypeptides comprising immunogenic or antigenic epitopes are at least 5, 10, 15, 20, 25, 30, 35, 40, 45, 50, 55, 60, 65, 70, 75, 80, 85, 90, 95, or 100 amino acid residues in length. Antigenic as well as immunogenic epitopes may be linear, i.e., be comprised of contiguous amino acids in a polypeptide, or may be three dimensional, i.e., where an epitope is comprised of non-contiguous amino acids which come together due to the secondary or tertiary structure of the polypeptide, thereby forming an epitope.

As to the selection of peptides or polypeptides bearing an antigenic epitope (e.g., that contain a region of a protein molecule to which an antibody or T cell receptor can bind), it is well known in that art that relatively short synthetic peptides that mimic part of a protein sequence are routinely capable of eliciting an antiserum that reacts with the partially mimicked protein. See, e.g., Sutcliffe, J. G., et al., *Science* 219:660-666 (1983).

Peptides capable of eliciting an immunogenic response are frequently represented in the primary sequence of a protein, can be characterized by a set of simple chemical rules, and are confined neither to immunodominant regions of intact proteins nor to the amino or carboxyl terminals. Peptides that are extremely hydrophobic and those of six or fewer residues generally are ineffective at inducing antibodies that bind to the mimicked protein; longer peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Codon Optimization

"Codon optimization" is defined as modifying a nucleic acid sequence for enhanced expression in the cells of the vertebrate of interest, e.g., human, by replacing at least one, more than one, or a significant number, of codons of the native sequence with codons that are more frequently or most frequently used in the genes of that vertebrate. Various species exhibit particular biases for certain codons of a particular amino acid.

In one aspect, the present invention relates to polynucleotides comprising nucleic acid fragments of codon-optimized coding regions which encode SARS-CoV polypeptides, or fragments, variants, or derivatives thereof, with the codon usage adapted for optimized expression in the cells of a given vertebrate, e.g., humans. These polynucleotides are prepared by incorporating codons preferred for use in the genes of the vertebrate of interest into the DNA sequence. Also provided are polynucleotide expression constructs, vectors, and host cells comprising nucleic acid fragments of codon-optimized coding regions which encode SARS-CoV polypeptides, and fragments, variants, or derivatives thereof, and various methods of using the polynucleotide expression constructs, vectors, and/or host cells to treat or prevent SARS disease in a vertebrate.

As used herein the term "codon-optimized coding region" means a nucleic acid coding region that has been adapted for expression in the cells of a given vertebrate by replacing at least one, or more than one, or a significant number, of codons with one or more codons that are more frequently used in the genes of that vertebrate.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code," which shows which codons encode which amino acids, is reproduced herein as Table 3. As a result, many amino acids are designated by more than one codon. For example, the amino acids alanine and proline are coded for by four triplets, serine and arginine by six triplets, whereas tryptophan and methionine are coded by just one triplet. This degeneracy allows for DNA base composition to vary over a wide range without altering the amino acid sequence of the proteins encoded by the DNA.

TABLE 3

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA **Ter** | TGA **Ter** |
| | TTG Leu (L) | TCG Ser (S) | TAG **Ter** | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | **ATG** Met (M) | ACG Thr (T) | AAG Lys (K) | AAG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database," available at www.kazusa.or.jp/codon/ (visited Jul. 9, 2002), and these tables can be adapted in a number of ways. See Nakamura, Y., et al. "Codon usage tabulated from the international DNA sequence databases: status for the year 2000" Nucl. Acids Res. 28:292 (2000). As examples, the codon usage tables for human, mouse, domestic cat, and cow, calculated from GenBank Release 128.0 (15 Feb. 2002), are reproduced below as Tables 4-7. These tables use mRNA nomenclature, and so instead of thymine (T) which is found in DNA, the tables use uracil (U) which is found in RNA. The tables have been adapted so that frequencies are calculated for each amino acid, rather than for all 64 codons.

TABLE 4

Codon Usage Table for Human Genes (*Homo sapiens*)

| Amino Acid | Codon | Number | Frequency |
|---|---|---|---|
| Phe | UUU | 326146 | 0.4525 |
| Phe | UUC | 394680 | 0.5475 |
| Total | | 720826 | |
| Leu | UUA | 139249 | 0.0728 |
| Leu | UUG | 242151 | 0.1266 |
| Leu | CUU | 246206 | 0.1287 |
| Leu | CUC | 374262 | 0.1956 |
| Leu | CUA | 133980 | 0.0700 |
| Leu | CUG | 777077 | 0.4062 |
| Total | | 1912925 | |
| Ile | AUU | 303721 | 0.3554 |
| Ile | AUC | 414483 | 0.4850 |
| Ile | AUA | 136399 | 0.1596 |
| Total | | 854603 | |
| Met | AUG | 430946 | 1.0000 |
| Total | | 430946 | |
| Val | GUU | 210423 | 0.1773 |
| Val | GUC | 282445 | 0.2380 |
| Val | GUA | 134991 | 0.1137 |
| Val | GUG | 559044 | 0.4710 |
| Total | | 1186903 | |
| Ser | UCU | 282407 | 0.1840 |
| Ser | UCC | 336349 | 0.2191 |
| Ser | UCA | 225963 | 0.1472 |
| Ser | UCG | 86761 | 0.0565 |
| Ser | AGU | 230047 | 0.1499 |
| Ser | AGC | 373362 | 0.2433 |
| Total | | 1534889 | |
| Pro | CCU | 333705 | 0.2834 |
| Pro | CCC | 386462 | 0.3281 |
| Pro | CCA | 322220 | 0.2736 |
| Pro | CCG | 135317 | 0.1149 |
| Total | | 1177704 | |
| Thr | ACU | 247913 | 0.2419 |
| Thr | ACC | 371420 | 0.3624 |
| Thr | ACA | 285655 | 0.2787 |
| Thr | ACG | 120022 | 0.1171 |
| Total | | 1025010 | |
| Ala | GCU | 360146 | 0.2637 |
| Ala | GCC | 551452 | 0.4037 |
| Ala | GCA | 308034 | 0.2255 |
| Ala | GCG | 146233 | 0.1071 |
| Total | | 1365865 | |
| Tyr | UAU | 232240 | 0.4347 |
| Tyr | UAC | 301978 | 0.5653 |
| Total | | 534218 | |
| His | CAU | 201389 | 0.4113 |
| His | CAC | 288200 | 0.5887 |
| Total | | 489589 | |

TABLE 4-continued

Codon Usage Table for Human Genes (*Homo sapiens*)

| Amino Acid | Codon | Number | Frequency |
|---|---|---|---|
| Gln | CAA | 227742 | 0.2541 |
| Gln | CAG | 668391 | 0.7459 |
| Total | | 896133 | |
| Asn | AAU | 322271 | 0.4614 |
| Asn | AAC | 376210 | 0.5386 |
| Total | | 698481 | |
| Lys | AAA | 462660 | 0.4212 |
| Lys | AAG | 635755 | 0.5788 |
| Total | | 1098415 | |
| Asp | GAU | 430744 | 0.4613 |
| Asp | GAC | 502940 | 0.5387 |
| Total | | 933684 | |
| Glu | GAA | 561277 | 0.4161 |
| Glu | GAG | 787712 | 0.5839 |
| Total | | 1348989 | |
| Cys | UGU | 190962 | 0.4468 |
| Cys | UGC | 236400 | 0.5532 |
| Total | | 427362 | |
| Trp | UGG | 248083 | 1.0000 |
| Total | | 248083 | |
| Arg | CGU | 90899 | 0.0830 |
| Arg | CGC | 210931 | 0.1927 |
| Arg | CGA | 122555 | 0.1120 |
| Arg | CGG | 228970 | 0.2092 |
| Arg | AGA | 221221 | 0.2021 |
| Arg | AGG | 220119 | 0.2011 |
| Total | | 1094695 | |
| Gly | GGU | 209450 | 0.1632 |
| Gly | GGC | 441320 | 0.3438 |
| Gly | GGA | 315726 | 0.2459 |
| Gly | GGG | 317263 | 0.2471 |
| Total | | 1283759 | |
| Stop | UAA | 13963 | |
| Stop | UAG | 10631 | |
| Stop | UGA | 24607 | |

TABLE 5

Codon Usage Table for Mouse Genes (*Mus musculus*)

| Amino Acid | Codon | Number | Frequency |
|---|---|---|---|
| Phe | UUU | 150467 | 0.4321 |
| Phe | UUC | 197795 | 0.5679 |
| Total | | 348262 | |
| Leu | UUA | 55635 | 0.0625 |
| Leu | UUG | 116210 | 0.1306 |
| Leu | CUU | 114699 | 0.1289 |
| Leu | CUC | 179248 | 0.2015 |
| Leu | CUA | 69237 | 0.0778 |
| Leu | CUG | 354743 | 0.3987 |
| Total | | 889772 | |
| Ile | AUU | 137513 | 0.3367 |
| Ile | AUC | 208533 | 0.5106 |
| Ile | AUA | 62349 | 0.1527 |
| Total | | 408395 | |
| Met | AUG | 204546 | 1.0000 |
| Total | | 204546 | |
| Val | GUU | 93754 | 0.1673 |
| Val | GUC | 140762 | 0.2513 |

TABLE 5-continued

Codon Usage Table for Mouse Genes (*Mus musculus*)

| Amino Acid | Codon | Number | Frequency |
|---|---|---|---|
| Val | GUA | 64417 | 0.1150 |
| Val | GUG | 261308 | 0.4664 |
| Total | | 560241 | |
| Ser | UCU | 139576 | 0.1936 |
| Ser | UCC | 160313 | 0.2224 |
| Ser | UCA | 100524 | 0.1394 |
| Ser | UCG | 38632 | 0.0536 |
| Ser | AGU | 108413 | 0.1504 |
| Ser | AGC | 173518 | 0.2407 |
| Total | | 720976 | |
| Pro | CCU | 162613 | 0.3036 |
| Pro | CCC | 164796 | 0.3077 |
| Pro | CCA | 151091 | 0.2821 |
| Pro | CCG | 57032 | 0.1065 |
| Total | | 535532 | |
| Thr | ACU | 119832 | 0.2472 |
| Thr | ACC | 172415 | 0.3556 |
| Thr | ACA | 140420 | 0.2896 |
| Thr | ACG | 52142 | 0.1076 |
| Total | | 484809 | |
| Ala | GCU | 178593 | 0.2905 |
| Ala | GCC | 236018 | 0.3839 |
| Ala | GCA | 139697 | 0.2272 |
| Ala | GCG | 60444 | 0.0983 |
| Total | | 614752 | |
| Tyr | UAU | 108556 | 0.4219 |
| Tyr | UAC | 148772 | 0.5781 |
| Total | | 257328 | |
| His | CAU | 88786 | 0.3973 |
| His | CAC | 134705 | 0.6027 |
| Total | | 223491 | |
| Gln | CAA | 101783 | 0.2520 |
| Gln | CAG | 302064 | 0.7480 |
| Total | | 403847 | |
| Asn | AAU | 138868 | 0.4254 |
| Asn | AAC | 187541 | 0.5746 |
| Total | | 326409 | |
| Lys | AAA | 188707 | 0.3839 |
| Lys | AAG | 302799 | 0.6161 |
| Total | | 491506 | |
| Asp | GAU | 189372 | 0.4414 |
| Asp | GAC | 239670 | 0.5586 |
| Total | | 429042 | |
| Glu | GAA | 235842 | 0.4015 |
| Glu | GAG | 351582 | 0.5985 |
| Total | | 587424 | |
| Cys | UGU | 97385 | 0.4716 |
| Cys | UGC | 109130 | 0.5284 |
| Total | | 206515 | |
| Trp | UGG | 112588 | 1.0000 |
| Total | | 112588 | |
| Arg | CGU | 41703 | 0.0863 |
| Arg | CGC | 86351 | 0.1787 |
| Arg | CGA | 58928 | 0.1220 |
| Arg | CGG | 92277 | 0.1910 |
| Arg | AGA | 101029 | 0.2091 |
| Arg | AGG | 102859 | 0.2129 |
| Total | | 483147 | |
| Gly | GGU | 103673 | 0.1750 |
| Gly | GGC | 198604 | 0.3352 |
| Gly | GGA | 151497 | 0.2557 |

TABLE 5-continued

| Codon Usage Table for Mouse Genes (*Mus musculus*) | | | |
|---|---|---|---|
| Amino Acid | Codon | Number | Frequency |
| Gly | GGG | 138700 | 0.2341 |
| Total | | 592474 | |
| Stop | UAA | 5499 | |
| Stop | UAG | 4661 | |
| Stop | UGA | 10356 | |

TABLE 6

| Codon Usage Table for Domestic Cat Genes (*Felis cattus*) | | | |
|---|---|---|---|
| Amino Acid | Codon | Number | Frequency of usage |
| Phe | UUU | 1204.00 | 0.4039 |
| Phe | UUC | 1777.00 | 0.5961 |
| Total | | 2981 | |
| Leu | UUA | 404.00 | 0.0570 |
| Leu | UUG | 857.00 | 0.1209 |
| Leu | CUU | 791.00 | 0.1116 |
| Leu | CUC | 1513.00 | 0.2135 |
| Leu | CUA | 488.00 | 0.0688 |
| Leu | CUG | 3035.00 | 0.4282 |
| Total | | 7088 | |
| Ile | AUU | 1018.00 | 0.2984 |
| Ile | AUC | 1835.00 | 0.5380 |
| Ile | AUA | 558.00 | 0.1636 |
| Total | | 3411 | |
| Met | AUG | 1553.00 | 0.0036 |
| Total | | 1553 | |
| Val | GUU | 696.00 | 0.1512 |
| Val | GUC | 1279.00 | 0.2779 |
| Val | GUA | 463.00 | 0.1006 |
| Val | GUG | 2164.00 | 0.4702 |
| Total | | 4602 | |
| Ser | UCU | 940.00 | 0.1875 |
| Ser | UCC | 1260.00 | 0.2513 |
| Ser | UCA | 608.00 | 0.1213 |
| Ser | UCG | 332.00 | 0.0662 |
| Ser | AGU | 672.00 | 0.1340 |
| Ser | AGC | 1202.00 | 0.2397 |
| Total | | 5014 | |
| Pro | CCU | 958.00 | 0.2626 |
| Pro | CCC | 1375.00 | 0.3769 |
| Pro | CCA | 850.00 | 0.2330 |
| Pro | CCG | 465.00 | 0.1275 |
| Total | | 3648 | |
| Thr | ACU | 822.00 | 0.2127 |
| Thr | ACC | 1574.00 | 0.4072 |
| Thr | ACA | 903.00 | 0.2336 |
| Thr | ACG | 566.00 | 0.1464 |
| Total | | 3865 | |
| Ala | GCU | 1129.00 | 0.2496 |
| Ala | GCC | 1951.00 | 0.4313 |
| Ala | GCA | 883.00 | 0.1952 |
| Ala | GCG | 561.00 | 0.1240 |
| Total | | 4524 | |
| Tyr | UAU | 837.00 | 0.3779 |
| Tyr | UAC | 1378.00 | 0.6221 |
| Total | | 2215 | |
| His | CAU | 594.00 | 0.3738 |
| His | CAC | 995.00 | 0.6262 |
| Total | | 1589 | |

TABLE 6-continued

| Codon Usage Table for Domestic Cat Genes (*Felis cattus*) | | | |
|---|---|---|---|
| Amino Acid | Codon | Number | Frequency of usage |
| Gln | CAA | 747.00 | 0.2783 |
| Gln | CAG | 1937.00 | 0.7217 |
| Total | | 2684 | |
| Asn | AAU | 1109.00 | 0.3949 |
| Asn | AAC | 1699.00 | 0.6051 |
| Total | | 2808 | |
| Lys | AAA | 1445.00 | 0.4088 |
| Lys | AAG | 2090.00 | 0.5912 |
| Total | | 3535 | |
| Asp | GAU | 1255.00 | 0.4055 |
| Asp | GAC | 1840.00 | 0.5945 |
| Total | | 3095 | |
| Glu | GAA | 1637.00 | 0.4164 |
| Glu | GAG | 2294.00 | 0.5836 |
| Total | | 3931 | |
| Cys | UGU | 719.00 | 0.4425 |
| Cys | UGC | 906.00 | 0.5575 |
| Total | | 1625 | |
| Trp | UGG | 1073.00 | 1.0000 |
| Total | | 1073 | |
| Arg | CGU | 236.00 | 0.0700 |
| Arg | CGC | 629.00 | 0.1865 |
| Arg | CGA | 354.00 | 0.1050 |
| Arg | CGG | 662.00 | 0.1963 |
| Arg | AGA | 712.00 | 0.2112 |
| Arg | AGG | 779.00 | 0.2310 |
| Total | | 3372 | |
| Gly | GGU | 648.00 | 0.1498 |
| Gly | GGC | 1536.00 | 0.3551 |
| Gly | GGA | 1065.00 | 0.2462 |
| Gly | GGG | 1077.00 | 0.2490 |
| Total | | 4326 | |
| Stop | UAA | 55 | |
| Stop | UAG | 36 | |
| Stop | UGA | 110 | |

TABLE 7

| Codon Usage Table for Cow Genes (*Bos taurus*) | | | |
|---|---|---|---|
| Amino Acid | Codon | Number | Frequency of usage |
| Phe | UUU | 13002 | 0.4112 |
| Phe | UUC | 18614 | 0.5888 |
| Total | | 31616 | |
| Leu | UUA | 4467 | 0.0590 |
| Leu | UUG | 9024 | 0.1192 |
| Leu | CUU | 9069 | 0.1198 |
| Leu | CUC | 16003 | 0.2114 |
| Leu | CUA | 4608 | 0.0609 |
| Leu | CUG | 32536 | 0.4298 |
| Total | | 75707 | |
| Ile | AUU | 12474 | 0.3313 |
| Ile | AUC | 19800 | 0.5258 |
| Ile | AUA | 5381 | 0.1429 |
| Total | | 37655 | |
| Met | AUG | 17770 | 1.0000 |
| Total | | 17770 | |
| Val | GUU | 8212 | 0.1635 |
| Val | GUC | 12846 | 0.2558 |

TABLE 7-continued

Codon Usage Table for Cow Genes (*Bos taurus*)

| Amino Acid | Codon | Number | Frequency of usage |
|---|---|---|---|
| Val | GUA | 4932 | 0.0982 |
| Val | GUG | 24222 | 0.4824 |
| Total | | 50212 | |
| Ser | UCU | 10287 | 0.1804 |
| Ser | UCC | 13258 | 0.2325 |
| Ser | UCA | 7678 | 0.1347 |
| Ser | UCG | 3470 | 0.0609 |
| Ser | AGU | 8040 | 0.1410 |
| Ser | AGC | 14279 | 0.2505 |
| Total | | 57012 | |
| Pro | CCU | 11695 | 0.2684 |
| Pro | CCC | 15221 | 0.3493 |
| Pro | CCA | 11039 | 0.2533 |
| Pro | CCG | 5621 | 0.1290 |
| Total | | 43576 | |
| Thr | ACU | 9372 | 0.2203 |
| Thr | ACC | 16574 | 0.3895 |
| Thr | ACA | 10892 | 0.2560 |
| Thr | ACG | 5712 | 0.1342 |
| Total | | 42550 | |
| Ala | GCU | 13923 | 0.2592 |
| Ala | GCC | 23073 | 0.4295 |
| Ala | GCA | 10704 | 0.1992 |
| Ala | GCG | 6025 | 0.1121 |
| Total | | 53725 | |
| Tyr | UAU | 9441 | 0.3882 |
| Tyr | UAC | 14882 | 0.6118 |
| Total | | 24323 | |
| His | CAU | 6528 | 0.3649 |
| His | CAC | 11363 | 0.6351 |
| Total | | 17891 | |
| Gln | CAA | 8060 | 0.2430 |
| Gln | CAG | 25108 | 0.7570 |
| Total | | 33168 | |
| Asn | AAU | 12491 | 0.4088 |
| Asn | AAC | 18063 | 0.5912 |
| Total | | 30554 | |
| Lys | AAA | 17244 | 0.3897 |
| Lys | AAG | 27000 | 0.6103 |
| Total | | 44244 | |
| Asp | GAU | 16615 | 0.4239 |
| Asp | GAC | 22580 | 0.5761 |
| Total | | 39195 | |
| Glu | GAA | 21102 | 0.4007 |
| Glu | GAG | 31555 | 0.5993 |
| Total | | 52657 | |
| Cys | UGU | 7556 | 0.4200 |
| Cys | UGC | 10436 | 0.5800 |
| Total | | 17992 | |
| Trp | UGG | 10706 | 1.0000 |
| Total | | 10706 | |
| Arg | CGU | 3391 | 0.0824 |
| Arg | CGC | 7998 | 0.1943 |
| Arg | CGA | 4558 | 0.1108 |
| Arg | CGG | 8300 | 0.2017 |
| Arg | AGA | 8237 | 0.2001 |
| Arg | AGG | 8671 | 0.2107 |
| Total | | 41155 | |
| Gly | GGU | 8508 | 0.1616 |
| Gly | GGC | 18517 | 0.3518 |
| Gly | GGA | 12838 | 0.2439 |
| Gly | GGG | 12772 | 0.2427 |
| Total | | 52635 | |
| Stop | UAA | 555 | |
| Stop | UAG | 394 | |
| Stop | UGA | 392 | |

By utilizing these or similar tables, one of ordinary skill in the art can apply the frequencies to any given polypeptide sequence, and produce a nucleic acid fragment of a codon-optimized coding region which encodes the polypeptide, but which uses codons more optimal for a given species. Codon-optimized coding regions can be designed by various different methods.

In one method, termed "uniform optimization," a codon usage table is used to find the single most frequent codon used for any given amino acid, and that codon is used each time that particular amino acid appears in the polypeptide sequence. For example, referring to Table 4 above, the most frequent codon for leucine in humans is CUG, which is used 41% of the time. Thus, all of the leucine residues in a given amino acid sequence would be assigned the codon CUG. A coding region for SARS-CoV soluble S protein (SEQ ID NO:1) optimized by the "uniform optimization" method is presented herein as SEQ ID NO:25.

In another method, termed "full-optimization," the actual frequencies of the codons are distributed randomly throughout the coding region. Thus, using this method for optimization, if a hypothetical polypeptide sequence had 100 leucine residues, referring to Table 4 for frequency of usage in humans, about 7, or 7% of the leucine codons would be UUA, about 13, or 13% of the leucine codons would be UUG, about 13, or 13% of the leucine codons would be CUU, about 20, or 20% of the leucine codons would be CUC, about 7, or 7% of the leucine codons would be CUA, and about 41, or 41% of the leucine codons would be CUG. These frequencies would be distributed randomly throughout the leucine codons in the coding region encoding the hypothetical polypeptide. As will be understood by those of ordinary skill in the art, the distribution of codons in the sequence can vary significantly using this method, however, the sequence always encodes the same polypeptide.

As an example, a nucleotide sequence for soluble S (SEQ ID NO:1) fully optimized for human codon usage, is shown as SEQ ID NO:24.

In using the "full-optimization" method, an entire polypeptide sequence may be codon-optimized as described above. With respect to various desired fragments, variants, or derivatives of the complete polypeptide, the fragment, variant, or derivative may first be designed, and is then codon-optimized individually. Alternatively, a full-length polypeptide sequence is codon-optimized for a given species, resulting in a codon-optimized coding region encoding the entire polypeptide; then nucleic acid fragments of the codon-optimized coding region, which encode fragments, variants, and derivatives of the polypeptide, are made from the original codon-optimized coding region. As will be well understood by those of ordinary skill in the art, if codons have been randomly assigned to the full-length coding region based on their frequency of use in a given species, nucleic acid fragments encoding fragments, variants, and derivatives would not necessarily be fully codon-optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

When using the "full-optimization" method, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes, for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," ie., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

In a third method termed "minimal optimization," coding regions are only partially optimized. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a vertebrate species, e.g., humans, in place of a codon that is normally used in the native nucleic acid sequence. Codons that are rarely found in the genes of the vertebrate of interest are changed to codons more commonly utilized in the coding regions of the vertebrate of interest.

Thus, those codons which are used more frequently in the SARS-CoV gene of interest than in genes of the vertebrate of interest are substituted with more frequently-used codons. The difference in frequency at which the SARS-CoV codons are substituted may vary based on a number factors as discussed below. For example, codons used at least twice more per thousand in SARS-CoV genes as compared to genes of the vertebrate of interest are substituted with the most frequently used codon for that amino acid in the vertebrate of interest. This ratio may be adjusted higher or lower depending on various factors such as those discussed below. Accordingly, a codon in a SARS-CoV native coding region would be substituted with a codon used more frequently for that amino acid in coding regions of the vertebrate of interest if the codon is used 1.1 times, 1.2 times, 1.3 times, 1.4 times, 1.5 times, 1.6 times, 1.7 times, 1.8 times, 1.9 times, 2.0 times, 2.1 times, 2.2 times, 2.3 times, 2.4 times, 2.5 times, 2.6 times, 2.7 times, 2.8 times, 2.9 times, 3.0 times, 3.1 times, 3.2 times, 3.3. times, 3.4 times, 3.5 times, 3.6 times. 3.7 times, 3.8 times, 3.9 times, 4.0 times, 4.1 times, 4.2 times, 4.3 times, 4.4 times, 4.5 times, 4.6 times, 4.7 times, 4.8 times, 4.9 times, 5.0 times, 5.5 times, 6.0 times, 6.5 times, 7.0 times, 7.5 times, 8.0 times, 8.5 times, 9.0 times, 9.5 times, 10.0 times, 10.5 times, 11.0 times, 11.5 times, 12.0 times, 12.5 times, 13.0 times, 13.5 times, 14.0 times, 14.5 times, 15.0 times, 15.5 times, 16.0 times, 16.5 times, 17.0 times, 17.5 times, 18.0 times, 18.5 times, 19.0 times, 19.5 times, 20 times, 21 times, 22 times, 23 times, 24 times, 25 times, or greater more frequently in SARS-CoV coding regions than in coding regions of the vertebrate of interest.

This minimal human codon optimization for highly variant codons has several advantages, which include but are not limited to the following examples. Since fewer changes are made to the nucleotide sequence of the gene of interest, fewer manipulations are required, which leads to reduced risk of introducing unwanted mutations and lower cost, as well as allowing the use of commercially available site-directed mutagenesis kits, and reducing the need for expensive oligonucleotide synthesis. Further, decreasing the number of changes in the nucleotide sequence decreases the potential of altering the secondary structure of the sequence, which can have a significant impact on gene expression in certain host cells. The introduction of undesirable restriction sites is also reduced, facilitating the subcloning of the genes of interest into the plasmid expression vector.

In a fourth method, termed "standardized optimization," a Codon Usage Table (CUT) for the sequence to be optimized is generated and compared to the CUT for human genomic DNA (see, e.g., Table 8 below). Codons are identified for which there is a difference of at least 10 percentage points in codon usage between human and query DNA. When such a codon is found, all of the wild type codons for that amino acid are modified to conform to predominant human codon.

The codon usage frequencies for all established SARS-CoV open reading frames (ORFs) is compared to the codon usage frequencies for humans in Table 8 below.

TABLE 8

SARS CoV Urbani Codon Frequencies using all established ORFs

| Amino Acid | Codon | Urbani Number | Urbani Frequency of usage | Human Number | Human Frequency of usage |
|---|---|---|---|---|---|
| Phe | UUU | 272 | 0.6154 | 326146 | 0.4525 |
| Phe | UUC | 170 | 0.3846 | 394680 | 0.5475 |
| Total | | 442 | | 720826 | |
| Leu | UUA | 150 | 0.1777 | 139249 | 0.0728 |
| Leu | UUG | 150 | 0.1777 | 242151 | 0.1266 |
| Leu | CUU | 254 | 0.3009 | 246206 | 0.1287 |
| Leu | CUC | 119 | 0.1410 | 374262 | 0.1956 |
| Leu | CUA | 90 | 0.1066 | 133980 | 0.0700 |
| Leu | CUG | 81 | 0.0960 | 777077 | 0.4062 |
| Total | | 844 | | 1912925 | |
| Ile | AUU | 262 | 0.5784 | 303721 | 0.3554 |
| Ile | AUC | 98 | 0.2163 | 414483 | 0.4850 |
| Ile | AUA | 93 | 0.2053 | 136399 | 0.1596 |
| Total | | 453 | | 854603 | |
| Met | AUG | 212 | 0.0005 | 430946 | 1.0000 |
| Total | | 212 | | 430946 | |
| Val | GUU | 299 | 0.4194 | 210423 | 0.1773 |
| Val | GUC | 126 | 0.1767 | 282445 | 0.2380 |
| Val | GUA | 152 | 0.2132 | 134991 | 0.1137 |
| Val | GUG | 136 | 0.1907 | 559044 | 0.4710 |
| Total | | 713 | | 1186903 | |
| Ser | UCU | 202 | 0.3328 | 282407 | 0.1840 |
| Ser | UCC | 41 | 0.0675 | 336349 | 0.2191 |
| Ser | UCA | 176 | 0.2900 | 225963 | 0.1472 |
| Ser | UCG | 20 | 0.0329 | 86761 | 0.0565 |
| Ser | AGU | 118 | 0.1944 | 230047 | 0.1499 |
| Ser | AGC | 50 | 0.0824 | 373362 | 0.2433 |
| Total | | 607 | | 1534889 | |

TABLE 8-continued

| SARS CoV Urbani Codon Frequencies using all established ORFs | | | | | |
|---|---|---|---|---|---|
| Amino Acid | Codon | Urbani Number | Urbani Frequency of usage | Human Number | Human Frequency of usage |
| Pro | CCU | 163 | 0.4405 | 333705 | 0.2834 |
| Pro | CCC | 38 | 0.1027 | 386462 | 0.3281 |
| Pro | CCA | 156 | 0.4216 | 322220 | 0.2736 |
| Pro | CCG | 13 | 0.0351 | 135317 | 0.1149 |
| Total | | 370 | | 1177704 | |
| Thr | ACU | 275 | 0.4264 | 247913 | 0.2419 |
| Thr | ACC | 86 | 0.1333 | 371420 | 0.3624 |
| Thr | ACA | 257 | 0.3985 | 285655 | 0.2787 |
| Thr | ACG | 27 | 0.0419 | 120022 | 0.1171 |
| Total | | 645 | | 1025010 | |

The present invention provides isolated polynucleotides comprising codon-optimized coding regions of SARS-CoV polypeptides, e.g., S, S1, S2 N, E, or M, or fragments, variants, or derivatives thereof.

Additionally, a minimally codon-optimized nucleotide sequence can be designed by changing only certain codons found more frequently in SARS-CoV genes than in human genes. For example, if it is desired to substitute more frequently used codons in humans for those codons that occur at least 2 times more frequently in SARS-CoV genes.

In another form of minimal optimization, a Codon Usage Table (CUT) for the specific SARS-CoV sequence in question is generated and compared to the CUT for human genomic DNA. Amino acids are identified for which there is a difference of at least 10 percentage points in codon usage between human and SARS-CoV DNA (either more or less). Then, the wild type SARS-CoV codon is modified to conform to the predominant human codon for each such amino acid. Furthermore, the remainder of codons for that amino acid are also modified such that they conform to the predominant human codon for each such amino acid.

In certain embodiments described herein, a codon-optimized coding region encoding SEQ ID NO:2 is optimized according to codon usage in humans (*Homo sapiens*). Alternatively, a codon-optimized coding region encoding SEQ ID NO:2 may be optimized according to codon usage in any plant, animal, or microbial species. Codon-optimized coding regions encoding SEQ ID NO:2, optimized according to codon usage in humans are designed as follows. The amino acid composition of SEQ ID NO:2 is shown in Table 9.

TABLE 9

| AMINO ACID | | Number in SEQ ID NO: 2 |
|---|---|---|
| A | Ala | 81 |
| R | Arg | 39 |
| C | Cys | 30 |
| G | Gly | 74 |
| H | His | 14 |
| I | Ile | 74 |
| L | Leu | 92 |
| K | Lys | 56 |
| M | Met | 18 |
| F | Phe | 81 |
| P | Pro | 56 |
| S | Ser | 91 |
| T | Thr | 96 |
| W | Trp | 10 |
| Y | Tyr | 52 |
| V | Val | 86 |

TABLE 9-continued

| AMINO ACID | | Number in SEQ ID NO: 2 |
|---|---|---|
| N | Asn | 81 |
| D | Asp | 70 |
| Q | Gln | 55 |
| E | Glu | 40 |

Using the amino acid composition shown in Table 9, a human codon-optimized coding region which encodes SEQ ID NO:2 can be designed by any of the methods discussed herein. For "uniform" optimization, each amino acid is assigned the most frequent codon used in the human genome for that amino acid. According to this method, codons are assigned to the coding region encoding SEQ ID NO:2 as follows: the 81 phenylalanine codons are TTC, the 92 leucine codons are CTG, the 74 isoleucine codons are ATC, the 18 methionine codons are ATG, the 86 valine codons are GTG, the 91 serine codons are AGC, the 56 proline codons are CCC, the 96 threonine codons are ACC, the 81 alanine codons are GCC, the 52 tyrosine codons are TAC, the 14 histidine codons are CAC, the 55 glutamine codons are CAG, the 81 asparagine codons are AAC, the 56 lysine codons are AAG, the 70 aspartic acid codons are GAC, the 40 glutamic acid codons are GAG, the 30 cysteine codons are TGC, the 10 tryptophan codon is TGG, the 39 arginine codons are CGG, AGA, or AGG (the frequencies of usage of these three codons in the human genome are not significantly different), and the 74 glycine codons are GGC. The codon-optimized coding region designed by this method is presented herein as SEQ ID NO:25.

```
ATGTTCATCTTCCTGCTGTTCCTGACCCTGACCAGCGGCAGCGACCTGGA

CCGGTGCACCACCTTCGACGACGTGCAGGCCCCCAACTACACCCAGCACA

CCAGCAGCATGCGGGGCGTGTACTACCCCGACGAGATCTTCCGGAGCGAC

ACCCTGTACCTGACCCAGGACCTGTTCCTGCCCTTCTACAGCAACGTGAC

CGGCTTCCACACCATCAACCACACCTTCGGCAACCCCGTGATCCCCTTCA

AGGACGGCATCTACTTCGCCGCCACCGAGAAGAGCAACGTGGTGCGGGGC

TGGGTGTTCGGCAGCACCATGAACAACAAGAGCCAGAGCGTGATCATCAT

CAACAACAGCACCAACGTGGTGATCCGGGCCTGCAACTTCGAGCTGTGCG

ACAACCCCTTCTTCGCCGTGAGCAAGCCCATGGGCACCCAGACCCACACC

ATGATCTTCGACAACGCCTTCAACTGCACCTTCGAGTACATCAGCGACGC

CTTCAGCCTGGACGTGAGCGAGAAGAGCGGCAACTTCAAGCACCTGCGGG

AGTTCGTGTTCAAGAACAAGGACGGCTTCCTGTACGTGTACAAGGGCTAC

CAGCCCATCGACGTGGTGCGGGACCTGCCCAGCGGCTTCAACACCCTGAA

GCCCATCTTCAAGCTGCCCCTGGGCATCAACATCACCAACTTCCGGGCCA

TCCTGACCGCCTTCAGCCCCGCCCAGGACATCTGGGGCACCAGCGCCGCC

GCCTACTTCGTGGGCTACCTGAAGCCCACCACCTTCATGCTGAAGTACGA

CGAGAACGGCACCATCACCGACGCCGTGGACTGCAGCCAGAACCCCCTGG

CCGAGCTGAAGTGCAGCGTGAAGAGCTTCGAGATCGACAAGGGCATCTAC

CAGACCAGCAACTTCCGGGTGGTGCCCAGCGGCGACGTGGTGCGGTTCCC

CAACATCACCAACCTGTGCCCCTTCGGCGAGGTGTTCAACGCCACCAAGT
```

-continued

```
TCCCCAGCGTGTACGCCTGGGAGCGGAAGAAGATCAGCAACTGCGTGGCC
GACTACAGCGTGCTGTACAACAGCACCTTCTTCAGCACCTTCAAGTGCTA
CGGCGTGAGCGCCACCAAGCTGAACGACCTGTGCTTCAGCAACGTGTACG
CCGACAGCTTCGTGGTGAAGGGCGACGACGTGCGGCAGATCGCCCCCGGC
CAGACCGGCGTGATCGCCGACTACAACTACAAGCTGCCCGACGACTTCAT
GGGCTGCGTGCTGGCCTGGAACACCCGGAACATCGACGCCACCAGCACCG
GCAACTACAACTACAAGTACCGGTACCTGCGGCACGGCAAGCTGCGGCCC
TTCGAGCGGGACATCAGCAACGTGCCCTTCAGCCCCGACGGCAAGCCCTG
CACCCCCCCCGCCCTGAACTGCTACTGGCCCCTGAACGACTACGGCTTCT
ACACCACCACCGGCATCGGCTACCAGCCCTACCGGGTGGTGGTGCTGAGC
TTCGAGCTGCTGAACGCCCCCGCCACCGTGTGCGGCCCCAAGCTGAGCAC
CGACCTGATCAAGAACCAGTGCGTGAACTTCAACTTCAACGGCCTGACCG
GCACCGGCGTGCTGACCCCCAGCAGCAAGCGGTTCCAGCCCTTCCAGCAG
TTCGGCCGGGACGTGAGCGACTTCACCGACAGCGTGCGGGACCCCAAGAC
CAGCGAGATCCTGGACATCAGCCCCTGCAGCTTCGGCGGCGTGAGCGTGA
TCACCCCCGGCACCAACGCCAGCAGCGAGGTGGCCGTGCTGTACCAGGAC
GTGAACTGCACCGACGTGAGCACCGCCATCCACGCCGACCAGCTGACCCC
CGCCTGGCGGATCTACAGCACCGGCAACAACGTGTTCCAGACCCAGGCCG
GCTGCCTGATCGGCGCCGAGCACGTGGACACCAGCTACGAGTGCGACATC
CCCATCGGCGCCGGCATCTGCGCCAGCTACCACACCGTGAGCCTGCTGCG
GAGCACCAGCCAGAAGAGCATCGTGGCCTACACCATGAGCCTGGGCGCCG
ACAGCAGCATCGCCTACAGCAACAACACCATCGCCATCCCCACCAACTTC
AGCATCAGCATCACCACCGAGGTGATGCCCGTGAGCATGGCCAAGACCAG
CGTGGACTGCAACATGTACATCTGCGGCGACAGCACCGAGTGCGCCAACC
TGCTGCTGCAGTACGGCAGCTTCTGCACCCAGCTGAACCGGGCCCTGAGC
GGCATCGCCGCCGAGCAGGACCGGAACACCCGGGAGGTGTTCGCCCAGGT
GAAGCAGATGTACAAGACCCCCACCCTGAAGTACTTCGGCGGCTTCAACT
TCAGCCAGATCCTGCCCGACCCCCTGAAGCCCACCAAGCGGAGCTTCATC
GAGGACCTGCTGTTCAACAAGGTGACCCTGGCCGACGCCGGCTTCATGAA
GCAGTACGGCGAGTGCCTGGGCGACATCAACGCCCGGGACCTGATCTGCG
CCCAGAAGTTCAACGGCCTGACCGTGCTGCCCCCCCTGCTGACCGACGAC
ATGATCGCCGCCTACACCGCCGCCCTGGTGAGCGGCACCGCCACCGCCGG
CTGGACCTTCGGCGCCGGCGCCGCCCTGCAGATCCCCTTCGCCATGCAGA
TGGCCTACCGGTTCAACGGCATCGGCGTGACCCAGAACGTGCTGTACGAG
AACCAGAAGCAGATCGCCAACCAGTTCAACAAGGCCATCAGCCAGATCCA
GGAGAGCCTGACCACCACCAGCACCGCCCTGGGCAAGCTGCAGGACGTGG
TGAACCAGAACGCCCAGGCCCTGAACACCCTGGTGAAGCAGCTGAGCAGC
AACTTCGGCGCCATCAGCAGCGTGCTGAACGACATCCTGAGCCGGCTGGA
CAAGGTGGAGGCCGAGGTGCAGATCGACCGGCTGATCACCGGCCGGCTGC
AGAGCCTGCAGACCTACGTGACCCAGCAGCTGATCCGGGCCGCCGAGATC
CGGGCCAGCGCCAACCTGGCCGCCACCAAGATGAGCGAGTGCGTGCTGGG
```

-continued

```
CCAGAGCAAGCGGGTGGACTTCTGCGGCAAGGGCTACCACCTGATGAGCT
TCCCCCAGGCCGCCCCCCACGGCGTGGTGTTCCTGCACGTGACCTACGTG
CCCAGCCAGGAGCGGAACTTCACCACCGCCCCCGCCATCTGCCACGAGGG
CAAGGCCTACTTCCCCCGGGAGGGCGTGTTCGTGTTCAACGGCACCAGCT
GGTTCATCACCCAGCGGAACTTCTTCAGCCCCCAGATCATCACCACCGAC
AACACCTTCGTGAGCGGCAACTGCGACGTGGTGATCGGCATCATCAACAA
CACCGTGTACGACCCCCTGCAGCCCGAGCTGGACAGCTTCAAGGAGGAGC
TGGACAAGTACTTCAAGAACCACACCAGCCCCGACGTGGACCTGGGCGAC
ATCAGCGGCATCAACGCCAGCGTGGTGAACATCCAGAAGGAGATCGACCG
GCTGAACGAGGTGGCCAAGAACCTGAACGAGAGCCTGATCGACCTGCAGG
AGCTGGGCAAGTACGAGCAGTACATCAAGTGGCCCTGG
```

Alternatively, a human codon-optimized coding region which encodes SEQ ID NO:2 can be designed by the "full optimization" method, where each amino acid is assigned codons based on the frequency of usage in the human genome. These frequencies are shown in Table 4 above. Using this latter method, codons are assigned to the coding region encoding SEQ ID NO:2 as follows: about 37 of the 81 phenylalanine codons are TTT, and about 44 of the phenylalanine codons are TTC; about 7 of the 92 leucine codons are TTA, about 12 of the leucine codons are TTG, about 12 of the leucine codons are CTT, about 18 of the leucine codons are CTC, about 7 of the leucine codons are CTA, and about 36 of the leucine codons are CTG; about 26 of the 74 isoleucine codons are ATT, about 35 of the isoleucine codons are ATC, and about 13 of the isoleucine codons are ATA; the 18 methionine codons are ATG; about 15 of the 86 valine codons are GTT, about 40 of the valine codons are GTG, about 10 of the valine codons are GTA, and about 21 of the valine codons are GTC; about 17 of the 91 serine codons are TCT, about 20 of the serine codons are TCC, about 14 of the serine codons are TCA, about 5 of the serine codons are TCG, about 13 of the serine codons are AGT, and about 22 of the serine codons are AGC; about 16 of the 56 proline codons are CCT, about 18 of the proline codons are CCC, about 16 of the proline codons are CCA, and about 6 of the proline codons are CCG; about 23 of the 96 threonine codons are ACT, about 35 of the threonine codons are ACC, about 27 of the threonine codons are ACA, and about 11 of the threonine codons are ACG; about 21 of the 81 alanine codons are GCT, about 33 of the alanine codons are GCC, about 18 of the alanine codons are GCA, and about 9 of the alanine codons are GCG; about 23 of the 52 tyrosine codons are TAT and about 29 of the tyrosine codons are TAC; about 6 of the 14 histidine codons are CAT and about 8 of the histidine codons are CAC; about 14 of the 55 glutamine codons are CAA and about 41 of the glutamine codons are CAG; about 37 of the 81 asparagine codons are AAT and about 44 of the asparagine codons are AAC; about 24 of the 56 lysine codons are AAA and about 32 of the lysine codons are AAG; about 32 of the 70 aspartic acid codons are GAT and about 38 of the aspartic acid codons are GAC; about 17 of the 40 glutamic acid codons are GAA and about 23 of the glutamic acid codons are GAG; about 14 of the 30 cysteine codons are TGT and about 16 of the cysteine codons are TGC; the 10 tryptophan codons are TGG; about 3 of the 39 arginine codons are CGT, about 7 of the arginine codons are CGC, about 4 of the arginine codons are CGA, about 8 of the arginine codons are CGG, about 9 of the arginine codons are AGA, and about 8 of the arginine codons are AGG; and about 12 of the 74 glycine codons are GGT, about 25 of the glycine codons are GGC, about 19 of the glycine codons are GGA, and about 18 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:2, optimized according to codon usage in humans is presented herein as SEQ ID NO:24.

```
ATG TTT ATC TTC CTC CTC TTC CTG ACG CTC ACT AGC
GGA TCC GAC TTA GAT CGG TGT ACC ACT TTC GAC GAC
GTC CAG GCC CCT AAC TAT ACT CAA CAT ACC TCC AGT
ATG CGC GGG GTG TAC TAT CCA GAT GAG ATT TTT CGG
AGC GAC ACT CTG TAC TTA ACA CAG GAC CTG TTT CTA
CCG TTT TAT TCA AAT GTA ACC GGC TTC CAC ACC ATT
AAC CAT ACA TTT GGC AAT CCC GTG ATA CCA TTC AAA
GAC GGC ATT TAC TTC GCC GCA ACA GAA AAG AGC AAT
GTT GTG AGG GGG TGG GTC TTC GGC TCC ACA ATG AAC
AAT AAA TCT CAG TCT GTC ATC ATC ATC AAT AAC AGC
ACT AAC GTG GTA ATC CGT GCC TGC AAT TTC GAG CTT
TGT GAC AAC CCA TTC TTC GCC GTG TCT AAG CCT ATG
GGC ACC CAG ACT CAC ACA ATG ATC TTT GAC AAT GCT
TTC AAC TGC ACC TTC GAA TAC ATA TCA GAT GCA TTC
TCT TTG GAT GTC AGT GAA AAG TCT GGA AAC TTT AAA
CAT CTG AGA GAG TTT GTC TTC AAA AAC AAG GAC GGC
TTT CTC TAC GTT TAC AAG GGT TAT CAG CCC ATT GAT
GTG GTG CGG GAC CTC CCT TCA GGG TTT AAC ACA TTG
AAA CCA ATA TTC AAA CTG CCC CTG GGT ATC AAT ATT
ACT AAC TTT CGA GCC ATC TTG ACC GCC TTT TCC CCC
GCG CAA GAC ATA TGG GGA ACC AGC GCG GCA GCC TAT
TTC GTC GGT TAT CTG AAG CCC ACT ACA TTT ATG CTG
AAG TAC GAC GAG AAC GGA ACC ATT ACC GAT GCT GTC
GAT TGT TCA CAG AAT CCA CTG GCT GAA TTG AAA TGC
TCC GTG AAG AGC TTT GAG ATC GAT AAG GGG ATT TAC
CAG ACG TCT AAT TTT CGA GTG GTT CCC TCA GGA GAT
GTG GTT AGA TTC CCC AAT ATC ACA AAT TTG TGC CCC
TTC GGT GAA GTG TTC AAT GCC ACA AAG TTC CCG TCT
GTC TAC GCT TGG GAG CGG AAA AAG ATA AGC AAC TGT
GTC GCG GAT TAC AGT GTC CTA TAT AAC TCG ACC TTT
TTT AGC ACG TTC AAG TGT TAC GGG GTG AGT GCT ACT
```

-continued

```
AAA CTG AAT GAT TTA TGT TTT AGT AAC GTT TAT GCA
GAC TCC TTT GTT GTA AAG GGT GAT GAC GTG CGC CAA
ATT GCA CCT GGG CAG ACC GGA GTG ATG GCA GAT TAT
AAC TAC AAA CTT CCA GAC GAC TTT ATG GGA TGC GTG
CTC GCC TGG AAC ACT CGC AAC ATC GAC GCA ACC AGC
ACC GGG AAC TAT AAT TAC AAA TAC AGA TAC CTC AGG
CAC GGC AAG CTG CGG CCT TTT GAG CGG GAT ATC TCA
AAC GTC CCA TTT AGC CCG GAC GGC AAG CCC TGT ACT
CCT CCC GCA CTT AAC TGT TAC TGG CCA CTG AAC GAT
TAT GGC TTT TAT ACC ACA ACC GGC ATC GGC TAC CAG
CCC TAC CGG GTG GTG GTG CTA TCT TTC GAG CTG CTG
AAC GCG CCT GCC ACC GTA TGT GGG CCC AAG CTT TCG
ACA GAT CTC ATC AAG AAC CAA TGC GTA AAT TTC AAT
TTC AAT GGC CTT ACA GGA ACC GGT GTG CTG ACA CCC
TCC TCC AAG AGG TTT CAA CCT TTC CAG CAG TTT GGA
CGT GAC GTC TCA GAC TTT ACT GAC AGT GTG AGG GAT
CCT AAG ACC TCT GAA ATC CTG GAT ATA TCT CCC TGT
TCC TTC GGT GGG GTT AGT GTG ATA ACC CCT GGG ACA
AAT GCT AGT TCC GAA GTG GCC GTA CTC TAT CAA GAC
GTG AAC TGC ACA GAC GTG TCA ACC GCC ATC CAC GCT
GAT CAA CTC ACA CCG GCT TGG CGG ATC TAT AGC ACT
GGC AAT AAC GTG TTC CAA ACG CAG GCC GGC TGC CTT
ATA GGG GCA GAG CAT GTC GAC ACT TCT TAC GAG TGT
GAT ATA CCA ATC GGA GCC GGC ATC TGC GCC TCA TAC
CAC ACG GTG AGC TTG CTG CGC TCC ACC AGT CAG AAG
AGT ATT GTC GCA TAC ACC ATG TCA CTC GGC GCA GAT
TCA AGT ATC GCC TAC AGC AAT AAC ACT ATC GCT ATT
CCT ACC AAC TTT TCC ATT TCC ATC ACA ACT GAG GTT
ATG CCT GTC TCC ATG GCT AAG ACT TCC GTG GAC TGC
AAT ATG TAC ATT TGT GGG GAC TCT ACC GAG TGC GCT
AAC CTT TTA CTG CAG TAT GGC TCC TTC TGC ACA CAG
CTG AAT AGA GCC CTG AGC GGA ATT GCC GCT GAG CAG
GAT AGA AAT ACG AGA GAA GTG TTT GCC CAG GTG AAA
CAG ATG TAT AAG ACT CCA ACC TTG AAG TAT TTC GGA
GGG TTC AAT TTT AGC CAG ATC CTT CCT GAC CCC TTG
AAG CCG ACC AAA AGG ACC TTC ATC GAA GAT CTT CTG
TTC AAC AAA GTT ACT TTA GCG GAC GCC GGG TTC ATG
AAA CAG TAT GGC GAG TGT CTC GGG GAT ATT AAT GCC
CGC GAT CTC ATC TGT GCT CAG AAA TTC AAC GGC CTC
ACA GTG CTC CCC CCA CTT CTG ACG GAT GAT ATG ATC
```

-continued

GCC GCT TAC ACA GCC GCA CTC GTG AGC GGC ACC GCC
ACA GCC GGT TGG ACA TTC GGA GCT GGA GCC GCA TTA
CAG ATT CCA TTC GCT ATG CAG ATG GCG TAC AGG TTC
AAC GGA ATA GGC GTG ACC CAG AAC GTG TTG TAT GAA
AAT CAG AAG CAG ATT GCG AAC CAG TTC AAC AAA GCC
ATT TCT CAA ATC CAG GAG TCC CTG ACC ACC ACA AGC
ACG GCA CTG GGA AAG CTG CAA GAC GTG GTC AAC CAG
AAC GCC CAA GCC CTA AAT ACC CTG GTT AAG CAG CTG
TCT AGC AAT TTT GGA GCG ATT TCA TCT GTC CTT AAC
GAT ATA CTA TCA AGA CTG GAC AAA GTG GAG GCA GAG
GTC CAA ATC GAC CGC CTG ATT ACG GGC CGC CTC CAG
AGC CTT CAG ACG TAT GTG ACA CAG CAG CTG ATA AGA
GCT GCT GAA ATA CGA GCC TCG GCT AAT CTG GCC GCA
ACC AAA ATG TCC GAA TGC GTC CTG GGG CAG TCC AAA
CGT GTC GAT TTC TGC GGC AAA GGT TAC CAT TTG ATG
TCA TTT CCA CAG GCG GCT CCT CAC GGC GTA GTG TTT
CTG CAC GTG ACT TAT GTA CCT TCG CAG GAA AGG AAC
TTC ACA ACT GCC CCA GCC ATC TGC CAT GAG GGA AAA
GCA TAT TTC CCC CGA GAA GGT GTT TTC GTT TTC AAC
GGG ACA AGC TGG TTC ATT ACT CAA AGG AAT TTT TTT
TCG CCA CAG ATC ATT ACC ACT GAT AAC ACA TTT GTA
TCT GGT AAC TGC GAC GTA GTT ATC GGG ATT ATC AAT
AAT ACG GTC TAT GAC CCC TTG CAA CCT GAG CTG GAT
AGC TTT AAG GAA GAG CTG GAC AAG TAC TTT AAG AAT
CAC ACC TCT CCA GAC GTG GAC CTG GGA GAC ATC TCC
GGC ATT AAT GCA AGT GTT GTG AAT ATT CAG AAA GAG
ATT GAT AGA CTA AAC GAA GTT GCT AAG AAC TTG AAT
GAG AGT TTA ATT GAC CTA CAG GAG CTC GGT AAG TAC
GAA CAG TAC ATC AAA TGG CCG TGG

Another representative codon-optimized coding region encoding SEQ ID NO:2 is presented herein as SEQ ID NO: 44.

ATG TTT ATC TTC CTG CTG TTT CTG ACA CTG ACA AGC
GGC AGT GAC CTG GAT AGA TGC ACA ACG TTT GAC GAC
GTG CAG GCC CCC AAC TAC ACC CAG CAT ACA TCC AGC
ATG AGG GGC GTT TAC TAC CCC GAT GAG ATC TTT AGA
AGT GAT ACT CTG TAT CTG ACT CAG GAC CTG TTT CTG
CCC TTC TAT TCT AAC GTT ACT GGC TTC CAT ACA ATC
AAC CAC ACC TTC GGC AAC CCC GTA ATA CCC TTT AAG
GAT GGC ATC TAC TTT GCC GCC ACC GAG AAG TCT AAC
GTA GTG AGA GGC TGG GTG TTC GGC AGT ACT ATG AAC

-continued

AAC AAG TCT CAG TCT GTG ATA ATA ATC AAC AAC TCC
ACT AAC GTC GTC ATC AGA GCC TGT AAC TTC GAG CTG
TGC GAT AAC CCC TTC TTC GCC GTT TCG AAG CCC ATG
GGC ACT CAG ACC CAT ACA ATG ATC TTT GAT AAC GCC
TTC AAC TGC ACC TTT GAG TAT ATC TGC GAT GCC TTC
AGT CTG GAT GTG TCC GAG AAG TCA GGC AAC TTC AAG
CAT CTG AGA GAG TTT GTG TTC AAG AAC AAG GAT GGC
TTT CTG TAC GTC TAC AAG GGC TAC CAG CCC ATA GAT
GTG GTA CGT GAC CTG CCC AGC GGC TTC AAC ACT CTG
AAG CCC ATA TTC AAG CTG CCC CTG GGC ATA AAC ATT
ACC AAC TTT AGA GCC ATT CTG ACG GCC TTC TCC CCC
GCC CAG GAT ATC TGG GGC ACA AGT GCC GCC GCC TAC
TTC GTG GGC TAC CTG AAG CCC ACA ACT TTT ATG CTG
AAG TAC GAC GAG AAC GGC ACC ATA ACA GAT GCC GTG
GAC TGT TCT CAG AAC CCC CTG GCC GAG CTG AAG TGC
TCA GTT AAG AGT TTT GAG ATA GAT AAG GGC ATC TAT
CAG ACA AGC AAC TTC CGC GTG GTC CCC AGC GGC GAT
GTG GTG AGG TTT CCC AAC ATT ACC AAC CTG TGC CCC
TTC GGC GAG GTA TTC AAC GCC ACA AAG TTC CCC TCC
GTT TAC GCC TGG GAG AGG AAG AAG ATT TCA AAC TGC
GTG GCC GAC TAC TCG GTG CTG TAT AAC TCT ACT TTC
TTC AGT ACC TTT AAG TGC TAC GGC GTG TCT GCC ACA
AAG CTG AAC GAT CTG TGC TTT AGC AAC GTG TAT GCC
GAT AGC TTC GTC GTC AAG GGC GAC GAC GTC AGA CAG
ATC GCC CCC GGC CAG ACA GGC GTC ATC GCC GAC TAC
AAC TAC AAG CTG CCC GAC GAT TTC ATG GGC TGC GTG
CTG GCC TGG AAC ACG AGG AAC ATA GAT GCC ACC AGC
ACT GGC AAC TAC AAC TAC AAG TAC AGA TAT CTG CGG
CAC GGC AAG CTG AGG CCC TTC GAG AGA GAC ATC TCT
AAC GTT CCC TTT TCC CCC GAT GGC AAG CCC TGC ACT
CCC CCC GCC CTG AAC TGC TAC TGG CCC CTG AAC GAC
TAT GGC TTC TAC ACC ACA ACT GGC ATC GGC TAT CAG
CCC TAC CGC GTA GTC GTG CTG TCG TTC GAG CTG CTG
AAC GCC CCC GCC ACA GTC TGC GGC CCC AAG CTG TCC
ACT GAC CTG ATT AAG AAC CAG TGT GTG AAC TTC AAC
TTT AAC GGC CTG ACT GGC ACC GGC GTG CTG ACA CCC
AGC AGC AAG CGG TTC CAG CCC TTC CAG CAG TTT GGC
AGA GAC GTG TCT GAT TTC ACA GAT TCC GTG AGA GAT
CCC AAG ACT TCC GAG ATA CTG GAT ATC AGT CCC TGC
TCC TTC GGC GGC GTG TCA GTT ATT ACA CCC GGC ACT

-continued

AAC GCC TCG TCC GAG GTA GCC GTT CTG TAT CAG GAC

GTG AAC TGC ACT GAT GTG AGT ACA GCC ATC CAC GCC

GAC CAG CTG ACC CCC GCC TGG CGG ATT TAT AGT ACG

GGC AAC AAC GTC TTT CAG ACT CAG GCC GGC TGC CTG

ATC GGC GCC GAG CAT GTA GAT ACG TCT TAT GAG TGC

GAC ATC CCC ATC GGC GCC GGC ATC TGC GCC AGC TAT

CAC ACC GTT TCT CTG CTG CGA AGT ACT TCT CAG AAG

TCT ATA GTG GCC TAC ACC ATG TCT CTG GGC GCC GAT

AGC TCT ATC GCC TAT AGC AAC AAC ACT ATA GCC ATC

CCC ACA AAC TTC TCT ATT TCT ATC ACT ACA GAG GTG

ATG CCC GTC TCC ATG GCC AAG ACC AGC GTT GAT TGC

AAC ATG TAC ATC TGC GGC GAT AGT ACA GAG TGC GCC

AAC CTG CTG CTG CAG TAT GGC AGC TTC TGC ACC CAG

CTG AAC AGA GCC CTG TCT GGC ATC GCC GCC GAG CAG

GAT AGG AAC ACA AGA GAG GTT TTC GCC CAG GTT AAG

CAG ATG TAC AAG ACT CCC ACT CTG AAG TAC TTT GGC

GGC TTT AAC TTT TCT CAG ATT CTG CCC GAT CCC CTG

AAG CCC ACT AAG AGG AGT TTC ATA GAG GAC CTG CTG

TTC AAC AAG GTG ACT CTG GCC GAC GCC GGC TTT ATG

AAG CAG TAC GGC GAG TGC CTG GGC GAT ATC AAC GCC

AGA GAC CTG ATC TGT GCC CAG AAG TTT AAC GGC CTG

ACA GTA CTG CCC CCC CTG CTG ACT GAT GAC ATG ATT

GCC GCC TAT ACG GCC GCC CTG GTG TCT GGC ACT GCC

ACC GCC GGC TGG ACC TTT GGC GCC GGC GCC GCC CTG

CAG ATA CCC TTT GCC ATG CAG ATG GCC TAC CGA TTC

AAC GGC ATA GGC GTA ACC CAG AAC GTT CTG TAT GAG

AAC CAG AAG CAG ATA GCC AAC CAG TTC AAC AAG GCC

ATC TCT CAG ATT CAG GAG TCT CTG ACC ACT ACA TCT

ACT GCC CTG GGC AAG CTG CAG GAC GTA GTG AAC CAG

AAC GCC CAG GCC CTG AAC ACC CTG GTT AAG CAG CTG

TCA AGT AAC TTC GGC GCC ATC TCT AGC GTT CTG AAC

GAT ATA CTG AGT CGG CTG GAT AAG GTG GAG GCC GAG

GTG CAG ATT GAC AGA CTG ATC ACA GGC AGA CTG CAG

TCT CTG CAG ACA TAT GTT ACT CAG CAG CTG ATA AGG

GCC GCC GAG ATT AGA GCC AGT GCC AAC CTG GCC GCC

ACT AAG ATG TCC GAG TGC GTC CTG GGC CAG AGT AAG

AGG GTA GAC TTT TGT GGC AAG GGC TAT CAC CTG ATG

TCC TTC CCC CAG GCC GCC CCC CAC GGC GTC GTG TTT

CTG CAT GTC ACT TAT GTT CCC TCA CAG GAG AGG AAC

TTC ACG ACC GCC CCC GCC ATC TGC CAC GAG GGC AAG

GCC TAT TTC CCC AGG GAG GGC GTC TTC GTA TTC AAC

-continued

GGC ACG AGT TGG TTC ATC ACC CAG CGA AAC TTC TTT

TCG CCC CAG ATA ATT ACA ACG GAC AAC ACT TTT GTA

AGT GGC AAC TGC GAT GTC GTC ATC GGC ATA ATC AAC

AAC ACG GTT TAC GAC CCC CTG CAG CCC GAG CTG GAT

TCA TTC AAG GAG GAG CTG GAC AAG TAC TTC AAG AAC

CAT ACT AGC CCC GAC GTT GAT CTG GGC GAC ATA AGC

GGC ATC AAC GCC AGT GTA GTC AAC ATA CAG AAG GAG

ATC GAT AGA CTG AAC GAG GTG GCC AAG AAC CTG AAC

GAG TCT CTG ATA GAC CTG CAG GAG CTG GGC AAG TAC

GAG CAG TAC ATC AAG TGG CCC TGG

A representative codon-optimized coding region encoding SEQ ID NO:2 according to the "standardized optimization" method is presented herein as SEQ ID NO: 67.

ATG TTC ATC TTC CTG CTG TTC CTG ACC CTG ACC AGC

GGC AGC GAC CTG GAT CGC TGC ACC ACC TTC GAT GAC

GTG CAG GCC CCC AAC TAC ACC CAG CAT ACC AGC AGC

ATG CGC GGC GTG TAC TAC CCC GAT GAG ATC TTC CGC

AGC GAC ACC CTG TAC CTG ACC CAG GAC CTG TTC CTG

CCC TTC TAC AGC AAC GTG ACC GGC TTC CAC ACC ATC

AAC CAT ACC TTC GGC AAC CCC GTG ATC CCC TTC AAG

GAC GGC ATC TAC TTC GCC GCC ACC GAG AAG AGC AAC

GTG GTG CGC GGC TGG GTG TTC GGC AGC ACC ATG AAC

AAC AAG AGC CAG AGC GTG ATC ATC ATC AAC AAC AGC

ACC AAC GTG GTG ATC CGC GCC TGC AAC TTC GAG CTG

TGC GAC AAC CCC TTC TTC GCC GTG AGC AAG CCC ATG

GGC ACC CAG ACC CAT ACC ATG ATC TTC GAT AAC GCC

TTC AAC TGC ACC TTC GAG TAC ATC AGC GAC GCC TTC

AGC CTG GAC GTG AGC GAG AAG AGC GGC AAC TTC AAG

CAT CTG CGC GAG TTC GTG TTC AAG AAC AAG GAT GGC

TTC CTG TAC GTG TAC AAG GGC TAC CAG CCC ATC GAC

GTG GTG CGC GAT CTG CCC AGC GGC TTC AAC ACC CTG

AAG CCC ATC TTC AAG CTG CCC CTG GGC ATC AAC ATC

ACC AAC TTC CGC GCC ATC CTG ACC GCC TTC AGC CCC

GCC CAG GAC ATC TGG GGC ACC AGC GCC GCC GCC TAC

TTC GTG GGC TAC CTG AAG CCC ACC ACC TTC ATG CTG

AAG TAC GAT GAG AAC GGC ACC ATC ACC GAC GCC GTG

GAC TGC AGC CAG AAC CCC CTG GCC GAG CTG AAG TGC

AGC GTG AAG AGC TTC GAG ATC GAT AAG GGC ATC TAC

CAG ACC AGC AAC TTC CGC GTG GTG CCC AGC GGC GAC

GTG GTG CGC TTC CCC AAC ATC ACC AAC CTG TGT CCC

-continued

TTC GGC GAG GTG TTC AAC GCC ACC AAG TTC CCC AGC

GTG TAC GCC TGG GAG CGC AAG AAG ATC AGC AAC TGC

GTG GCC GAC TAC AGC GTG CTG TAC AAC AGC ACC TTC

TTC AGC ACC TTC AAG TGC TAC GGC GTG AGC GCC ACC

AAG CTG AAC GAT CTG TGC TTC AGC AAC GTG TAC GCC

GAC AGC TTC GTG GTG AAG GGC GAT GAT GTG CGC CAG

ATC GCC CCC GGC CAG ACC GGC GTG ATC GCC GAT TAC

AAC TAC AAG CTG CCC GAC GAC TTC ATG GGC TGC GTG

CTG GCC TGG AAC ACC CGC AAC ATC GAC GCC ACC AGC

ACC GGC AAC TAC AAC TAC AAG TAC CGC TAC CTG CGC

CAT GGC AAG CTG CGC CCC TTC GAG CGC GAT ATC AGC

AAC GTG CCC TTC AGC CCC GAT GGC AAG CCC TGC ACC

CCC CCC GCC CTG AAC TGT TAC TGG CCC CTG AAC GAC

TAC GGC TTC TAC ACC ACC ACC GGC ATC GGC TAC CAG

CCC TAC CGC GTG GTG GTG CTG AGC TTC GAG CTG CTG

AAC GCC CCC GCC ACC GTG TGC GGC CCC AAG CTG AGC

ACC GAC CTG ATC AAG AAC CAG TGC GTG AAC TTC AAC

TTC AAC GGC CTG ACC GGC ACC GGC GTG CTG ACC CCC

AGC AGC AAG CGC TTC CAG CCC TTC CAG CAG TTC GGC

CGC GAT GTG AGC GAC TTC ACC GAT AGC GTG CGC GAC

CCC AAG ACC AGC GAG ATC CTG GAT ATC AGC CCC TGC

AGC TTC GGC GGC GTG AGC GTG ATC ACC CCC GGC ACC

AAC GCC AGC AGC GAG GTG GCC GTG CTG TAC CAG GAT

GTG AAC TGT ACC GAT GTG AGC ACC GCC ATC CAC GCC

GAT CAG CTG ACC CCC GCC TGG CGC ATC TAC AGC ACC

GGC AAC AAC GTG TTC CAG ACC CAG GCC GGC TGC CTG

ATC GGC GCC GAG CAT GTG GAC ACC AGC TAC GAG TGT

GAC ATC CCC ATC GGC GCC GGC ATC TGT GCC AGC TAC

CAC ACC GTG AGC CTG CTG CGC AGC ACC AGC CAG AAG

AGC ATC GTG GCC TAC ACC ATG AGC CTG GGC GCC GAT

AGC AGC ATC GCC TAC AGC AAC AAC ACC ATC GCC ATC

CCC ACC AAC TTC AGC ATC AGC ATC ACC ACC GAG GTG

ATG CCC GTG AGC ATG GCC AAG ACC AGC GTG GAC TGC

AAC ATG TAC ATC TGC GGC GAT AGC ACC GAG TGC GCC

AAC CTG CTG CTG CAG TAC GGC AGC TTC TGC ACC CAG

CTG AAC CGC GCC CTG AGC GGC ATC GCC GCC GAG CAG

GAT CGC AAC ACC CGC GAG GTG TTC GCC CAG GTG AAG

CAG ATG TAC AAG ACC CCC ACC CTG AAG TAC TTC GGC

GGC TTC AAC TTC AGC CAG ATC CTG CCC GAT CCC CTG

AAG CCC ACC AAG CGC AGC TTC ATC GAG GAT CTG CTG

TTC AAC AAG GTG ACC CTG GCC GAT GCC GGC TTC ATG

-continued

AAG CAG TAC GGC GAG TGC CTG GGC GAT ATC AAC GCC

CGC GAT CTG ATC TGC GCC CAG AAG TTC AAC GGC CTG

ACC GTG CTG CCC CCC CTG CTG ACC GAC GAC ATG ATC

GCC GCC TAC ACC GCC GCC CTG GTG AGC GGC ACC GCC

ACC GCC GGC TGG ACC TTC GGC GCC GGC GCC GCC CTG

CAG ATC CCC TTC GCC ATG CAG ATG GCC TAC CGC TTC

AAC GGC ATC GGC GTG ACC CAG AAC GTG CTG TAC GAG

AAC CAG AAG CAG ATC GCC AAC CAG TTC AAC AAG GCC

ATC AGC CAG ATC CAG GAG AGC CTG ACC ACC ACC AGC

ACC GCC CTG GGC AAG CTG CAG GAC GTG GTG AAC CAG

AAC GCC CAG GCC CTG AAC ACC CTG GTG AAG CAG CTG

AGC AGC AAC TTC GGC GCC ATC AGC AGC GTG CTG AAC

GAC ATC CTG AGC CGC CTG GAT AAG GTG GAG GCC GAG

GTG CAG ATC GAT CGC CTG ATC ACC GGC CGC CTG CAG

AGC CTG CAG ACC TAC GTG ACC CAG CAG CTG ATC CGC

GCC GCC GAG ATC CGC GCC AGC GCC AAC CTG GCC GCC

ACC AAG ATG AGC GAG TGC GTG CTG GGC CAG AGC AAG

CGC GTG GAT TTC TGC GGC AAG GGC TAC CAC CTG ATG

AGC TTC CCC CAG GCC GCC CCC CAT GGC GTG GTG TTC

CTG CAC GTG ACC TAC GTG CCC AGC CAG GAG CGC AAC

TTC ACC ACC GCC CCC GCC ATC TGC CAC GAG GGC AAG

GCC TAC TTC CCC CGC GAG GGC GTG TTC GTG TTC AAC

GGC ACC AGC TGG TTC ATC ACC CAG CGC AAC TTC TTC

AGC CCC CAG ATC ATC ACC ACC GAT AAC ACC TTC GTG

AGC GGC AAC TGC GAT GTG GTG ATC GGC ATC ATC AAC

AAC ACC GTG TAC GAT CCC CTG CAG CCC GAG CTG GAC

AGC TTC AAG GAG GAG CTG GAT AAG TAC TTC AAG AAC

CAC ACC AGC CCC GAC GTG GAT CTG GGC GAT ATC AGC

GGC ATC AAC GCC AGC GTG GTG AAC ATC CAG AAG GAG

ATC GAT CGC CTG AAC GAG GTG GCC AAG AAC CTG AAC

GAG AGC CTG ATC GAC CTG CAG GAG CTG GGC AAG TAC

GAG CAG TAC ATC AAG TGG CCC TGG

In certain embodiments described herein, a codon-optimized coding region encoding SEQ ID NO:4 is optimized according to codon usage in humans (*Homo sapiens*). Alternatively, a codon-optimized coding region encoding SEQ ID NO:4 may be optimized according to codon usage in any plant, animal, or microbial species. Codon-optimized coding regions encoding SEQ ID NO:4, optimized according to codon usage in humans are designed as follows. The amino acid composition of SEQ ID NO:4 is shown in Table 10.

TABLE 10

| AMINO ACID | | Number in SEQ ID NO: 4 |
|---|---|---|
| A | Ala | 38 |
| R | Arg | 23 |
| C | Cys | 20 |
| G | Gly | 44 |
| H | His | 9 |
| I | Ile | 38 |
| L | Leu | 46 |
| K | Lys | 31 |
| M | Met | 8 |
| F | Phe | 53 |
| P | Pro | 37 |
| S | Ser | 56 |
| T | Thr | 58 |
| W | Trp | 6 |
| Y | Tyr | 35 |
| V | Val | 53 |
| N | Asn | 46 |
| D | Asp | 44 |
| Q | Gln | 21 |
| E | Glu | 17 |

Using the amino acid composition shown in Table 10, a human codon-optimized coding region which encodes SEQ ID NO:4 can be designed by any of the methods discussed herein. For "uniform" optimization, each amino acid is assigned the most frequent codon used in the human genome for that amino acid. According to this method, codons are assigned to the coding region encoding SEQ ID NO:4 as follows: the 53 phenylalanine codons are TTC, the 46 leucine codons are CTG, the 38 isoleucine codons are ATC, the 8 methionine codons are ATG, the 53 valine codons are GTG, the 56 serine codons are AGC, the 37 proline codons are CCC, the 58 threonine codons are ACC, the 38 alanine codons are GCC, the 35 tyrosine codons are TAC, the 9 histidine codons are CAC, the 21 glutamine codons are CAG, the 46 asparagine codons are AAC, the 31 lysine codons are AAG, the 44 aspartic acid codons are GAC, the 17 glutamic acid codons are GAG, the 20 cysteine codons are TGC; the 6 tryptophan codons are TGG, the 23 arginine codons are CGG, AGA, or AGG (the frequencies of usage of these three codons in the human genome are not significantly different), and the 44 glycine codons are GGC. The codon-optimized S1 coding region designed by this method is presented herein as SEQ I) NO:27.

```
ATGTTCATCTTCCTGCTGTTCCTGACCCTGACCAGCGGCAGCGACCTGGA

CAGATGCACCACCTTCGACGACGTGCAGGCCCCCAACTACACCCAGCACA

CCAGCAGCATGAGAGGCGTGTACTACCCCGACGAGATCTTCAGAAGCGAC

ACCCTGTACCTGACCCAGGACCTGTTCCTGCCCTTCTACAGCAACGTGAC

CGGCTTCCACACCATCAACCACACCTTCGGCAACCCCGTGATCCCCTTCA

AGGACGGCATCTACTTCGCCGCCACCGAGAAGAGCAACGTGGTGAGAGGC

TGGGTGTTCGGCAGCACCATGAACAACAAGAGCCAGAGCGTGATCATCAT

CAACAACAGCACCAACGTGGTGATCAGAGCCTGCAACTTCGAGCTGTGCG

ACAACCCCTTCTTCGCCGTGAGCAAGCCCATGGGCACCCAGACCCACACC

ATGATCTTCGACAACGCCTTCAACTGCACCTTCGAGTACATCAGCGACGC

CTTCAGCCTGGACGTGAGCGAGAAGAGCGGCAACTTCAAGCACCTGAGAG

AGTTCGTGTTCAAGAACAAGGACGGCTTCCTGTACGTGTACAAGGGCTAC
```

-continued

```
CAGCCCATCGACGTGGTGAGAGACCTGCCCAGCGGCTTCAACACCCTGAA

GCCCATCTTCAAGCTGCCCCTGGGCATCAACATCACCAACTTCAGAGCCA

TCCTGACCGCCTTCAGCCCCGCCCAGGACATCTGGGGCACCAGCGCCGCC

GCCTACTTCGTGGGCTACCTGAAGCCCACCACCTTCATGCTGAAGTACGA

CGAGAACGGCACCATCACCGACGCCGTGGACTGCAGCCAGAACCCCCTGG

CCGAGCTGAAGTGCAGCGTGAAGAGCTTCGAGATCGACAAGGGCATCTAC

CAGACCAGCAACTTCAGAGTGGTGCCCAGCGGCGACGTGGTGAGATTCCC

CAACATCACCAACCTGTGCCCCTTCGGCGAGGTGTTCAACGCCACCAAGT

TCCCCAGCGTGTACGCCTGGGAGAGAAAGAAGATCAGCAACTGCGTGGCC

GACTACAGCGTGCTGTACAACAGCACCTTCTTCAGCACCTTCAAGTGCTA

CGGCGTGAGCGCCACCAAGCTGAACGACCTGTGCTTCAGCAACGTGTACG

CCGACAGCTTCGTGGTGAAGGGCGACGACGTGAGACAGATCGCCCCCGGC

CAGACCGGCGTGATCGCCGACTACAACTACAAGCTGCCCGACGACTTCAT

GGGCTGCGTGCTGGCCTGGAACACCAGAAACATCGACGCCACCAGCACCG

GCAACTACAACTACAAGTACAGATACCTGAGACACGGCAAGCTGAGACCC

TTCGAGAGAGACATCAGCAACGTGCCCTTCAGCCCCGACGGCAAGCCCTG

CACCCCCCCCGCCCTGAACTGCTACTGGCCCCTGAACGACTACGGCTTCT

ACACCACCACCGGCATCGGCTACCAGCCCTACAGAGTGGTGGTGCTGAGC

TTCGAGCTGCTGAACGCCCCCGCCACCGTGTGCGGCCCCAAGCTGAGCAC

CGACCTGATCAAGAACCAGTGCGTGAACTTCAACTTCAACGGCCTGACCG

GCACCGGCGTGCTGACCCCCAGCAGCAAGAGATTCCAGCCCTTCCAGCAG

TTCGGCAGAGACGTGAGCGACTTCACCGACAGCGTGAGAGACCCCAAGAC

CAGCGAGATCCTGGACATCAGCCCCTGCAGCTTCGGCGGCGTGAGCGTGA

TCACCCCCGGCACCAACGCCAGCAGCGAGGTGGCCGTGCTGTACCAGGAC

GTGAACTGCACCGACGTGAGCACCGCCATCCACGCCGACCAGCTGACCCC

CGCCTGGAGAATCTACAGCACCGGCAACAACGTGTTCCAGACCCAGGCCG

GCTGCCTGATCGGCGCCGAGCACGTGGACACCAGCTACGAGTGCGACATC

CCCATCGGCGCCGGCATCTGCGCCAGCTACCACACCGTGAGCCTGCTGAG

AAGCACCAGCCAGAAGAGCATCGTGGCCTACACCATGAGCCTGGGCGCC
```

Alternatively, a human codon-optimized coding region which encodes SEQ ID NO:4 can be designed by the "full optimization" method, where each amino acid is assigned codons based on the frequency of usage in the human genome. These frequencies are shown in Table 4 above. Using this latter method, codons are assigned to the coding region encoding SEQ ID NO:4 as follows: about 24 of the 53 phenylalanine codons are TTT, and about 29 of the phenylalanine codons are TTC; about 3 of the 46 leucine codons are TTA, about 6 of the leucine codons are TTG, about 6 of the leucine codons are CTT, about 9 of the leucine codons are CTC, about 4 of the leucine codons are CTA, and about 18 of the leucine codons are CTG; about 13 of the 38 isoleucine codons are ATT, about 18 of the isoleucine codons are ATC, and about 7 of the isoleucine codons are ATA; the 8 methionine codons are ATG; about 10 of the 53 valine codons are GTT, about 13 of the valine codons are GTC, about 5 of the valine codons are GTA, and about 25 of the valine codons are GTG; about 10 of the 56 serine codons are TCT, about 12 of the serine codons are TCC, about 8 of the serine codons are TCA, about 3 of the serine codons are TCG, about 9 of the serine codons are AGT, and about 14 of the serine codons are AGC; about 10 of the 37 proline codons are CCT, about 12 of the proline codons are CCC, about 11 of the proline codons are CCA, and about 4 of the proline codons are CCG; about 14 of the 58 threonine codons are ACT, about 21 of the threonine codons are ACC, about 16 of the threonine codons are ACA, and about 7 of the threonine codons are ACG; about 10 of the 38 alanine codons are GCT, about 15 of the alanine codons are GCC, about 9 of the alanine codons are GCA, and about 4 of the alanine codons are GCG; about 15 of the 35 tyrosine codons are TAT and about 20 of the tyrosine codons are TAC; about 4 of the 9 histidine codons are CAT and about 5 of the histidine codons are CAC; about 5 of the 21 glutamine codons are CAA and about 16 of the glutamine codons are CAG; about 21 of the 46 asparagine codons are AAT and about 25 of the asparagine codons are AAC; about 13 of the 31 lysine codons are AAA and about 18 of the lysine codons are AAG; about 20 of the 44 aspartic acid codons are GAT and about 24 of the aspartic acid codons are GAC; about 7 of the 17 glutamic acid codons are GAA and about 10 of the glutamic acid codons are GAG; about 9 of the 20 cysteine codons are TGT and about 11 of the cysteine codons are TGC; the 6 tryptophan codons are TGG; about 2 of the 23 arginine codons are CGT, about 4 of the arginine codons are CGC, about 3 of the arginine codons are CGA, about 5 of the arginine codons are CGG, about 4 of the arginine codons are AGA, and about 5 of the arginine codons are AGG; and about 7 of the 44 glycine codons are GGT, about 15 of the glycine codons are GGC, about 11 of the glycine codons are GGA, and about 11 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:4, optimized according to codon usage in humans is presented herein as SEQ ID NO:26.

```
ATG TTT ATC TTT TTG CTG TTT CTC ACA TTA ACT TCG
GGG TCT GAC CTG GAC CGG TGC ACC ACA TTC GAT GAC
GTC CAA GCC CCC AAC TAC ACT CAG CAT ACA TCT AGC
ATG CGC GGC GTG TAC TAC CCA GAT GAG ATC TTT AGG
TCC GAC ACC CTT TAT CTG ACC CAG GAC CTT TTT CTT
CCT TTC TAC TCT AAT GTA ACT GGG TTC CAT ACC ATC
AAC CAT ACC TTT GGC AAC CCA GTG ATT CCA TTT AAG
GAT GGT ATT TAC TTC GCC GCG ACC GAG AAA TCA AAT
GTT GTG CGC GGC TGG GTT TTC GGC TCC ACC ATG AAC
AAT AAG AGT CAG TCC GTA ATT ATC ATT AAC AAT AGT
ACA AAC GTG GTG ATC AGG GCA TGT AAT TTT GAA TTG
TGC GAC AAC CCT TTC TTC GCT GTA AGC AAA CCC ATG
GGG ACG CAG ACT CAC ACG ATG ATC TTC GAT AAC GCT
```

-continued

```
TTC AAT TGC ACG TTT GAG TAC ATA TCC GAT GCC TTT
TCT CTA GAT GTG TCC GAA AAA TCA GGG AAT TTT AAG
CAC CTG AGA GAG TTC GTC TTT AAG AAC AAG GAC GGT
TTC TTG TAC GTG TAC AAG GGA TAC CAG CCG ATC GAC
GTG GTG CGG GAC CTA CCC AGC GGA TTC AAC ACC CTC
AAG CCC ATT TTT AAG CTC CCA CTG GGT ATC AAT ATA
ACT AAC TTC AGA GCC ATT CTC ACA GCT TTC TCT CCA
GCT CAG GAT ATT TGG GGG ACT AGT GCG GCA GCT TAT
TTC GTG GGA TAC CTT AAG CCC ACA ACC TTC ATG TTG
AAA TAC GAT GAG AAC GGA ACC ATA ACT GAC GCA GTT
GAC TGC TCA CAG AAC CCC CTC GCA GAG TTG AAA TGC
TCA GTT AAA TCC TTT GAG ATC GAC AAG GGT ATT TAC
CAG ACC AGT AAC TTT AGA GTC GTG CCG TCA GGC GAC
GTC GTG AGG TTT CCT AAC ATC ACA AAT CTA TGT CCT
TTC GGA GAA GTG TTC AAT GCC ACA AAG TTC CCC AGC
GTG TAC GCC TGG GAG CGA AAA AAG ATA TCT AAC TGC
GTC GCA GAC TAC AGC GTA CTG TAT AAC AGC ACT TTT
TTC AGC ACC TTT AAG TGT TAT GGG GTG TCA GCA ACA
AAA CTG AAC GAT CTC TGC TTT TCA AAC GTT TAT GCC
GAT TCC TTC GTT GTC AAG GGA GAC GAT GTC CGT CAA
ATT GCT CCC GGG CAA ACT GGC GTT ATC GCT GAC TAT
AAC TAT AAA CTG CCA GAC GAT TTT ATG GGG TGT GTC
CTC GCA TGG AAT ACG CGC AAC ATC GAT GCG ACC TCT
ACC GGA AAC TAC AAC TAT AAA TAT AGG TAT CTT CGG
CAC GGG AAA TTA CGG CCG TTC GAG CGA GAT ATT TCG
AAC GTG CCT TTC AGT CCC GAT GGA AAA CCA TGT ACT
CCT CCA GCC CTC AAT TGT TAC TGG CCA TTG AAT GAC
TAC GGG TTC TAC ACG ACA ACT GGA ATA GGC TAT CAG
CCT TAT CGT GTC GTC GTT CTT TCT TTC GAA CTG CTG
AAT GCT CCC GCC ACG GTG TGC GGT CCA AAA CTC AGC
ACC GAC CTG ATC AAG AAT CAG TGC GTG AAT TTC AAT
TTC AAC GGC CTG ACA GGC ACA GGC GTT CTG ACC CCA
AGC TCC AAG CGC TTC CAG CCC TTC CAG CAA TTT GGC
AGG GAT GTG TCC GAC TTT ACC GAT TCA GTG CGA GAT
CCC AAG ACC AGT GAA ATA CTA GAC ATT TCT CCG TGT
AGC TTT GGC GGC GTG TCT GTC ATT ACT CCT GGG ACG
AAT GCC TCG AGC GAG GTG GCG GTG TTA TAT CAG GAC
GTT AAT TGT ACA GAC GTC AGT ACC GCC ATA CAT GCT
GAT CAG CTG ACT CCT GCA TGG AGA ATC TAC TCC ACA
GGA AAT AAT GTG TTT CAG ACA CAA GCA GGT TGC CTG
ATC GGA GCC GAA CAC GTC GAC ACC AGC TAC GAA TGT
```

-continued

GAT ATC CCT ATC GGT GCC GGC ATC TGC GCT AGT TAT

CAC ACA GTA AGC CTG CTG CGG AGC ACC AGT CAG AAG

TCC ATT GTG GCC TAT ACT ATG TCC CTG GGC GCC

Another representative codon-optimized coding region encoding SEQ ID NO:4 is presented herein as SEQ ID NO:45.

ATG TTC ATC TTC CTG CTG TTT CTG ACA CTG ACT TCT

GGC TCA GAT CTG GAT AGA TGC ACT ACC TTT GAC GAT

GTA CAG GCC CCC AAC TAC ACT CAG CAC ACA TCG TCC

ATG CGA GGC GTG TAT TAC CCC GAC GAG ATC TTC AGA

AGT GAC ACT CTG TAC CTG ACA CAG GAC CTG TTC CTG

CCC TTT TAC TCT AAC GTG ACT GGC TTT CAC ACT ATC

AAC CAT ACC TTC GGC AAC CCC GTA ATC CCC TTC AAG

GAT GGC ATC TAT TTT GCC GCC ACC GAG AAG TCC AAC

GTG GTG AGG GGC TGG GTC TTC GGC AGT ACG ATG AAC

AAC AAG TCT CAG TCC GTG ATA ATC ATA AAC AAC AGT

ACT AAC GTG GTT ATA AGA GCC TGC AAC TTC GAG CTG

TGC GAC AAC CCC TTC TTC GCC GTG TCC AAG CCC ATG

GGC ACA CAG ACC CAC ACC ATG ATA TTC GAC AAC GCC

TTT AAC TGT ACT TTC GAG TAT ATA AGC GAT GCC TTC

AGT CTG GAT GTT TCT GAG AAG TCA GGC AAC TTT AAG

CAT CTG AGA GAG TTC GTA TTC AAG AAC AAG GAC GGC

TTT CTG TAT GTT TAT AAG GGC TAC CAG CCC ATA GAT

GTC GTG CGG GAT CTG CCC AGC GGC TTC AAC ACA CTG

AAG CCC ATT TTT AAG CTG CCC CTG GGC ATC AAC ATA

ACC AAC TTT AGA GCC ATC CTG ACT GCC TTT AGC CCC

GCC CAG GAT ATA TGG GGC ACT AGC GCC GCC GCC TAT

TTC GTC GGC TAC CTG AAG CCC ACC ACA TTC ATG CTG

AAG TAC GAT AGA AAC GGC ACA ATT ACG GAT GCC GTA

GAT TGC AGT CAG AAC CCC CTG GCC GAG CTG AAG TGC

AGT GTG AAG TCT TTC GAG ATC GAC AAG GGC ATA TAC

CAG ACT TCT AAC TTT CGG GTG GTT CCC AGC GGC GAC

GTT GTT AGG TTT CCC AAC ATC ACC AAC CTG TGC CCC

TTC GGC GAG GTG TTT AAC GCC ACA AAG TTC CCC TCC

GTA TAT GCC TGG GAG AGG AAG AAG ATT TCG AAC TGC

GTG GCC GAC TAT AGC GTC CTG TAC AAC TCT ACA TTC

TTT TCT ACA TTC AAG TGC TAC GGC GTC AGT GCC ACT

AAG CTG AAC GAC CTG TGC TTC AGC AAC GTG TAT GCC

GAC TCA TTT GTA GTT AAG GGC GAT GAT GTG AGA CAG

ATT GCC CCC GGC CAG ACA GGC GTG ATC GCC GAT TAT

-continued

AAC TAT AAG CTG CCC GAC GAT TTC ATG GGC TGC GTT

CTG GCC TGG AAC ACA AGG AAC ATC GAT GCC ACT AGC

ACT GGC AAC TAC AAC TAC AAG TAC AGG TAT CTG AGA

CAC GGC AAG CTG AGG CCC TTC GAG CGA GAT ATC AGT

AAC GTA CCC TTC AGT CCC GAC GGC AAG CCC TGC ACT

CCC CCC GCC CTG AAC TGC TAT TGG CCC CTG AAC GAC

TAC GGC TTT TAT ACC ACT ACA GGC ATC GGC TAC CAG

CCC TAC AGG GTT GTG GTG CTG AGC TTC GAG CTG CTG

AAC GCC CCC GCC ACT GTT TGC GGC CCC AAG CTG TCA

ACG GAT CTG ATC AAG AAC CAG TGC GTA AAC TTT AAC

TTT AAC GGC CTG ACA GGC ACA GGC GTC CTG ACT CCC

TCT AGT AAG AGA TTC CAG CCC TTT CAG CAG TTC GGC

CGC GAC GTC AGC GAT TTT ACG GAT AGT GTG AGA GAT

CCC AAG ACC AGC GAG ATC CTG GAC ATT AGT CCC TGT

TCT TTC GGC GGC GTG TCT GTC ATA ACG CCC GGC ACG

AAC GCC TCT TCT GAG GTC GCC GTT CTG TAC CAG GAC

GTC AAC TGT ACA GAC GTC TCC ACA GCC ATA CAC GCC

GAT CAG CTG ACT CCC GCC TGG AGA ATT TAC TCT ACC

GGC AAC AAC GTC TTC CAG ACC CAG GCC GGC TGC CTG

ATC GGC GCC GAG CAT GTG GAT ACT TCC TAC GAG TGC

GAC ATA CCC ATC GGC GCC GGC ATT TGC GCC TCG TAC

CAT ACC GTG TCT CTG CTG AGA TCT ACC TCT CAG AAG

AGT ATC GTT GCC TAC ACT ATG TCC CTG GGC GCC

A representative codon-optimized coding region encoding SEQ ID NO:4 according to the “standardized optimization” method is presented herein as SEQ ID NO: 68.

ATG TTC ATC TTC CTG CTG TTC CTG ACC CTG ACC AGC

GGC AGC GAT CTG GAC CGC TGC ACC ACC TTC GAC GAT

GTG CAG GCC CCC AAC TAC ACC CAG CAC ACC AGC AGC

ATG CGC GGC GTG TAC TAC CCC GAT GAG ATC TTC CGC

AGC GAT ACC CTG TAC CTG ACC CAG GAT CTG TTC CTG

CCC TTC TAC AGC AAC GTG ACC GGC TTC CAT ACC ATC

AAC CAC ACC TTC GGC AAC CCC GTG ATC CCC TTC AAG

GAT GGC ATC TAC TTC GCC GCC ACC GAG AAG AGC AAC

GTG GTG CGC GGC TGG GTG TTC GGC AGC ACC ATG AAC

AAC AAG AGC CAG AGC GTG ATC ATC ATC AAC AAC AGC

ACC AAC GTG GTG ATC CGC GCC TGC AAC TTC GAG CTG

TGC GAC AAC CCC TTC TTC GCC GTG AGC AAG CCC ATG

GGC ACC CAG ACC CAC ACC ATG ATC TTC GAC AAC GCC

TTC AAC TGC ACC TTC GAG TAC ATC AGC GAT GCC TTC

AGC CTG GAC GTG AGC GAG AAG AGC GGC AAC TTC AAG

-continued

CAT CTG CGC GAG TTC GTG TTC AAG AAC AAG GAT GGC

TTC CTG TAC GTG TAC AAG GGC TAC CAG CCC ATC GAC

GTG GTG CGC GAC CTG CCC AGC GGC TTC AAC ACC CTG

AAG CCC ATC TTC AAG CTG CCC CTG GGC ATC AAC ATC

ACC AAC TTC CGC GCC ATC CTG ACC GCC TTC AGC CCC

GCC CAG GAT ATC TGG GGC ACC AGC GCC GCC GCC TAC

TTC GTG GGC TAC CTG AAG CCC ACC ACC TTC ATG CTG

AAG TAC GAC GAG AAC GGC ACC ATC ACC GAT GCC GTG

GAT TGC AGC CAG AAC CCC CTG GCC GAG CTG AAG TGC

AGC GTG AAG AGC TTC GAG ATC GAT AAG GGC ATC TAC

CAG ACC AGC AAC TTC CGC GTG GTG CCC AGC GGC GAC

GTG GTG CGC TTC CCC AAC ATC ACC AAC CTG TGC CCC

TTC GGC GAG GTG TTC AAC GCC ACC AAG TTC CCC AGC

GTG TAC GCC TGG GAG CGC AAG AAG ATC AGC AAC TGC

GTG GCC GAT TAC AGC GTG CTG TAC AAC AGC ACC TTC

TTC AGC ACC TTC AAG TGC TAC GGC GTG AGC GCC ACC

AAG CTG AAC GAC CTG TGC TTC AGC AAC GTG TAC GCC

GAC AGC TTC GTG GTG AAG GGC GAC GAC GTG CGC CAG

ATC GCC CCC GGC CAG ACC GGC GTG ATC GCC GAT TAC

AAC TAC AAG CTG CCC GAT GAC TTC ATG GGC TGC GTG

CTG GCC TGG AAC ACC CGC AAC ATC GAT GCC ACC AGC

ACC GGC AAC TAC AAC TAC AAG TAC CGC TAC CTG CGC

CAC GGC AAG CTG CGC CCC TTC GAG CGC GAT ATC AGC

AAC GTG CCC TTC AGC CCC GAT GGC AAG CCC TGC ACC

CCC CCC GCC CTG AAC TGT TAC TGG CCC CTG AAC GAT

TAC GGC TTC TAC ACC ACC ACC GGC ATC GGC TAC CAG

CCC TAC CGC GTG GTG GTG CTG AGC TTC GAG CTG CTG

AAC GCC CCC GCC ACC GTG TGC GGC CCC AAG CTG AGC

ACC GAC CTG ATC AAA AAC CAG TGC GTG AAC TTC AAC

TTC AAC GGC CTG ACC GGC ACC GGC GTG CTG ACC CCC

AGC AGC AAG CGC TTC CAG CCC TTC CAG CAG TTC GGC

CGC GAC GTG AGC GAC TTC ACC GAC AGC GTG CGC GAT

CCC AAG ACC AGC GAG ATC CTG GAT ATC AGC CCC TGC

AGC TTC GGC GGC GTG AGC GTG ATC ACC CCC GGC ACC

AAC GCC AGC AGC GAG GTG GCC GTG CTG TAC CAG GAC

GTG AAC TGC ACC GAT GTG AGC ACC GCC ATC CAC GCC

GAT CAG CTG ACC CCC GCC TGG CGC ATC TAC AGC ACC

GGC AAC AAC GTG TTC CAG ACC CAG GCC GGC TGT CTG

ATC GGC GCC GAG CAT GTG GAC ACC AGC TAC GAG TGT

GAT ATC CCC ATC GGC GCC GGC ATC TGC GCC AGC TAC

-continued

CAT ACC GTG AGC CTG CTG CGC AGC ACC AGC CAG AAG

AGC ATC GTG GCC TAC ACC ATG AGC CTG GGC GCC

In certain embodiments described herein, a codon-optimized coding region encoding SEQ ID NO:6 is optimized according to codon usage in humans (*Homo sapiens*). Alternatively, a codon-optimized coding region encoding SEQ ID NO:6 may be optimized according to codon usage in any plant, animal, or microbial species. Codon-optimized coding regions encoding SEQ ID NO:6, optimized according to codon usage in humans are designed as follows. The amino acid composition of SEQ ID NO:6 is shown in Table 11.

TABLE 11

| AMINO ACID | | Number in SEQ ID NO: 6 |
|---|---|---|
| A | Ala | 43 |
| R | Arg | 16 |
| C | Cys | 10 |
| G | Gly | 30 |
| H | His | 5 |
| I | Ile | 36 |
| L | Leu | 46 |
| K | Lys | 25 |
| M | Met | 10 |
| F | Phe | 28 |
| P | Pro | 19 |
| S | Ser | 35 |
| T | Thr | 38 |
| W | Trp | 4 |
| Y | Tyr | 17 |
| V | Val | 33 |
| N | Asn | 35 |
| D | Asp | 26 |
| Q | Gln | 34 |
| E | Glu | 23 |

Using the amino acid composition shown in Table 11, a human codon-optimized coding region which encodes SEQ ID NO:6 can be designed by any of the methods discussed herein. For "uniform" optimization, each amino acid is assigned the most frequent codon used in the human genome for that amino acid. According to this method, codons are assigned to the coding region encoding SEQ ID NO:6 as follows: the 28 phenylalanine codons are TTC, the 46 leucine codons are CTG, the 36 isoleucine codons are ATC, the 10 methionine codons are ATG, the 33 valine codons are GTG, the 35 serine codons are AGC, the 19 proline codons are CCC, the 38 threonine codons are ACC, the 43 alanine codons are GCC, the 17 tyrosine codons are TAC, the 5 histidine codons are CAC, the 34 glutamine codons are CAG, the 35 asparagine codons are AAC, the 25 lysine codons are AAG, the 26 aspartic acid codons are GAC, the 23 glutamic acid codons are GAG, the 10 cysteine codons are TGC, the 4 tryptophan codon is TGG, the 16 arginine codons are CGG, AGA, or AGG (the frequencies of usage of these three codons in the human genome are not significantly different), and the 30 glycine codons are GGC. The codon-optimized coding region designed by this method is presented herein as SEQ ID NO:29.

GAC AGC AGC ATC GCC TAC AGC AAC AAC ACC ATC GCC

ATC CCC ACC AAC TTC AGC ATC AGC ATC ACC ACC GAG

GTG ATG CCC GTG AGC ATG GCC AAG ACC AGC GTG GAC

-continued

TGC AAC ATG TAC ATC TGC GGC GAC AGC ACC GAG TGC
GCC AAC CTG CTG CTG CAG TAC GGC AGC TTC TGC ACC
CAG CTG AAC CGG GCC CTG AGC GGC ATC GCC GCC GAG
CAG GAC CGG AAC ACC CGG GAG GTG TTC GCC CAG GTG
AAG CAG ATG TAC AAG ACC CCC ACC CTG AAG TAC TTC
GGC GGC TTC AAC TTC AGC CAG ATC CTG CCC GAC CCC
CTG AAG CCC ACC AAG CGG AGC TTC ATC GAG GAC CTG
CTG TTC AAC AAG GTG ACC CTG GCC GAC GCC GGC TTC
ATG AAG CAG TAC GGC GAG TGC CTG GGC GAC ATC AAC
GCC CGG GAC CTG ATC TGC GCC CAG AAG TTC AAC GGC
CTG ACC GTG CTG CCC CCC CTG CTG ACC GAC GAC ATG
ATC GCC GCC TAC ACC GCC GCC CTG GTG AGC GGC ACC
GCC ACC GCC GGC TGG ACC TTC GGC GCC GGC GCC GCC
CTG CAG ATC CCC TTC GCC ATG CAG ATG GCC TAC CGG
TTC AAC GGC ATC GGC GTG ACC CAG AAC GTG CTG TAC
GAG AAC CAG AAG CAG ATC GCC AAC CAG TTC AAC AAG
GCC ATC AGC CAG ATC CAG GAG AGC CTG ACC ACC ACC
AGC ACC GCC CTG GGC AAG CTG CAG GAC GTG GTG AAC
CAG AAC GCC CAG GCC CTG AAC ACC CTG GTG AAG CAG
CTG AGC AGC AAC TTC GGC GCC ATC AGC AGC GTG CTG
AAC GAC ATC CTG AGC CGG CTG GAC AAG GTG GAG GCC
GAG GTG CAG ATC GAC CGG CTG ATC ACC GGC CGG CTG
CAG AGC CTG CAG ACC TAC GTG ACC CAG CAG CTG ATC
CGG GCC GCC GAG ATC CGG GCC AGC GCC AAC CTG GCC
GCC ACC AAG ATG AGC GAG TGC GTG CTG GGC CAG AGC
AAG CGG GTG GAC TTC TGC GGC AAG GGC TAC CAC CTG
ATG AGC TTC CCC CAG GCC GCC CCC CAC GGC GTG GTG
TTC CTG CAC GTG ACC TAC GTG CCC AGC CAG GAG CGG
AAC TTC ACC ACC GCC CCC GCC ATC TGC CAC GAG GGC
AAG GCC TAC TTC CCC CGG GAG GGC GTG TTC GTG TTC
AAC GGC ACC AGC TGG TTC ATC ACC CAG CGG AAC TTC
TTC AGC CCC CAG ATC ATC ACC ACC GAC AAC ACC TTC
GTG AGC GGC AAC TGC GAC GTG GTG ATC GGC ATC ATC
AAC AAC ACC GTG TAC GAC CCC CTG CAG CCC GAG CTG
GAC AGC TTC AAG GAG GAG CTG GAC AAG TAC TTC AAG
AAC CAC ACC AGC CCC GAC GTG GAC CTG GGC GAC ATC
AGC GGC ATC AAC GCC AGC GTG GTG AAC ATC CAG AAG
GAG ATC GAC CGG CTG AAC GAG GTG GCC AAG AAC CTG
AAC GAG AGC CTG ATC GAC CTG CAG GAG CTG GGC AAG
TAC GAG CAG TAC ATC AAG TGG CCC TGG

A codon-optimized coding region encoding SEQ ID NO:56 designed by this method is presented herein as SEQ ID NO:64.

ATG GAC AGC AGC ATC GCC TAC AGC AAC AAC ACC ATC
GCC ATC CCC ACC AAC TTC AGC ATC AGC ATC ACC ACC
GAG GTG ATG CCC GTG AGC ATG GCC AAG ACC AGC GTG
GAC TGC AAC ATG TAC ATC TGC GGC GAC AGC ACC GAG
TGC GCC AAC CTG CTG CTG CAG TAC GGC AGC TTC TGC
ACC CAG CTG AAC CGG GCC CTG AGC GGC ATC GCC GCC
GAG CAG GAC CGG AAC ACC CGG GAG GTG TTC GCC CAG
GTG AAG CAG ATG TAC AAG ACC CCC ACC CTG AAG TAC
TTC GGC GGC TTC AAC TTC AGC CAG ATC CTG CCC GAC
CCC CTG AAG CCC ACC AAG CGG AGC TTC ATC GAG GAC
CTG CTG TTC AAC AAG GTG ACC CTG GCC GAC GCC GGC
TTC ATG AAG CAG TAC GGC GAG TGC CTG GGC GAC ATC
AAC GCC CGG GAC CTG ATC TGC GCC CAG AAG TTC AAC
GGC CTG ACC GTG CTG CCC CCC CTG CTG ACC GAC GAC
ATG ATC GCC GCC TAC ACC GCC GCC CTG GTG AGC GGC
ACC GCC ACC GCC GGC TGG ACC TTC GGC GCC GGC GCC
GCC CTG CAG ATC CCC TTC GCC ATG CAG ATG GCC TAC
CGG TTC AAC GGC ATC GGC GTG ACC CAG AAC GTG CTG
TAC GAG AAC CAG AAG CAG ATC GCC AAC CAG TTC AAC
AAG GCC ATC AGC CAG ATC CAG GAG AGC CTG ACC ACC
ACC AGC ACC GCC CTG GGC AAG CTG CAG GAC GTG GTG
AAC CAG AAC GCC CAG GCC CTG AAC ACC CTG GTG AAG
CAG CTG AGC AGC AAC TTC GGC GCC ATC AGC AGC GTG
CTG AAC GAC ATC CTG AGC CGG CTG GAC AAG GTG GAG
GCC GAG GTG CAG ATC GAC CGG CTG ATC ACC GGC CGG
CTG CAG AGC CTG CAG ACC TAC GTG ACC CAG CAG CTG
ATC CGG GCC GCC GAG ATC CGG GCC AGC GCC AAC CTG
GCC GCC ACC AAG ATG AGC GAG TGC GTG CTG GGC CAG
AGC AAG CGG GTG GAC TTC TGC GGC AAG GGC TAC CAC
CTG ATG AGC TTC CCC CAG GCC GCC CCC CAC GGC GTG
GTG TTC CTG CAC GTG ACC TAC GTG CCC AGC CAG GAG
CGG AAC TTC ACC ACC GCC CCC GCC ATC TGC CAC GAG
GGC AAG GCC TAC TTC CCC CGG GAG GGC GTG TTC GTG
TTC AAC GGC ACC AGC TGG TTC ATC ACC CAG CGG AAC
TTC TTC AGC CCC CAG ATC ATC ACC ACC GAC AAC ACC
TTC GTG AGC GGC AAC TGC GAC GTG GTG ATC GGC ATC
ATC AAC AAC ACC GTG TAC GAC CCC CTG CAG CCC GAG
CTG GAC AGC TTC AAG GAG GAG CTG GAC AAG TAC TTC

-continued

AAG AAC CAC ACC AGC CCC GAC GTG GAC CTG GGC GAC

ATC AGC GGC ATC AAC GCC AGC GTG GTG AAC ATC CAG

AAG GAG ATC GAC CGG CTG AAC GAG GTG GCC AAG AAC

CTG AAC GAG AGC CTG ATC GAC CTG CAG GAG CTG GGC

AAG TAC GAG CAG TAC ATC AAG TGG CCC TGG

Alternatively, a human codon-optimized coding region which encodes SEQ ID NO:6 can be designed by the "full optimization" method, where each amino acid is assigned codons based on the frequency of usage in the human genome. These frequencies are shown in Table 4 above. Using this latter method, codons are assigned to the coding region encoding SEQ ID NO:6 as follows: about 13 of the 28 phenylalanine codons are TTT, and about 15 of the phenylalanine codons are TTC; about 3 of the 46 leucine codons are TTA, about 6 of the leucine codons are TTG, about 6 of the leucine codons are CTT, about 9 of the leucine codons are CTC, about 4 of the leucine codons are CTA, and about 18 of the leucine codons are CTG; about 13 of the 36 isoleucine codons are ATT, about 17 of the isoleucine codons are ATC, and about 6 of the isoleucine codons are ATA; the 10 methionine codons are ATG; about 6 of the 33 valine codons are GTT, about 15 of the valine codons are GTG, about 4 of the valine codons are GTA, and about 8 of the valine codons are GTC; about 6 of the 35 serine codons are TCT, about 8 of the serine codons are TCC, about 5 of the serine codons are TCA, about 2 of the serine codons are TCG, about 6 of the serine codons are AGT, and about 8 of the serine codons are AGC; about 5 of the 19 proline codons are CCT, about 6 of the proline codons are CCC, about 6 of the proline codons are CCA, and about 2 of the proline codons are CCG; about 9 of the 38 threonine codons are ACT, about 14 of the threonine codons are ACC, about 11 of the threonine codons are ACA, and about 4 of the threonine codons are ACG; about 11 of the 43 alanine codons are GCT, about 17 of the alanine codons are GCC, about 10 of the alanine codons are GCA, and about 5 of the alanine codons are GCG; about 7 of the 17 tyrosine codons are TAT and about 10 of the tyrosine codons are TAC; about 2 of the 5 histidine codons are CAT and about 3 of the histidine codons are CAC; about 9 of the 34 glutamine codons are CAA and about 25 of the glutarnine codons are CAG; about 16 of the 35 asparagine codons are AAT and about 19 of the asparagine codons are AAC; about 11 of the 25 lysine codons are AAA and about 14 of the lysine codons are AAG; about 12 of the 26 aspartic acid codons are GAT and about 14 of the aspartic acid codons are GAC; about 10 of the 23 glutamic acid codons are GAA and about 13 of the glutarnic acid codons are GAG; about 5 of the 10 cysteine codons are TGT and about 5 of the cysteine codons are TGC; the 4 tryptophan codons are TGG; about 1 of the 16 arginine codons is CGT, about 3 of the arginine codons are CGC, about 2 of the arginine codons are CGA, about 3 of the arginine codons are CGG, about 4 of the arginine codons are AGA, and about 3 of the arginine codons are AGG; and about 5 of the 30 glycine codons are GGT, about 10 of the glycine codons are GGC, about 8 of the glycine codons are GGA, and about 7 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:6, optimized according to codon usage in humans is presented herein as SEQ ID NO:28.

GAC AGT TCA ATC GCC TAT TCG AAC AAC ACT ATA GCA

ATC CCA ACA AAT TTT TCA ATT TCT ATA ACA ACA GAG

GTG ATG CCA GTG TCC ATG GCA AAG ACT AGC GTA GAC

TGC AAT ATG TAC ATC TGC GGA GAT TCT ACA GAA TGT

GCA AAC TTG CTG CTA CAG TAT GGA TCG TTC TGT ACC

CAG CTC AAC CGG GCG CTG AGC GGC ATT GCT GCC GAA

CAG GAT CGC AAT ACG AGA GAG GTG TTT GCT CAA GTG

AAA CAA ATG TAT AAG ACC CCA ACA TTG AAA TAC TTC

GGT GGA TTC AAT TTC AGT CAG ATT CTG CCA GAC CCA

CTC AAA CCC ACC AAG AGG AGC TTT ATT GAA GAT CTT

CTG TTC AAC AAA GTT ACC TTG GCC GAC GCT GGG TTT

ATG AAG CAA TAC GGT GAG TGC CTG GGC GAC ATT AAC

GCA CGA GAC CTG ATC TGC GCC CAG AAG TTT AAC GGG

CTC ACG GTT TTA CCG CCA CTG CTG ACT GAT GAT ATG

ATT GCC GCT TAC ACT GCG GCC CTT GTG AGT GGT ACC

GCA ACT GCT GGC TGG ACG TTT GGC GCT GGG GCG GCC

TTA CAG ATC CCT TTT GCC ATG CAG ATG GCC TAC AGG

TTC AAT GGA ATT GGT GTC ACT CAG AAT GTC CTG TAC

GAG AAC CAG AAA CAG ATC GCC AAC CAG TTC AAT AAA

GCT ATT TCA CAG ATT CAG GAA TCA CTT ACC ACA ACT

TCC ACG GCA CTC GGT AAA CTG CAG GAC GTG GTG AAT

CAG AAC GCT CAG GCA CTA AAT ACA CTC GTC AAG CAA

CTG AGT TCC AAT TTC GGG GCC ATA TCT AGC GTA TTG

AAC GAC ATC CTC AGT CGG CTC GAC AAA GTG GAG GCC

GAA GTC CAA ATA GAC CGT CTT ATC ACA GGC AGA CTA

CAG TCA TTG CAG ACC TAC GTT ACC CAG CAG TTG ATC

CGC GCC GCT GAG ATA CGA GCC TCC GCC AAT CTG GCC

GCT ACC AAA ATG TCT GAG TGT GTG CTC GGA CAA AGT

AAG CGG GTG GAT TTT TGC GGC AAG GGC TAT CAC CTC

ATG TCC TTC CCT CAA GCA GCA CCC CAC GGA GTC GTT

TTT CTG CAT GTG ACA TAC GTG CCT AGC CAG GAG AGA

AAC TTT ACC ACT GCG CCT GCC ATT TGT CAT GAA GGC

AAA GCT TAT TTT CCC CGC GAG GGG GTG TTC GTT TTC

AAC GGA ACT AGC TGG TTT ATC ACA CAA AGG AAT TTC

TTC TCC CCC CAG ATC ATC ACC ACC GAC AAC ACC TTT

GTC TCT GGA AAC TGT GAC GTC GTT ATA GGC ATC ATC

AAT AAT ACA GTA TAC GAT CCC CTG CAG CCC GAA CTT

-continued

GAC TCT TTC AAG GAG GAA CTA GAT AAG TAC TTC AAG

AAT CAC ACC AGC CCG GAT GTA GAT TTA GGG GAT ATT

AGC GGG ATT AAC GCA TCC GTG GTC AAC ATC CAA AAA

GAG ATT GAC AGA CTG AAC GAA GTG GCG AAG AAC CTG

AAT GAG TCC CTG ATC GAT CTT CAG GAG CTG GGC AAG

TAT GAA CAG TAT ATC AAG TGG CCT TGG

A representative "fully optimized" codon-optimized coding region encoding SEQ ID NO:56, optimized according to codon usage in humans is presented herein as SEQ ID NO:65.

ATG GAC AGT TCA ATC GCC TAT TCG AAC AAC ACT ATA

GCA ATC CCA ACA AAT TTT TCA ATT TCT ATA ACA ACA

GAG GTG ATG CCA GTG TCC ATG GCA AAG ACT AGC GTA

GAC TGC AAT ATG TAC ATC TGC GGA GAT TCT ACA GAA

TGT GCA AAC TTG CTG CTA CAG TAT GGA TCG TTC TGT

ACC CAG CTC AAC CGG GCG CTG AGC GGC ATT GCT GCC

GAA CAG GAT CGC AAT ACG AGA GAG GTG TTT GCT CAA

GTG AAA CAA ATG TAT AAG ACC CCA ACA TTG AAA TAC

TTC GGT GGA TTC AAT TTC AGT CAG ATT CTG CCA GAC

CCA CTC AAA CCC ACC AAG AGG AGC TTT ATT GAA GAT

CTT CTG TTC AAC AAA GTT ACC TTG GCC GAC GCT GGG

TTT ATG AAG CAA TAC GGT GAG TGC CTG GGC GAC ATT

AAC GCA CGA GAC CTG ATC TGC GCC CAG AAG TTT AAC

GGG CTC ACG GTT TTA CCG CCA CTG CTG ACT GAT GAT

ATG ATT GCC GCT TAC ACT GCG GCC CTT GTG AGT GGT

ACC GCA ACT GCT GGC TGG ACG TTT GGC GCT GGG GCG

GCC TTA CAG ATC CCT TTT GCC ATG CAG ATG GCC TAC

AGG TTC AAT GGA ATT GGT GTC ACT CAG AAT GTC CTG

TAC GAG AAC CAG AAA CAG ATC GCC AAC CAG TTC AAT

AAA GCT ATT TCA CAG ATT CAG GAA TCA CTT ACC ACA

ACT TCC ACG GCA CTC GGT AAA CTG CAG GAC GTG GTG

AAT CAG AAC GCT CAG GCA CTA AAT ACA CTC GTC AAG

CAA CTG AGT TCC AAT TTC GGG GCC ATA TCT AGC GTA

TTG AAC GAC ATC CTC AGT CGG CTC GAC AAA GTG GAG

GCC GAA GTC CAA ATA GAC CGT CTT ATC ACA GGC AGA

CTA CAG TCA TTG CAG ACC TAC GTT ACC CAG CAG TTG

ATC CGC GCC GCT GAG ATA CGA GCC TCC GCC AAT CTG

GCC GCT ACC AAA ATG TCT GAG TGT GTG CTC GGA CAA

AGT AAG CGG GTG GAT TTT TGC GGC AAG GGC TAT CAC

CTC ATG TCC TTC CCT CAA GCA GCA CCC CAC GGA GTC

GTT TTT CTG CAT GTG ACA TAC GTG CCT AGC CAG GAG

-continued

AGA AAC TTT ACC ACT GCG CCT GCC ATT TGT CAT GAA

GGC AAA GCT TAT TTT CCC CGC GAG GGG GTG TTC GTT

TTC AAC GGA ACT AGC TGG TTT ATC ACA CAA AGG AAT

TTC TTC TCC CCC CAG ATC ATC ACC ACC GAC AAC ACC

TTT GTC TCT GGA AAC TGT GAC GTC GTT ATA GGC ATC

ATC AAT AAT ACA GTA TAC GAT CCC CTG CAG CCC GAA

CTT GAC TCT TTC AAG GAG GAA CTA GAT AAG TAC TTC

AAG AAT CAC ACC AGC CCG GAT GTA GAT TTA GGG GAT

ATT AGC GGG ATT AAC GCA TCC GTG GTC AAC ATC CAA

AAA GAG ATT GAC AGA CTG AAC GAA GTG GCG AAG AAC

CTG AAT GAG TCC CTG ATC GAT CTT CAG GAG CTG GGC

AAG TAT GAA CAG TAT ATC AAG TGG CCT TGG

Another representative codon-optimized coding region encoding SEQ ID NO:6 is presented herein as SEQ ID NO:46.

GAT AGC AGC ATA GCC TAC TCA AAC AAC ACG ATC GCC

ATC CCC ACA AAC TTT TCC ATT TCC ATA ACT ACC GAG

GTG ATG CCC GTG AGC ATG GCC AAG ACA TCG GTA GAT

TGC AAC ATG TAC ATC TGT GGC GAT TCT ACA GAG TGT

GCC AAC CTG CTG CTG CAG TAC GGC TCT TTC TGC ACG

CAG CTG AAC AGG GCC CTG TCT GGC ATC GCC GCC GAG

CAG GAT CGG AAC ACA CGG GAG GTT TTC GCC CAG GTA

AAG CAG ATG TAT AAG ACG CCC ACT CTG AAG TAC TTC

GGC GGC TTC AAC TTC TCT CAG ATA CTG CCC GAC CCC

CTG AAG CCC ACT AAG AGG TCT TTT ATC GAG GAT CTG

CTG TTC AAC AAG GTT ACC CTG GCC GAT GCC GGC TTT

ATG AAG CAG TAT GGC GAG TGC CTG GGC GAC ATC AAC

GCC AGA GAT CTG ATA TGC GCC CAG AAG TTC AAC GGC

CTG ACT GTG CTG CCC CCC CTG CTG ACT GAC GAC ATG

ATC GCC GCC TAT ACC GCC GCC CTG GTG AGT GGC ACA

GCC ACT GCC GGC TGG ACA TTC GGC GCC GGC GCC GCC

CTG CAG ATC CCC TTC GCC ATG CAG ATG GCC TAC AGA

TTT AAC GGC ATT GGC GTC ACT CAG AAC GTC CTG TAT

GAG AAC CAG AAG CAG ATC GCC AAC CAG TTT AAC AAG

GCC ATA AGC CAG ATC CAG GAG TCA CTG ACA ACG ACA

AGT ACC GCC CTG GGC AAG CTG CAG GAT GTA GTG AAC

CAG AAC GCC CAG GCC CTG AAC ACT CTG GTT AAG CAG

CTG TCT AGC AAC TTC GGC GCC ATC AGT AGT GTT CTG

AAC GAT ATT CTG TCT AGG CTG GAC AAG GTC GAG GCC

GAG GTG CAG ATT GAT CGC CTG ATT ACC GGC AGA CTG

CAG AGT CTG CAG ACT TAT GTA ACT CAG CAG CTG ATC

-continued

AGA GCC GCC GAG ATT CGA GCC TCC GCC AAC CTG GCC
GCC ACA AAG ATG TCT GAG TGC GTC CTG GGC CAG AGT
AAG AGG GTT GAC TTC TGC GGC AAG GGC TAT CAT CTG
ATG TCT TTT CCC CAG GCC GCC CCC CAC GGC GTC GTG
TTC CTG CAC GTA ACT TAC GTG CCC AGT CAG GAG AGA
AAC TTT ACC ACT GCC CCC GCC ATC TGC CAC GAG GGC
AAG GCC TAC TTC CCC AGA GAG GGC GTG TTT GTG TTC
AAC GGC ACA TCT TGG TTC ATC ACC CAG AGG AAC TTT
TTC AGC CCC CAG ATC ATA ACA ACT GAC AAC ACT TTC
GTT TCG GGC AAC TGC GAC GTA GTG ATC GGC ATA ATA
AAC AAC ACC GTG TAC GAT CCC CTG CAG CCC GAG CTG
GAC AGC TTT AAG GAG GAG CTG GAC AAG TAC TTT AAG
AAC CAT ACC TCA CCC GAT GTG GAC CTG GGC GAC ATT
TCT GGC ATA AAC GCC TCC GTC GTC AAC ATC CAG AAG
GAG ATA GAT AGA CTG AAC GAG GTT GCG AAG AAC CTG
AAC GAG TCC CTG ATC GAT CTG CAG GAG CTG GGC AAG
TAC GAG CAG TAT ATA AAG TGG CCC TGG

Another representative codon-optimized coding region encoding SEQ ID NO:56 is presented herein as SEQ ID NO:66.

ATG GAT AGC AGC ATA GCC TAC TCA AAC AAC ACG ATC
GCC ATC CCC ACA AAC TTT TCC ATT TCC ATA ACT ACC
GAG GTG ATG CCC GTG AGC ATG GCC AAG ACA TCG GTA
GAT TGC AAC ATG TAC ATC TGT GGC GAT TCT ACA GAG
TGT GCC AAC CTG CTG CTG CAG TAC GGC TCT TTC TGC
ACG CAG CTG AAC AGG GCC CTG TCT GGC ATC GCC GCC
GAG CAG GAT CGG AAC ACA CGG GAG GTT TTC GCC CAG
GTA AAG CAG ATG TAT AAG ACG CCC ACT CTG AAG TAC
TTC GGC GGC TTC AAC TTC TCT CAG ATA CTG CCC GAC
CCC CTG AAG CCC ACT AAG AGG TCT TTT ATC GAG GAT
CTG CTG TTC AAC AAG GTT ACC CTG GCC GAT GCC GGC
TTT ATG AAG CAG TAT GGC GAG TGC CTG GGC GAC ATC
AAC GCC AGA GAT CTG ATA TGC GCC CAG AAG TTC AAC
GGC CTG ACT GTG CTG CCC CCC CTG CTG ACT GAC GAC
ATG ATC GCC GCC TAT ACC GCC GCC CTG GTG AGT GGC
ACA GCC ACT GCC GGC TGG ACA TTC GGC GCC GGC GCC
GCC CTG CAG ATC CCC TTC GCC ATG CAG ATG GCC TAC
AGA TTT AAC GGC ATT GGC GTC ACT CAG AAC GTC CTG
TAT GAG AAC CAG AAG CAG ATC GCC AAC CAG TTT AAC
AAG GCC ATA AGC CAG ATC CAG GAG TCA CTG ACA ACG

-continued

ACA AGT ACC GCC CTG GGC AAG CTG CAG GAT GTA GTG
AAC CAG AAC GCC CAG GCC CTG AAC ACT CTG GTT AAG
CAG CTG TCT AGC AAC TTC GGC GCC ATC AGT AGT GTT
CTG AAC GAT ATT CTG TCT AGG CTG GAC AAG GTC GAG
GCC GAG GTG CAG ATT GAT CGC CTG ATT ACC GGC AGA
CTG CAG AGT CTG CAG ACT TAT GTA ACT CAG CAG CTG
ATC AGA GCC GCC GAG ATT CGA GCC TCC GCC AAC CTG
GCC GCC ACA AAG ATG TCT GAG TGC GTC CTG GGC CAG
AGT AAG AGG GTT GAC TTC TGC GGC AAG GGC TAT CAT
CTG ATG TCT TTT CCC CAG GCC GCC CCC CAC GGC GTC
GTG TTC CTG CAC GTA ACT TAC GTG CCC AGT CAG GAG
AGA AAC TTT ACC ACT GCC CCC GCC ATC TGC CAC GAG
GGC AAG GCC TAC TTC CCC AGA GAG GGC GTG TTT GTG
TTC AAC GGC ACA TCT TGG TTC ATC ACC CAG AGG AAC
TTT TTC AGC CCC CAG ATC ATA ACA ACT GAC AAC ACT
TTC GTT TCG GGC AAC TGC GAC GTA GTG ATC GGC ATA
ATA AAC AAC ACC GTG TAC GAT CCC CTG CAG CCC GAG
CTG GAC AGC TTT AAG GAG GAG CTG GAC AAG TAC TTT
AAG AAC CAT ACC TCA CCC GAT GTG GAC CTG GGC GAC
ATT TCT GGC ATA AAC GCC TCC GTC GTC AAC ATC CAG
AAG GAG ATA GAT AGA CTG AAC GAG GTT GCC AAG AAC
CTG AAC GAG TCC CTG ATC GAT CTG CAG GAG CTG GGC
AAG TAC GAG CAG TAT ATA AAG TGG CCC TGG

In certain embodiments, a codon-optimized coding region encoding the full-length SARS-CoV spike protein (SEQ ID NO:23) is optimized according to any plant, animal, or microbial species, including humans. A codon-optimized coding region encoding SEQ ID NO:23 was first established using the "uniform" optimization protocol described above. However, certain additional adjustments to the sequence were carried out in order to eliminate, for example, newly opened reading frames being created on the opposite strand, splice acceptors, stretches of identical bases, or unwanted restriction enzyme sites. Making such adjustments is well within the capabilities of a person of ordinary skill in the art.

A codon-optimized coding region encoding SEQ ID NO:23 is conveniently synthesized as smaller fragments, which are then spliced together using restriction enzyme sites engineered into the sequence fragments. Examples of fragments of codon-optimized coding regions encoding SEQ ID NO:23 are as follows.

SEQ ID NO:57 has the following sequence:

GTCGACATGGTTATCTTTCTGCTGTTCCTCACCCTCACCAGCGGCAGCGA
TCTGGATAGGTGCACCACCTTCGACGACGTGCAGGCCCCCAACTACACCC
AGCACACCAGCAGCATGAGGGGCGTGTACTACCCCGACGAGATTTTCAGA
AGCGACACCCTGTACCTCACCCAGGACCTGTTCCTGCCCTTCTACAGCAA
CGTGACCGGCTTCCACACCATCAACCACACCTTCGGCAACCCCGTGATCC

-continued

CTTTCAAGGACGGCATCTACTTCGCCGCCACCGAGAAGAGCAATGTGGTG

CGGGGCTGGGTGTTCGGCAGCACCATGAACAACAAGAGCCAGAGCGTGAT

CATCATCAACAACAGCACCAACGTGGTGATCCGGGCCTGCAATTTCGAGC

TGTGCGACAACCCTTTCTTCGCCGTGTCCAAACCTATGGGCACCCAGACC

CACACCATGATCTTCGACAACGCCTTCAACTGCACCTTCGAGTACATCAG

CGACGCCTTCAGCCTGGATGTGAGCGAGAAGAGCGGCAACTTCAAGCACC

TGCGGGAGTTCGTGTTCAAGAACAAGGACGGCTTCCTGTACGTGTACAAG

GGCTACCAGCCCATCGACGTGGTGAGAGACCTGCCCAGCGGCTTCAACAC

CCTGAAGCCCATCTTCAAGCTGCCCCTGGGCATCAACATCACCAACTTCC

GGGCCATCCTCACCGCCTTTAGCCCTGCCCAGGATATCTGGGGCACCAGC

GCCGCTGCCTACTTCGTGGGCTACCTGAAGCCTACCACCTTCATGCTGAA

GTACGACGAGAACGGCACCATCACCGATGCCGTGGACTGCAGCCAGAACC

CCCTGGCCGAGCTGAAGTGCAGCGTGAAGAGCTTCGAGATCGACAAGGGC

ATCTACCAGACCAGCAACTTCAGAGTGGTGCCTAGCGGCGATGTGGTGAG

GTTCCCCAATATCACCAACCTGTGCCCCTTCGGCGAGGTGTTCAACGCCA

CCAAGTTCCCTAGCGTGTACGCCTGGGAGCGGAAGAAGATCAGCAACTGC

GTGGCCGATTACAGCGTGCTGTACAACTCCACCTTCTTCAGCACCTTCAA

GTGCTACGGCGTGAGCGCCACCAAGCTGAACGACCTGTGCTTCAGCAACG

TGTACGCCGACTCATTCGTGGTGAAGGGCGACGACGTGAGACAGATCGCC

CCTGGCCAGACCGGCGTGATCGCCGACTACAACTACAAGCTT

Nucleotides 7 to 1242 of SEQ ID NO:57 encode amino acids 1 to 412 of SEQ ID NO:23, with the exception that amino acid 2 (Phenylalanine, (F)) of SEQ ID NO:23 is replaced with valine (V). The translation product of nucleotides 7 to 1242 of SEQ ID NO:57 is presented herein as SEQ ID NO:58.

MVIFLLFLTLTSGSDLDRCTTFDDVQALPNYTQHTSSMRGVYYPDEIFRS

DTLYLTQDLFLPFYSNVTGFHTINHTFGNPVIPFKDGIYFAATEKSNVVR

GWVFGSTMNNKSQSVIIINNSTNVVIRACNFELCDNPFFAVSKPMGTQTH

TMIFDNAFNCTFEYISDAFSLDVSEKSGNFKHLREFVFKNKDGFLYVYKG

YQPIDVVRDLPSGFNTLKLPIFKLPLGINITNFRAILTAFSPAQDIWGTS

AAAYFVGYLKPTTFMLKYDENGTITDAVDCSQNPLAELKCSVKSFEIDKG

IYQTSNFRVVPSGDVVRFPNITNLCPFGEVFNATKFPSVYAWERKKISNC

VADYSVLYNSTFFSTFKCYGVSATKLNDLCFSNVYADSFVVKGDDVRQIA

PGQTGVIADYNYKL

Nucleotides 1 to 6 of SEQ ID NO:57, GTCGAC, is a recognition site for the restriction enzyme Sal I. Nucleotides 1237 to 1242 of SEQ ID NO:57, AAGCTT, is a recognition site for the restriction enzyme Hind III.

SEQ ID NO:59 has the following sequence:

AAGCTTCCCGACGACTTCATGGGCTGCGTGCTGGCCTGGAACACCAGAAA

CATCGACGCCACCTCCACCGGCAACTACAATTACAAGTACCGCTACCTGA

-continued

GGCACGGCAAGCTGAGACCCTTCGAGCGGGACATCTCCAACGTGCCCTTC

AGCCCCGACGGCAAGCCCTGCACCCCCCCTGCCCTGAACTGCTACTGGCC

CCTGAACGACTACGGCTTCTACACCACCACCGGCATCGGCTATCAGCCCT

ACAGAGTGGTGGTGCTGAGCTTCGAGCTGCTGAACGCCCCTGCCACCGTG

TGCGGCCCCAAGCTGAGCACCGACCTCATCAAGAACCAGTGCGTGAACTT

CAACTTCAACGGCCTCACCGGCACCGGCGTGCTCACCCCCAGCAGCAAGA

GATTCCAGCCCTTCCAGCAGTTCGGCAGGGACGTGAGCGATTTCACCGAC

AGCGTGAGGGATCCTAAGACCAGCGAGATCCTGGACATCAGCCCTTGCAG

CTTCGGCGGCGTGTCCGTGATCACCCCCGGCACCAACGCCAGCAGCGAGG

TGGCCGTGCTGTACCAGGACGTGAACTGCACCGACGTGAGCACCGCCATC

CACGCCGACCAGCTCACCCCCGCCTGGAGAATCTACAGCACCGGCAACAA

CGTGTTCCAGACCCAGGCCGGCTGCCTCATCGGCGCCGAGCACGTGGACA

CCAGCTACGAGTGCGACATCCCCATCGGAGCCGGCATCTGCGCCAGCTAC

CACACCGTGAGCCTGCTGAGAAGCACCAGCCAGAAGAGCATCGTGGCCTA

CACCATGAGCCTGGGCGCCGACAGCAGCATCGCCTACAGCAACAACACCA

TCGCCATCCCCACCAACTTCAGCATCTCCATCACCACCGAGGTGATGCCC

GTGAGCATGGCCAAGACCAGCGTGGATTGCAACATGTACATCTGCGGCGA

CAGCACCGAGTGCGCCAACCTGCTGCTGCAGTACGGCAGCTTCTGCACCC

AGCTGAACAGAGCCCTGAGCGGCATTGCCGCCGAGCAGGACAGAAACACC

AGGGAGGTGTTCGCCCAGGTGAAGCAGATGTATAAGACCCCCACCCTGAA

GTACTTCGGCGGGTTCAACTTCAGCCAGATCCTGCCCGATCCTCTGAAGC

CCACCAAGCGGAGCTTCATCGAGGACCTGCTGTTCAACAAGGTGACCCTG

GCCGACGCCGGCTTTATGAAGCAGTACGGCGAGTGCCTGGGCGATATCAA

CGCCAGGGACCTCATCTGCGCCCAGAAGTTCAACGGCTTGACCGTGCTGC

CCCCTCTGCTCACCGATGATATGATCGCCGCCTATACAGCCGCCCTGGTG

TCAGGCACCGCCACCGCCGGCTGGACCTTTGGCGCCGGAGCCGCCCTGCA

GATCCCCTTCGCCATGCAGATGGCCTACCGGT

Nucleotides 1 to 1431 of SEQ ID NO:59 encode amino acids 411 to 887 of SEQ ID NO:23. Nucleotides 1 to 6 of SEQ ID NO:59, AAGCTT, is a recognition site for the restriction enzyrne Hind III. Nucleotides 1237 to 1242 of SEQ ID NO:59, ACCGGT, is a recognition site for the restriction enzymes Age I and PinA I.

SEQ ID NO:60 has the following sequence:

ACCGGTTCAATGGCATCGGCGTGACCCAGAACGTGCTGTACGAGAACCAG

AAGCAGATCGCCAACCAGTTCAATAAGGCCATCTCCCAGATCCAGGAGAG

CCTCACCACCACAAGCACCGCCCTGGGCAAGCTGCAGGACGTGGTGAACC

AGAACGCCCAGGCCCTGAATACCCTGGTGAAGCAGCTGAGCAGCAACTTC

GGCGCCATCAGCAGCGTGCTGAACGACATCCTGAGCAGGCTGGATAAGGT

GGAGGCCGAGGTGCAGATCGACAGACTCATCACCGGCAGACTGCAGAGCC

TGCAGACCTACGTGACCCAGCAGCTCATCAGAGCCGCCGAGATCAGAGCC

AGCGCCAATCTGGCCGCCACCAAGATGAGCGAGTGCGTGCTGGGCCAGAG

-continued

CAAGAGAGTGGACTTCTGCGGCAAGGGCTATCACCTCATGAGCTTCCCTC

AGGCCGCTCCCCACGGCGTGGTGTTCCTGCACGTGACCTACGTGCCTAGC

CAGGAGAGGAATTTCACCACCGCCCCAGCCATCTGCCACGAGGGCAAGGC

CTACTTCCCCAGAGAGGGCGTGTTCGTGTTTAACGGCACCAGCTGGTTCA

TCACCCAGCGGAACTTCTTCAGCCCCCAGATCATCACCACAGACAACACC

TTCGTGTCCGGCAATTGCGACGTGGTCATCGGCATCATCAAATAACACCG

TGTACGACCCCCTGCAGCCCGAGCTGGATAGCTTCAAGGAGGAGCTGGAC

AAGTACTTCAAGAACCACACCTCCCCCGACGTGGACCTGGGCGACATCAG

CGGCATCAATGCCAGCGTGGTGAACATCCAGAAGGAGATCGACCGGCTGA

ACGAGGTGGCCAAGAACCTGAACGAGAGCCTCATCGACCTGCAGGAGCTG

GGAAAGTACGAGCAGTACATCAAGTGGCCCTGGTACGTGTGGCTGGGCTT

CATCGCCGGCCTCATCGCCATCGTGATGGTGACCATCCTGCTGTGCTGCA

TGACCAGCTGCTGCTCCTGCCTGAAGGGCGCCTGCAGCTGTGGCAGCTGC

TGCAAGTTCGACGAGGACGACTCAGAGCCCGTGCTGAAGGGCGTGAAGCT

GCACTACACCTGAAGATCT

Nucleotides 3 to 1109 of SEQ ID NO:60 encode amino acids 887 to 1255 of SEQ ID NO:23. Nucleotides 1 to 6 of SEQ ID NO:60, ACCGGT, is a recognition site for the restriction enzymes Age I and PinA I. Nucleotides 1113 to 1118 of SEQ ID NO:59, AGATCT, is a recognition site for the restriction enzyme Bgl II.

SEQ ID NOs 57, 59, and 60 are then spliced together using the restriction enzyme sites described above to produce a codon-optimized coding region encoding SEQ ID NO:23 in its entirety, with the exception that amino acid 2 (Phenylalanine, (F)) of SEQ ID NO:23 is replaced with valine (V). The spliced sequence is presented herein as SEQ ID NO:61.

GTCGACATGGTTATCTTTCTGCTGTTCCTCACCCTCACCAGCGGCAGCGA

TCTGGATAGGTGCACCACCTTCGACGACGTGCAGGCCCCCAACTACACCC

AGCACACCAGCAGCATGAGGGGCGTGTACTACCCCGACGAGATTTTCAGA

AGCGACACCCTGTACCTCACCCAGGACCTGTTCCTGCCCTTCTACAGCAA

CGTGACCGGCTTCCACACCATCAACCACACCTTCGGCAACCCCGTGATCC

CTTTCAAGGACGGCATCTACTTCGCCGCCACCGAGAAGAGCAATGTGGTG

CGGGGCTGGGTGTTCGGCAGCACCATGAACAACAAGAGCCAGAGCGTGAT

CATCATCAACAACAGCACCAACGTGGTGATCCGGGCCTGCAATTTCGAGC

TGTGCGACAACCCTTTCTTCGCCGTGTCCAAACCTATGGGCACCCAGACC

CACACCATGATCTTCGACAACGCCTTCAACTGCACCTTCGAGTACATCAG

CGACGCCTTCAGCCTGGATGTGAGCGAGAAGAGCGGCAACTTCAAGCACC

TGCGGGAGTTCGTGTTCAAGAACAAGGACGGCTTCCTGTACGTGTACAAG

GGCTACCAGCCCATCGACGTGGTGAGAGACCTGCCCAGCGGCTTCAACAC

CCTGAAGCCCATCTTCAAGCTGCCCCTGGGCATCAACATCACCAACTTCC

GGGCCATCCTCACCGCCTTTAGCCCTGCCCAGGATATCTGGGGCACCAGC

GCCGCTGCCTACTTCGTGGGCTACCTGAAGCCTACCACCTTCATGCTGAA

-continued

GTACGACGAGAACGGCACCATCACCGATGCCGTGGACTGCAGCCAGAACC

CCCTGGCCGAGCTGAAGTGCAGCGTGAAGAGCTTCGAGATCGACAAGGGC

ATCTACCAGACCAGCAACTTCAGAGTGGTGCCTAGCGGCGATGTGGTGAG

GTTCCCCAATATCACCAACCTGTGCCCCTTCGGCGAGGTGTTCAACGCCA

CCAAGTTCCCTAGCGTGTACGCCTGGGAGCGGAAGAAGATCAGCAACTGC

GTGGCCGATTACAGCGTGCTGTACAACTCCACCTTCTTCAGCACCTTCAA

GTGCTACGGCGTGAGCGCCACCAAGCTGAACGACCTGTGCTTCAGCAACG

TGTACGCCGACTCATTCGTGGTGAAGGGCGACGACGTGAGACAGATCGCC

CCTGGCCAGACCGGCGTGATCGCCGACTACAACTACAAGCTTCCCGACGA

CTTCATGGGCTGCGTGCTGGCCTGGAACACCAGAAACATCGACGCCACCT

CCACCGGCAACTACAATTACAAGTACCGCTACCTGAGGCACGGCAAGCTG

AGACCCTTCGAGCGGGACATCTCCAACGTGCCCTTCAGCCCCGACGGCAA

GCCCTGCACCCCCCCTGCCCTGAACTGCTACTGGCCCCTGAACGACTACG

GCTTCTACACCACCACCGGCATCGGCTATCAGCCCTACAGAGTGGTGGTG

CTGAGCTTCGAGCTGCTGAACGCCCCTGCCACCGTGTGCGGCCCCAAGCT

GAGCACCGACCTCATCAAGAACCAGTGCGTGAACTTCAACTTCAACGGCC

TCACCGGCACCGGCGTGCTCACCCCCAGCAGCAAGAGATTCCAGCCCTTC

CAGCAGTTCGGCAGGGACGTGAGCGATTTCACCGACAGCGTGAGGGATCC

TAAGACCAGCGAGATCCTGGACATCAGCCCTTGCAGCTTCGGCGGCGTGT

CCGTGATCACCCCCGGCACCAACGCCAGCAGCGAGGTGGCCGTGCTGTAC

CAGGACGTGAACTGCACCGACGTGAGCACCGCCATCCACGCCGACCAGCT

CACCCCCGCCTGGAGAATCTACAGCACCGGCAACAACGTGTTCCAGACCC

AGGCCGGCTGCCTCATCGGCGCCGAGCACGTGGACACCAGCTACGAGTGC

GACATCCCCATCGGAGCCGGCATCTGCGCCAGCTACCACACCGTGAGCCT

GCTGAGAAGCACCAGCCAGAAGAGCATCGTGGCCTACACCATGAGCCTGG

GCGCCGACAGCAGCATCGCCTACAGCAACAACACCATCGCCATCCCCACC

AACTTCAGCATCTCCATCACCACCGAGGTGATGCCCGTGAGCATGGCCAA

GACCAGCGTGGATTGCAACATGTACATCTGCGGCGACAGCACCGAGTGCG

CCAACCTGCTGCTGCAGTACGGCAGCTTCTGCACCCAGCTGAACAGAGCC

CTGAGCGGCATTGCCGCCGAGCAGGACAGAAACACCAGGGAGGTGTTCGC

CCAGGTGAAGCAGATGTATAAGACCCCCACCCTGAAGTACTTCGGCGGGT

TCAACTTCAGCCAGATCCTGCCCGATCCTCTGAAGCCCACCAAGCGGAGC

TTCATCGAGGACCTGCTGTTCAACAAGGTGACCCTGGCCGACGCCGGCTT

TATGAAGCAGTACGGCGAGTGCCTGGGCGATATCAACGCCAGGGACCTCA

TCTGCGCCCAGAAGTTCAACGGCTTGACCGTGCTGCCCCCTCTGCTCACC

GATGATATGATCGCCGCCTATACAGCCGCCCTGGTGTCAGGCACCGCCAC

CGCCGGCTGGACCTTTGGCGCCGGAGCCGCCCTGCAGATCCCCTTCGCCA

TGCAGATGGCCTACCGGTTCAATGGCATCGGCGTGACCCAGAACGTGCTG

TACGAGAACCAGAAGCAGATCGCCAACCAGTTCAATAAGGCCATCTCCCA

GATCCAGGAGAGCCTCACCACCACAAGCACCGCCCTGGGCAAGCTGCAGG

ACGTGGTGAACCAGAACGCCCAGGCCCTGAATACCCTGGTGAAGCAGCTG

-continued

AGCAGCAACTTCGGCGCCATCAGCAGCGTGCTGAACGACATCCTGAGCAG

GCTGGATAAGGTGGAGGCCGAGGTGCAGATCGACAGACTCATCACCGGCA

GACTGCAGAGCCTGCAGACCTACGTGACCCAGCAGCTCATCAGAGCCGCC

GAGATCAGAGCCAGCGCCAATCTGUCCGCCACCAAGATGAGCGAGTGCGT

GCTGGGCCAGAGCAAGAGAGTGGACTTCTGCGGCAAGGGCTATCACCTCA

TGAGCTTCCCTCAGGCCGCTCCCCACGGCGTGGTGTTCCTGCACGTGACC

TACGTGCCTAGCCAGGAGAGGAATTTCACCACCGCCCCAGCCATCTGCCA

CGAGGGCAAGGCCTACTTCCCCAGAGAGGGCGTGTTCGTGTTTAACGGCA

CCAGCTGCTTCATCACCCAGCGGAACTTCTTCAGCCCCCAGATCATCACC

ACAGACAACACCTTCGTGTCCGGCAATTGCGACGTGGTCATCGGCATCAT

CAATAACACCGTGTACGACCCCCTGCAGCCCGAGCTGGATAGCTTCAAGG

AGGAGCTGGACAAGTACTTCAAGAACCACACCTCCCCCGACGTGGACCTG

GGCGACATCAGCGGCATCAATGCCAGCGTGGTGAACATCCAGAAGGAGAT

CGACCGGCTGAACGAGGTGGCCAAGAACCTGAACGAGAGCCTCATCGACC

TGCAGGAGCTGGGAAAGTACGAGCAGTACATCAAGTGGCCCTGGTACGTG

TGGCTGGGCTTCATCGCCGGCCTCATCGCCATCGTGATGGTGACCATCCT

GCTGTGCTGCATGACCAGCTGCTGCTCCTGCCTGAAGGGCGCCTGCAGCT

GTGGCAGCTGCTGCAAGTTCGACGAGGACGACTCAGAGCCCGTGCTGAAG

GGCGTGAAGCTGCACTACACCTGAAGATCT

The translation product of nucleotides 7 to 3771 of SEQ ID NO:61 is presented herein as SEQ ID NO:62

MVIFLLFLTLTSGSDLDRCTTFDDVQAPNYTQHTSSMRGVYYPDEIFRSD

TLYLTQDLFLPFYSNVTGFHTINHTFGNPVIPFKDGIYFAATEKSNVVRG

WVFGSTMNNKSQSVIIINNSTNVVRACNFELCDNPFFAVSKPMGTQTHTM

IFDNAFNCTFEYISDAFSLDVSEKSGNFKHLREFVFKNKDGFLYVYKGYQ

PIDVVRDLPSGFNTLKPIFKLPLGINITNFRAILTAFSPAQDIWGTSAAA

YFVGYLKPTTFMLKYDENGTTTDAVDCSQNPLAELKCSVKSFEIDKGIYQ

TSNFRVVPSGDVVRFPNITNLCPFGEVFNATKFPSVYAWERKKISNCVAD

YSVLYNSTFFSTFKCYGVSATKLNDLCFSNVYADSFVVKGDDVRQIAPGQ

TGVIADYNYKLPDDFMGCVLAWNTRNIDATSTGNYNYKYRYLRHGKLRPF

ERDISNVPFSPDGKPCTPPALNCYWPLNDYGFYTTTGIGYQPYRVVVLSF

ELLNAPATVCGPKLSTDLIKNQCVNFNFNGLTGTGVLTPSSKRFQPFQQF

GRDVSDFTDSVRDPKTSEILDISPCSFGGVSVITPGTNASSEVAVLYQDV

NCTDVSTAIHADQLTPAWRIYSTGNNVFQTQAGCLIGAEHVDTSYECDIP

IGAGICASYHTVSLLRSTSQKSIVAYTMSLGADSSIAYSNNTIAIPTNFS

ISITTEVMPVSMAKTSVDCNMYICGDSTECANLLLQYGSFCTQLNRALSG

IAAEQDRNTREVFAQVKQMYKTPTLKYFGGFNFSQILPDPLKPTKRSFIE

DLLFNKVTLADAGFMKQYGECLGDINARDLICAQKFNGLTVLPPLLTDDM

IAAYTAALVSGTATAGWTFGAGAALQIPFAMQMAYRFNGIGVTQNVLYEN

QKQIANQFNKAISQIQESLTTTSTALGKLQDVVNQNAQALNTLVKQLSSN

-continued

FGAISSVLNDILSRLDKVEAEVQIDRLITGRLQSLQTYVTQQLIRAAEIR

ASANLAATKMSECVLGQSKRVDFCGKGYHLMSFPQAAPHGVVFLHVTYVP

SQERNFTTAPAICHEGKAYFPREGVFVFNGTSWFITQRNFFSPQIITTDN

TFVSGNCDVVIGIINNTVYDPLQPELDSFKEELDKYFKNHTSPDVDLGDI

SGINASVVNIQKEIDRLNEVAKNLNESLIDLQELGKYEQYIKWPWYVWLG

FIAGLIALIVMVTILLCCMTSCCSCLKGACSCGSCCKFDEDDSEPVLKGV

KLHYT

In certain embodiments described herein, a codon-optimized coding region encoding SEQ ID NO:8 is optimized according to codon usage in humans (*Homo sapiens*). Alternatively, a codon-optimized coding region encoding SEQ ID NO:8 may be optimized according to codon usage in any plant, animal, or microbial species. Codon-optimized coding regions encoding SEQ ID NO:8, optimized according to codon usage in humans are designed as follows. The amino acid composition of SEQ ID NO:8 is shown in Table 12.

TABLE 12

| | AMINO ACID | Number in SEQ ID NO: 8 |
|---|---|---|
| A | Ala | 84 |
| R | Arg | 41 |
| C | Cys | 33 |
| G | Gly | 77 |
| H | His | 14 |
| I | Ile | 73 |
| L | Leu | 92 |
| K | Lys | 57 |
| M | Met | 19 |
| F | Phe | 79 |
| P | Pro | 57 |
| S | Ser | 93 |
| T | Thr | 94 |
| W | Trp | 10 |
| Y | Tyr | 52 |
| V | Val | 89 |
| N | Asn | 81 |
| D | Asp | 71 |
| Q | Gln | 55 |
| E | Glu | 40 |

Using the amino acid composition shown in Table 12, a human codon-optimized coding region which encodes SEQ ID NO:8 can be designed by any of the methods discussed herein. For “uniform” optimization, each amino acid is assigned the most frequent codon used in the human genome for that amino acid. According to this method, codons are assigned to the coding region encoding SEQ ID NO:8 as follows: the 79 phenylalanine codons are TTC, the 92 leucine codons are CTG, the 73 isoleucine codons are ATC, the 19 methionine codons are ATG, the 89 valine codons are GTG, the 93 serine codons are AGC, the 57 proline codons are CCC, the 94 threonine codons are ACC, the 84 alanine codons are GCC, the 52 tyrosine codons are TAC, the 14 histidine codons are CAC, the 55 glutamine codons are CAG, the 81 asparagine codons are AAC, the 57 lysine codons are AAG, the 71 aspartic acid codons are GAC, the 40 glutamic acid codons are GAG, the 33 cysteine codons are TGC, the 10 tryptophan codon is TGG, the 41 arginine codons are CGG, AGA, or AGG (the frequencies of usage of these three codons in the human genome are not significantly different), and the 77 glycine codons are GGC. The codon-optimized coding region designed by this method is presented herein as SEQ ID NO:31.

ATG GAC GCC ATG AAG CGG GGC CTG TGC TGC GTG CTG
CTG CTG TGC GGC GCC GTG TTC GTG AGC CCC AGC GCC
CGG GGC AGC GGC AGC GAC CTG GAC CGG TGC ACC ACC
TTC GAC GAC GTG CAG GCC CCC AAC TAC ACC CAG CAC
ACC AGC AGC ATG CGG GGC GTG TAC TAC CCC GAC GAG
ATC TTC CGG AGC GAC ACC CTG TAC CTG ACC CAG GAC
CTG TTC CTG CCC TTC TAC AGC AAC GTG ACC GGC TTC
CAC ACC ATC AAC CAC ACC TTC GGC AAC CCC GTG ATC
CCC TTC AAG GAC GGC ATC TAC TTC GCC GCC ACC GAG
AAG AGC AAC GTG GTG CGG GGC TGG GTG TTC GGC AGC
ACC ATG AAC AAC AAG AGC CAG AGC GTG ATC ATC ATC
AAC AAC AGC ACC AAC GTG GTG ATC CGG GCC TGC AAC
TTC GAG CTG TGC GAC AAC CCC TTC TTC GCC GTG AGC
AAG CCC ATG GGC ACC CAG ACC CAC ACC ATG ATC TTC
GAC AAC GCC TTC AAC TGC ACC TTC GAG TAC ATC AGC
GAC GCC TTC AGC CTG GAC GTG AGC GAG AAG AGC GGC
AAC TTC AAG CAC CTG CGG GAG TTC GTG TTC AAG AAC
AAC GAC GGC TTC CTG TAC GTG TAC AAG GGC TAC CAG
CCC ATC GAC GTG GTG CGG GAC CTG CCC AGC GGC TTC
AAC ACC CTG AAG CCC ATC TTC AAG CTG CCC CTG GGC
ATC AAC ATC ACC AAC TTC CGG GCC ATC CTG ACC GCC
TTC AGC CCC GCC CAG GAC ATC TGG GGC ACC AGC GCC
GCC GCC TAC TTC GTG GGC TAC CTG AAG CCC ACC ACC
TTC ATG CTG AAG TAC GAC GAG AAC GGC ACC ATC ACC
GAC GCC GTG GAC TGC AGC CAG AAC CCC CTG GCC GAG
CTG AAG TGC AGC GTG AAG AGC TTC GAG ATC GAC AAG
GGC ATC TAC CAG ACC AGC AAC TTC CGG GTG GTG CCC
AGC GGC GAC GTG GTG CGG TTC CCC AAC ATC ACC AAC
CTG TGC CCC TTC GGC GAG GTG TTC AAC GCC ACC AAG
TTC CCC AGC GTG TAC GCC TGG GAG CGG AAG AAG ATC
AGC AAC TGC GTG GCC GAC TAC AGC GTG CTG TAC AAC
AGC ACC TTC TTC AGC ACC TTC AAG TGC TAC GGC GTG
AGC GCC ACC AAG CTG AAC GAC CTG TGC TTC AGC AAC
GTG TAC GCC GAC AGC TTC GTG GTG AAG GGC GAC GAC
GTG CGG CAG ATC GCC CCC GGC CAG ACC GGC GTG ATC
GCC GAC TAC AAC TAC AAG CTG CCC GAC GAC TTC ATG
GGC TGC GTG CTG GCC TGG AAC ACC CGG AAC ATC GAC
GCC ACC AGC ACC GGC AAC TAC AAC TAC AAG TAC CGG
TAC CTG CGG CAC GGC AAG CTG CGG CCC TTC GAG CGG
GAC ATC AGC AAC GTG CCC TTC AGC CCC GAC GGC AAG
CCC TGC ACC CCC CCC GCC CTG AAC TGC TAC TGG CCC

-continued

CTG AAC GAC TAC GGC TTC TAC ACC ACC ACC GGC ATC
GGC TAC CAG CCC TAC CGG GTG GTG GTG CTG AGC TTC
GAG CTG CTG AAC GCC CCC GCC ACC GTG TGC GGC CCC
AAG CTG AGC ACC GAC CTG ATC AAG AAC CAG TGC GTG
AAC TTC AAC TTC AAC GGC CTG ACC GGC ACC GGC GTG
CTG ACC CCC AGC AGC AAG CGG TTC CAG CCC TTC CAG
CAG TTC GGC CGG GAC GTG AGC GAC TTC ACC GAC AGC
GTG CGG GAC CCC AAG ACC AGC GAG ATC CTG GAC ATC
AGC CCC TGC AGC TTC GGC GGC GTG AGC GTG ATC ACC
CCC GGC ACC AAC GCC AGC AGC GAG GTG GCC GTG CTG
TAC CAG GAC GTG AAC TGC ACC GAC GTG AGC ACC GCC
ATC CAC GCC GAC CAG CTG ACC CCC GCC TGG CGG ATC
TAC AGC ACC GGC AAC AAC GTG TTC CAG ACC CAG GCC
GGC TGC CTG ATC GGC GCC GAG CAC GTG GAC ACC AGC
TAC GAG TGC GAC ATC CCC ATC GGC GCC GGC ATC TGC
GCC AGC TAC CAC ACC GTG AGC CTG CTG CGG AGC ACC
AGC CAG AAG AGC ATC GTG GCC TAC ACC ATG AGC CTG
GGC GCC GAC AGC AGC ATC GCC TAC AGC AAC AAC ACC
ATC GCC ATC CCC ACC AAC TTC AGC ATC AGC ATC ACC
ACC GAG GTG ATG CCC GTG AGC ATG GCC AAG ACC AGC
GTG GAC TGC AAC ATG TAC ATC TGC GGC GAC AGC ACC
GAG TGC GCC AAC CTG CTG CTG CAG TAC GGC AGC TTC
TGC ACC CAG CTG AAC CGG GCC CTG AGC GGC ATC GCC
GCC GAG CAG GAC CGG AAC ACC CGG GAG GTG TTC GCC
CAG GTG AAG CAG ATG TAC AAG ACC CCC ACC CTG AAG
TAC TTC GGC GGC TTC AAC TTC AGC CAG ATC CTG CCC
GAC CCC CTG AAG CCC ACC AAG CGG AGC TTC ATC GAG
GAC CTG CTG TTC AAC AAG GTG ACC CTG GCC GAC GCC
GGC TTC ATG AAG CAG TAC GGC GAG TGC CTG GGC GAC
ATC AAC GCC CGG GAC CTG ATC TGC GCC CAG AAG TTC
AAC GGC CTG ACC GTG CTG CCC CCC CTG CTG ACC GAC
GAC ATG ATC GCC GCC TAC ACC GCC GCC CTG GTG AGC
GGC ACC GCC ACC GCC GGC TGG ACC TTC GGC GCC GGC
GCC GCC CTG CAG ATC CCC TTC GCC ATG CAG ATG GCC
TAC CGG TTC AAC GGC ATC GGC GTG ACC CAG AAC GTG
CTG TAC GAG AAC CAG AAG CAG ATC GCC AAC CAG TTC
AAC AAG GCC ATC AGC CAG ATC CAG GAG AGC CTG ACC
ACC ACC AGC ACC GCC CTG GGC AAG CTG CAG GAC GTG
GTG AAC CAG AAC GCC CAG GCC CTG AAC ACC CTG GTG
AAG CAG CTG AGC AGC AAC TTC GGC GCC ATC AGC AGC

-continued

```
GTG CTG AAC GAC ATC CTG AGC CGG CTG GAC AAG GTG

GAG GCC GAG GTG CAG ATC GAC CGG CTG ATC ACC GGC

CGG CTG CAG AGC CTG CAG ACC TAC GTG ACC CAG CAG

CTG ATC CGG GCC GCC GAG ATC CGG GCC AGC GCC AAC

CTG GCC GCC ACC AAG ATG AGC GAG TGC GTG CTG GGC

CAG AGC AAG CGG GTG GAC TTC TGC GGC AAG GGC TAC

CAC CTG ATG AGC TTC CCC CAG GCC GCC CCC CAC GGC

GTG GTG TTC CTG CAC GTG ACC TAC GTG CCC AGC CAG

GAG CGG AAC TTC ACC ACC GCC CCC GCC ATC TGC CAC

GAG GGC AAG GCC TAC TTC CCC CGG GAG GGC GTG TTC

GTG TTC AAC GGC ACC AGC TGG TTC ATC ACC CAG CGG

AAC TTC TTC AGC CCC CAG ATC ATC ACC ACC GAC AAC

ACC TTC GTG AGC GGC AAC TGC GAC GTG GTG ATC GGC

ATC ATC AAC AAC ACC GTG TAC GAC CCC CTG CAG CCC

GAG CTG GAC AGC TTC AAG GAG GAG CTG GAC AAG TAC

TTC AAG AAC CAC ACC AGC CCC GAC GTG GAC CTG GGC

GAC ATC AGC GGC ATC AAC GCC AGC GTG GTG AAC ATC

CAG AAG GAG ATC GAC CGG CTG AAC GAG GTG GCC AAG

AAC CTG AAC GAG AGC CTG ATC GAC CTG CAG GAG CTG

GGC AAG TAC GAG CAG TAC ATC AAG TGG CCC TGG
```

Alternatively, a human codon-optimized coding region which encodes SEQ ID NO:8 can be designed by the "full optimization" method, where each amino acid is assigned codons based on the frequency of usage in the human genome. These frequencies are shown in Table 4 above. Using this latter method, codons are assigned to the coding region encoding SEQ ID NO:8 as follows: about 36 of the 79 phenylalanine codons are TTT, and about 43 of the phenylalanine codons are TTC; about 7 of the 92 leucine codons are TTA, about 12 of the leucine codons are TTG, about 12 of the leucine codons are CTT, about 18 of the leucine codons are CTC, about 7 of the leucine codons are CTA, and about 36 of the leucine codons are CTG; about 26 of the 73 isoleucine codons are ATT, about 35 of the isoleucine codons are ATC, and about 12 of the isoleucine codons are ATA; the 19 methionine codons are ATG; about 16 of the 89 valine codons are GTT, about 41 of the valine codons are GTG, about 11 of the valine codons are GTA, and about 21 of the valine codons are GTC; about 17 of the 93 serine codons are TCT, about 20 of the serine codons are TCC, about 14 of the serine codons are TCA, about 5 of the serine codons are TCG, about 15 of the serine codons are AGT, and about 22 of the serine codons are AGC; about 16 of the 57 proline codons are CCT, about 19 of the proline codons are CCC, about 16 of the proline codons are CCA, and about 6 of the proline codons are CCG; about 23 of the 94 threonine codons are ACT, about 34 of the threonine codons are ACC, about 26 of the threonine codons are ACA, and about 11 of the threonine codons are ACG; about 22 of the 84 alanine codons are GCT, about 34 of the alanine codons are GCC, about 19 of the alanine codons are GCA, and about 9 of the alanine codons are GCG; about 23 of the 52 tyrosine codons are TAT and about 29 of the tyrosine codons are TAC; about 6 of the 14 histidine codons are CAT and about 8 of the histidine codons are CAC; about 14 of the 55 glutamine codons are CAA and about 41 of the glutamine codons are CAG; about 37 of the 81 asparagine codons are AAT and about 44 of the asparagine codons are AAC; about 24 of the 57 lysine codons are AAA and about 33 of the lysine codons are AAG; about 33 of the 71 aspartic acid codons are GAT and about 38 of the aspartic acid codons are GAC; about 17 of the 40 glutamic acid codons are GAA and about 23 of the glutamic acid codons are GAG; about 15 of the 33 cysteine codons are TGT and about 18 of the cysteine codons are TGC; the 10 tryptophan codons are TGG; about 3 of the 41 arginine codons are CGT, about 8 of the arginine codons are CGC, about 5 of the arginine codons are CGA, about 8 of the arginine codons are CGG, about 9 of the arginine codons are AGA, and about 8 of the arginine codons are AGG; and about 13 of the 77 glycine codons are GGT, about 26 of the glycine codons are GGC, about 19 of the glycine codons are GGA, and about 19 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:8, optimized according to codon usage in humans is presented herein as SEQ ID NO:30.

```
ATG GAT GCA ATG AAG CGG GGC CTG TGC TGC GTG CTC

CTG CTC TGC GGG GCG GTG TTT GTG AGC CCC AGT GCC

AGA GGT AGC GGC AGC GAT TTG GAT AGG TGC ACC ACA

TTT GAT GAC GTG CAG GCT CCC AAT TAC ACC CAG CAC

ACC AGT TCT ATG AGA GGA GTA TAC TAC CCT GAC GAG

ATC TTC CGC AGT GAT ACC CTA TAT TTA ACA CAA GAT

TTA TTC TTA CCC TTC TAC TCC AAC GTC ACA GGG TTT

CAC ACC ATC AAC CAC ACC TTC GGC AAC CCC GTG ATC

CCG TTT AAA GAT GGC ATT TAT TTC GCA GCC ACA GAG

AAG TCG AAT GTA GTG CGG GGT TGG GTG TTT GGA TCA

ACA ATG AAT AAT AAA TCT CAG TCC GTG ATC ATT ATT

AAC AAC TCT ACG AAT GTG GTT ATA CGA GCC TGT AAT

TTC GAG TTA TGC GAT AAT CCA TTT TTC GCG GTC AGT

AAA CCA ATG GGC ACT CAG ACC CAT ACG ATG ATT TTC

GAT AAC GCA TTC AAT TGT ACG TTT GAA TAC ATT TCT

GAT GCT TTT TCA CTC GAC GTT TCA GAA AAG TCT GGG

AAC TTC AAG CAT TTA AGA GAG TTC GTC TTT AAA AAT

AAA GAC GGG TTC CTG TAC GTG TAT AAA GGA TAC CAG

CCT ATC GAC GTG GTG CGG GAC CTG CCA AGC GGT TTT

AAT ACC CTG AAG CCC ATC TTT AAG CTG CCC CTG GGA

ATC AAT ATT ACA AAC TTC AGG GCT ATC CTC ACC GCT

TTT AGC CCA GCT CAG GAC ATA TGG GGA ACC TCC GCC

GCC GCC TAC TTC GTC GGA TAT TTG AAA CCA ACC ACA
```

-continued

```
TTC ATG CTG AAG TAT GAC GAA AAT GGG ACG ATT ACC
GAC GCC GTA GAC TGT AGT CAG AAC CCT TTG GCG GAG
TTG AAG TGC TCA GTC AAG AGC TTT GAG ATC GAC AAG
GGA ATT TAT CAA ACT AGC AAC TTC AGG GTG GTG CCC
TCC GGA GAT GTA GTT CGC TTC CCC AAC ATC ACC AAC
CTG TGC CCG TTC GGT GAG GTG TTT AAT GCA ACT AAA
TTC CCC TCA GTG TAT GCC TGG GAA AGA AAG AAA ATT
AGC AAC TGT GTT GCC GAT TAC AGC GTC CTT TAT AAC
TCA ACA TTC TTC TCT ACC TTT AAG TGC TAT GGT GTG
TCC GCC ACT AAG TTG AAC GAC CTC TGC TTT AGT AAC
GTG TAC GCT GAT TCC TTC GTG GTG AAA GGG GAT GAC
GTG CGT CAG ATT GCA CCG GGC CAG ACC GGA GTA ATC
GCC GAT TAC AAT TAC AAG TTG CCT GAC GAC TTC ATG
GGC TGC GTT CTA GCA TGG AAT ACC CGC AAC ATA GAT
GCC ACC TCA ACG GGG AAC TAC AAC TAC AAG TAC AGA
TAT CTG AGA CAC GGT AAG CTG CGG CCT TTT GAG CGG
GAT ATC TCC AAT GTG CCT TTT AGC CCC GAT GGC AAA
CCA TGC ACC CCA CCT GCC CTG AAT TGT TAT TGG CCT
TTG AAC GAT TAT GGA TTC TAC ACT ACC ACT GGG ATC
GGT TAT CAA CCC TAC CGG GTC GTC GTC CTG AGT TTT
GAA CTC TTG AAC GCG CCT GCA ACA GTC TGC GGA CCC
AAG CTG TCG ACA GAC CTT ATC AAG AAT CAG TGT GTG
AAC TTT AAC TTC AAT GGG CTC ACC GGT ACC GGT GTT
CTG ACT CCA TCT AGT AAG CGA TTT CAA CCA TTC CAA
CAG TTC GGC CGT GAC GTT TCC GAT TTT ACG GAT TCG
GTG CGT GAT CCA AAA ACA TCA GAG ATC CTT GAC ATA
TCG CCG TGT TCT TTT GGA GGC GTG TCT GTG ATT ACA
CCA GGC ACT AAT GCT AGT AGC GAA GTC GCT GTA CTA
TAC CAG GAC GTG AAC TGC ACC GAC GTG AGC ACG GCA
ATC CAC GCT GAC CAG CTG ACC CCC GCC TGG CGC ATC
TAC AGT ACA GGC AAT AAC GTC TTT CAG ACC CAG GCC
GGC TGT CTG ATT GGG GCT GAG CAC GTC GAC ACT TCC
TAT GAA TGT GAT ATT CCC ATC GGC GCT GGA ATT TGT
GCT AGC TAT CAC ACA GTC TCC CTT TTA AGA TCA ACC
AGC CAG AAA TCT ATT GTG GCT TAC ACA ATG TCT CTC
GGC GCA GAC TCA TCA ATT GCC TAT AGC AAC AAT ACC
ATT GCA ATC CCT ACC AAT TTT AGT ATA TCC ATA ACC
ACC GAG GTG ATG CCC GTG TCT ATG GCG AAA ACT TCC
GTC GAT TGC AAC ATG TAT ATC TGC GGG GAC TCC ACA
GAA TGC GCC AAC CTG CTT CTG CAG TAT GGA AGC TTC
```

-continued

```
TGT ACT CAA CTC AAC CGC GCA TTG TCT GGG ATT GCC
GCC GAG CAG GAT AGG AAT ACT AGA GAG GTG TTC GCT
CAG GTT AAA CAA ATG TAC AAG ACA CCG ACA CTT AAG
TAC TTC GGA GGT TTT AAC TTT TCC CAG ATA CTC CCT
GAC CCT CTA AAG CCT ACT AAA CGC AGT TTC ATC GAG
GAT CTC CTG TTT AAT AAG GTG ACA CTC GCC GAT GCT
GGC TTC ATG AAA CAA TAC GGA GAA TGC CTG GGA GAC
ATT AAC GCC AGA GAC CTG ATC TGT GCC CAG AAG TTC
AAC GGT CTG ACA GTA CTT CCT CCC CTT CTG ACG GAC
GAC ATG ATT GCT GCA TAC ACA GCC GCC CTA GTT AGC
GGC ACA GCC ACA GCT GGG TGG ACC TTT GGC GCT GGC
GCA GCG TTG CAG ATT CCA TTC GCG ATG CAG ATG GCT
TAC CGA TTT AAC GGG ATC GGC GTG ACT CAG AAT GTT
TTG TAT GAG AAC CAG AAA CAG ATC GCT AAT CAG TTT
AAC AAG GCA ATC AGC CAG ATA CAA GAA TCT CTG ACT
ACC ACA AGC ACC GCT CTG GGA AAA CTG CAG GAC GTG
GTG AAT CAG AAT GCA CAG GCC CTC AAC ACG CTC GTG
AAG CAG CTT AGT TCC AAT TTC GGG GCC ATC TCC TCC
GTT TTA AAT GAT ATC CTG AGT CGC CTG GAC AAG GTC
GAG GCC GAA GTT CAG ATC GAC CGC CTG ATC ACA GGG
AGG CTA CAA TCA TTG CAG ACT TAC GTG ACT CAG CAG
CTC ATA AGG GCT GCA GAG ATT AGG GCC TCT GCA AAC
CTT GCC GCG ACC AAG ATG TCC GAG TGT GTT CTC GGT
CAG TCC AAA CGG GTT GAC TTT TGT GGC AAA GGC TAC
CAT CTG ATG AGC TTC CCC CAG GCC GCA CCC CAT GGC
GTA GTC TTT CTG CAC GTA ACT TAT GTG CCA TCC CAA
GAA AGG AAC TTC ACT ACG GCG CCA GCC ATA TGC CAT
GAA GGT AAA GCA TAT TTC CCT CGA GAA GGG GTA TTT
GTT TTC AAC GGG ACT AGC TGG TTT ATT ACG CAG CGG
AAT TTC TTC TCA CCA CAA ATC ATC ACT ACT GAT AAC
ACA TTC GTC AGC GGC AAT TGT GAC GTC GTC ATT GGA
ATT ATA AAC AAC ACT GTG TAC GAT CCT CTG CAG CCG
GAA CTG GAT TCT TTT AAG GAG GAG CTC GAC AAG TAC
TTC AAA AAC CAT ACC TCG CCC GAC GTG GAC CTA GGC
GAT ATC TCT GGG ATT AAT GCC TCA GTA GTC AAC ATC
CAG AAG GAG ATA GAC CGA CTT AAT GAG GTT GCC AAG
AAT CTG AAT GAG AGT CTC ATC GAT CTG CAA GAA CTT
GGC AAG TAT GAA CAA TAT ATC AAA TGG CCA TGG
```

In certain embodiments described herein, a codon-optimized coding region encoding SEQ ID NO:10 is optimized according to codon usage in humans (*Homo sapiens*). Alternatively, a codon-optimized coding region encoding SEQ ID NO:10 may be optimized according to codon usage in any plant, animal, or microbial species. Codon-optimized coding regions encoding SEQ ID NO:10, optimized according to codon usage in humans are designed as follows. The amino acid composition of SEQ ID NO:10 is shown in Table 13.

TABLE 13

| AMINO ACID | | Number in SEQ ID NO: 10 |
|---|---|---|
| A | Ala | 41 |
| R | Arg | 25 |
| C | Cys | 23 |
| G | Gly | 47 |
| H | His | 9 |
| I | Ile | 37 |
| L | Leu | 46 |
| K | Lys | 32 |
| M | Met | 9 |
| F | Phe | 51 |
| P | Pro | 38 |
| S | Ser | 58 |
| T | Thr | 56 |
| W | Trp | 6 |
| Y | Tyr | 35 |
| V | Val | 56 |
| N | Asn | 46 |
| D | Asp | 45 |
| Q | Gln | 21 |
| E | Glu | 17 |

Using the amino acid composition shown in Table 13, a human codon-optimized coding region which encodes SEQ ID NO:10 can be designed by any of the methods discussed herein. For "uniform" optimization, each amino acid is assigned the most frequent codon used in the human genome for that amino acid. According to this method, codons are assigned to the coding region encoding SEQ ID NO:10 as follows: the 51 phenylalanine codons are TTC, the 46 leucine codons are CTG, the 37 isoleucine codons are ATC, the 9 methionine codons are ATG, the 56 valine codons are GTG, the 58 serine codons are AGC, the 38 proline codons are CCC, the 56 threonine codons are ACC, the 41 alanine codons are GCC, the 35 tyrosine codons are TAC, the 9 histidine codons are CAC, the 21 glutamine codons are CAG, the 46 asparagine codons are AAC, the 32 lysine codons are AAG, the 45 aspartic acid codons are GAC, the 17 glutamic acid codons are GAG, the 23 cysteine codons are TGC, the 6 tryptophan codons are TGG, the 25 arginine codons are CGG, AGA, or AGG (the frequencies of usage of these three codons in the human genome are not significantly different), and the 47 glycine codons are GGC. The codon-optimized coding region designed by this method is presented herein as SEQ ID NO:33.

```
ATG GAC GCC ATG AAG CGG GGC CTG TGC TGC GTG CTG

CTG CTG TGC GGC GCC GTG TTC GTG AGC CCC AGC GCC

CGG GGC AGC GGC AGC GAC CTG GAC CGG TGC ACC ACC

TTC GAC GAC GTG CAG GCC CCC AAC TAC ACC CAG CAC

ACC AGC AGC ATG CGG GGC GTG TAC TAC CCC GAC GAG

ATC TTC CGG AGC GAC ACC CTG TAC CTG ACC CAG GAC

CTG TTC CTG CCC TTC TAC AGC AAC GTG ACC GGC TTC

CAC ACC ATC AAC CAC ACC TTC GGC AAC CCC GTG ATC

CCC TTC AAG GAC GGC ATC TAC TTC GCC GCC ACC GAG
```

-continued

```
AAG AGC AAC GTG GTG CGG GGC TGG GTG TTC GGC AGC

ACC ATG AAC AAC AAG AGC CAG AGC GTG ATC ATC ATC

AAC AAC AGC ACC AAC GTG GTG ATC CGG GCC TGC AAC

TTC GAG CTG TGC GAC AAC CCC TTC TTC GCC GTG AGC

AAG CCC ATG GGC ACC CAG ACC CAC ACC ATG ATC TTC

GAC AAC GCC TTC AAC TGC ACC TTC GAG TAC ATC AGC

GAC GCC TTC AGC CTG GAC GTG AGC GAG AAG AGC GGC

AAC TTC AAG CAC CTG CGG GAG TTC GTG TTC AAG AAC

AAG GAC GGC TTC CTG TAC GTG TAC AAG GGC TAC CAG

CCC ATC GAC GTG GTG CGG GAC CTG CCC AGC GGC TTC

AAC ACC CTG AAG CCC ATC TTC AAG CTG CCC CTG GGC

ATC AAC ATC ACC AAC TTC CGG GCC ATC CTG ACC GCC

TTC AGC CCC GCC CAG GAC ATC TGG GGC ACC AGC GCC

GCC GCC TAC TTC GTG GGC TAC CTG AAG CCC ACC ACC

TTC ATG CTG AAG TAC GAC GAG AAC GGC ACC ATC ACC

GAC GCC GTG GAC TGC AGC CAG AAC CCC CTG GCC GAG

CTG AAG TGC AGC GTG AAG AGC TTC GAG ATC GAC AAG

GGC ATC TAC CAG ACC AGC AAC TTC CGG GTG GTG CCC

AGC GGC GAC GTG GTG CGG TTC CCC AAC ATC ACC AAC

CTG TGC CCC TTC GGC GAG GTG TTC AAC GCC ACC AAG

TTC CCC AGC GTG TAC GCC TGG GAG CGG AAG AAG ATC

AGC AAC TGC GTG GCC GAC TAC AGC GTG CTG TAC AAC

AGC ACC TTC TTC AGC ACC TTC AAG TGC TAC GGC GTG

AGC GCC ACC AAG CTG AAC GAC CTG TGC TTC AGC AAC

GTG TAC GCC GAC AGC TTC GTG GTG AAG GGC GAC GAC

GTG CGG CAG ATC GCC CCC GGC CAG ACC GGC GTG ATC

GCC GAC TAC AAC TAC AAG CTG CCC GAC GAC TTC ATG

GGC TGC GTG CTG GCC TGG AAC ACC CGG AAC ATC GAC

GCC ACC AGC ACC GGC AAC TAC AAC TAC AAG TAC CGG

TAC CTG CGG CAC GGC AAG CTG CGG CCC TTC GAG CGG

GAC ATC AGC AAC GTG CCC TTC AGC CCC GAC GGC AAG

CCC TGC ACC CCC CCC GCC CTG AAC TGC TAC TGG CCC

CTG AAC GAC TAC GGC TTC TAC ACC ACC ACC GGC ATC

GGC TAC CAG CCC TAC CGG GTG GTG GTG CTG AGC TTC

GAG CTG CTG AAC GCC CCC GCC ACC GTG TGC GGC CCC

AAG CTG AGC ACC GAC CTG ATC AAG AAC CAG TGC GTG

AAC TTC AAC TTC AAC GGC CTG ACC GGC ACC GGC GTG

CTG ACC CCC AGC AGC AAG CGG TTC CAG CCC TTC CAG

CAG TTC GGC CGG GAC GTG AGC GAC TTC ACC GAC AGC

GTG CGG GAC CCC AAG ACC AGC GAG ATC CTG GAC ATC

AGC CCC TGC AGC TTC GGC GGC GTG AGC GTG ATC ACC
```

-continued

CCC GGC ACC AAC GCC AGC AGC GAG GTG GCC GTG CTG

TAC CAG GAC GTG AAC TGC ACC GAC GTG AGC ACC GCC

ATC CAC GCC GAC CAG CTG ACC CCC GCC TGG CGG ATC

TAC AGC ACC GGC AAC AAC GTG TTC CAG ACC CAG GCC

GGC TGC CTG ATC GGC GCC GAG CAC GTG GAC ACC AGC

TAC GAG TGC GAC ATC CCC ATC GGC GCC GGC ATC TGC

GCC AGC TAC CAC ACC GTG AGC CTG CTG CGG AGC ACC

AGC CAG AAG AGC ATC GTG GCC TAC ACC ATG AGC CTG

GGC

Alternatively, a human codon-optimized coding region which encodes SEQ ID NO:10 can be designed by the "full optimization" method, where each amino acid is assigned codons based on the frequency of usage in the human genome. These frequencies are shown in Table 4 above. Using this latter method, codons are assigned to the coding region encoding SEQ ID NO:10 as follows: about 23 of the 51 phenylalanine codons are TTT, and about 28 of the phenylalanine codons are TTC; about 3 of the 46 leucine codons are TTA, about 6 of the leucine codons are TTG, about 6 of the leucine codons are CTT, about 9 of the leucine codons are CTC, about 4 of the leucine codons are CTA, and about 18 of the leucine codons are CTG; about 13 of the 37 isoleucine codons are ATT, about 18 of the isoleucine codons are ATC, and about 6 of the isoleucine codons are ATA; the 9 methionine codons are ATG; about 10 of the 56 valine codons are GTT, about 26 of the valine codons are GTG, about 7 of the valine codons are GTA, and about 13 of the valine codons are GTC; about 11 of the 58 serine codons are TCT, about 13 of the serine codons are TCC, about 9 of the serine codons are TCA, about 3 of the serine codons are TCG, about 8 of the serine codons are AGT, and about 14 of the serine codons are AGC; about 11 of the 38 proline codons are CCT, about 13 of the proline codons are CCC, about 10 of the proline codons are CCA, and about 4 of the proline codons are CCG; about 14 of the 56 threonine codons are ACT, about 20 of the threonine codons are ACC, about 16 of the threonine codons are ACA, and about 6 of the threonine codons are ACG; about 11 of the 41 alanine codons are GCT, about 16 of the alanine codons are GCC, about 10 of the alanine codons are GCA, and about 4 of the alanine codons are GCG; about 15 of the 35 tyrosine codons are TAT and about 20 of the tyrosine codons are TAC; about 4 of the 9 histidine codons are CAT and about 5 of the histidine codons are CAC; about 5 of the 21 glutamine codons are CAA and about 16 of the glutarnine codons are CAG; about 21 of the 46 asparagine codons are AAT and about 25 of the asparagine codons are AAC; about 14 of the 32 lysine codons are AAA and about 18 of the lysine codons are AAG; about 21 of the 45 aspartic acid codons are GAT and about 24 of the aspartic acid codons are GAC; about 7 of the 17 glutamic acid codons are GAA and about 10 of the glutarnic acid codons are GAG; about 10 of the 23 cysteine codons are TGT and about 13 of the cysteine codons are TGC; the 6 tryptophan codons are TGG; about 2 of the 25 arginine codons are CGT, about 5 of the arginine codons are CGC, about 3 of the arginine codons are CGA, about 5 of the arginine codons are CGG, about 5 of the arginine codons are AGA, and about 5 of the arginine codons are AGG; and about 8 of the 47 glycine codons are GGT, about 16 of the glycine codons are GGC, about 11 of the glycine codons are GGA, and about 12 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO: 10, optimized according to codon usage in humans is presented herein as SEQ ID NO:32.

ATG GAC GCC ATG AAG CGA GGA CTG TGC TGC GTT TTG

TTG CTG TGC GGC GCA GTT TTT GTC AGT CCA TCC GCC

CGG GGG TCG GGA TCT GAC CTA GAT AGA TGC ACG ACC

TTC GAT GAC GTG CAG GCA CCA AAT TAC ACC CAA CAT

ACT TCA TCC ATG CGC GGC GTT TAC TAC CCC GAC GAA

ATC TTC CGG AGT GAC ACC CTG TAT CTG ACT CAG GAC

CTG TTT CTG CCC TTC TAC AGC AAT GTG ACA GGC TTT

CAC ACC ATT AAC CAT ACC TTC GGG AAT CCA GTA ATC

CCT TTT AAG GAT GGG ATT TAC TTT GCT GCT ACT GAG

AAA AGT AAT GTT GTC AGG GGG TGG GTT TTT GGC TCA

ACA ATG AAC AAT AAG TCT CAG AGT GTC ATC ATC ATT

AAC AAT TCT ACC AAT GTA GTC ATC AGA GCA TGC AAC

TTC GAG CTC TGT GAT AAC CCT TTC TTT GCT GTG TCT

AAG CCC ATG GGC ACT CAA ACA CAT ACC ATG ATC TTC

GAC AAT GCG TTC AAT TGT ACC TTT GAG TAT ATA TCA

GAC GCC TTC AGC CTA GAC GTC TCG GAA AAG TCC GGA

AAC TTT AAA CAC CTG CGG GAA TTC GTG TTT AAG AAC

AAA GAT GGA TTT TTG TAC GTA TAC AAG GGT TAT CAG

CCT ATC GAT GTC GTG CGT GAT CTG CCC TCC GGC TTC

AAC ACC CTG AAG CCT ATA TTC AAA CTA CCC CTA GGG

ATC AAC ATC ACC AAT TTT AGG GCA ATA CTT ACG GCA

TTT TCC CCA GCC CAG GAC ATC TGG GGA ACT TCC GCC

GCT GCC TAC TTT GTG GGC TAT CTC AAG CCT ACT ACT

TTC ATG CTT AAG TAT GAT GAG AAT GGC ACA ATC ACG

GAT GCA GTG GAT TGC TCG CAG AAT CCA CTT GCT GAG

CTG AAA TGC TCC GTA AAG AGC TTC GAA ATT GAT AAA

GGA ATC TAT CAG ACC AGC AAC TTC CGG GTC GTG CCC

TCT GGC GAC GTT GTC CGG TTC CCC AAC ATC ACC AAC

CTC TGC CCA TTC GGC GAG GTG TTC AAC GCT ACA AAA

TTC CCA AGT GTC TAC GCC TGG GAG AGG AAA AAG ATC

TCT AAT TGT GTG GCA GAT TAT TCC GTG TTA TAC AAC

AGC ACA TTC TTC TCA ACG TTC AAG TGT TAT GGC GTG

-continued

```
AGC GCC ACC AAG CTT AAC GAC CTC TGC TTC TCC AAT
GTA TAC GCT GAC TCT TTT GTG GTT AAG GGA GAC GAT
GTG CGA CAG ATC GCC CCG GGG CAA ACC GGA GTG ATT
GCG GAC TAC AAC TAT AAA CTG CCC GAC GAT TTC ATG
GGT TGT GTG CTT GCT TGG AAT ACG AGG AAC ATT GAC
GCA ACG AGC ACC GGG AAC TAT AAT TAC AAA TAT CGT
TAC CTG CGC CAT GGG AAA CTC AGA CCT TTT GAA CGA
GAT ATT AGC AAC GTC CCT TTC TCA CCG GAT GGG AAG
CCC TGT ACC CCA CCT GCC CTG AAC TGC TAT TGG CCT
CTC AAC GAC TAC GGC TTC TAC ACT ACC ACA GGG ATC
GGG TAC CAG CCC TAT CGC GTG GTG GTT CTC TCC TTT
GAA CTC CTT AAT GCT CCC GCG ACT GTG TGT GGG CCG
AAG TTG AGT ACT GAC TTA ATA AAA AAT CAA TGC GTA
AAC TTT AAC TTT AAT GGC TTG ACA GGT ACA GGT GTG
CTC ACA CCG AGT AGC AAA AGG TTC CAG CCA TTT CAG
CAA TTT GGC AGA GAT GTG TCT GAC TTT ACA GAC AGC
GTG CGC GAT CCT AAG ACT TCT GAG ATT TTA GAC ATC
TCA CCT TGT TCC TTT GGA GGA GTG AGC GTG ATA ACT
CCC GGT ACC AAC GCC TCA TCC GAA GTG GCT GTC CTG
TAT CAG GAC GTT AAT TGC ACC GAT GTC TCT ACA GCC
ATT CAC GCC GAT CAG CTG ACA CCA GCT TGG CGC ATC
TAC AGT ACC GGT AAC AAT GTT TTC CAG ACT CAG GCC
GGT TGT CTG ATT GGC GCC GAG CAC GTC GAC ACA TCT
TAC GAG TGC GAT ATT CCC ATA GGT GCC GGC ATT TGT
GCG AGC TAC CAC ACT GTA TCA CTG CTG AGA AGC ACA
AGC CAG AAA TCA ATT GTG GCA TAC ACA ATG TCC TTG
GGA GCA
```

In certain embodiments described herein, a codon-optimized coding region encoding SEQ ID NO:12 is optimized according to codon usage in humans (*Homo sapiens*). Alternatively, a codon-optimized coding region encoding SEQ ID NO:12 may be optimized according to codon usage in any plant, animal, or microbial species. Codon-optimized coding regions encoding SEQ ID NO:12, optimized according to codon usage in humans are designed as follows. The amino acid composition of SEQ ID NO:12 is shown in Table 14.

TABLE 14

| AMINO ACID | | Number in SEQ ID NO: 12 |
|---|---|---|
| A | Ala | 46 |
| R | Arg | 18 |
| C | Cys | 13 |
| G | Gly | 34 |
| H | His | 5 |
| I | Ile | 36 |
| L | Leu | 50 |
| K | Lys | 26 |
| M | Met | 12 |
| F | Phe | 29 |
| P | Pro | 20 |
| S | Ser | 38 |
| T | Thr | 38 |
| W | Trp | 4 |
| Y | Tyr | 17 |
| V | Val | 36 |
| N | Asn | 35 |
| D | Asp | 27 |
| Q | Gln | 34 |
| E | Glu | 23 |

Using the amino acid composition shown in Table 14, a human codon-optimized coding region which encodes SEQ ID NO:12 can be designed by any of the methods discussed herein. For "uniform" optimization, each amino acid is assigned the most frequent codon used in the human genome for that amino acid. According to this method, codons are assigned to the coding region encoding SEQ ID NO:12 as follows: the 29 phenylalanine codons are TTC, the 50 leucine codons are CTG, the 36 isoleucine codons are ATC, the 12 methionine codons are ATG, the 36 valine codons are GTG, the 38 serine codons are AGC, the 20 proline codons are CCC, the 38 threonine codons are ACC, the 46 alanine codons are GCC, the 17 tyrosine codons are TAC, the 5 histidine codons are CAC, the 34 glutamine codons are CAG, the 35 asparagine codons are AAC, the 26 lysine codons are AAG, the 35 aspartic acid codons are GAC, the 23 glutamic acid codons are GAG, the 13 cysteine codons are TGC, the 4 tryptophan codon is TGG, the 18 arginine codons are CGG, AGA, or AGG (the frequencies of usage of these three codons in the human genome are not significantly different), and the 34 glycine codons are GGC. The codon-optimized coding region designed by this method is presented herein as SEQ ID NO:35.

```
ATG GAC GCC ATG AAG CGG GGC CTG TGC TGC GTG CTG
CTG CTG TGC GGC GCC GTG TTC GTG AGC CCC AGC GCC
CGG GGC AGC GGC GAC AGC AGC ATC GCC TAC AGC AAC
AAC ACC ATC GCC ATC CCC ACC AAC TTC AGC ATC AGC
ATC ACC ACC GAG GTG ATG CCC GTG AGC ATG GCC AAG
ACC AGC GTG GAC TGC AAC ATG TAC ATC TGC GGC GAC
AGC ACC GAG TGC GCC AAC CTG CTG CTG CAG TAC GGC
AGC TTC TGC ACC CAG CTG AAC CGG GCC CTG AGC GGC
ATC GCC GCC GAG CAG GAC CGG AAC ACC CGG GAG GTG
TTC GCC CAG GTG AAG CAG ATG TAC AAG ACC CCC ACC
CTG AAG TAC TTC GGC GGC TTC AAC TTC AGC CAG ATC
CTG CCC GAC CCC CTG AAG CCC ACC AAG CGG AGC TTC
ATC GAG GAC CTG CTG TTC AAC AAG GTG ACC CTG GCC
GAC GCC GGC TTC ATG AAG CAG TAC GGC GAG TGC CTG
GGC GAC ATC AAC GCC CGG GAC CTG ATC TGC GCC CAG
AAG TTC AAC GGC CTG ACC GTG CTG CCC CCC CTG CTG
```

```
ACC GAC GAC ATG ATC GCC GCC TAC ACC GCC GCC CTG

GTG AGC GGC ACC GCC ACC GCC GGC TGG ACC TTC GGC

GCC GGC GCC GCC CTG CAG ATC CCC TTC GCC ATG CAG

ATG GCC TAC CGG TTC AAC GGC ATC GGC GTG ACC CAG

AAC GTG CTG TAC GAG AAC CAG AAG CAG ATC GCC AAC

CAG TTC AAC AAG GCC ATC AGC CAG ATC CAG GAG AGC

CTG ACC ACC ACC AGC ACC GCC CTG GGC AAG CTG CAG

GAC GTG GTG AAC CAG AAC GCC CAG GCC CTG AAC ACC

CTG GTG AAG CAG CTG AGC AGC AAC TTC GGC GCC ATC

AGC AGC GTG CTG AAC GAC ATC CTG AGC CGG CTG GAC

AAG GTG GAG GCC GAG GTG CAG ATC GAC CGG CTG ATC

ACC GGC CGG CTG CAG AGC CTG CAG ACC TAC GTG ACC

CAG CAG CTG ATC CGG GCC GCC GAG ATC CGG GCC AGC

GCC AAC CTG GCC GCC ACC AAG ATG AGC GAG TGC GTG

CTG GGC CAG AGC AAG CGG GTG GAC TTC TGC GGC AAG

GGC TAC CAC CTG ATG AGC TTC CCC CAG GCC GCC CCC

CAC GGC GTG GTG TTC CTG CAC GTG ACC TAC GTG CCC

AGC CAG GAG CGG AAC TTC ACC ACC GCC CCC GCC ATC

TGC CAC GAG GGC AAG GCC TAC TTC CCC CGG GAG GGC

GTG TTC GTG TTC AAC GGC ACC AGC TGG TTC ATC ACC

CAG CGG AAC TTC TTC AGC CCC CAG ATC ATC ACC ACC

GAC AAC ACC TTC GTG AGC GGC AAC TGC GAC GTG GTG

ATC GGC ATC ATC AAC AAC ACC GTG TAC GAC CCC CTG

CAG CCC GAG CTG GAC AGC TTC AAG GAG GAG CTG GAC

AAG TAC TTC AAG AAC CAC ACC AGC CCC GAC GTG GAC

CTG GGC GAC ATC AGC GGC ATC AAC GCC AGC GTG GTG

AAC ATC CAG AAG GAG ATC GAC CGG CTG AAC GAG GTG

GCC AAG AAC CTG AAC GAG AGC CTG ATC GAC CTG CAG

GAG CTG GGC AAG TAC GAG CAG TAC ATC AAG TGG CCC

TGG
```

Alternatively, a human codon-optimized coding region which encodes SEQ ID NO:12 can be designed by the "full optimization" method, where each amino acid is assigned codons based on the frequency of usage in the human genome. These frequencies are shown in Table 4 above. Using this latter method, codons are assigned to the coding region encoding SEQ ID NO:12 as follows: about 13 of the 29 phenylalanine codons are TTT, and about 16 of the phenylalanine codons are TTC; about 4 of the 50 leucine codons are TTA, about 6 of the leucine codons are TTG, about 6 of the leucine codons are CTT, about 10 of the leucine codons are CTC, about 4 of the leucine codons are CTA, and about 20 of the leucine codons are CTG; about 13 of the 36 isoleucine codons are ATT, about 17 of the isoleucine codons are ATC, and about 6 of the isoleucine codons are ATA; the 12 methionine codons are ATG; about 6 of the 36 valine codons are GTT, about 9 of the valine codons are GTG, about 4 of the valine codons are GTA, and about 17 of the valine codons are GTG; about 7 of the 38 serine codons are TCT, about 8 of the serine codons are TCC, about 6 of the serine codons are TCA, about 2 of the serine codons are TCG, about 6 of the serine codons are AGT, and about 9 of the serine codons are AGC; about 6 of the 20 proline codons are CCT, about 7 of the proline codons are CCC, about 5 of the proline codons are CCA, and about 2 of the proline codons are CCG; about 9 of the 38 threonine codons are ACT, about 14 of the threonine codons are ACC, about 11 of the threonine codons are ACA, and about 4 of the threonine codons are ACG; about 12 of the 46 alanine codons are GCT, about 19 of the alanine codons are GCC, about 10 of the alanine codons are GCA, and about 5 of the alanine codons are GCG; about 7 of the 17 tyrosine codons are TAT and about 10 of the tyrosine codons are TAC; about 2 of the 5 histidine codons are CAT and about 3 of the histidine codons are CAC; about 9 of the 34 glutamine codons are CAA and about 25 of the glutamine codons are CAG; about 16 of the 35 asparagine codons are AAT and about 19 of the asparagine codons are AAC; about 11 of the 26 lysine codons are AAA and about 15 of the lysine codons are AAG; about 12 of the 27 aspartic acid codons are GAT and about 15 of the aspartic acid codons are GAC; about 16 of the 23 glutamic acid codons are GAA and about 13 of the glutamic acid codons are GAG; about 6 of the 13 cysteine codons are TGT and about 7 of the cysteine codons are TGC; the 4 tryptophan codons are TGG; about 1 of the 18 arginine codons are CGT, about 3 of the arginine codons are CGC, about 2 of the arginine codons are CGA, about 4 of the arginine codons are CGG, about 4 of the arginine codons are AGA, and about 4 of the arginine codons are AGG; and about 6 of the 34 glycine codons are GGT, about 12 of the glycine codons are GGC, about 8 of the glycine codons are GGA, and about 8 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:12, optimized according to codon usage in humans is presented herein as SEQ ID NO:34.

```
ATG GAT GCA ATG AAA AGA GGC CTG TGT TGT GTT CTG

CTG CTG TGT GGG GCG GTA TTT GTG AGT CCC TCT GCC

AGG GGA AGC GGC GAC AGC AGT ATA GCC TAC TCA AAC

AAT ACC ATC GCC ATT CCT ACA AAT TTT TCC ATC TCA

ATC ACG ACG GAA GTC ATG CCA GTT AGC ATG GCC AAA

ACC TCT GTC GAC TGC AAC ATG TAC ATC TGC GGA GAC

TCT ACT GAG TGC GCA AAC CTG CTC TTG CAG TAT GGC

TCG TTT TGC ACC CAG TTG AAT CGG GCC CTC AGT GGC

ATT GCC GCA GAA CAA GAT CGG AAT ACC AGG GAG GTC

TTC GCG CAA GTC AAG CAG ATG TAC AAA ACC CCT ACA

CTC AAA TAC TTC GGG GGG TTC AAC TTT AGC CAA ATC

CTG CCA GAC CCC CTC AAG CCT ACT AAG CGC AGT TTT

ATC GAA GAC TTA CTC TTT AAT AAG GTG ACA TTA GCT
```

-continued

GAT GCC GGA TTC ATG AAG CAG TAC GGA GAG TGC CTG
GGG GAT ATC AAC GCG CGG GAC CTA ATC TGT GCC CAG
AAG TTC AAC GGT CTG ACA GTG CTT CCG CCT CTC CTG
ACC GAT GAT ATG ATC GCA GCT TAC ACC GCC GCA CTG
GTT AGT GGT ACG GCC ACA GCA GGC TGG ACC TTC GGT
GCC GGT GCT GCC CTG CAA ATC CCA TTC GCG ATG CAG
ATG GCA TAC AGA TTT AAC GGC ATT GGA GTC ACC CAG
AAT GTC CTA TAC GAG AAC CAG AAG CAA ATC GCT AAC
CAG TTC AAC AAA GCC ATA TCC CAG ATT CAG GAG TCC
CTT ACT ACA ACC AGT ACT GCT TTA GGT AAA CTG CAA
GAT GTA GTG AAC CAG AAC GCT CAG GCC TTA AAT ACC
CTT GTT AAA CAG CTA TCC TCA AAC TTT GGG GCT ATC
TCC TCC GTG CTC AAC GAT ATC CTG AGC CGC CTC GAT
AAG GTG GAA GCG GAG GTC CAG ATC GAT AGA CTT ATT
ACA GGC AGG CTT CAG TCT CTC CAG ACC TAT GTC ACA
CAA CAG CTC ATT CGT GCT GCA GAG ATC CGC GCT TCC
GCC AAC TTG GCT GCA ACA AAG ATG TCT GAA TGT GTG
CTG GGA CAG AGC AAG AGA GTG GAC TTT TGT GGG AAA
GGC TAT CAC TTG ATG AGC TTC CCC CAG GCC GCC CCC
CAT GGA GTG GTA TTC CTA CAC GTG ACG TAC GTT CCA
TCT CAA GAA CGA AAT TTC ACC ACC GCA CCT GCC ATT
TGC CAC GAA GGG AAG GCT TAT TTC CCT CGA GAG GGC
GTG TTC GTT TTT AAC GGG ACT TCA TGG TTT ATA ACT
CAA AGG AAT TTC TTC TCG CCC CAG ATA ATT ACA ACA
GAC AAC ACT TTT GTG AGC GGC AAT TGC GAC GTG GTC
ATA GGT ATT ATT AAT AAT ACT GTG TAT GAC CCG CTG
CAG CCC GAA CTG GAC AGC TTT AAA GAG GAG CTG GAC
AAA TAC TTC AAG AAT CAT ACT TCA CCC GAC GTG GAT
CTG GGC GAC ATA TCC GGA ATC AAT GCC TCT GTG GTA
AAC ATT CAG AAG GAG ATC GAT CGG CTG AAC GAA GTG
GCT AAG AAT CTG AAT GAA TCA TTG ATT GAC CTT CAG
GAG TTG GGC AAG TAT GAG CAG TAT ATT AAA TGG CCA
TGG

Another representative codon-optimized coding region encoding SEQ ID NO:12 is presented herein as SEQ ID NO:47.

ATG GAT GCC ATG AAG CGA GGC CTG TGT TGC GTA CTG
CTG CTG TGC GGC GCC GTG TTT GTG AGC CCC AGC GCC
CGG GGC AGT GGC GAC AGC AGC ATC GCC TAT TCG AAC
AAC ACT ATT GCC ATA CCC ACA AAC TTC TCT ATA TCT

-continued

ATA ACT ACG GAG GTG ATG CCC GTG TCT ATG GCC AAG
ACT AGT GTA GAC TGC AAC ATG TAC ATC TGC GGC GAC
TCT ACT GAG TGC GCC AAC CTG CTG CTG CAG TAT GGC
TCT TTC TGC ACC CAG CTG AAC AGA GCC CTG AGT GGC
ATC GCC GCC GAG CAG GAC CGG AAC ACA AGA GAG GTT
TTC GCC CAG GTA AAG CAG ATG TAC AAG ACC CCC ACT
CTG AAG TAT TTT GGC GGC TTC AAC TTC TCT CAG ATC
CTG CCC GAT CCC CTG AAG CCC ACC AAG AGG TCT TTC
ATC GAG GAC CTG CTG TTC AAC AAG GTC ACT CTG GCC
GAT GCC GGC TTC ATG AAG CAG TAC GGC GAG TGC CTG
GGC GAC ATT AAC GCC CGC GAC CTG ATC TGT GCC CAG
AAG TTT AAC GGC CTG ACG GTC CTG CCC CCC CTG CTG
ACA GAT GAT ATG ATC GCC GCC TAC ACT GCC GCC CTG
GTC TCT GGC ACC GCC ACC GCC GGC TGG ACT TTC GGC
GCC GGC GCC GCC CTG CAG ATC CCC TTC GCC ATG CAG
ATG GCC TAT AGA TTT AAC GGC ATA GGC GTA ACT CAG
AAC GTC CTG TAC GAG AAC CAG AAG CAG ATC GCC AAC
CAG TTT AAC AAG GCC ATC TCC CAG ATT CAG GAG AGC
CTG ACA ACC ACT AGC ACT GCC CTG GGC AAG CTG CAG
GAC GTG GTG AAC CAG AAC GCC CAG GCC CTG AAC ACA
CTG GTT AAG CAG CTG AGT TCT AAC TTT GGC GCC ATA
TCC TCG GTG CTG AAC GAC ATA CTG TCA AGG CTG GAC
AAG GTC GAG GCC GAG GTT CAG ATA GAT AGA CTG ATC
ACA GGC AGA CTG CAG AGC CTG CAG ACC TAC GTT ACA
CAG CAG CTG ATC AGA GCC GCC GAG ATC AGA GCC TCA
GCC AAC CTG GCC GCC ACG AAG ATG TCT GAG TGC GTC
CTG GGC CAG TCT AAG AGA GTC GAT TTC TGC GGC AAG
GGC TAC CAC CTG ATG AGT TTC CCC CAG GCC GCC CCC
CAT GGC GTT GTA TTC CTG CAT GTG ACA TAT GTT CCC
TCC CAG GAG AGG AAC TTT ACC ACG GCC CCC GCC ATC
TGC CAC GAG GGC AAG GCC TAC TTC CCC AGA GAG GGC
GTG TTC GTT TTT AAC GGC ACT AGC TGG TTT ATT ACC
CAG AGG AAC TTC TTC TCC CCC CAG ATT ATA ACA ACA
GAT AAC ACT TTC GTG TCC GGC AAC TGC GAT GTT GTG
ATA GGC ATC ATT AAC AAC ACA GTG TAC GAT CCC CTG
CAG CCC GAG CTG GAT AGT TTT AAG GAG GAG CTG GAC
AAG TAT TTT AAG AAC CAC ACT TCC CCC GAT GTA GAC
CTG GGC GAT ATC AGT GGC ATA AAC GCC AGT GTC GTG
AAC ATA CAG AAG GAG ATC GAT AGG CTG AAC GAG GTG
GCC AAG AAC CTG AAC GAG TCA CTG ATC GAT CTG CAG
GAG CTG GGC AAG TAC GAG CAG TAT ATT AAG TGG CCC

A representative codon-optimized coding region encoding SEQ ID NO:12 according to the "standardized optimization" method is presented herein as SEQ ID NO: 69.

ATG GAT GCC ATG AAG CGC GGC CTG TGC TGT GTG CTG

CTG CTG TGT GGC GCC GTG TTC GTG AGC CCC AGC GCC

CGC GGC AGC GGC GAT AGC AGC ATC GCC TAC AGC AAC

AAC ACC ATC GCC ATC CCC ACC AAC TTC AGC ATC AGC

ATC ACC ACC GAG GTG ATG CCC GTG AGC ATG GCC AAG

ACC AGC GTG GAT TGC AAC ATG TAC ATC TGC GGC GAC

AGC ACC GAG TGC GCC AAC CTG CTG CTG CAG TAC GGC

AGC TTC TGC ACC CAG CTG AAC CGC GCC CTG AGC GGC

ATC GCC GCC GAG CAG GAC CGC AAC ACC CGC GAG GTG

TTC GCC CAG GTG AAG CAG ATG TAC AAG ACC CCC ACC

CTG AAG TAC TTC GGC GGC TTC AAC TTC AGC CAG ATC

CTG CCC GAC CCC CTG AAG CCC ACC AAG CGC AGC TTC

ATC GAG GAT CTG CTG TTC AAC AAG GTG ACC CTG GCC

GAC GCC GGC TTC ATG AAG CAG TAC GGC GAG TGC CTG

GGC GAC ATC AAC GCC CGC GAC CTG ATC TGC GCC GAC

AAG TTC AAC GGC CTG ACC GTG CTG CCC CCC CTG CTG

ACC GAT GAC ATG ATC GCC GCC TAC ACC GCC GCC CTG

GTG AGC GGC ACC GCC ACC GCC GGC TGG ACC TTC GGC

GCC GGC GCC GCC CTG CAG ATC CCC TTC GCC ATG CAG

ATG GCC TAC CGC TTC AAC GGC ATC GGC GTG ACC CAG

AAC GTG CTG TAC GAG AAC CAG AAG CAG ATC GCC AAC

CAG TTC AAC AAG GCC ATC AGC CAG ATC CAG GAG AGC

CTG ACC ACC ACC AGC ACC GCC CTG GGC AAG CTG CAG

GAT GTG GTG AAC CAG AAC GCC CAG GCC CTG AAC ACC

CTG GTG AAG CAG CTG AGC AGC AAC TTC GGC GCC ATC

AGC AGC GTG CTG AAC GAT ATC CTG AGC CGC CTG GAT

AAG GTG GAG GCC GAG GTG CAG ATC GAC CGC CTG ATC

ACC GGC CGC CTG CAG AGC CTG CAG ACC TAC GTG ACC

CAG CAG CTG ATC CGC GCC GCC GAG ATC CGC GCC AGC

GCC AAC CTG GCC GCC ACC AAG ATG AGC GAG TGC GTG

CTG GGC CAG AGC AAG CGC GTG GAT TTC TGC GGC AAG

GGC TAC CAC CTG ATG AGC TTC CCC CAG GCC GCC CCC

CAC GGC GTG GTG TTC CTG CAT GTG ACC TAC GTG CCC

AGC CAG GAG CGC AAC TTC ACC ACC GCC CCC GCC ATC

TGC CAC GAG GGC AAG GCC TAC TTC CCC CGC GAG GGC

GTG TTC GTG TTC AAC GGC ACC AGC TGG TTC ATC ACC

CAG CGC AAC TTC TTC AGC CCC CAG ATC ATC ACC ACC

GAC AAC ACC TTC GTG AGC GGC AAC TGC GAC GTG GTG

-continued

ATC GGC ATC ATC AAC AAC ACC GTG TAC GAT CCC CTG

CAG CCC GAG CTG GAT AGC TTC AAG GAG GAG CTG GAC

AAG TAC TTC AAG AAC CAT ACC AGC CCC GAT GTG GAT

CTG GGC GAC ATC AGC GGC ATC AAC GCC AGC GTG GTG

AAC ATC CAG AAG GAG ATC GAT CGC CTG AAC GAG GTG

GCC AAG AAC CTG AAC GAG AGC CTG ATC GAT CTG CAG

GAG CTG GGC AAG TAC GAG CAG TAC ATC AAG TGG CCC

TGG

In certain embodiments described herein, a codon-optimized coding region encoding SEQ ID NO:14 is optimized according to codon usage in humans (*Homo sapiens*). Alternatively, a codon-optimized coding region encoding SEQ ID NO:14 may be optimized according to codon usage in any plant, animal, or microbial species. Codon-optimized coding regions encoding SEQ ID NO:14, optimized according to codon usage in humans are designed as follows. The amino acid composition of SEQ ID NO:14 is shown in Table 15.

TABLE 15

| AMINO ACID | | Number in SEQ ID NO: 14 |
|---|---|---|
| A | Ala | 34 |
| R | Arg | 31 |
| C | Cys | 0 |
| G | Gly | 45 |
| H | His | 5 |
| I | Ile | 11 |
| L | Leu | 26 |
| K | Lys | 29 |
| M | Met | 7 |
| F | Phe | 13 |
| P | Pro | 31 |
| S | Ser | 35 |
| T | Thr | 33 |
| W | Trp | 5 |
| Y | Tyr | 11 |
| V | Val | 11 |
| N | Asn | 25 |
| D | Asp | 22 |
| Q | Gln | 34 |
| E | Glu | 14 |

Using the amino acid composition shown in Table 15, a human codon-optimized coding region which encodes SEQ ID NO:14 can be designed by any of the methods discussed herein. For "uniform" optimization, each amino acid is assigned the most frequent codon used in the human genome for that amino acid. According to this method, codons are assigned to the coding region encoding SEQ ID NO:14 as follows: the 13 phenylalanine codons are TTC, the 26 leucine codons are CTG, the 11 isoleucine codons are ATC, the 7 methionine codons are ATG, the 11 valine codons are GTG, the 35 serine codons are AGC, the 31 proline codons are CCC, the 33 threonine codons are ACC, the 34 alanine codons are GCC, the 11 tyrosine codons are TAC, the 5 histidine codons are CAC, the 34 glutamine codons are CAG, the 25 asparagine codons are AAC, the 29 lysine codons are AAG, the 22 aspartic acid codons are GAC, the 14 glutamic acid codons are GAG, the 5 tryptophan codons are TGG, the 31 arginine codons are CGG, AGA, or AGG (the frequencies of usage of these three codons in the human genome are not significantly different), and the 45 glycine codons are GGC. The codon-optimized N coding region designed by this method is presented herein as SEQ ID NO:37.

```
ATGAGCGACAACGGCCCCCAGAGCAACCAGAGAAGCGCCCGCAGAATCAC

CTTCGGCGGCCCCACCGACAGCACCGACAACAACCAGAACGGCGGCAGAA

ACGGCGCCAGACCCAAGCAGAGAAGACCCCAGGGCCTGCCCAACAACACC

GCCAGCTGGTTCACCGCCCTGACCCAGCACGGCAAGGAGGAGCTGAGATT

CCCCAGAGGCCAGGGCGTGCCCATCAACACCAACAGCGGCCCCGACGACC

AGATCGGCTACTACAGAAGAGCCACCAGAAGAGTGAGAGGCGGCGACGGC

AAGATGAAGGAGCTGAGCCCCAGATGGTACTTCTACTACCTGGGCACCGG

CCCCGAGGCCAGCCTGCCCTACGGCGCCAACAAGGAGGGCATCGTGTGGG

TGGCCACCGAGGGCGCCCTGAACACCCCCAAGGACCACATCGGCACCAGA

AACCCCAACAACAACGCCGCCACCGTGCTGCAGCTGCCCCAGGGCACCAC

CCTGCCCAAGGGCTTCTACGCCGAGGGCAGCAGAGGCGGCAGCCAGGCCA

GCAGCAGAAGCAGCAGCAGAAGCAGAGGCAACAGCAGAAACAGCACCCCC

GGCAGCAGCAGAGGCAACAGCCCCGCCAGAATGGCCAGCGGCGGCGGCGA

GACCGCCCTGGCCCTGCTGCTGCTGGACAGACTGAACCAGCTGGAGAGCA

AGGTGAGCGGCAAGGGCCAGCAGCAGCAGGGCCAGACCGTGACCAAGAAG

AGCGCCGCCGAGGCCAGCAAGAAGCCCAGACAGAAGAGAACCGCCACCAA

GCAGTACAACGTGACCCAGGCCTTCGGCAGAAGAGGCCCCGAGCAGACCC

AGGGCAACTTCGGCGACCAGGACCTGATCAGACAGGGCACCGACTACAAG

CACTGGCCCCAGATCGCCCAGTTCGCCCCCAGCGCCAGCGCCTTCTTCGG

CATGAGCAGAATCGGCATGGAGGTGACCCCCAGCGGCACCTGGCTGACCT

ACCACGGCGCCATCAAGCTGGACGACAAGGACCCCCAGTTCAAGGACAAC

GTGATCCTGCTGAACAAGCACATCGACGCCTACAAGACCTTCCCCCCCAC

CGAGCCCAAGAAGGACAAGAAGAAGAAGACCGACGAGGCCCAGCCCCTGC

CCCAGAGACAGAAGAAGCAGCCCACCGTGACCCTGCTGCCCGCCGCCGAC

ATGGACGACTTCAGCAGACAGCTGCAGAACAGCATGAGCGGCGCCAGCGC

CGACAGCACCCAGGCC
```

Alternatively, a human codon-optimized coding region which encodes SEQ ID NO:14 can be designed by the "full optimization" method, where each amino acid is assigned codons based on the frequency of usage in the human genome. These frequencies are shown in Table 4 above. Using this latter method, codons are assigned to the coding region encoding SEQ ID NO:14 as follows: about 4 of the 13 phenylalanine codons are TTT, and about 9 of the phenylalanine codons are TTC; about 1 of the 26 leucine codons are TTA, about 6 of the leucine codons are TTG, about 7 of the leucine codons are CTT, about 3 of the leucine codons are CTC, about 5 of the leucine codons are CTA, and about 4 of the leucine codons are CTG; about 7 of the 11 isoleucine codons are ATT, about 3 of the isoleucine codons are ATC, and about 1 of the isoleucine codons are ATA; the 7 methionine codons are ATG; about 4 of the 11 valine codons are GTT, about 4 of the valine codons are GTC, about 1 of the valine codons is GTA, and about 2 of the valine codons are GTG; about 10 of the 35 serine codons are TCT, about 3 of the serine codons are TCC, about 9 of the serine codons are TCA, about 1 of the serine codons is TCG, about 7 of the serine codons are AGT, and about 5 of the serine codons are AGC; about 10 of the 31 proline codons are CCT, about 9 of the proline codons are CCC, about 10 of the proline codons are CCA, and about 2 of the proline codons are CCG; about 17 of the 33 threonine codons are ACT, about 5 of the threonine codons are ACC, about 11 of the threonine codons are ACA, and about 0 of the threonine codons is ACG; about 14 of the 34 alanine codons are GCT, about 8 of the alanine codons are GCC, about 9 of the alanine codons are GCA, and about 3 of the alanine codons are GCG; about 2 of the 11 tyrosine codons are TAT and about 9 of the tyrosine codons are TAC; about 3 of the 5 histidine codons are CAT and about 2 of the histidine codons are CAC; about 24 of the 34 glutamine codons are CAA and about 10 of the glutamine codons are CAG; about 16 of the 25 asparagine codons are AAT and about 9 of the asparagine codons are AAC; about 20 of the 29 lysine codons are AAA and about 9 of the lysine codons are AAG; about 10 of the 22 aspartic acid codons are GAT and about 12 of the aspartic acid codons are GAC; about 7 of the 14 glutamic acid codons are GAA and about 7 of the glutamic acid codons are GAG; the 5 tryptophan codons are TGG; about 5 of the 31 arginine codons are CGT, about 8 of the arginine codons are CGC, about 6 of the arginine codons are CGA, about 0 of the arginine codons are CGG, about 10 of the arginine codons are AGA, and about 2 of the arginine codons are AGG; and about 10 of the 45 glycine codons are GGT, about 16 of the glycine codons are GGC, about 16 of the glycine codons are GGA, and about 3 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:14, optimized according to codon usage in humans is presented herein as SEQ ID NO:36.

```
ATG TCC GAT AAT GGT CCC CAG TCT AAC CAG AGG TCG

GCG CCA AGA ATC ACA TTC GGG GGC CCA ACA GAC AGT

ACC GAT AAC AAC CAG AAC GGC GGA AGA AAC GGG GCC

AGG CCC AAG CAG CGG AGA CCT CAG GGA TTA CCA AAT

AAT ACC GCA AGC TGG TTC ACA GCC CTG ACC CAG CAT

GGA AAA GAG GAA CTG AGA TTC CCT AGA GGA CAA GGG

GTG CCT ATT AAT ACT AAT AGC GGG CCT GAC GAT CAA

ATT GGC TAT TAT CGA CGT GCG ACT CGC CGT GTT AGA

GGG GGG GAC GGG AAG ATG AAG GAG CTT AGC CCA CGC

TGG TAC TTT TAC TAT CTG GGA ACC GGA CCT GAA GCT

AGT CTG CCC TAC GGC GCT AAC AAG GAG GGA ATA GTA

TGG GTC GCC ACG GAA GGT GCG TTG AAT ACT CCG AAA

GAT CAC ATC GGC ACC AGA AAT CCT AAC AAT AAC GCC

GCA ACC GTG CTA CAA TTA CCC CAG GGA ACT ACT CTG

CCG AAG GGG TTC TAT GCG GAG GGA AGC CGC GGC GGC

TCA CAA GCC AGT TCA CGC TCC AGC TCC CGG TCG AGG

GGT AAT TCC CGA AAC AGC ACC CCG GGA TCA TCT AGG

GGA AAC TCT CCC GCC CGG ATG GCC TCA GGC GGC GGC
```

-continued

GAA ACA GCT CTG GCT CTG CTA TTG CTG GAC CGG CTC

AAC CAG CTC GAG TCC AAA GTC TCT GGT AAA GGT CAG

CAG CAG CAG GGT CAA ACA GTG ACC AAA AAA AGT GCA

GCC GAG GCC AGC AAG AAA CCA CGC CAG AAA CGT ACG

GCC ACA AAG CAA TAC AAT GTG ACC CAA GCC TTT GGA

AGG CGG GGG CCC GAA CAG ACA CAG GGC AAT TTC GGC

GAT CAA GAT TTG ATA CGA CAG GGC ACT GAC TAC AAA

CAC TGG CCG CAG ATC GCT CAG TTT GCA CCT AGC GCC

TCC GCT TTC TTT GGC ATG AGT CGG ATT GGC ATG GAG

GTG ACA CCA TCA GGT ACT TGG TTA ACG TAC CAC GGG

GCA ATC AAA CTT GAT GAT AAA GAT CCC CAG TTT AAG

GAC AAC GTT ATC CTC CTG AAT AAG CAT ATT GAC GCC

TAT AAG ACC TTC CCC CCA ACC GAA CCA AAG AAG GAC

AAG AAG AAG AAG ACA GAC GAG GCA CAG CCT CTC CCC

CAG AGG CAG AAA AAG CAG CCT ACT GTC ACC CTT CTG

CCC GCT GCA GAC ATG GAT GAC TTT TCC CGC CAA CTC

CAG AAC TCT ATG AGT GGG GCT TCC GCT GAC TCT ACG

CAG GCC TGA

Another representative codon-optimized coding region encoding SEQ ID NO:14 is presented herein as SEQ ID NO:63. SEQ ID NO:14 is encoded by nucleotides 7 to 1275 of SEQ ID NO:63.

GTCGACATGAGCGACAACGGCCCCCAGAGCAACCAGAGAAGCGCCCCCAG

AATCACCTTTGGCGGCCCTACCGACAGCACCGACAACAACCAGAACGGCG

GCAGAAACGGCGCCAGACCCAAGCAGAGGAGACCCCAGGGCCTGCCCAAC

AACACCGCCAGCTGGTTCACCGCCCTCACCCAGCACGGCAAGGAGGAGCT

GAGATTCCCCAGAGGCCAGGGCGTGCCCATCAATACCAACAGCGGCCCAG

ACGATCAGATCGGCTACTACCGGAGGGCCACCAGAAGAGTGAGAGGCGGC

GACGGCAAGATGAAGGAGCTGAGCCCCCGGTGGTACTTCTACTACCTGGG

CACCGGCCCTGAGGCCAGCCTGCCCTACGGCGCCAACAAGGAGGGCATCG

TGTGGGTGGCCACCGAGGGCGCCCTGAATACCCCCAAGGACCACATCGGC

ACCAGGAACCCCAACAACAATGCCGCCACCGTGCTGCAGCTGCCCCAGGG

CACCACCCTGCCCAAGGGCTTCTACGCCGAGGGCAGCAGAGGCGGCAGCC

AGGCCAGCAGCAGAAGCAGCAGCAGGAGCAGGGGCAACAGCAGAAATAGC

ACCCCCGGCAGCAGCAGAGGAAATTCACCCGCCAGAATGGCCAGCGGCGG

AGGCGAGACCGCCCTGGCCCTGCTGCTCCTGGACAGGCTGAATCAGCTGG

AGAGCAAGGTGAGCGGCAAGGGCCAGCAACAGCAGGGACAGACCGTGACC

AAGAAGTCTGCCGCCGAGGCCAGCAAGAAGCCCAGGCAGAAGAGAACCGC

CACCAAGCAGTACAATGTGACCCAGGCCTTCGGCAGAAGAGGCCCCGAGC

AGACCCAGGGCAATTTCGGCGACCAGGACCTCATCAGACAGGGCACCGAC

-continued

TACAAGCACTGGCCTCAGATCGCCCAGTTCGCCCCCAGCGCCAGCGCCTT

CTTCGGCATGAGCCGGATCGGCATGGAGGTGACCCCCAGCGGCACCTGGC

TCACCTACCACGGCGCCATCAAGCTGGACGACAAGGACCCCCAGTTCAAG

GACAACGTGATCCTGCTGAACAAGCACATCGACGCCTACAAGACCTTCCC

ACCCACCGAGCCCAAGAAGGACAAGAAGAAGAAAACCGACGAGGCCCAGC

CCCTGCCCCAGAGACAGAAGAAGCAGCCCACCGTGACCCTGCTGCCTGCC

GCCGACATGGACGACTTCAGCCGCCAGCTGCAGAATAGCATGAGCGGCGC

CTCTGCCGATTCAACCCAGGCCTGAAGATCT

In certain embodiments described herein, a codon-optimized coding region encoding SEQ ID NO:16 is optimized according to codon usage in humans (*Homo sapiens*). Alternatively, a codon-optimized coding region encoding SEQ ID NO:16 may be optimized according to codon usage in any plant, animal, or microbial species. Codon-optimized coding regions encoding SEQ ID NO:16, optimized according to codon usage in humans are designed as follows. The amino acid composition of SEQ ID NO:16 is shown in Table 16.

TABLE 16

| AMINO ACID | | Number in SEQ ID NO: 16 |
|---|---|---|
| A | Ala | 33 |
| R | Arg | 31 |
| C | Cys | 0 |
| G | Gly | 45 |
| H | His | 5 |
| I | Ile | 11 |
| L | Leu | 26 |
| K | Lys | 22 |
| M | Met | 7 |
| F | Phe | 12 |
| P | Pro | 28 |
| S | Ser | 35 |
| T | Thr | 30 |
| W | Trp | 5 |
| Y | Tyr | 11 |
| V | Val | 11 |
| N | Asn | 25 |
| D | Asp | 20 |
| Q | Gln | 33 |
| E | Glu | 12 |

Using the amino acid composition shown in Table 16, a human codon-optimized coding region which encodes SEQ ID NO:16 can be designed by any of the methods discussed herein. For "uniform" optimization, each amino acid is assigned the most frequent codon used in the human genome for that amino acid. According to this method, codons are assigned to the coding region encoding SEQ ID NO:16 as follows: the 12 phenylalanine codons are TTC, the 26 leucine codons are CTG, the 11 isoleucine codons are ATC, the 7 methionine codons are ATG, the 11 valine codons are GTG, the 35 serine codons are AGC, the 28 proline codons are CCC, the 30 threonine codons are ACC, the 33 alanine codons are GCC, the 11 tyrosine codons are TAC, the 5 histidine codons are CAC, the 33 glutamine codons are CAG, the 25 asparagine codons are AAC, the 22 lysine codons are AAG, the 20 aspartic acid codons are GAC, the 12 glutamic acid codons are GAG, the 5 tryptophan codons are TGG, the 31 arginine codons are CGG, AGA, or AGG (the frequencies of usage of these three codons in the human genome are not significantly different), and the 45 glycine codons are GGC. The codon-optimized N (minus NLS) coding region designed by this method is presented herein as SEQ ID NO:39.

ATGAGCGACAACGGCCCCCAGAGCAACCAGAGAAGCGCCCCCAGAATCAC
CTTCGGCGGCCCCACCGACAGCACCGACAACAACCAGAACGGCGGCAGAA
ACGGCGCCAGACCCAAGCAGAGAAGACCCCAGGGCCTGCCCAACAACACC
GCCAGCTGGTTCACCGCCCTGACCCAGCACGGCAAGGAGGAGCTGAGATT
CCCCAGAGGCCAGGGCGTGCCCATCAACACCAACAGCGGCCCCGACGACC
AGATCGGCTACTACAGAAGAGCCACCAGAAGAGTGAGAGGCGGCGACGGC
AAGATGAAGGAGCTGAGCCCCAGATGGTACTTCTACTACCTGGGCACCGG
CCCCGAGGCCAGCCTGCCCTACGGCGCCAACAAGGAGGGCATCGTGTGGG
TGGCCACCGAGGGCGCCCTGAACACCCCCAAGGACCACATCGGCACCAGA
AACCCCAACAACAACGCCGCCACCGTGCTGCAGCTGCCCCAGGGCACCAC
CCTGCCCAAGGGCTTCTACGCCGAGGGCAGCAGAGGCGGCAGCCAGGCCA
GCAGCAGAAGCAGCAGCAGAAGCAGAGGCAACAGCAGAAACAGCACCCCC
GGCAGCAGCAGAGGCAACAGCCCCGCCAGAATGGCCAGCGGCGGCGGCGA
GACCGCCCTGGCCCTGCTGCTGCTGGACAGACTGAACCAGCTGGAGAGCA
AGGTGAGCGGCAAGGGCCAGCAGCAGCAGGGCCAGACCGTGACCAAGAAG
AGCGCCGCCGAGGCCAGCAAGAAGCCCAGACAGAAGAGAACCGCCACCAA
GCAGTACAACGTGACCCAGGCCTTCGGCAGAAGAGGCCCCGAGCAGACCC
AGGGCAACTTCGGCGACCAGGACCTGATCAGACAGGGCACCGACTACAAG
CACTGGCCCCAGATCGCCCAGTTCGCCCCCAGCGCCAGCGCCTTCTTCGG
CATGAGCAGAATCGGCATGGAGGTGACCCCCAGCGGCACCTGGCTGACCT
ACCACGGCGCCATCAAGCTGGACGACAAGGACCCCCAGTTCAAGGACAAC
GTGATCCTGCTGAACAAGCACATCGACGCCTACCCCCTGCCCCAGAGACA
GAAGAAGCAGCCCACCGTGACCCTGCTGCCCGCCGCCGACATGGACGACT
TCAGCAGACAGCTGCAGAACAGCATGAGCGGCGCCAGCGCCGACAGCACC
CAGGCC

Alternatively, a human codon-optimized coding region which encodes SEQ ID NO:16 can be designed by the "full optimization" method, where each amino acid is assigned codons based on the frequency of usage in the human genome. These frequencies are shown in Table 4 above. Using this latter method, codons are assigned to the coding region encoding SEQ ID NO:16 as follows: about 5 of the 12 phenylalanine codons are TTT, and about 7 of the phenylalanine codons are TTC; about 3 of the 26 leucine codons are TTA, about 3 of the leucine codons are TTG, about 3 of the leucine codons are CTT, about 5 of the leucine codons are CTC, about 2 of the leucine codons are CTA, and about 10 of the leucine codons are CTG; about 4 of the 11 isoleucine codons are ATT, about 5 of the isoleucine codons are ATC, and about 2 of the isoleucine codons are ATA; the 7 methionine codons are ATG; about 2 of the 11 valine codons are GTT, about 3 of the valine codons are GTC, about 1 of the valine codons is GTA, and about 5 of the valine codons are GTG; about 6 of the 35 serine codons are TCT, about 8 of the serine codons are TCC, about 5 of the serine codons are TCA, about 2 of the serine codons are TCG, about 6 of the serine codons are AGT, and about 8 of the serine codons are AGC; about 8 of the 28 proline codons are CCT, about 9 of the proline codons are CCC, about 8 of the proline codons are CCA, and about 3 of the proline codons are CCG; about 7 of the 30 threonine codons are ACT, about 11 of the threonine codons are ACC, about 9 of the threonine codons are ACA, and about 3 of the threonine codons are ACG; about 9 of the 33 alanine codons are GCT, about 13 of the alanine codons are GCC, about 7 of the alanine codons are GCA, and about 4 of the alanine codons are GCG; about 5 of the 11 tyrosine codons are TAT and about 6 of the tyrosine codons are TAC; about 2 of the 5 histidine codons are CAT and about 3 of the histidine codons are CAC; about 9 of the 33 glutamine codons are CAA and about 24 of the glutarnine codons are CAG; about 12 of the 25 asparagine codons are AAT and about 13 of the asparagine codons are AAC; about 9 of the 22 lysine codons are AAA and about 13 of the lysine codons are AAG; about 9 of the 20 aspartic acid codons are GAT and about 11 of the aspartic acid codons are GAC; about 5 of the 12 glutamic acid codons are GAA and about 7 of the glutamic acid codons are GAG; the 5 tryptophan codons are TGG; about 3 of the 31 arginine codons are CGT, about 6 of the arginine codons are CGC, about 3 of the arginine codons are CGA, about 6 of the arginine codons are CGG, about 7 of the arginine codons are AGA, and about 6 of the arginine codons are AGG; and about 7 of the 45 glycine codons are GGT, about 15 of the glycine codons are GGC, about 12 of the glycine codons are GGA, and about 11 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:16, optimized according to codon usage in humans is presented herein as SEQ ID NO:38.

ATG AGT GAT AAT GGC CCC CAG TCT AAC CAG AGG AGC
GCA CCG CGG ATC ACG TTC GGT GGC CCA ACC GAC TCA
ACA GAC AAT AAT CAG AAC GGA GGA CGC AAT GGT GCA
CGT CCT AAG CAG AGA CGC CCC CAA GGG CTG CCT AAT
AAT ACA GCA AGT TGG TTT ACC GCA CTC ACA CAA CAT
GGA AAG GAA GAG TTG CGG TTC CCC CGC GGC CAG GGC
GTG CCC ATC AAC ACA AAT AGC GGA CCC GAC GAT CAG
ATC GGA TAT TAC CGA AGA GCT ACA AGG AGA GTT CGC
GGC GGG GAT GGC AAG ATG AAG GAG CTA TCA CCA CGA
TGG TAC TTC TAT TAC CTC GGG ACA GGC CCA GAG GCC
TCG CTA CCA TAC GGG GCC AAC AAG GAG GGT ATT GTC
TGG GTC GCT ACC GAA GGG GCC CTG AAT ACA CCT AAA
GAC CAC ATA GGT ACC AGA AAT CCC AAC AAT AAC GCC
GCG ACC GTG TTA CAG CTT CCT CAG GGA ACG ACC CTT
CCA AAA GGG TTT TAC GCC GAA GGA TCT CGG GGA GGG
TCA CAG GCT AGC TCC CGT AGC TCC TCA AGG TCC AGG
GGG AAT TCT AGA AAC AGT ACA CCC GGC TCT AGC CGT
GGT AAC TCC CCA GCT CGC ATG GCA TCC GGC GGA GGG
GAA ACC GCT CTG GCT CTG CTC CTG TTA GAT CGG TTG

-continued

```
AAC CAA CTG GAA TCG AAG GTA TCC GGA AAG GGA CAG
CAG CAG CAA GGC CAG ACT GTG ACT AAG AAG TCC GCG
GCC GAG GCC AGT AAG AAA CCC CGC CAG AAA CGA ACT
GCC ACC AAA CAG TAT AAT GTG ACA CAG GCC TTC GGC
AGA CGG GGT CCA GAG CAG ACC CAA GGC AAC TTC GGG
GAT CAG GAC CTG ATT CGG CAG GGT ACC GAC TAT AAG
CAC TGG CCG CAA ATT GCT CAG TTT GCT CCC AGT GCG
AGT GCC TTC TTC GGC ATG TCT AGG ATC GGG ATG GAG
GTT ACT CCT AGC GGC ACT TGG CTT ACT TAT CAC GGA
GCC ATC AAA CTC GAT GAT AAG GAC CCA CAG TTT AAG
GAT AAC GTG ATT CTG CTG AAC AAA CAT ATA GAC GCG
TAC CCT CTC CCG CAA AGG CAG AAA AAA CAG CCT ACC
GTC ACG TTA CTG CCT GCC GCA GAC ATG GAC GAC TTT
TCT AGA CAG TTG CAA AAC AGC ATG TCA GGC GCA TCC
GCC GAT AGC ACT CAA GCT TGA
```

In certain embodiments described herein, a codon-optimized coding region encoding SEQ ID NO:19 is optimized according to codon usage in humans (*Homo sapiens*). Alternatively, a codon-optimized coding region encoding SEQ ID NO:19 may be optimized according to codon usage in any plant, animal, or microbial species. Codon-optimized coding regions encoding SEQ ID NO:19, optimized according to codon usage in humans are designed as follows. The amino acid composition of SEQ ID NO:19 is shown in Table 17.

TABLE 17

| AMINO ACID | | Number in SEQ ID NO: 19 |
|---|---|---|
| A | Ala | 19 |
| R | Arg | 15 |
| C | Cys | 3 |
| G | Gly | 15 |
| H | His | 3 |
| I | Ile | 18 |
| L | Leu | 31 |
| K | Lys | 6 |
| M | Met | 7 |
| F | Phe | 11 |
| P | Pro | 6 |
| S | Ser | 11 |
| T | Thr | 13 |
| W | Trp | 7 |
| Y | Tyr | 9 |
| V | Val | 16 |
| N | Asn | 13 |
| D | Asp | 6 |
| Q | Gln | 5 |
| E | Glu | 7 |

Using the amino acid composition shown in Table 17, a human codon-optimized coding region which encodes SEQ ID NO:19 can be designed by any of the methods discussed herein. For "uniform" optimization, each amino acid is assigned the most frequent codon used in the human genome for that amino acid. According to this method, codons are assigned to the coding region encoding SEQ ID NO:19 as follows: the 11 phenylalanine codons are TTC, the 31 leucine codons are CTG, the 18 isoleucine codons are ATC, the 7 methionine codons are ATG, the 16 valine codons are GTG, the 11 serine codons are AGC, the 6 proline codons are CCC, the 13 threonine codons are ACC, the 19 alanine codons are GCC, the 19 tyrosine codons are TAC, the 3 histidine codons are CAC, the 5 glutamine codons are CAG, the 13 asparagine codons are AAC, the 6 lysine codons are AAG, the 6 aspartic acid codons are GAC, the 7 glutamic acid codons are GAG, the 3 cysteine codons are TGC, the 7 tryptophan codons are TGG, the 15 arginine codons are CGG, AGA, or AGG (the frequencies of usage of these three codons in the human genome are not significantly different), and the 43 glycine codons are GGC. The codon-optimized M coding region designed by this method is presented herein as SEQ ID NO:41.

```
ATGGCCGACAACGGCACCATCACCGTGGAGGAGCTGAAGCAGCTGCTGGA
GCAGTGGAACCTGGTGATCGGCTTCCTGTTCCTGGCCTGGATCATGCTGC
TGCAGTTCGCCTACAGCAACAGAAACAGATTCCTGTACATCATCAAGCTG
GTGTTCCTGTGGCTGCTGTGGCCCGTGACCCTGGCCTGCTTCGTGCTGGC
CGCCGTGTACAGAATCAACTGGGTGACCGGCGGCATCGCCATCGCCATGG
CCTGCATCGTGGGCCTGATGTGGCTGAGCTACTTCGTGGCCAGCTTCAGA
CTGTTCGCCAGAACCAGAAGCATGTGGAGCTTCAACCCCGAGACCAACAT
CCTGCTGAACGTGCCCCTGAGAGGCACCATCGTGACCAGACCCCTGATGG
AGAGCGAGCTGGTGATCGGCGCCGTGATCATCAGAGGCCACCTGAGAATG
GCCGGCCACCCCCTGGGCAGATGCGACATCAAGGACCTGCCCAAGGAGAT
CACCGTGGCCACCAGCAGAACCCTGAGCTACTACAAGCTGGGCGCCAGCC
AGAGAGTGGGCACCGACAGCGGCTTCGCCGCCTACAACAGATACAGAATC
GGCAACTACAAGCTGAACACCGACCACGCCGGCAGCAACGACAACATCGC
CCTGCTGGTGCAG
```

Alternatively, a human codon-optimized coding region which encodes SEQ ID NO:19 can be designed by the "full optimization" method, where each amino acid is assigned codons based on the frequency of usage in the human genome. These frequencies are shown in Table 4 above. Using this latter method, codons are assigned to the coding region encoding SEQ ID NO:19 as follows: about 5 of the 11 phenylalanine codons are TTT, and about 6 of the phenylalanine codons are TTC; about 3 of the 31 leucine codons are TTA, about 4 of the leucine codons are TTG, about 4 of the leucine codons are CTT, about 6 of the leucine codons are CTC, about 2 of the leucine codons are CTA, and about 12 of the leucine codons are CTG; about 6 of the 18 isoleucine codons are ATT, about 9 of the isoleucine codons are ATC, and about 3 of the isoleucine codons are ATA; the 7 methionine codons are ATG; about 3 of the 16 valine codons are GTT, about 4 of the valine codons are GTC, about 2 of the valine codons are GTA, and about 7 of the valine codons are GTG; about 2 of the 11 serine codons are TCT, about 2 of the serine codons are TCC, about 2 of the serine codons are TCA, about 1 of the serine codons is TCG, about 1 of the serine codons is AGT, and about 3 of the serine codons are AGC; about 2 of the 6 proline codons are CCT, about 2 of the proline codons are CCC, about 1 of the proline codons is CCA, and about 1 of the proline codons is CCG; about 3 of the 13 threonine codons are ACT, about 5 of the threonine codons are ACC, about 4 of the threonine codons are ACA, and about 1 of the threonine codons is ACG; about 5 of the 19 alanine codons are GCT, about 8 of the alanine codons are GCC, about 4 of the alanine codons are GCA, and about 2 of the alanine codons are GCG; about 4 of the 9 tyrosine codons are TAT and about 5 of the tyrosine codons are TAC; about 1 of the 3 histidine codons is CAT and about 2 of the histidine codons are CAC; about 1 of the 5 glutamine codons is CAA and about 4 of the glutamine codons are CAG; about 6 of the 13 asparagine codons are AAT and about 7 of the asparagine codons are AAC; about 3 of the 6 lysine codons are AAA and about 3 of the lysine codons are AAG; about 3 of the 6 aspartic acid codons are GAT and about 3 of the aspartic acid codons are GAC; about 3 of the 7 glutamic acid codons are GAA and about 4 of the glutamic acid codons are GAG; about 1 of the 3 cysteine codons is TGT and about 2 of the cysteine codons are TGC; the 7 tryptophan codons are TGG; about 1 of the 15 arginine codons is CGT, about 3 of the arginine codons are CGC, about 2 of the arginine codons are CGA, about 3 of the arginine codons are CGG, about 3 of the arginine codons are AGA, and about 3 of the arginine codons are AGG; and about 2 of the 15 glycine codons are GGT, about 5 of the glycine codons are GGC, about 4 of the glycine codons are GGA, and about 4 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative "fully optimized" codon-optimized coding region encoding SEQ ID NO:19, optimized according to codon usage in humans is presented herein as SEQ ID NO:40.

```
ATG GCT GAC AAC GGC ACC ATA ACC GTC GAG GAG CTT

AAA CAG TTA TTA GAA CAA TGG AAC TTG GTG ATA GGA

TTC CTC TTT CTG GCA TGG ATC ATG TTG CTT CAG TTC

GCC TAT TCT AAC CGC AAT AGG TTT TTG TAC ATT ATC

AAG CTG GTC TTC CTT TGG CTG CTC TGG CCC GTA ACA

CTA GCC TGT TTT GTT TTG GCG GCC GTG TAT CGG ATC

AAT TGG GTG ACA GGT GGC ATT GCT ATT GCG ATG GCT

TGC ATC GTG GGG CTG ATG TGG CTG TCG TAT TTC GTT

GCC TCA TTC CGG CTG TTT GCC CGA ACA AGG AGT ATG

TGG TCT TTT AAC CCC GAG ACC AAT ATT CTG CTC AAT

GTG CCT TTA CGC GGC ACT ATC GTG ACC CGG CCT CTA

ATG GAA TCC GAG CTG GTA ATT GGC GCA GTC ATC ATA

AGG GGG CAC CTC AGA ATG GCC GGG CAC CCA CTT GGG

AGA TGC GAC ATC AAG GAT CTG CCG AAG GAA ATT ACT

GTT GCA ACT TCA CGA ACG CTG AGC TAT TAC AAA CTG

GGA GCT AGC CAG AGA GTG GGT ACC GAC TCC GGC TTC

GCT GCC TAC AAC CGC TAC CGT ATC GGA AAT TAC AAA

CTC AAC ACA GAT CAT GCA GGA AGC AAT GAT AAC ATC

GCC CTC CTG GTC CAG TGA
```

In certain embodiments described herein, a codon-optimized coding region encoding SEQ ID NO:21 is optimized according to codon usage in humans (*Homo sapiens*). Alternatively, a codon-optimized coding region encoding SEQ ID NO:21 may be optimized according to codon usage in any plant, animal, or microbial species. Codon-optimized coding regions encoding SEQ ID NO:21, optimized according to codon usage in humans are designed as follows. The amino acid composition of SEQ ID NO:21 is shown in Table 18.

TABLE 18

| AMINO ACID | | Number in SEQ ID NO: 21 |
|---|---|---|
| A | Ala | 4 |
| R | Arg | 2 |
| C | Cys | 3 |
| G | Gly | 2 |
| H | His | 0 |
| I | Ile | 3 |
| L | Leu | 14 |
| K | Lys | 2 |
| M | Met | 1 |
| F | Phe | 4 |
| P | Pro | 2 |
| S | Ser | 7 |
| T | Thr | 5 |
| W | Trp | 0 |
| Y | Tyr | 4 |
| V | Val | 14 |
| N | Asn | 5 |
| D | Asp | 1 |
| Q | Gln | 0 |
| E | Glu | 3 |

Using the amino acid composition shown in Table 18, a human codon-optimized coding region which encodes SEQ ID NO:21 can be designed by any of the methods discussed herein. For "uniform" optimization, each amino acid is assigned the most frequent codon used in the human genome for that amino acid. According to this method, codons are assigned to the coding region encoding SEQ ID NO:21 as follows: the 4 phenylalanine codons are TTC, the 14 leucine codons are CTG, the 18 isoleucine codons are 3, the 1 methionine codon is ATG, the 14 valine codons are GTG, the 7 serine codons are AGC, the 2 proline codons are CCC, the 5 threonine codons are ACC, the 4 alanine codons are GCC, the 4 tyrosine codons are TAC, the 5 asparagine codons are AAC, the 2 lysine codons are AAG, the 1 aspartic acid codon is GAC, the 3 glutamic acid codons are GAG, the 3 cysteine codons are TGC, the 1 tryptophan codon is TGG, the 2 arginine codons are CGG, AGA, or AGG (the frequencies of usage of these three codons in the human genome are not significantly different), and the 2 glycine codons are GGC. The codon-optimized E coding region designed by this method is presented herein as SEQ ID NO:43.

```
ATG TAC AGC TTC GTG AGC GAG GAG ACC GGC ACC CTG

ATC GTG AAC AGC GTG CTG CTG TTC CTG GCC TTC GTG

GTG TTC CTG CTG GTG ACC CTG GCC ATC CTG ACC GCC

CTG CGG CTG TGC GCC TAC TGC TGC AAC ATC GTG AAC

GTG AGC CTG GTG AAG CCC ACC GTG TAC GTG TAC AGC

CGG GTG AAG AAC CTG AAC AGC AGC GAG GGC GTG CCC

GAC CTG CTG GTG TGA
```

Alternatively, a human codon-optimized coding region which encodes SEQ ID NO:21 can be designed by an optimization method, where each amino acid is assigned codons based on the frequency of usage in the human genome. These frequencies are shown in Table 4 above. Using this latter method, codons are assigned to the coding region encoding SEQ ID NO:21 as follows: about 1 of the 4 phenylalanine codons are TTT, and about 3 of the phenylalanine codons are TTC; about 2 of the 14 leucine codons are TTA, about 2 of the leucine codons are TTG, about 6 of the leucine codons are CTT, about 0 of the leucine codons are CTC, about 2 of the leucine codons are CTA, and about 2 of the leucine codons are CTG; about 1 of the 3 isoleucine codons are ATT, about 1 of the isoleucine codons are ATC, and about 1 of the isoleucine codons are ATA; the 1 methionine codons are ATG; about 6 of the 14 valine codons are GTT, about 3 of the valine codons are GTC, about 3 of the valine codons are GTA, and about 2 of the valine codons are GTG; about 2 of the 7 serine codons are TCT, about 0 of the serine codons are TCC, about 1 of the serine codons are TCA, about 2 of the serine codons is TCG, about 1 of the serine codons is AGT, and about 1 of the serine codons are AGC; about 1 of the 2 proline codons are CCT, about 0 of the proline codons are CCC, about 1 of the proline codons is CCA, and about 0 of the proline codons is CCG; about 1 of the 5 threonine codons are ACT, about 0 of the threonine codons are ACC, about 2 of the threonine codons are ACA, and about 2 of the threonine codons is ACG; about 1 of the 4 alanine codons are GCT, about 1 of the alanine codons are GCC, about 0 of the alanine codons are GCA, and about 2 of the alanine codons are GCG; about 0 of the 4 tyrosine codons are TAT and about 4 of the tyrosine codons are TAC; about 3 of the 5 asparagine codons are AAT and about 2 of the asparagine codons are AAC; about 2 of the 2 lysine codons are AAA and about 0 of the lysine codons are AAG; about 1 of the 1 aspartic acid codons are GAT and about 0 of the aspartic acid codons are GAC; about 3 of the 3 glutamic acid codons are GAA and about 0 of the glutamic acid codons are GAG; about 1 of the 3 cysteine codons is TGT and about 2 of the cysteine codons are TGC; about 1 of the 2 arginine codons is CGT, about 0 of the arginine codons are CGC, about 1 of the arginine codons are CGA, about 0 of the arginine codons are CGG, about 0 of the arginine codons are AGA, and about 0 of the arginine codons are AGG; and about 1 of the 2 glycine codons are GGT, about 0 of the glycine codons are GGC, about 1 of the glycine codons are GGA, and about 0 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

A representative fully codon-optimized coding region encoding SEQ ID NO:21, optimized according to codon usage in humans is presented herein as SEQ ID NO:42.

```
ATG TAC AGC TTT GTG TCT GAA GAA ACA GGA ACG TTG

ATA GTT AAT AGT GTT TTG CTT TTC TTA GCG TTC GTA

GTC TTC CTT CTT GTC ACA CTT GCC ATT TTA ACT GCG

CTT CGT CTA TGC GCT TAC TGT TGC AAT ATC GTA AAC
```

-continued

```
GTG TCG CTT GTT AAA CCA ACG GTT TAC GTA TAC TCG

CGA GTT AAA AAC CTG AAT TCT TCA GAA GGT GTT CCT

GAT CTG CTA GTC TAA
```

Another representative codon-optimized coding region encoding SEQ ID NO:21 is presented herein as SEQ ID NO:48.

```
ATG TAT AGT TTT GTG AGT GAG GAG ACG GGC ACC CTG

ATT GTC AAC TCA GTG CTG CTG TTC CTG GCC TTT GTT

GTC TTC CTG CTG GTA ACT CTG GCC ATC CTG ACT GCC

CTG AGA CTG TGC GCC TAC TGC TGC AAC ATC GTG AAC

GTC TCT CTG GTA AAG CCC ACA GTT TAC GTG TAT TCT

AGG GTG AAG AAC CTG AAC TCC AGC GAG GGC GTT CCC

GAT CTG CTG GTA TGA
```

Randomly assigning codons at an optimized frequency to encode a given polypeptide sequence using the "uniform optimization," "full optimization," "minimal optimization," or other optimization methods, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, WI, the backtranslation function in the VectorNTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences. For example, the "backtranslation" function found on the Entelechon website at www.entelechon.com/eng/backtranslation.html (visited Jul. 9, 2002), and the "backtranseq" function available on the Institute of Pasteur website at bioinfo.pbi.nrc.ca:8090/EMBOSS/index.html (visited Oct. 15, 2002). Constructing a rudimentary algorithm to assign codons based on a given frequency can also easily be accomplished with basic mathematical functions by one of ordinary skill in the art.

A number of options are available for synthesizing codon-optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

The codon-optimized coding regions can be versions encoding any gene products from any strain, derivative, or variant of SARS-CoV, or fragments, variants, or derivatives of such gene products. For example, nucleic acid fragments of codon-optimized coding regions encoding the S, N, E or M polypeptides, or fragments, variants or derivatives thereof. Codon-optimized coding regions encoding other SARS-CoV polypeptides or fragments, variants, or derivatives thereof (e.g., those encoding certain predicted open reading frames in the SARS-CoV genome), are included within the present invention. Additional, non-codon-optimized polynucleotides encoding SARS-CoV polypeptides or other polypeptides may be included as well.

Compositions and Methods

In certain embodiments, the present invention is directed to compositions and methods of raising a detectable immune in a vertebrate by administering in vivo, into a tissue of a vertebrate, one or more polynucleotides comprising at least one wild-type coding region encoding a SARS-CoV polypeptide, or a fragment, variant, or derivative thereof, and/or at least one codon-optimized coding region encoding a SARS-CoV polypeptide, or a fragment, variant, or derivative thereof. In addition, the present invention is directed to compositions and methods of raising a detectable immune response in a vertebrate by administering to the vertebrate a composition comprising one or more polynucleotides as described herein, and at least one isolated SARS-CoV component, or isolated polypeptide. The SARS-CoV component may be inactivated virus, attenuated virus, a viral vector expressing an isolated SARS-CoV polypeptide, or a SARS-CoV virus protein, fragment, variant or derivative thereof.

The polynucleotides comprising at least one coding region encoding a SARS-CoV polypeptide, or a fragment, variant, or derivative thereof, and/or at least one codon-optimized coding region encoding a SARS-CoV polypeptide may be administered either prior to, at the same time (simultaneously), or subsequent to the administration of the SARS-CoV component, or isolated polypeptide.

The SARS-CoV component, or isolated polypeptide in combination with polynucleotides comprising at least one coding region encoding a SARS-CoV polypeptide, or a fragment, variant, or derivative thereof, and/or at least one codon-optimized coding region encoding a SARS-CoV polypeptide compositions may be referred to as "combinatorial polynucleotide vaccine compositions" or "single formulation heterologous prime-boost vaccine compositions."

The isolated SARS-CoV polypeptides of the invention may be in any form, and are generated using techniques well known in the art. Examples include isolated SARS-CoV proteins produced recombinantly, isolated SARS-CoV proteins directly purified from their natural milieu, recombinant (non-SARS-COV) virus vectors expressing an isolated SARS-CoV protein, or proteins delivered in the form of an inactivated SARS-CoV vaccine, such as conventional vaccines.

When utilized, an isolated SARS-CoV component, or polypeptide or fragment, variant or derivative thereof is administered in an immunologically effective amount. Canine coronavirus, known to infect swine, turkeys, mice, calves, dogs, cats, rodents, avians and humans, may be administered as a live viral vector vaccine at a dose rate per dog of $10^5$-$10^8$ pfu, or as a typical subunit vaccine at 10 ug-1 mg of polypeptide, according to U.S. Pat. No. 5,661,006, incorporated by reference herein in its entirety. Similarly, Bovine coronavirus is administered to animals in an antigen vaccine composition at dose of about 1 to about 100 micrograms of subunit antigen, according to U.S. Pat. No. 5,369,026, incorporated by reference herein in its entirety. The effective amount of SARS-CoV component or isolated polypeptide, and polynucleotides as described herein are determinable by one of ordinary skill in the art based upon several factors, including the antigen being expressed, the age and weight of the subject, and the precise condition requiring treatment and its severity, and route of administration.

In the instant invention, the combination of conventional antigen vaccine compositions with the polynucleotides comprising at least one coding region encoding a SARS-CoV polypeptide, or a fragment, variant, or derivative thereof, and/or at least one codon-optimized coding region encoding a SARS-CoV polypeptide compositions provides for therapeutically beneficial effects at dose sparing concentrations. For example, immunological responses sufficient for a therapeutically beneficial effect in patients predetermined for an approved commercial product, such as for the typical animal coronavirus products described above, may be attained by using less of the product when supplemented or enhanced with the appropriate amount of polynucleotides comprising at least one coding region encoding a SARS-CoV or codon-optimized nucleic acid. Thus, dose sparing is contemplated by administration of conventional coronavirus vaccines administered in combination with the nucleic acids of the invention.

In particular, the dose of an antigen SARS-CoV vaccine may be reduced by at least 5%, at least 10%, at least 20%, at least 30%, at least 40%, at least 50%, at least 60% or at least 70% when administered in combination with the nucleic acid compositions of the invention.

Similarly, a desirable level of an immunological response afforded by a DNA-based pharmaceutical alone may be attained with less DNA by including an aliquot of antigen SARS-CoV vaccine. Further, using a combination of conventional and DNA-based pharmaceuticals may allow both materials to be used in lesser amounts, while still affording the desired level of immune response arising from administration of either component alone in higher amounts (e.g., one may use less of either immunological product when they are used in combination). This may be manifest not only by using lower amounts of materials being delivered at any time, but also to leads to reducing the number of administrations in a vaccination regime (e.g., 2 versus 3 or 4 injections), and/or to reducing the kinetics of the immunological response (e.g., desired response levels are attained in 3 weeks instead of 6 weeks after immunization).

In particular, the dose of DNA-based pharmaceuticals, may be reduced by at least 5%, at least 10%, at least 20%, at least 30%, at least 40%, at least 50%, at least 60% or at least 70% when administered in combination with antigen SARS-CoV vaccines.

Determining the precise amounts of DNA based pharmaceutical and SARS-CoV antigen is based on a number of factors as described above, and is readily determined by one of ordinary skill in the art.

In addition to dose sparing, the claimed combinatorial compositions provide for a broadening of the immune response and/or enhanced beneficial immune responses. Such broadened or enhanced immune responses are achieved by: adding DNA to enhance cellular responses to a conventional vaccine; adding a conventional vaccine to a DNA pharmaceutical to enhance humoral response; using a combination that induces additional epitopes (both humoral and/or cellular) to be recognized and/or responded to in a more desirable way (epitope broadening); employing a DNA-conventional vaccine combination designed for a particular desired spectrum of immunological responses; and/or obtaining a desirable spectrum by using higher amounts of either component. The broadened immune response is measurable by one of ordinary skill in the art by standard immunological assays specific for the desirable response spectrum.

Both broadening and dose sparing may be obtained simultaneously.

In addition, the present invention is directed to compositions and methods of raising a detectable immune response in a vertebrate by administering to the vertebrate a composition comprising one or more SARS-CoV polynucleotides as described herein. The compositions of the invention may comprise at least 1, at least 2, at least 3, at least 4, at least 5, at least 6, at least 7, at least 8, at least 9, at least 10 polynucleotides, as described herein, encoding different SARS-CoV polypeptides or fragments, variants or derivatives thereof in the same composition.

The coding regions encoding SARS-CoV polypeptides or fragments, variants, or derivatives thereof may be codon optimized for a particular vertebrate. Codon optimization is carried out by the methods described herein; for example, in certain embodiments codon-optimized coding regions encoding polypeptides of SARS-CoV, or nucleic acid fragments of such coding regions encoding fragments, variants, or derivatives thereof are optimized according to the codon usage of the particular vertebrate. The polynucleotides of the invention are incorporated into the cells of the vertebrate in vivo, and an immunologically effective amount of a SARS-CoV polypeptide or a fragment, variant, or derivative thereof is produced in vivo. The coding regions encoding a SARS-CoV polypeptide or a fragment, variant, or derivative thereof may be codon optimized for mammals, e.g., humans, apes, monkeys (e.g., owl, squirrel, cebus, rhesus, African green, patas, cynomolgus, and cercopithecus), orangutans, baboons, gibbons, and chimpanzees, dogs, wolves, cats, lions, and tigers, horses, donkeys, zebras, cows, pigs, sheep, deer, giraffes, bears, rabbits, mice, ferrets, seals, whales; birds, e.g., ducks, geese, terns, shearwaters, gulls, turkeys, chickens, quail, pheasants, geese, starlings and budgerigars; or other vertebrates.

In particular, the present invention relates to codon-optimized coding regions encoding polypeptides of SARS-CoV, or fragments, variants, or derivatives thereof, or nucleic acid fragments of such coding regions or fragments, variants, or derivatives thereof, which have been optimized according to human codon usage. For example, human codon-optimized coding regions encoding polypeptides of SARS-CoV, or fragments, variants, or derivatives thereof are prepared by substituting one or more codons preferred for use in human genes for the codons naturally used in the DNA sequence encoding the SARS-CoV polypeptide or a fragment, variant, or derivative thereof. Also provided are polynucleotides, vectors, and other expression constructs comprising wild-type coding regions or codon-optimized coding regions encoding polypeptides of SARS-CoV, or nucleic acid fragments of such wild-type coding regions or codon-optimized coding regions including variants, or derivatives thereof. Also provided are pharmaceutical compositions comprising polynucleotides, vectors, and other expression constructs comprising wild-type coding regions or codon-optimized coding regions encoding polypeptides of SARS-CoV, or nucleic acid fragments of such coding regions encoding variants, or derivatives thereof; and various methods of using such polynucleotides, vectors and other expression constructs. Coding regions encoding SARS-CoV polypeptides may be uniformly optimized, fully optimized, or minimally optimized, or otherwise optimized, as described herein.

The present invention is further directed towards polynucleotides comprising coding regions or codon-optimized coding regions encoding polypeptides of SARS-CoV antigens, for example, (predicted ORF's), optionally in conjunction with other antigens. The invention is also directed to polynucleotides comprising nucleic acid fragments or codon-optimized nucleic acid fragments encoding fragments, variants and derivatives of these polypeptides.

In certain embodiments, the present invention provides an isolated polynucleotide comprising a nucleic acid fragment, where the nucleic acid fragment is a fragment of a coding region or a codon optimized coding region encoding a polypeptide at least 60%, 65%, 70%, 75%, 80%, 85%, 86%, 87%, 88%, 89%, 90%, 91%, 92%, 93%, 94%, 95%, 96%, 97%, 98%, or 99% identical to a SARS-CoV polypeptide, e.g., S, N, E or M, and where the nucleic acid fragment is a variant of a coding region or a codon optimized coding region encoding an SARS-CoV polypeptide, e.g., S, N, E or M. The human codon-optimized coding region can be optimized for any vertebrate species and by any of the methods described herein.

As a practical matter, whether any particular nucleic acid molecule or polypeptide is at least 80%, 85%, 90%, 95%, 96%, 97%, 98% or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237-245 (1990)). In a sequence alignment the query and subject sequences are both DNA sequences. An RNA sequence can be compared by converting U's to T's. The result of said global sequence alignment is expressed as percent identity. Preferred parameters used in a FASTDB alignment of DNA sequences to calculate percent identity are: Matrix=Unitary, k-tuple=4, Mismatch Penalty=1, Joining, Penalty=30 Randomization Group Length=0, Cutoff Score=1, Gap Penalty=5, Gap Size Penalty 0.05, Window Size=500 or the length of the subject nucleotide sequence, whichever is shorter.

Isolated SARS-CoV Polypeptides

The present invention is further drawn to compositions which include at least one polynucleotide comprising one or more nucleic acid fragments, where each nucleic acid fragment is a fragment of a coding region or a codon-optimized coding region operably encoding an SARS-CoV polypeptide or fragment, variant, or derivative thereof; together with and one or more isolated SARS-CoV, components, polypeptides or fragments, variants or derivatives thereof, i.e., “combinatorial polynucleotide vaccine compositions” or “single formulation heterologous prime-boost vaccine compositions.” The isolated SARS-CoV polypeptides of the invention may be in any form, and are generated using techniques well known in the art. Examples include isolated SARS-CoV proteins produced recombinantly, isolated SARS-CoV proteins directly purified from their natural milieu, and recombinant (non-SARS-CoV) virus vectors expressing an isolated SARS-CoV protein.

Similarly, the isolated SARS-CoV polypeptide or fragment, variant, or derivative thereof to be delivered (either a recombinant protein, a purified subunit, or viral vector expressing an isolated SARS-CoV polypeptide) may be any isolated SARS-CoV polypeptide or fragment, variant, or derivative thereof, including but not limited to the S, S1, S2, N, E or M proteins or fragments, variants or derivatives thereof. Fragments include, but are not limited to the soluble portion of the S protein and the S1 and S2 domains of the S protein. In certain embodiments, a derivative protein may be a fusion protein. It should be noted that any isolated SARS-CoV polypeptide or fragment, variant, or derivative thereof described herein may be combined in a composition with any polynucleotide comprising a nucleic acid fragment, where the nucleic acid fragment is a fragment of a coding region or a codon-optimized coding region operably encoding a SARS-CoV polypeptide or fragment, variant, or derivative thereof. The proteins may be different, the same, or may be combined in any combination of one or more isolated SARS-CoV proteins and one or more polynucleotides.

In certain embodiments, the isolated SARS-CoV polypeptides, or fragments, derivatives or variants thereof may be fused to or conjugated to a second isolated SARS-CoV polypeptide, or fragment, derivative or variant thereof, or may be fused to other heterologous proteins, including for example, hepatitis B proteins including, but not limited to the hepatitis B core antigen (HBcAg), or those derived from diphtheria or tetanus. The second isolated SARS-CoV polypeptide or other heterologous protein may act as a "carrier" that potentiates the immunogenicity of the SARS-CoV polypeptide or a fragment, variant, or derivative thereof to which it is attached. Hepatitis B virus proteins and fragments and variants thereof useful as carriers within the scope of the invention are disclosed in U.S. Pat. Nos. 6,231,864 and 5,143,726, incorporated by reference in their entireties. Polynucleotides comprising coding regions encoding said fused or conjugated proteins are also within the scope of the invention.

Methods and Administration

The present invention also provides methods for delivering a SARS-CoV polypeptide or a fragment, variant, or derivative thereof to a human, which comprise administering to a human one or more of the polynucleotide compositions described herein such that upon administration of polynucleotide compositions such as those described herein, a SARS-CoV polypeptide or a fragment, variant, or derivative thereof is expressed in human cells, in an amount sufficient to generate an immune response to SARS-CoV; or administering the SARS-CoV polypeptide or a fragment, variant, or derivative thereof itself to the human in an amount sufficient to generate an immune response.

The present invention further provides methods for delivering a SARS-CoV polypeptide or a fragment, variant, or derivative thereof to a human, which comprise administering to a vertebrate one or more of the compositions described herein; such that upon administration of compositions such as those described herein, an immune response is generated in the vertebrate.

The term "vertebrate" is intended to encompass a singular "vertebrate" as well as plural "vertebrates" and comprises mammals and birds, as well as fish, reptiles, and amphibians.

The term "mammal" is intended to encompass a singular "mammal" and plural "mammals," and includes, but is not limited to humans; primates such as apes, monkeys (e.g., owl, squirrel, cebus, rhesus, African green, patas, cynomolgus, and cercopithecus), orangutans, baboons, gibbons, and chimpanzees; canids such as dogs and wolves; felids such as cats, lions, and tigers; equines such as horses, donkeys, and zebras, food animals such as cows, pigs, and sheep; ungulates such as deer and giraffes; ursids such as bears; and others such as rabbits, mice, ferrets, seals, whales. In particular, the mammal can be a human subject, a food animal or a companion animal.

The term "bird" is intended to encompass a singular "bird" and plural "birds," and includes, but is not limited to feral water birds such as ducks, geese, terns, shearwaters, and gulls; as well as domestic avian species such as turkeys, chickens, quail, pheasants, geese, and ducks. The term "bird" also encompasses passerine birds such as starlings and budgerigars.

The present invention further provides a method for generating, enhancing or modulating an immune response to SARS-CoV comprising administering to a vertebrate one or more of the compositions described herein. In this method, the compositions may include one or more isolated polynucleotides comprising at least one nucleic acid fragment where the nucleic acid fragment is a fragment of a coding region or a codon-optimized coding region encoding an SARS-CoV polypeptide, or a fragment, variant, or derivative thereof. In another embodiment, the compositions may include multiple (e.g., 2, 3, 4, 5, 6, 7, 8, 9, or 10) polynucleotides as described herein, such polynucleotides encoding different SARS CoV polypeptides in the same composition.

In another embodiment, the compositions may include both a polynucleotide as described above; and also an isolated SARS-CoV polypeptide, or a fragment, variant, or derivative thereof, wherein the protein is provided as a recombinant protein, in particular, a fusion protein, a purified subunit, viral vector expressing the protein, or inactivated virus. Thus, the latter compositions include both a polynucleotide encoding a SARS-CoV polypeptide or a fragment, variant, or derivative thereof and an isolated SARS-CoV polypeptide or a fragment, variant, or derivative thereof. The SARS-CoV polypeptide or a fragment, variant, or derivative thereof encoded by the polynucleotide of the compositions need not be the same as the isolated SARS-CoV polypeptide or a fragment, variant, or derivative thereof of the compositions. Compositions to be used according to this method may be univalent, bivalent, trivalent or multivalent.

The polynucleotides of the compositions may comprise a fragment of a coding region or a human (or other vertebrate) codon-optimized coding region encoding a protein of SARS-CoV, or a fragment, variant, or derivative thereof. The polynucleotides are incorporated into the cells of the vertebrate in vivo, and an antigenic amount of the SARS-CoV polypeptide, or fragment, variant, or derivative thereof, is produced in vivo. Upon administration of the composition according to this method, the SARS-CoV polypeptide or a fragment, variant, or derivative thereof is expressed in the vertebrate in an amount sufficient to elicit an immune response. Such an immune response might be used, for example, to generate antibodies to the SARS-CoV for use in diagnostic assays or as laboratory reagents, or as therapeutic or preventative vaccines as described herein.

The present invention further provides a method for generating, enhancing, or modulating a protective and/or therapeutic immune response to SARS-CoV in a vertebrate, comprising administering to a vertebrate in need of therapeutic and/or preventative immunity one or more of the compositions described herein. In this method, the compositions include one or more polynucleotides comprising at least one nucleic acid fragment, where the nucleic acid fragment is a fragment of a wild-type coding region or a codon-optimized coding region encoding a SARS-CoV polypeptide, or a fragment, variant, or derivative thereof. In a further embodiment, the composition used in this method includes both an isolated polynucleotide comprising at least one nucleic acid fragment, where the nucleic acid fragment is a fragment of a wild-type coding region or a codon-optimized coding region encoding a SARS-CoV polypeptide, or a fragment, variant, or derivative thereof; and at least one isolated SARS-CoV polypeptide, or a fragment, variant, or derivative thereof. Thus, the latter composition includes both an isolated polynucleotide encoding a SARS-CoV polypeptide or a fragment, variant, or derivative thereof and an isolated SARS-CoV polypeptide or a fragment, variant, or derivative thereof, for example, a recombinant protein, a purified subunit, or viral vector expressing the protein. Upon administration of the composition according to this method, the SARS-CoV polypeptide or a fragment, variant, or derivative thereof is expressed in the vertebrate in a therapeutically or prophylactically effective amount.

In certain embodiments, the polynucleotide or polypeptide compositions of the present invention may be administered to a vertebrate where the vertebrate is used as an in vivo model to observe the effects of individual or multiple SARS-CoV polypeptides in vivo. This approach would not only eliminate the species specific barrier to studying SARS-CoV, but would allow for the study of the immunopathology of SARS-CoV polypeptides as well as SARS-CoV polypeptide specific effects with out using infectious SARS-CoV virus. An in vivo vertebrate model of SARS infection would be useful, for example, in developing treatments for one or more aspects of SARS infection by mimicking those aspects of infection without the potential hazards associated with handling the infectious virus As used herein, an "immune response" refers to the ability of a vertebrate to elicit an immune reaction to a composition delivered to that vertebrate. Examples of immune responses include an antibody response or a cellular, e.g., T-cell, response. One or more compositions of the present invention may be used to prevent SARS-CoV infection in vertebrates, e.g., as a prophylactic or prevenative vaccine (also sometimes referred to in the art as a "protective" vaccine), to establish or enhance immunity to SARS-CoV in a healthy individual prior to exposure to SARS-CoV or contraction of Severe Acute Respiratory Syndrome (SARS), thus preventing the syndrome or reducing the severity of SARS symptoms. As used herein, "a detectable immune response" refers to an immunogenic response to the polynucleotides and polypeptides of the present invention, which can be measured or observed by standard protocols. These protocols include, but are not limited to, immunoblot analysis (western), fluorescence-activated cell sorting (FACS), immunoprecipitation analysis, ELISA, cytolytic T-cell response, ELISPOT, and chromium release assay. An immune response may also be "detected" through challenge of immunized animals with virulent SARS-CoV, either before or after vaccination. ELISA assays are performed as described by Ausubel et al., *Current Protocols in Molecular Biology*, John Wiley and Sons, Baltimore, Md. (1989). Cytolytic T-cell responses are measured as described in Hartikka et al. "Vaxfectin Enhances the Humoral Response to Plasmid DNA-encoded Antigens." *Vaccine* 19: 1911-1923 (2001), which is hereby incorporated in its entirety by reference. Standard ELISPOT technology is used for the CD4+ and CD8+ T-cell assays as described in Example 6A. Standard chromium release assays are used to measure specific cytotoxic T lymphocyte (CTL) activity against the various SARS-CoV antigens.

As mentioned above, compositions of the present invention may be used both to prevent SARS-CoV infection, and also to therapeutically treat SARS-CoV infection. In individuals already exposed to SARS-CoV, or already suffering from SARS, the present invention is used to further stimulate the immune system of the vertebrate, thus reducing or eliminating the symptoms associated with that disease or disorder. As defined herein, "treatment " refers to the use of one or more compositions of the present invention to prevent, cure, retard, or reduce the severity of SARS symptoms in a vertebrate, and/or result in no worsening of SARS over a specified period of time in a vertebrate which has already been exposed to SARS-CoV and is thus in need of therapy. The term "prevention" refers to the use of one or more compositions of the present invention to generate immunity in a vertebrate which has not yet been exposed to a particular strain of SARS-CoV, thereby preventing or reducing disease symptoms if the vertebrate is later exposed to the particular strain of SARS-CoV. The methods of the present invention therefore may be referred to as therapeutic vaccination or preventative or prophylactic vaccination. It is not required that any composition of the present invention provide total immunity to SARS-CoV or totally cure or eliminate all SARS symptoms. As used herein, a "vertebrate in need of therapeutic and/or preventative immunity" refers to an individual for whom it is desirable to treat, i.e., to prevent, cure, retard, or reduce the severity of SARS symptoms, and/or result in no worsening of SARS over a specified period of time. Vertebrates to treat and/or vaccinate include humans, apes, monkeys (e.g., owl, squirrel, cebus, rhesus, African green, patas, cynomolgus, and cercopithecus), orangutans, baboons, gibbons, and chimpanzees, dogs, wolves, cats, lions, and tigers, horses, donkeys, zebras, cows, pigs, sheep, deer, giraffes, bears, rabbits, mice, ferrets, seals, whales, ducks, geese, terns, shearwaters, gulls, turkeys, chickens, quail, pheasants, geese, starlings and budgerigars.

One or more compositions of the present invention are utilized in a "prime boost" regimen. An example of a "prime boost" regimen may be found in Yang, Z. et al. *J. Virol.* 77:799-803 (2002). In these embodiments, one or more polynucleotide vaccine compositions of the present invention are delivered to a vertebrate, thereby priming the immune response of the vertebrate to SARS-CoV, and then a second immunogenic composition is utilized as a boost vaccination. One or more compositions of the present invention are used to prime immunity, and then a second immunogenic composition, e.g., a recombinant viral vaccine or vaccines, a different polynucleotide vaccine, or one or more purified subunit isolated SARS-CoV polypeptides or fragments, variants or derivatives thereof is used to boost the anti-SARS-CoV immune response.

In one embodiment, a priming composition and a boosting composition are delivered to a vertebrate in separate doses and vaccinations. For example, a single composition may comprise one or more polynucleotides encoding SARS-CoV protein(s), fragment(s), variant(s), or derivative(s) thereof and/or one or more isolated SARS-CoV polypeptide(s) or fragment(s), variant(s), or derivative(s) thereof as the priming component. The polynucleotides encoding the SARS-CoV polypeptides fragments, variants, or derivatives thereof may be contained in a single plasmid or viral vector or in multiple plasmids or viral vectors. At least one polynucleotide encoding a SARS-CoV protein and/or one or more SARS-CoV isolated polypeptide can serve as the boosting component. In this embodiment, the compositions of the priming component and the compositions of the boosting component may be contained in separate vials. In one example, the boosting component is administered approximately 1 to 6 months after administration of the priming component.

In one embodiment, a priming composition and a boosting composition are combined in a single composition or single formulation. For example, a single composition may comprise an isolated SARS-CoV polypeptide or a fragment, variant, or derivative thereof as the priming component and a polynucleotide encoding an SARS-CoV protein as the boosting component. In this embodiment, the compositions may be contained in a single vial where the priming component and boosting component are mixed together. In general, because the peak levels of expression of protein from the polynucleotide does not occur until later (e.g., 7-10 days) after administration, the polynucleotide component may provide a boost to the isolated protein component. Compositions comprising both a priming component and a boosting component are referred to herein as "combinatorial vaccine compositions" or "single formulation heterologous prime-boost vaccine compositions." In addition, the priming composition may be administered before the boosting composition, or even after the boosting composition, if the boosting composition is expected to take longer to act.

In another embodiment, the priming composition may be administered simultaneously with the boosting composition, but in separate formulations where the priming component and the boosting component are separated.

The terms "priming" or "primary" and "boost" or "boosting" as used herein may refer to the initial and subsequent immunizations, respectively, i.e., in accordance with the definitions these terms normally have in immunology. However, in certain embodiments, e.g., where the priming component and boosting component are in a single formulation, initial and subsequent immunizations may not be necessary as both the "prime" and the "boost" compositions are administered simultaneously.

In certain embodiments, one or more compositions of the present invention are delivered to a vertebrate by methods described herein, thereby achieving an effective therapeutic and/or an effective preventative immune response. More specifically, the compositions of the present invention may be administered to any tissue of a vertebrate, including, but not limited to, muscle, skin, brain tissue, lung tissue, liver tissue, spleen tissue, bone marrow tissue, thymus tissue, heart tissue, e.g., myocardium, endocardium, and pericardium, lymph tissue, blood tissue, bone tissue, pancreas tissue, kidney tissue, gall bladder tissue, stomach tissue, intestinal tissue, testicular tissue, ovarian tissue, uterine tissue, vaginal tissue, rectal tissue, nervous system tissue, eye tissue, glandular tissue, tongue tissue, and connective tissue, e.g., cartilage.

Furthermore, the compositions of the present invention may be administered to any internal cavity of a vertebrate, including, but not limited to, the lungs, the mouth, the nasal cavity, the stomach, the peritoneal cavity, the intestine, any heart chamber, veins, arteries, capillaries, lymphatic cavities, the uterine cavity, the vaginal cavity, the rectal cavity, joint cavities, ventricles in brain, spinal canal in spinal cord, the ocular cavities, the lumen of a duct of a salivary gland or a liver. When the compositions of the present invention are administered to the lumen of a duct of a salivary gland or liver, the desired polypeptide is expressed in the salivary gland and the liver such that the polypeptide is delivered into the blood stream of the vertebrate from each of the salivary gland or the liver. Certain modes for administration to secretory organs of a gastrointestinal system using the salivary gland, liver and pancreas to release a desired polypeptide into the bloodstream are disclosed in U.S. Pat. Nos. 5,837,693 and 6,004,944, both of which are incorporated herein by reference in their entireties.

In certain embodiments, the compositions are administered to muscle, either skeletal muscle or cardiac muscle, or to lung tissue. Specific, but non-limiting modes for administration to lung tissue are disclosed in Wheeler, C. J., et al., *Proc. Natl. Acad. Sci. USA* 93:11454-11459 (1996), which is incorporated herein by reference in its entirety.

According to the disclosed methods, compositions of the present invention can be administered by intramuscular (i.m.), subcutaneous (s.c.), or intrapulmonary routes. Other suitable routes of administration include, but are not limited to intratracheal, transdermal, intraocular, intranasal, inhalation, intracavity, intravenous (i.v.), intraductal (e.g., into the pancreas) and intraparenchymal (i.e., into any tissue) administration. Transdermal delivery includes, but is not limited to intradermal (e.g., into the dermis or epidermis), transdermal (e.g., percutaneous) and transmucosal administration (i.e., into or through skin or mucosal tissue). Intracavity administration includes, but is not limited to administration into oral, vaginal, rectal, nasal, peritoneal, or intestinal cavities as well as, intrathecal (i.e., into spinal canal), intraventricular (i.e., into the brain ventricles or the heart ventricles), inraatrial (i.e., into the heart atrium) and sub arachnoid (i.e., into the sub arachnoid spaces of the brain) administration.

Any mode of administration can be used so long as the mode results in the expression of the desired peptide or protein, in the desired tissue, in an amount sufficient to generate an immune response to SARS-CoV and/or to generate a prophylactically or therapeutically effective immune response to SARS-CoV in a vertebrate in need of such response. Administration means of the present invention include needle injection, catheter infusion, biolistic injectors, particle accelerators (e.g., "gene guns" or pneumatic "needleless" injectors) Med-E-Jet (Vahlsing, H., et al., *J. Immunol. Methods* 171:11-22 (1994)), Pigjet (Schrijver, R., et al., *Vaccine* 15: 1908-1916 (1997)), Biojector (Davis, H., et al., *Vaccine* 12: 1503-1509 (1994); Gramzinski, R., et al., *Mol. Med.* 4: 109-118 (1998)), AdvantaJet (Linmayer, I., et al., *Diabetes Care* 9:294-297 (1986)), Medi-jector (Martins, J., and Roedl, E. J. *Occup. Med.* 21:821-824 (1979)), gelfoam sponge depots, other commercially available depot materials (e.g., hydrogels), osmotic pumps (e.g., Alza minipumps), oral or suppositorial solid (tablet or pill) pharmaceutical formulations, topical skin creams, and decanting, use of polynucleotide coated suture (Qin, Y., et al., *Life Sciences* 65: 2193-2203 (1999)) or topical applications during surgery. Certain modes of administration are intramuscular needle-based injection and pulmonary application via catheter infusion. Energy-assisted plasmid delivery (EAPD) methods may also be employed to administer the compositions of the invention. One such method involves the application of brief electrical pulses to injected tissues, a procedure commonly known as electroporation. See generally Mir, L. M. et al., *Proc. Natl. Acad. Sci USA* 96:4262-7 (1999); Hartikka, J. et al., *Mol. Ther.* 4:407-15 (2001); Mathiesen, I., *Gene Ther.* 6:508-14(1999); Rizzuto G. et al., *Hum. Gen. Ther.* 11:1891-900 (2000). Each of the references cited in this paragraph is incorporated herein by reference in its entirety.

Determining an effective amount of one or more compositions of the present invention depends upon a number of factors including, for example, the antigen being expressed or administered directly, (e.g., S, N, E or M, or fragments, variants, or derivatives thereof), the age and weight of the subject, the precise condition requiring treatment and its severity, and the route of administration. Based on the above factors, determining the precise amount, number of doses, and timing of doses are within the ordinary skill in the art and will be readily determined by the attending physician or veterinarian.

Compositions of the present invention may include various salts, excipients, delivery vehicles and/or auxiliary agents as are disclosed, e.g., in U.S. Patent Application Publication 2002/0019358, published Feb. 14, 2002, which is incorporated herein by reference in its entirety.

Furthermore, compositions of the present invention may include one or more transfection facilitating compounds that facilitate delivery of polynucleotides to the interior of a cell, and/or to a desired location within a cell. As used herein, the terms “transfection facilitating compound,” “transfection facilitating agent,” and “transfection facilitating material” are synonymous, and may be used interchangeably. It should be noted that certain transfection facilitating compounds may also be “adjuvants” as described infra, i.e., in addition to facilitating delivery of polynucleotides to the interior of a cell, the compound acts to alter or increase the immune response to the antigen encoded by that polynucleotide. Examples of the transfection facilitating compounds include, but are not limited to inorganic materials such as calcium phosphate, alum (aluminum sulfate), and gold particles (e.g., “powder” type delivery vehicles); peptides that are, for example, cationic, intercell targeting (for selective delivery to certain cell types), intracell targeting (for nuclear localization or endosomal escape), and ampipathic (helix forming or pore forming); proteins that are, for example, basic (e.g., positively charged) such as histones, targeting (e.g., asialoprotein), viral (e.g., Sendai virus coat protein), and pore-forming; lipids that are, for example, cationic (e.g., DMRIE, DOSPA, DC-Chol), basic (e.g., steryl amine), neutral (e.g., cholesterol), anionic (e.g., phosphatidyl serine), and zwitterionic (e.g., DOPE, DOPC); and polymers such as dendrimers, star-polymers, “homogenous” poly-amino acids (e.g., poly-lysine, poly-arginine), “heterogeneous” poly-amino acids (e.g., mixtures of lysine & glycine), co-polymers, polyvinylpyrrolidinone (PVP), poloxamers (e.g., CRL 1005) and polyethylene glycol (PEG). A transfection facilitating material can be used alone or in combination with one or more other transfection facilitating materials. Two or more transfection facilitating materials can be combined by chemical bonding (e.g., covalent and ionic such as in lipidated polylysine, PEGylated polylysine) (Toncheva, et al., *Biochim. Biophys. Acta* 1380(3):354-368 (1988)), mechanical mixing (e.g., free moving materials in liquid or solid phase such as “polylysine+cationic lipids”) (Gao and Huang, *Biochemistry* 35:1027-1036 (1996); Trubetskoy, et al., *Biochem. Biophys. Acta* 1131:311-313 (1992)), and aggregation (e.g., co-precipitation, gel forming such as in cationic lipids+poly-lactide, and polylysine+gelatin).

One category of transfection facilitating materials is cationic lipids. Examples of cationic lipids are 5-carboxyspermylglycine dioctadecylamide (DOGS) and dipalmitoyl-phophatidylethanolamine-5-carboxyspermylamide (DPPES). Cationic cholesterol derivatives are also useful, including {3β-[N-N',N'-dimethylamino)ethane]-carbomoyl}-cholesterol (DC-Chol). Dimethyldioctdecyl-ammonium bromide (DDAB), N-(3-aminopropyl)-N,N-(bis-(2-tetradecyloxyethyl))-N-methyl-ammonium bromide (PA-DEMO), N-(3-aminopropyl)-N,N-(bis-(2-dodecyloxyethyl))-N-methyl-ammonium bromide (PA-DELO), N,N,N-tris-(2-dodecyloxy)ethyl-N-(3-amino) propyl-ammonium bromide (PA-TELO), and N1-(3-aminopropyl)((2-dodecyloxy)ethyl)-N2-(2-dodecyloxy) ethyl-1-piperazinaminium bromide (GA-LOE-BP) can also be employed in the present invention.

Non-diether cationic lipids, such as DL-1,2-dioleoyl-3-dimethylaminopropyl-β-hydroxyethylammonium (DORI diester), 1-O-oleyl-2-oleoyl-3-dimethylaminopropyl-β-hydroxyethylammonium (DORI ester/ether), and their salts promote in vivo gene delivery. In some embodiments, cationic lipids comprise groups attached via a heteroatom attached to the quaternary ammonium moiety in the head group. A glycyl spacer can connect the linker to the hydroxyl group.

Specific, but non-limiting cationic lipids for use in certain embodiments of the present invention include DMRIE ((±)-N-(2-hydroxyethyl)-N,N-dimethyl-2,3-bis(tetradecyloxy)-1-propanaminium bromide), GAP-DMORIE ((±)-N-(3-aminopropyl)-N,N-dimethyl-2,3-bis(syn-9-tetradeceneyloxy)-1-propanaminium bromide), and GAP-DLRIE ((±)-N-(3-aminopropyl)-N,N-dimethyl-2,3-(bis-dodecyloxy)-1-propanaminium bromide).

Other specific but non-limiting cationic surfactants for use in certain embodiments of the present invention include Bn-DHRIE, DhxRIE, DhxRIE-OAc, DhxRIE-OBz and Pr-DOctRIE-OAc. These lipids are disclosed in U.S. patent application No. 60/435,303. In another aspect of the present invention, the cationic surfactant is Pr-DOctRIE-OAc.

Other cationic lipids include (±)-N,N-dimethyl-N-[2-(sperminecarboxamido) ethyl]-2,3-bis(dioleyloxy)-1-propaniminium pentahydrochloride (DOSPA), (±)-N-(2-aminoethyl)-N,N-dimethyl-2,3-bis(tetradecyloxy)-1-propaniminium bromide (β-aminoethyl-DMRIE or βAE-DMRIE) (Wheeler, et al., *Biochim. Biophys. Acta* 1280:1-11 (1996), and (±)-N-(3-aminopropyl)-N,N-dimethyl-2,3-bis (dodecyloxy)-1-propaniminium bromide (GAP-DLRIE) (Wheeler, et al., *Proc. Natl. Acad. Sci. USA* 93:11454-11459 (1996)), which have been developed from DMRIE.

Other examples of DMRIE-derived cationic lipids that are useful for the present invention are (±)-N-(3-aminopropyl)-N,N-dimethyl-2,3-(bis-decyloxy)-1-propanaminium bromide (GAP-DDRIE), (±)-N-(3-aminopropyl)-N,N-dimethyl-2,3-(bis-tetradecyloxy)-1-propanaminium bromide (GAP-DMRIE), (±)-N-((N''-methyl)-N'-ureyl)propyl-N,N-dimethyl-2,3-bis(tetradecyloxy)-1-propanaminium bromide (GMU-DMRIE), (±)-N-(2-hydroxyethyl)-N,N-dimethyl-2,3-bis(dodecyloxy)-1-propanaminium bromide (DLRIE), and (±)-N-(2-hydroxyethyl)-N,N-dimethyl-2,3-bis-([Z]-9-octadecenyloxy)propyl-1- propaniminium bromide (HP-DORIE).

In the embodiments where the immunogenic composition comprises a cationic lipid, the cationic lipid may be mixed with one or more co-lipids. For purposes of definition, the term “co-lipid” refers to any hydrophobic material which may be combined with the cationic lipid component and includes amphipathic lipids, such as phospholipids, and neutral lipids, such as cholesterol. Cationic lipids and co-lipids may be mixed or combined in a number of ways to produce a variety of non-covalently bonded macroscopic structures, including, for example, liposomes, multilamellar vesicles, unilamellar vesicles, micelles, and simple films. One non-limiting class of co-lipids are the zwitterionic phospholipids, which include the phosphatidylethanolamines and the phosphatidylcholines. Examples of phosphatidylethanolamines, include DOPE, DMPE and DPyPE. In certain embodiments, the co-lipid is DPyPE, which comprises two phytanoyl substituents incorporated into the diacylphosphatidylethanolamine skeleton.

In other embodiments, the co-lipid is DOPE, CAS name 1,2-diolyeoyl-sn-glycero-3-phosphoethanolamine.

When a composition of the present invention comprises a cationic lipid and co-lipid, the cationic lipid:co-lipid molar ratio may be from about 9:1 to about 1:9, from about 4:1 to about 1:4, from about 2:1 to about 1:2, or about 1:1.

In order to maximize homogeneity, the cationic lipid and co-lipid components may be dissolved in a solvent such as chloroform, followed by evaporation of the cationic lipid/co-lipid solution under vacuum to dryness as a film on the inner surface of a glass vessel (e.g., a Rotovap round-bottomed flask). Upon suspension in an aqueous solvent, the amphipathic lipid component molecules self-assemble into homogenous lipid vesicles. These lipid vesicles may subsequently be processed to have a selected mean diameter of uniform size prior to complexing with, for example, a polynucleotide or a codon-optimized polynucleotide of the present invention, according to methods known to those skilled in the art. For example, the sonication of a lipid solution is described in Felgner et al., *Proc. Natl. Acad. Sci. USA* 8:,7413-7417 (1987) and in U.S. Pat. No. 5,264,618, the disclosures of which are incorporated herein by reference.

In those embodiments where the composition includes a cationic lipid, polynucleotides of the present invention are complexed with lipids by mixing, for example, a plasmid in aqueous solution and a solution of cationic lipid:co-lipid as prepared herein are mixed. The concentration of each of the constituent solutions can be adjusted prior to mixing such that the desired final plasmid/cationic lipid:co-lipid ratio and the desired plasmid final concentration will be obtained upon mixing the two solutions. The cationic lipid:co-lipid mixtures are suitably prepared by hydrating a thin film of the mixed lipid materials in an appropriate volume of aqueous solvent by vortex mixing at ambient temperatures for about 1 minute. The thin films are prepared by admixing chloroform solutions of the individual components to afford a desired molar solute ratio followed by aliquoting the desired volume of the solutions into a suitable container. The solvent is removed by evaporation, first with a stream of dry, inert gas (e.g., argon) followed by high vacuum treatment.

Other hydrophobic and amphiphilic additives, such as, for example, sterols, fatty acids, gangliosides, glycolipids, lipopeptides, liposaccharides, neobees, niosomes, prostaglandins and sphingolipids, may also be included in compositions of the present invention. In such compositions, these additives may be included in an amount between about 0.1 mol % and about 99.9 mol % (relative to total lipid), about 1-50 mol %, or about 2-25 mol %.

Additional embodiments of the present invention are drawn to compositions comprising an auxiliary agent which is administered before, after, or concurrently with the polynucleotide. As used herein, an "auxiliary agent" is a substance included in a composition for its ability to enhance, relative to a composition which is identical except for the inclusion of the auxiliary agent, the entry of polynucleotides into vertebrate cells in vivo, and/or the in vivo expression of polypeptides encoded by such polynucleotides. Certain auxiliary agents may, in addition to enhancing entry of polynucleotides into cells, enhance an immune response to an immunogen encoded by the polynucleotide. Auxiliary agents of the present invention include nonionic, anionic, cationic, or zwitterionic surfactants or detergents, with nonionic surfactants or detergents being preferred, chelators, DNase inhibitors, poloxamers, agents that aggregate or condense nucleic acids, emulsifying or solubilizing agents, wetting agents, gel-forming agents, and buffers.

Auxiliary agents for use in compositions of the present invention include, but are not limited to non-ionic detergents and surfactants IGEPAL CA 630®, NONIDET NP-40, Nonidet® P40, Tween-20®, Tween-80™, Pluronic® F68 (ave. MW: 8400; approx. MW of hydrophobe, 1800; approx. wt. % of hydrophile, 80%), Pluronic F770® (ave. MW: 6600; approx. MW of hydrophobe, 2100; approx. wt. % of hydrophile, 70%), Pluronic P65® (ave. MW: 3400; approx. MW of hydrophobe, 1800; approx. wt. % of hydrophile, 50%), Triton X-100™, and Triton X-114™; the anionic detergent sodium dodecyl sulfate (SDS); the sugar stachyose; the condensing agent DMSO; and the chelator/DNAse inhibitor EDTA, CRL 1005 (12 kDa, 5% POE), and BAK (Benzalkonium chloride 50% solution, available from Ruger Chemical Co. Inc.). In certain specific embodiments, the auxiliary agent is DMSO, Nonidet P40, Pluronic F68® (ave. MW: 8400; approx. MW of hydrophobe, 1800; approx. wt. % of hydrophile, 80%), Pluronic F77® (ave. MW: 6600; approx. MW of hydrophobe, 2100; approx. wt. % of hydrophile, 70%), Pluronic P65® (ave. MW: 3400; approx. MW of hydrophobe, 1800; approx. wt. % of hydrophile, 50%), Pluronic L64® (ave. MW: 2900; approx. MW of hydrophobe, 1800; approx. wt. % of hydrophile, 40%), and Pluronic F108® (ave. MW: 14600; approx. MW of hydrophobe, 3000; approx. wt. % of hydrophile, 80%). See, e.g., U.S. Patent Application Publication No. 2002/0019358, published Feb. 14, 2002, which is incorporated herein by reference in its entirety.

Certain compositions of the present invention may further include one or more adjuvants before, after, or concurrently with the polynucleotide. The term "adjuvant" refers to any material having the ability to (1) alter or increase the immune response to a particular antigen or (2) increase or aid an effect of a pharmacological agent. It should be noted, with respect to polynucleotide vaccines, that an "adjuvant," may be a transfection facilitating material. Similarly, certain "transfection facilitating materials" described supra, may also be an "adjuvant." An adjuvant may be used with a composition comprising a polynucleotide of the present invention. In a prime-boost regimen, as described herein, an adjuvant may be used with either the priming immunization, the booster immunization, or both. Suitable adjuvants include, but are not limited to, cytokines and growth factors; bacterial components (e.g., endotoxins, in particular superantigens, exotoxins and cell wall components); aluminum-based salts; calcium-based salts; silica; polynucleotides; toxoids; serum proteins, viruses and virally-derived materials, poisons, venoms, imidazoquiniline compounds, poloxamers, and cationic lipids.

A great variety of materials have been shown to have adjuvant activity through a variety of mechanisms. Any compound which may increase the expression, antigenicity or immunogenicity of the polypeptide is a potential adjuvant. The present invention provides an assay to screen for improved immune responses to potential adjuvants. Potential adjuvants which may be screened for their ability to enhance the immune response according to the present invention include, but are not limited to: inert carriers, such as alum, bentonite, latex, and acrylic particles; pluronic block polymers, such as TiterMax® (block copolymer CRL-8941, squalene (a metabolizable oil) and a microparticulate silica stabilizer), depot formers, such as Freunds adjuvant, surface active materials, such as saponin, lysolecithin, retinal, Quil A, liposomes, and pluronic polymer formulations; macrophage stimulators, such as bacterial lipopolysaccharide; alternate pathway complement activators, such as insulin, zymosan, endotoxin, and levamisole; and non-ionic surfactants, such as poloxamers, poly(oxyethylene)-poly(oxypropylene) triblock copolymers. Also included as adjuvants are transfection-facilitating materials, such as those described above.

Poloxamers which may be screened for their ability to enhance the immune response according to the present invention include, but are not limited to, commercially available poloxamers such as Pluronic® surfactants, which are block copolymers of propylene oxide and ethylene oxide in which the propylene oxide block is sandwiched between two ethylene oxide blocks. Examples of Pluronic® surfactants include Pluronic® L121 (ave. MW: 4400; approx. MW of hydrophobe, 3600; approx. wt. % of hydrophile, 10%), Pluronic® L101 (ave. MW: 3800; approx. MW of hydrophobe, 3000; approx. wt. % of hydrophile, 10%), Pluronic® L81 (ave. MW: 2750; approx. MW of hydrophobe, 2400; approx. wt. % of hydrophile, 10%), Pluronic® L61 (ave. MW: 2000; approx. MW of hydrophobe, 1800; approx. wt. % of hydrophile, 10%), Pluronic® L31 (ave. MW: 1100; approx. MW of hydrophobe, 900; approx. wt. % of hydrophile, 10%), Pluronic® L122 (ave. MW: 5000; approx. MW of hydrophobe, 3600; approx. wt. % of hydrophile, 20%), Pluronic® L92 (ave. MW: 3650; approx. MW of hydrophobe, 2700; approx. wt. % of hydrophile, 20%), Pluronic® L72 (ave. MW: 2750; approx. MW of hydrophobe, 2100; approx. wt. % of hydrophile, 20%), Pluronic® L62 (ave. MW: 2500; approx. MW of hydrophobe, 1800; approx. wt. % of hydrophile, 20%), Pluronic® L42 (ave. MW: 1630; approx. MW of hydrophobe, 1200; approx. wt. % of hydrophile, 20%), Pluronic® L63 (ave. MW: 2650; approx. MW of hydrophobe, 1800; approx. wt. % of hydrophile, 30%), Pluronic® L43 (ave. MW: 1850; approx. MW of hydrophobe, 1200; approx. wt. % of hydrophile, 30%), Pluronic® L64 (ave. MW: 2900; approx. MW of hydrophobe, 1800; approx. wt. % of hydrophile, 40%), Pluronic® L44 (ave. MW: 2200; approx. MW of hydrophobe, 1200; approx. wt. % of hydrophile, 40%), Pluronic® L35 (ave. MW: 1900; approx. MW of hydrophobe, 900; approx. wt. % of hydrophile, 50%), Pluronic® P123 (ave. MW: 5750; approx. MW of hydrophobe, 3600; approx. wt. % of hydrophile, 30%), Pluronic® P103 (ave. MW: 4950; approx. MW of hydrophobe, 3000; approx. wt. % of hydrophile, 30%), Pluronic® P104 (ave. MW: 5900; approx. MW of hydrophobe, 3000; approx. wt. % of hydrophile, 40%), Pluronic® P84 (ave. MW: 4200; approx. MW of hydrophobe, 2400; approx. wt. % of hydrophile, 40%), Pluronic® P105 (ave. MW: 6500; approx. MW of hydrophobe, 3000; approx. wt. % of hydrophile, 50%), Pluronic® P85 (ave. MW: 4600; approx. MW of hydrophobe, 2400; approx. wt. % of hydrophile, 50%), Pluronic® P75 (ave. MW: 4150; approx. MW of hydrophobe, 2100; approx. wt. % of hydrophile, 50%), Pluronic® P65 (ave. MW: 3400; approx. MW of hydrophobe, 1800; approx. wt. % of hydrophile, 50%), Pluronic® F127 (ave. MW: 12600; approx. MW of hydrophobe, 3600; approx. wt. % of hydrophile, 70%), Pluronic® F98 (ave. MW: 13000; approx. MW of hydrophobe, 2700; approx. wt. % of hydrophile, 80%), Pluronic® F87 (ave. MW: 7700; approx. MW of hydrophobe, 2400; approx. wt. % of hydrophile, 70%), Pluronic® F77 (ave. MW: 6600; approx. MW of hydrophobe, 2100; approx. wt. % of hydrophile, 70%), Pluronic® F108 (ave. MW: 14600; approx. MW of hydrophobe, 3000; approx. wt. % of hydrophile, 80%), Pluronic® F98 (ave. MW: 13000; approx. MW of hydrophobe, 2700; approx. wt. % of hydrophile, 80%), Pluronic® F88 (ave. MW: 11400; approx. MW of hydrophobe, 2400; approx. wt. % of hydrophile, 80%), Pluronic® F68 (ave. MW: 8400; approx. MW of hydrophobe, 1800; approx. wt. % of hydrophile, 80%), Pluronic® F38 (ave. MW: 4700; approx. MW of hydrophobe, 900; approx. wt. % of hydrophile, 80%).

Reverse poloxamers which may be screened for their ability to enhance the immune response according to the present invention include, but are not limited to Pluronic® R 31R1 (ave. MW: 3250; approx. MW of hydrophobe, 3100; approx. wt. % of hydrophile, 10%), Pluronic® R 25R1 (aye. MW: 2700; approx. MW of hydrophobe, 2500; approx. wt. % of hydrophile, 10%), Pluronic® R 17R1 (ave. MW: 1900; approx. MW of hydrophobe, 1700; approx. wt. % of hydrophile, 10%), Pluronic® R 31R2 (ave. MW: 3300; approx. MW of hydrophobe, 3100; approx. wt. % of hydrophile, 20%), Pluronic® R 25R2 (ave. MW: 3100; approx. MW of hydrophobe, 2500; approx. wt. % of hydrophile, 20%), Pluronic® R 17R2 (ave. MW: 2150; approx. MW of hydrophobe, 1700; approx. wt. % of hydrophile, 20%), Pluronic® R 12R3 (ave. MW: 1800; approx. MW of hydrophobe, 1200; approx. wt. % of hydrophile, 30%), Pluronic® R 31R4 (ave. MW: 4150; approx. MW of hydrophobe, 3100; approx. wt. % of hydrophile, 40%), Pluronic® R 25R4 (ave. MW: 3600; approx. MW of hydrophobe, 2500; approx. wt. % of hydrophile, 40%), Pluronic® R 22R4 (ave. MW: 3350; approx. MW of hydrophobe, 2200; approx. wt. % of hydrophile, 40%), Pluronic® R 17R4 (ave. MW: 3650; approx. MW of hydrophobe, 1700; approx. wt. % of hydrophile, 40%), Pluronic® R 25R5 (ave. MW: 4320; approx. MW of hydrophobe, 2500; approx. wt. % of hydrophile, 50%), Pluronic® R 10R5 (ave. MW: 1950; approx. MW of hydrophobe, 1000; approx. wt. % of hydrophile, 50%), Pluronic® R 25R8 (ave. MW: 8550; approx. MW of hydrophobe, 2500; approx. wt. % of hydrophile, 80%), Pluronic® R 17R8 (ave. MW: 7000; approx. MW of hydrophobe, 1700; approx. wt. % of hydrophile, 80%), and Pluronic® R 10R8 (ave. MW: 4550; approx. MW of hydrophobe, 1000; approx. wt. % of hydrophile, 80%).

Other commercially available poloxamers which may be screened for their ability to enhance the immune response according to the present invention include compounds that are block copolymer of polyethylene and polypropylene glycol such as Synperonic® L121 (ave. MW: 4400), Synperonic® L122 (ave. MW: 5000), Synperonic® P104 (ave. MW: 5850), Synperonic® P105 (ave. MW: 6500), Synperonic® P123 (ave. MW: 5750), Synperonic® P85 (ave. MW: 4600) and Synperonic® P94 (ave. MW: 4600), in which L indicates that the surfactants are liquids, P that they are pastes, the first digit is a measure of the molecular weight of the polypropylene portion of the surfactant and the last digit of the number, multiplied by 10, gives the percent ethylene oxide content of the surfactant; and compounds that are nonylphenyl polyethylene glycol such as Synperonic® NP10 (nonylphenol ethoxylated surfactant—10% solution), Synperonic® NP30 (condensate of 1 mole of nonylphenol with 30 moles of ethylene oxide) and Synperonic® NP5 (condensate of 1 mole of nonylphenol with 5.5 moles of naphthalene oxide).

Other poloxamers which may be screened for their ability to enhance the immune response according to the present invention include: (a) a polyether block copolymer comprising an A-type segment and a B-type segment, wherein the A-type segment comprises a linear polymeric segment of relatively hydrophilic character, the repeating units of which contribute an average Hansch-Leo fragmental constant of about −0.4 or less and have molecular weight contributions between about 30 and about 500, wherein the B-type segment comprises a linear polymeric segment of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage; (b) a block copolymer having a polyether segment and a polycation segment, wherein the polyether segment comprises at least an A-type block, and the polycation segment comprises a plurality of cationic repeating units; and (c) a polyether-polycation copolymer comprising a polymer, a polyether segment and a polycationic segment comprising a plurality of cationic repeating units of formula —NH—$R^0$, wherein $R^0$ is a straight chain aliphatic group of 2 to 6 carbon atoms, which may be substituted, wherein said polyether segments comprise at least one of an A-type of B-type segment. See U.S. Pat. No. 5,656,611, by Kabonov, et al., which is incorporated herein by reference in its entirety. Other poloxamers of interest include CRL1005 (12 kDa, 5% POE), CRL8300 (11 kDa, 5% POE), CRL2690 (12 kDa, 10% POE), CRL4505 (15 kDa, 5% POE) and CRL1415 (9 kDa, 10% POE).

Other auxiliary agents which may be screened for their ability to enhance the immune response according to the present invention include, but are not limited to Acacia (gum arabic); the poloxyethylene ether R—O—$(C_2H_4O)_x$—H (BRIJ®), e.g., polyethylene glycol dodecyl ether (BRIJ® 35, x=23), polyethylene glycol dodecyl ether (BRIJ® 30, x=4), polyethylene glycol hexadecyl ether (BRIJ® 52 x=2), polyethylene glycol hexadecyl ether (BRIJ® 56, x=10), polyethylene glycol hexadecyl ether (BRIJ® 58P, x=20), polyethylene glycol octadecyl ether (BRIJ® 72, x=2), polyethylene glycol octadecyl ether (BRIJ® 76, x=10), polyethylene glycol octadecyl ether (BRIJ® 78P, x=20), polyethylene glycol oleyl ether (BRIJ® 92V, x=2), and polyoxyl 10 oleyl ether (BRIJ® 97, x=10); poly-D-glucosamine (chitosan); chlorbutanol; cholesterol; diethanolamine; digitonin; dimethylsulfoxide (DMSO), ethylenediamine tetraacetic acid (EDTA); glyceryl monosterate; lanolin alcohols; mono- and di-glycerides; monoethanolamine; nonylphenol polyoxyethylene ether (NP-40®); octylphenoxypolyethoxyethanol (NONIDET NP-40 from Amresco); ethyl phenol poly (ethylene glycol ether)$^n$, n=11 (Nonidet® P40 from Roche); octyl phenol ethylene oxide condensate with about 9 ethylene oxide units (nonidet P40); IGEPAL CA 630® ((octyl phenoxy) polyethoxyethanol; structurally same as NONIDET NP-40); oleic acid; oleyl alcohol; polyethylene glycol 8000; polyoxyl 20 cetostearyl ether; polyoxyl 35 castor oil; polyoxyl 40 hydrogenated castor oil; polyoxyl 40 stearate; polyoxyethylene sorbitan monolaurate (polysorbate 20, or TWEEN-20®; polyoxyethylene sorbitan monooleate (polysorbate 80, or TWEEN-80®); propylene glycol diacetate; propylene glycol monstearate; protamine sulfate; proteolytic enzymes; sodium dodecyl sulfate (SDS); sodium monolaurate; sodium stearate; sorbitan derivatives (SPAN®), e.g., sorbitan monopalmitate (SPAN® 40), sorbitan monostearate (SPAN® 60), sorbitan tristearate (SPAN® 65), sorbitan monooleate (SPAN® 80), and sorbitan trioleate (SPAN® 85); 2,6,10,15,19,23-hexamethyl-2,6,10,14,18,22-tetracosa-hexaene (squalene); stachyose; stearic acid; sucrose; surfactin (lipopeptide antibiotic from *Bacillus subtilis*); dodecylpoly(ethyleneglycolether)g (Thesit®) MW 582.9; octyl phenol ethylene oxide condensate with about 9-10 ethylene oxide units (Triton X-100™); octyl phenol ethylene oxide condensate with about 7-8 ethylene oxide units (Triton X-114™); tris(2-hydroxyethyl) amine (trolamine); and emulsifying wax.

In certain adjuvant compositions, the adjuvant is a cytokine. A composition of the present invention can comprise one or more cytokines, chemokines, or compounds that induce the production of cytokines and chemokines, or a polynucleotide encoding one or more cytokines, chemokines, or compounds that induce the production of cytokines and chemokines. Examples include, but are not limited to granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFNα), interferon beta (IFNβ), interferon gamma (IFNγ), interferon omega (IFNω), interferon tau (IFNθ), interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), *Leishmania* elongation initiating factor (LEIF), and Flt-3 ligand.

In certain compositions of the present invention, the polynucleotide construct may be complexed with an adjuvant composition comprising (±)-N-(3-aminopropyl)-N,N-dimethyl-2,3-bis(syn-9-tetradeceneyloxy)-1-propanaminium bromide (GAP-DMORIE). The composition may also comprise one or more co-lipids, e.g., 1,2-dioleoyl-sn-glycero-3-phosphoethanolamine (DOPE), 1,2-diphytanoyl-sn-glycero-3-phosphoethanolamine (DPyPE), and/or 1,2-dimyristoyl-glycer-3-phosphoethanolamine (DMPE). An adjuvant composition comprising; GAP-DMORIE and DPyPE at a 1:1 molar ratio is referred to herein as Vaxfectin™. See, e.g., PCT Publication No. WO 00/57917, which is incorporated herein by reference in its entirety.

In other embodiments, the polynucleotide itself may function as an adjuvant as is the case when the polynucleotides of the invention are derived, in whole or in part, from bacterial DNA. Bacterial DNA containing motifs of unmethylated CpG-dinucleotides (CpG-DNA) triggers innate immune cells in vertebrates through a pattern recognition receptor (including toll receptors such as TLR 9) and thus possesses potent immunostimulatory effects on macrophages, dendritic cells and B-lymphocytes. See, e.g., Wagner, H., *Curr. Opin. Microbiol.* 5:62-69 (2002); Jung, J. et al., *J. Immunol.* 169: 2368-73 (2002); see also Klinman, D. M. et al., *Proc. Natl Acad. Sci. U.S.A.* 93:2879-83 (1996). Methods of using unmethylated CpG-dinucleotides as adjuvants are described in, for example, U.S. Pat. Nos. 6,207,646, 6,406,705, and 6,429,199, the disclosures of which are herein incorporated by reference.

The ability of an adjuvant to increase the immune response to an antigen is typically manifested by a significant increase in immune-mediated protection. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or $Th_2$ response into a primarily cellular, or $Th_1$ response.

In certain embodiments, the compositions of the present invention may be administered in the absence of one or more transfection facilitating materials or auxiliary agents. It has been shown that, surprisingly, the cells of living vertebrates are capable of taking up and expressing polynucleotides that have been injected in vivo, even in the absence of any agent to facilitate transfection. Cohen, J., *Science* 259: 1691-1692; Felgner, P., *Scientific American* 276: 102-106 (1997). These references are hereby incorporated by reference in their entireties. Thus, by way of non-limiting examples, nucleic acid molecules and/or polynucleotides of the present invention (e.g., plasmid DNA, mRNA, linear DNA, or oligonucleotides) may be administered in the absence of any one of, or any combination of more than one of the following transfection facilitating materials or auxiliary agents as described herein: inorganic materials including but not limited to calcium phosphate, alum, and/or gold particles; peptides including, but not limited to cationic peptides, amphipathic peptides, intercell targeting peptides, and/or intracell targetting peptides; proteins, including, but not limited to basic (i.e., positively-charged) proteins, targeting proteins, viral proteins, and/or pore-forming proteins; lipids, including but not limited to cationic lipids, anionic lipids, basic lipids, neutral lipids, and/or zwitterionic lipids; polymers including but not limited to dendrimers, star-polymers, "homogeneous" poly-amino acids, "heterogenous" poly-amino acids, co-polymers, PVP, poloxamers, and/or PEG; surfactants, including but not limited to anionic surfactants, cationic surfactants, and zwitterionic surfactants; detergents, including but not limited to anionic detergents, cationic detergents, and zwitterionic detergents; chelators, including but not limited to EDTA; DNase inhibitors; condensing agents including, but not limited to DMSO; emulsifying or solublizing agents; gel-forming agents; buffers, and/or adjuvants.

Nucleic acid molecules and/or polynucleotides of the present invention, e.g., plasmid DNA, mRNA, linear DNA or oligonucleotides, may be solubilized in any of various buffers. Suitable buffers include, for example, phosphate buffered saline (PBS), normal saline, Tris buffer, and sodium phosphate (e.g., 150 mM sodium phosphate). Insoluble polynucleotides may be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art. For aqueous compositions used in vivo, sterile pyrogen-free water can be used. Such formulations will contain an effective amount of a polynucleotide together with a suitable amount of an aqueous solution in order to prepare pharmaceutically acceptable compositions suitable for administration to a human.

Compositions of the present invention can be formulated according to known methods. Suitable preparation methods are described, for example, in Remington's Pharmaceutical Sciences, 16th Edition, A. Osol, ed., Mack Publishing Co., Easton, Pa. (1980), and Remington's Pharmaceutical Sciences, 19th Edition, A. R. Gennaro, ed., Mack Publishing Co., Easton, Pa. (1995), both of which are incorporated herein by reference in their entireties. Although the composition may be administered as an aqueous solution, it can also be formulated as an emulsion, gel, solution, suspension, lyophilized form, or any other form known in the art. In addition, the composition may contain pharmaceutically acceptable additives including, for example, diluents, binders, stabilizers, and preservatives.

Passive Immunotherapy

Antibody therapy can be subdivided into two principally different activities: (i) passive immunotherapy using intact non-labeled antibodies or labeled antibodies and (ii) active immunotherapy using anti-idiotypes for re-establishment of network balance in autoimmunity In passive immunotherapy, naked antibodies are administered to neutralize an antigen or to direct effector functions to targeted membrane associated antigens. Neutralization would be of a lymphokine, a hormone, or an anaphylatoxin, i.e., C5a. Effector functions include complement fixation, macrophage activation and recruitment, and antibody-dependent cell-mediated cytotoxicity (ADCC). Naked antibodies have been used to treat leukemia (Ritz, S.F. et al *Blood,* 58:141-152 (1981)) and antibodies to GD2 have been used in treatments of neuroblastomas (Schulz et al. *Cancer Res.* 44:5914 (1984)) and melanomas (Irie et al., *Proc. Natl. Acad. Sci.* 83: 8694 (1986) One major advantage of passive antibody immunization is that it provides immediate immunity that can last for weeks and possibly months. Casadevall, A. "Passive Antibody Administration (Immediate Immunity) as a Specific Defense against Biological Weapons." *Emerging Infectious Diseases.* 8:833-841(2002).

The invention also provides for antibodies specifically reactive with SARS Co-V polypeptides which have been produced from an immune response elicited by the administration, to a vertebrate, of polynucleotide and polypeptides of the present invention. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A vertebrate such as a mouse, a hamster, a rabbit, a horse, a human, or non-human primate can be immunized with an immunogenic form of a SARS Co-V polypeptide or polynucleotide, of the present invention, encoding an immunogenic form of a SARS-CoV polypeptide. Techniques for conferring immunogenicity on a protein or peptide include conjugation to carriers or other techniques well known in the art. An immunogenic portion of the SARS-CoV polypeptide can be administered in the presence of adjuvant and as part of compositions described herein. The progress of immunization can be monitored by detection of antibody titers in plasma or serum. Standard ELISA or other immunoassays can be used with the immunogen as antigen to assess the levels of antibodies.

The antibodies of the invention are immunospecific for antigenic determinants of the SARS-CoV polypeptides of the invention, e.g., antigenic determinants of a polypeptide of the invention or a closely related human or non-human mammalian homolog (e.g., 90% homologous and at least about 95% homologous). In an alternative embodiment of the invention, the SARS Co-V antibodies do not substantially cross react (i.e., react specifically) with a protein which is for example, less than 80% percent homologous to a sequence of the invention. By "not substantially cross react," is meant that the antibody has a binding affinity for a non-homologous protein which is less than 10 percent, less than 5 percent, or less than 1 percent, of the binding affinity for a protein of the invention. In an alternative embodiment, there is no cross-reactivity between viral and mammalian antigens.

In one embodiment, purified monoclonal antibodies or polyclonal antibodies containing the variable heavy and light sequences are used as therapeutic and prophylactic agents to treat or prevent SARS-CoV infection by passive antibody therapy. In general, this will comprise administering a therapeutically or prophylactically effective amount of the monoclonal or polyclonal antibodies to a susceptible vertebrate or one exhibiting SARS Co-V infection. A dosage effective amount will range from about 50 to 20,000 μg/Kg, and from about 100 to 5000 μg/Kg. However, suitable dosages will vary dependening on factors such as the condition of the treated host, weight, etc. Suitable effective dosages may be determined by those skilled in the art.

In an alternative embodiment, purified antibodies and the polynucleotides or polypeptides of the present invention are administered simultaneously (at the same time) or subsequent to the administration of the isolated antibodies, thereby providing both immediate and long lasting protection.

The monoclonal or polyclonal antibodies may be administered by any mode of administration suitable for administering antibodies. Typically, the subject antibodies will be administered by injection, e.g., intravenous, intramuscular, or intraperitoneal injection (as described previously), or aerosol. Aerosol administration is particularly preferred if the subjects treated comprise newborn infants.

Formulation of antibodies in pharmaceutically acceptable form may be effected by known methods, using known pharmaceutical carriers and excipients. Suitable carriers and excipients include by way of non-limiting example buffered saline, and bovine serum albumin.

Any polynucleotides or polypeptides, as described herein, can be used to produce the isolated antibodies of the invention. For example, SARS-CoV proteins S, N, M, and E, fragments, variants and derivatives thereof, are purified as described in Example 2. The purified protein then serves as an antigen for producing SARS-CoV specific monoclonal and polyclonal antibodies.

Any vertebrate can serve as a host for antibody production. Preferred hosts include, but are not limited to human, non-human primate, mouse, rabbit, horse, goat, donkey, cow, sheep, chickens, cat, dog. Alternatively, antibodies can be produced by cultivation ex vivo of lymphocytes from primed donors stimulated with CD40 resulting in expansion of human B cells Banchereau et al., *Science* 251:70 (1991); Zhani et al., *J. Immunol.* 144:2955-2960, (1990); Tohma et al., *J. Immunol.* 146:2544-2552 (1991). Furthermore, an extra in vitro booster step can be used to obtain a higher yield of antibodies prior to immortalization of the cells. See Chaudhuri et al., *Cancer Supplement* 73: 1098-1104 (1994); Steenbakkers et al. *Hum. Antibod. Hybridomas* 4: 166-173 (1993); Ferrarro et al., *Hum. Antibod. Hybridomas* 4:80-85 (1993); Kwekkeboom et al., *Immunol. Methods* 160:117-127 (1993), which are herein incorporated by reference.

An alternative to human primed donors, is to "recreate" or mimic splenic conditions in an immunocompromised animal host, such as the "Severe Combined Immune Deficient" (SCID) mouse. Human lymphocytes are readily adopted by the SCID mouse (hu-SCID) and produce high levels of immunoglobulins Mosier et al, *Nature* 335:256 (1988); McCune et al, *Science* 241:1632-1639 (1988). Moreover, if the donor used for reconstitution has been exposed to a particular antigen, a strong secondary response to the same antigen can be elicited in such mice. Duchosal et al. *Nature* 355:258-262 (1992).

The term "antibody" as used herein is intended to include fragments thereof which are also specifically reactive with SARS-CoV polypeptides. Antibodies can be fragmented using conventional techniques and the fragments screened for utility in the same manner as described above for whole antibodies. For example. $F(ab')_2$ fragments can be generated by treating antibody with pepsin. The resulting $F(ab')_2$ fragment can be treated to reduce disulfide bridges to produce Fab' fragments. The antibody of the invention is further intended to include bispecific and chimeric molecules having an anti-SARS-CoV portion.

Both monoclonal and polyclonal antibodies (Ab) directed against SARS-CoV polypeptides or SARS-CoV polypeptide variants, and antibody fragments such as Fab' and $F(ab')_2$, can be used to block the action of SARS-CoV polypeptides and allow the study of the role of a particular SARS-CoV polypeptide of the invention in the infectious life cycle of the virus and in pathogenesis.

Moreover, the antibodies possess utility as immunoprobes for diagnosis of SARS Co-V infection. This generally comprises taking a sample, e.g., respiratory fluid, of a person suspected of having SARS-CoV infection and incubating the sample with the subject human monoclonal antibodies to detect the presence of SARS-CoV infected cells. This involves directly or indirectly labeling the subject human antibodies with a reporter molecule which provides for detection of human monoclonal antibody SARS-CoV immune complexes. Examples of known labels include by way of non-limiting example enzymes, e.g.,. β-lactamase, luciferase, and radiolabels. Methods for effecting immunodetection of antigens using monoclonal antibodies are well known in the art.

The following examples are included for purposes of illustration only and are not intended to limit the scope of the present invention, which is defined by the appended claims. All references cited in the Examples are incorporated herein by reference in their entireties.

EXAMPLES

Materials and Methods

The following materials and methods apply generally to all the examples disclosed herein. Specific materials and methods are disclosed in each example, as necessary.

The practice of the present invention will employ, unless otherwise indicated, conventional techniques of cell biology, cell culture, molecular biology (including PCR), vaccinology, microbiology, recombinant DNA, and immunology, which are within the skill of the art. Such techniques are explained fully in the literature. See, for example, *Molecular Cloning A Laboratory Manual,* 2nd Ed., Sambrook et al., ed., Cold Spring Harbor Laboratory Press: (1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); and in Ausubel et al., *Current Protocols in Molecular Biology*, John Wiley and Sons, Baltimore, Md. (1989).

Gene Construction

Constructs of the present invention are constructed based on the sequence information provided herein or in the art utilizing standard molecular biology techniques, including, but not limited to the following. First, a series complementary oligonucleotide pairs of 80-90 nucleotides each in length and spanning the length of the construct are synthesized by standard methods. These oligonucleotide pairs are synthesized such that upon annealing, they form double stranded fragments of 80-90 base pairs, containing cohesive ends. The single-stranded ends of each pair of oligonucleotides are designed to anneal with a single-stranded end of an adjacent oligonucleotide duplex. Several adjacent oligonucleotide pairs prepared in this manner are allowed to anneal, and approximately five to six adjacent oligonucleotide duplex fragments are then allowed to anneal together via the cohesive single stranded ends. This series of annealed oligonucleotide duplex fragments is then ligated together and cloned into a suitable plasmid, such as the TOPO® vector available from Invitrogen Corporation, Carlsbad, Calif. The construct is then sequenced by standard methods. Constructs prepared in this manner, comprising 5 to 6 adjacent 80 to 90 base pair fragments ligated together, i.e., fragments of about 500 base pairs, are prepared, such that the entire desired sequence of the construct is represented in a series of plasmid constructs. The inserts of these plasmids are then cut with appropriate restriction enzymes and ligated together to form the final construct. The final construct is then cloned into a standard bacterial cloning vector, and sequenced. The oligonucleotides and primers referred to herein can easily be designed by a person of skill in the art based on the sequence information provided herein and in the art, and such can be synthesized by any of a number of commercial nucleotide providers, for example Retrogen, San Diego, Calif.

Plasmid Vector

Constructs of the present invention can be inserted, for example, into eukaryotic expression vectors VR1012 or VR10551. These vectors are built on a modified pUC18 background (see Yanisch-Perron, C., et al. *Gene* 33:103-119 (1985)), and contain a kanamycin resistance gene, the human cytomegalovirus immediate early promoter/enhancer and intron A, and the bovine growth hormone transcription termination signal, and a polylinker for inserting foreign genes. See Hartikka, J., et al., *Hum. Gene Ther.* 7:1205-1217 (1996). However, other standard commercially available eukaryotic expression vectors may be used in the present invention, including, but not limited to: plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.).

An optimized backbone plasmid, termed VR-10551 has minor changes from the VR-1012 backbone described above. The VR-10551 vector is derived from and similar to VR-1012 in that it uses the human cytomegalovirus immediate early (hCMV-IE) gene enhancer/promoter and 5'untranslated region (UTR), including the hCMV-IE Intron A. The changes from the VR-1012 to the VR-10551 include some modifications to the multiple cloning site, and a modified rabbit ∃globin 3'untranslated region/polyadenylation signal sequence/transcriptional terminator has been substituted for the same functional domain derived from the bovine growth hormone gene.

Plasmid DNA Purification

Plasmid DNA may be transformed into competent cells of an appropriate Escherichia coli strain (including but not limited to the DH5α strain) and highly purified covalently closed circular plasmid DNA may be isolated by a modified lysis procedure (Horn, N. A., et al., *Hum. Gene Ther.* 6:565-573 (1995)) followed by standard double CsCl-ethidium bromide gradient ultracentrifugation (Sambrook, J., et al., *Molecular Cloning: A Laboratory Manual,* 2nd Ed., Cold Spring Harbor Laboratory Press, Plainview, N.Y. (1989)). Alternatively, plasmid DNAs are purified using Giga columns from Qiagen (Valencia, Calif.) according to the kit instructions. All plasmid preparations are free of detectable chromosomal DNA, RNA and protein impurities based on gel analysis and the bicinchoninic protein assay (Pierce Chem. Co., Rockford Ill.). Endotoxin levels are measured using *Limulus* Amebocyte Lysate assay (LAL, Associates of Cape Cod, Falmouth, Mass.) in Endotoxin Units/mg of plasmid DNA. The spectrophotometric $A_{260}/A_{280}$ ratios of the DNA solutions are also determined. Plasmids are ethanol precipitated and resuspended in an appropriate solution, e.g., 150 mM sodium phosphate (for other appropriate excipients and auxiliary agents, see U.S. Patent Application Publication 20020019358, published Feb. 14, 2002). DNA is stored at −20EC until use. DNA is diluted by mixing it with 300 mM salt solutions and by adding appropriate amount of USP water to obtain 1 mg/ml plasmid DNA in the desired salt at the desired molar concentration.

Injections of Plasmid DNA

The quadriceps muscles of restrained awake mice (e.g., female 6-12 week old BALB/c mice from Harlan Sprague Dawley, Indianapolis, Ind.) are injected bilaterally with 50 μg of DNA in 50 μl solution (100 μg in 100 μl total per mouse) using a disposable plastic insulin syringe and 28G ½ needle (Becton-Dickinson, Franklin Lakes, N.J., Cat. No. 329430) fitted with a plastic collar cut from a micropipette tip, as previously described (Hartikka, J., et al., *Hum. Gene Ther.* 7:1205-1217 (1996).

Animal care will comply with the "Guide for the Use and Care of Laboratory Animals," Institute of Laboratory Animal Resources, Commission on Life Sciences, National Research Council, National Academy Press, Washington, D.C., 1996 as well as with Vical's Institutional Animal Care and Use Committee.

Example 1

Construction of Expression Vectors

Plasmid constructs comprising the native coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg are constructed as follows. The S, S1, S2, N, M, or E genes from SARS-CoV Urbani or other strains (e.g., CUKH-Su10, TOR2 and BJ01) are isolated from viral RNA by RT PCR, or prepared by direct synthesis if the wildtype sequence is known, by standard methods and are inserted into the vector VR-10551 via standard restriction sites, by standard methods.

Plasmid constructs comprising human codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, are prepared as follows. The codon-optimized coding regions are generated using the full, minimal, uniform, or other codon optimization methods described herein. The coding regions or codon optimized coding regions are constructed using standard PCR methods described herein, or are ordered commercially. The coding regions or codon-optimized coding regions are inserted into the vector VR-10551 via standard restriction sites, by standard methods.

Examples of constructs to be made are listed in Table 19.

TABLE 19

| Gene | Strain | Backbone | Wild type/Codon optimized |
|---|---|---|---|
| S | Urbani | 10551 | Wild type |
| S | Urbani | 10551 | Codon optimized |
| S1 | Urbani | 1012 | Wild type |
| S1 | Urbani | 10551 | Codon optimized |
| S2 | Urbani | 10551 | Wild type |
| S2 | Urbani | 10551 | Codon optimized |
| N | Urbani | 10551 | Wild type |
| N | Urbani | 10551 | Codon optimized |
| M | Urbani | 10551 | Wild type |
| M | Urbani | 10551 | Codon optimized |
| E | Urbani | 10551 | Wild type |
| E | Urbani | 10551 | Codon optimized |

Plasmids constructed as above are propagated in *Escherichia coli* and purified by the alkaline lysis method (Sambrook, J., et al., *Molecular Cloning: A Laboratory Manual*, Cold Spring Harbor Laboratory Press, Cold Spring Harbor, N.Y., ed. 2 (1989)). CsCl-banded DNA are ethanol precipitated and resuspended in 0.9% saline to a final concentration of 2 mg/ml for injection. Alternately, plasmids are purified using any of a variety of commercial kits, or by other known procedures involving differential precipitation and/or chromatographic purification.

Expression is tested by formulating each of the plasmids in DMRIE/DOPE and transfecting cell lines including, but not limited to VM92 cells, fungal cells, including yeast cells such as *Saccharomyces* spp. cells; insect cells such as *Drosophila* S2, *Spodoptera* Sf9 or Sf21 cells and *Trichoplusa* High-Five cells; other animal cells (particularly mammalian cells and human cells) such as MDCK, CV1, 3T3, CPAE, A10, Sp2/0-Ag14, PC12, CHO, COS, VERO, HeLa, Bowes melanoma cells, SW-13, NCI-H295, RT4, HT-1376, UM-UC-3, IM-9, KG-1, R54;11, A-172, U-87MG, BT-20, MCF-7, SK-BR-3, ChaGo K-1, CCD-14Br, CaSki, ME-180, FHC, HT-29, Caco-2, SW480, HuTu8O, Tera 1, NTERA-2, AN3 CA, KLE, RL95-2, Caki-1, ACHN, 769 P, CCRF-CEM, Hut 78, MOLT 4, HL-60, Hep-3B, HepG2, SK-HEP1, A-549, NCI-H146, NCI-H82, NCI-H82, SK-LU-1, WI-38, MRC-5, HLF-a, CCD-19Lu, C39, Hs294T, SK-MEL5, COLO 829, U266B1, RPMI 2650, BeWo, JEG-3, JAR, SW 1353, MeKam, and SCC-4; and higher plant cells. Appropriate culture media and conditions for the above-described host cells are known in the art.

The supernatants are collected and the protein production tested by Western blot or ELISA. The relative expression of the wild type and codon optimized constructs are compared.

In addition to plasmids encoding single SARS-CoV proteins, single plasmids which contain a portion of a SARS-CoV coding region are constructed according to standard methods. For example, portions of a SARS-CoV coding region that is too large to be contained in a single plasmid may be inserted into two or more plasmids. Also, single plasmids which contain two or more SARS-CoV coding regions are constructed according to standard methods. For example, a polycistronic construct, where two or more SARS-CoV coding regions are transcribed as a single transcript in eukaryotic cells may be constructed by separating the various coding regions with IRES sequences (Jang et al. "A segment of the 5' nontranslated region of encephalomyocarditis virus RNA directs internal entry of ribosomes during in vitro translation." *J. Virol.* 62: 2636-43 (1988); Jang et al. "Cap-independent Translation of Picornavirus RNAs: Structure and Function of the Internal Ribosomal Entry Site." *Enzyme* 44:292-309(1990)).

Alternatively, two or more coding regions may be inserted into a single plasmid, each with their own promoter sequence.

Example 2

In Vitro Expression of SARS-CoV Subunit Proteins

Expression of SARS-CoV Nucleocapsid (N) and Spike (S) constructs were tested in vitro by transfection of a mouse melanoma cell line (VM92). The following expression constructs were transfected individually into VM92 cells and cultured for a period of time. All SARS-CoV sequences described below, were cloned into the VR1012 expression vector. The VR9208 expression plasmid contains a nucleotide sequence encoding the SARS-CoV S1 domain which was codon-optimized according to the full optimization method described herein and is disclosed in SEQ ID NO:50. The VR9204 expression plasmid contains a nucleotide sequence encoding a fragment of the SARS-CoV S1 which corresponds to amino acids 1-417 of the SARS-CoV S1 protein. The coding sequence in VR9204 was also codon optimized according to the full optimization method described herein.

VR9219—expressing full-length SARS-CoV N protein

VR9208—expressing SARS-CoV S1 domain of the S protein (amino acids 1-683 of the S protein)

VR9204—expressing a fragment of the SARS-CoV S1 domain (amino acids 1-417 of the S1 domain)

VR9209—expressing SARS-CoV S2 domain of the S protein

VR9210—expressing SARS-CoV secreted S protein

Both cell extracts and cell culture medium supernatants were analyzed by Western blot. The presence of the SARS-CoV N protein and S proteins were detected using commercial rabbit polyclonal antibodies which reconginze the N protein from SARS-CoV strain Urbani (IMG-543; Imgenex, San Diego, Calif.) and the S proteins from SARS-CoV strain Urbani (IMG-557, 542 and 541; Imgenex, Diego, Calif.). Western blot results are summarized below:

In both the supemantant and cell lystates from cells transfected with the VR9219 plasmid, protein bands of a molecular weight of between 37 and 50 kDa (as estimated by a protein molecular weight standard) were detectable. The SARS-CoV N protein has an expected molecule weight of 46 kDa. This result is consistent with efficient expression of the SARS-CoV N antigen.

The supernantant and cell lysates from cells transfected with four different SARS-CoV S antigen constructs were individually analyzed for the presence of the S antigen. The results are summarized below.

A protein band of 85-110 kDa (as estimated by a protein molecular weight standard) was detected by Western blot in both the lysate and supernatant of cells transfected with the VR9204 plasmid (S1 domain—fragment).

A protein band of about 150 kDa (as estimated by a protein molecular weight standard) was detected by Western blot in both the lysate and supernatant of cells transfected with the VR9208 plasmid (S1 domain).

A protein band of approximately 111 kDa (as estimated by a protein molecular weight standard) was detected by Western blot in both the lysate and supernatant of cells transfected with the VR9209 plasmid (S2 domain).

A protein band of about 190 kDa (as estimated by a protein molecular weight standard) was detected by Western blot in both the lysate and supernatant of cells transfected with the VR9210 plasmid (secreted S).

These results are consistent with efficient expression and secretion of SARS-CoV Spike protein. Due to the presence of glycosylation sites in the S protein, the molecular weight is difficult to acurrately predict.

Example 3

Preparation of SARS-CoV Subunit Proteins

Recombinantly prepared SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, for use as subunit proteins in the various combination therapies and compositions described herein, are prepared using the following procedure.

Eukaryotic cells transfected with expression plasmids such as those described in Example 1 are used to express SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg. Alternatively, a baculovirus system can be used wherein insect cells such as, but not limited to, Sf9, Sf21, or D.Mel-2 cells are infected with recombinant baculoviruses which can express SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg. Other in vitro expression systems may be used, and are well known to those of ordinary skill in the art. For baculovirus expression of non-secreted forms of these proteins, cells which are infected with recombinant baculoviruses capable of expressing SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, are collected by knocking and scraping cells off the bottom of the flask in which they are grown. Cells infected with baculoviruses for 24 or 48 hours are less easy to detach from flask and may lyse, thus care must be taken with their removal. Eukaryotic cells which are transfected, either transiently or permanently, with expression plasmids encoding non-secreted forms of SARS-CoV proteins are gently scraped of the bottom of the flasks in which they are grown. Flasks containing the cells are then rinsed with PBS and the cells are transferred to 250 ml conical tubes. The tubes are spun at 1000 rpm in J-6 centrifuge (300×g) for about 5-10 minutes. The cell pellets are washed two times with PBS and then resuspended in about 10-20 ml of PBS in order to count. The cells are fmally resuspended at a concentration of about $2\times10^7$ cells/ml in RSB (10 mM Tris pH=7.5, 1.5 mM $MgCl_2$, 10 mM KCl).

At this point either a total cell lysate is prepared, or cytoplasmic and nuclear fractions are separated. Approximately $10^6$ infected cells are used per lane of a standard SDS-PAGE mini-protein gel for gel analysis purposes. When separating cytoplasmic and nuclear fractions, 10% NP40 is added to the cells for a final concentration of 0.5%. The cell-NP40 mixture is vortexed and placed on ice for 10 minutes, vortexing occasionally. After ice incubation, the cells are spun at 1500 rpm in a J-6 centrifuge (600×1) for 10 minutes. The supemantant is removed, which is the cytoplasmic fraction. The remaining pellet, containing the nuclei, is washed two times with buffer C (20 mM HEPES pH=7.9, 1.5 mM $MgCl_2$, 0.2 mM EDTA, 0.5 mM PMSF, 0.5 mM DTT) to remove cytoplasmic proteins. The nuclei are resuspended in buffer C to $5\times10^7$ nuclei/ml. The nuclei are vortexed vigorously to break up particles and an aliquot is removed for the mini-protein gel, which is the nuclei fraction.

Whole cell lysates are prepared by simply resuspending the requisite number of cells in gel sample buffer.

For gel analysis, a small amount (about $10^6$ nuclear equivalents) of the nuclear pellet is resuspended directly in gel sample buffer and run with equivalent amounts of whole cells, cytoplasm, and nuclei. Those fractions containing the SARS-CoV protein of interest are detected by Western blot analysis as described herein.

Following analysis as described above, larger quantities of crude subunit proteins are prepared from batch cell cultures by protein purification methods well known by those of ordinary skill in the art, e.g., the use of HPLC.

Secreted versions of SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg are isolated from cell culture supernatants using various protein purification methods well known to those of ordinary skill in the art.

Example 4

Preparation of Vaccine Formulations

Plasmid constructs comprising codon-optimized and non-codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, as well as various controls, e.g., empty vector, are formulated with the poloxamer CRL 1005 and BAK (Benzalkonium chloride 50% solution, available from Ruger Chemical Co. Inc.) by the following methods. Specific final concentrations of each component of the formulae are described in the following methods, but for any of these methods, the concentrations of each component may be varied by basic stoichiometric calculations known by those of ordinary skill in the art to make a final solution having the desired concentrations.

For example, the concentration of CRL 1005 is adjusted depending on, for example, transfection efficiency, expression efficiency, or imunogenicity, to achieve a final concentration of between about 1 mg/ml to about 75 mg/ml, for example, about 1 mg/ml, about 2 mg/ml, about 3 mg/ml, about 4 mg/ml, about 5 mg/ml, about 6.5 mg/ml, about 7 mg/ml, about 7.5 mg/ml, about 8 mg/ml, about 9 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 75 mg/ml of CRL 1005.

Similarly, the concentration of DNA is adjusted depending on many factors, including the amount of a formulation to be delivered, the age and weight of the subject, the delivery method and route and the immunogenicity of the antigen being delivered. In general, formulations of the present invention are adjusted to have a final concentration from about 1 ng/ml to about 30 mg/ml of plasmid (or other polynucleotide). For example, a formulation of the present invention may have a final concentration of about 1 ng/ml, about 5 ng/ml, about 10 ng/ml, about 50 ng/ml, about 100 ng/ml, about 500 ng/ml, about 1 μg/ml, about 5 μg/ml, about 10 μg/ml, about 50 μg/ml, about 200 μg/ml, about 400 μg/ml, about 600 μg/ml, about 800 μg/ml, about 1 mg/ml, about 2 mg/ml, about 2.5, about 3 mg/ml, about 3.5, about 4 mg/ml, about 4.5, about 5 mg/ml, about 5.5 mg/ml, about 6 mg/ml, about 7 mg/ml, about 8 mg/ml, about 9 mg/ml, about 10 mg/ml, about 20 mg/ml, or about 30 mg/ml of a plasmid.

Certain formulations of the present invention include a cocktail of plasmids (see, e.g., Example 1 supra) of the present invention, e.g., comprising coding regions encoding SARS-CoV proteins, for example SARS-CoV S, S1, S2, N, M, or E and optionally, plasmids encoding immunity enhancing proteins, e.g., cytokines. Various plasmids desired in a cocktail are combined together in PBS or other diluent prior to the addition to the other ingredients. Furthermore, plasmids may be present in a cocktail at equal proportions, or the ratios may be adjusted based on, for example, relative expression levels of the antigens or the relative immunogenicity of the encoded antigens. Thus, various plasmids in the cocktail may be present in equal proportions, or up to twice or three times as much of one plasmid may be included relative to other plasmids in the cocktail.

Additionally, the concentration of BAK may be adjusted depending on, for example, a desired particle size and improved stability. Indeed, in certain embodiments, formulations of the present invention include CRL 1005 and DNA, but are free of BAK. In general BAK-containing formulations of the present invention are adjusted to have a final concentration of BAK from about 0.05 mM to about 0.5 mM. For example, a formulation of the present invention may have a final BAK concentration of about 0.05 mM, 0.1 mM, 0.2 mM, 0.3 mM, 0.4 mM, or 0.5 mM.

The total volume of the formulations produced by the methods below may be scaled up or down, by choosing apparatus of proportional size. Finally, in carrying out any of the methods described below, the three components of the formulation, BAK, CRL 1005, and plasmid DNA, may be added in any order. In each of these methods described below the term "cloud point" refers to the point in a temperature shift, or other titration, at which a clear solution becomes cloudy, ie., when a component dissolved in a solution begins to precipitate out of solution.

Thermal Cycling of a Pre-Mixed Formulation

Figure 2:
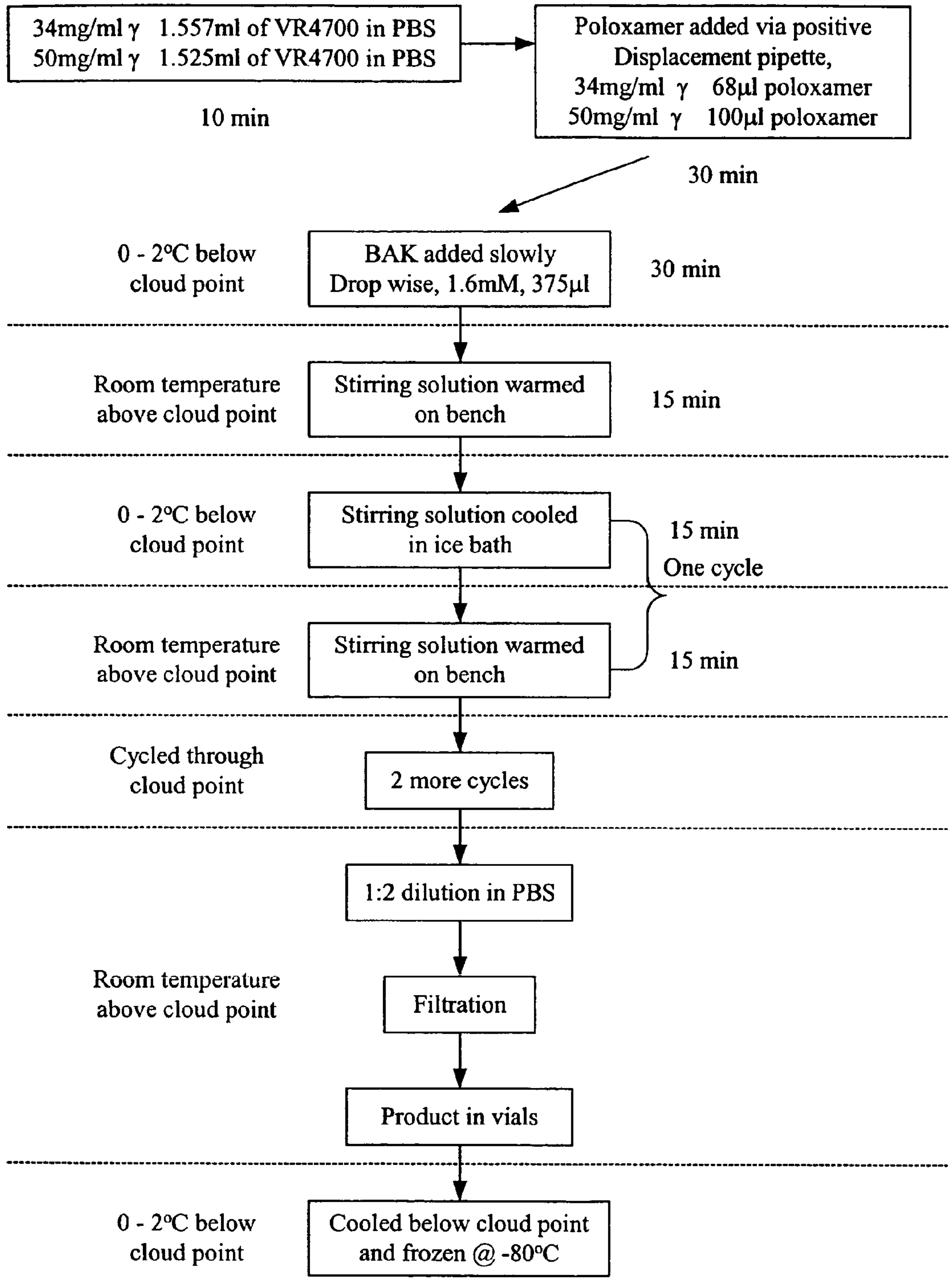
FIG. 2 shows the protocol for the preparation of a formulation comprising 0.3 mM BAK, 34 mg/ml or 50 mg/ml CRL 1005, and 2.5 mg/ml DNA in a final volume of 4.0 ml, through the use of thermal cycling.

This example describes the preparation of a formulation comprising 0.3 mM BAK, 7.5 mg/ml CRL 1005, and 5 mg/ml of DNA in a total volume of 3.6 ml. The ingredients are combined together at a temperature below the cloud point and then the formulation is thermally cycled to room temperature (above the cloud point) several times, according to the protocol outlined in FIG. 2.

A 1.28 mM solution of BAK is prepared in PBS, 846 μl of the solution is placed into a 15 ml round bottom flask fitted with a magnetic stirring bar, and the solution is stirred with moderate speed, in an ice bath on top of a stirrer/hotplate (hotplate off) for 10 minutes. CRL 1005 (27 μl) is then added using a 100 μl positive displacement pipette and the solution is stirred for a further 60 minutes on ice. Plasmids comprising coding regions or codon-optimized coding regions encoding SARS-CoV proteins, for example, S, S1, S2, N, M, or E, as described herein, and optionally, additional plasmids comprising codon-optimized or non-codon-optimized coding regions encoding, e.g., additional SARS-CoV proteins, and or other proteins, e.g., cytokines, are mixed together at desired proportions in PBS to achieve 6.4 mg/ml total DNA. This plasmid cocktail is added dropwise, slowly, to the stirring solution over 1 min using a 5 ml pipette. The solution at this point (on ice) is clear since it is below the cloud point of the poloxamer and is further stirred on ice for 15 min. The ice bath is then removed, and the solution is stirred at ambient temperature for 15 minutes to produce a cloudy solution as the poloxamer passes through the cloud point.

The flask is then placed back into the ice bath and stirred for a further 15 minutes to produce a clear solution as the mixture is cooled below the poloxamer cloud point. The ice bath is again removed and the solution stirred at ambient temperature for a further 15 minutes. Stirring for 15 minutes above and below the cloud point (total of 30 minutes), is defined as one thermal cycle. The mixture is cycled six more times. The resulting formulation may be used immediately, or may be placed in a glass vial, cooled below the cloud point, and frozen at −80° C. for use at a later time.

Thermal Cycling, Dilution and Filtration of a Pre-mixed Formulation, Using Increased Concentrations of CRL 1005

Figure 3:
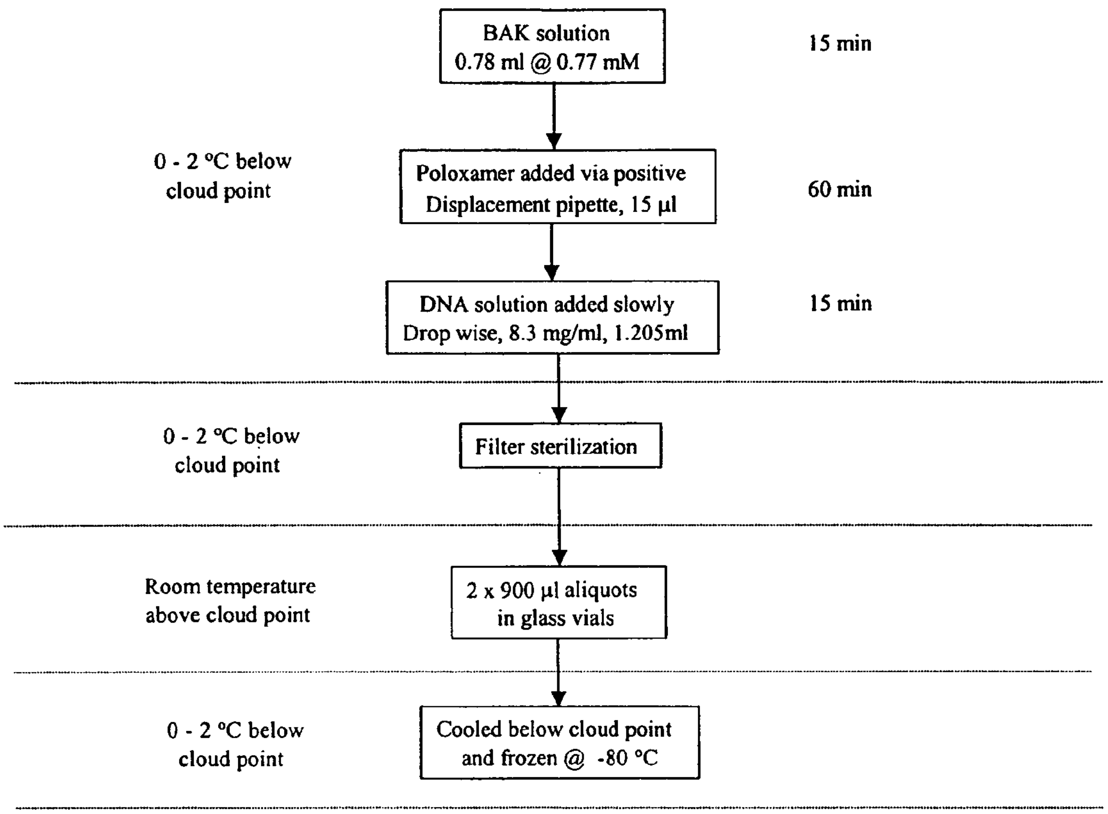
FIG. 3 shows the protocol for the simplified preparation (without thermal cycling) of a formulation comprising 0.3 mM BAK, 7.5 mg/ml CRL 1005, and 5 mg/ml DNA.

This example describes the preparation of a formulation comprising 0.3 mM BAK, 34 mg/ml or 50 mg/ml CRL 1005, and 2.5 mg/ml of DNA in a final volume of 4.0 ml. The ingredients are combined together at a temperature below the cloud point, then the formulation is thermally cycled to room temperature (above the cloud point) several times, diluted, and filtered according to the protocol outlined in FIG. 3.

Plasmids comprising wild-type or codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, and or other proteins, e.g., cytokines, are mixed together at desired proportions in PBS to achieve 6.4 mg/ml total DNA. This plasmid cocktail is placed into the 15 ml round bottom flask fitted with a magnetic stirring bar, and for the formulation containing 50 mg/ml CRL 1005, 3.13 ml of a solution containing about 3.2 mg/ml of e.g., S1 encoding plasmid and about 3.2 mg/ml S2 encoding plasmid (about 6.4 mg/ml total DNA) is placed into the 15 ml round bottom flask fitted with a magnetic stirring bar, and the solutions are stirred with moderate speed, in an ice bath on top of a stirrer/hotplate (hotplate off) for 10 minutes. CRL 1005 (136 μl for 34 mg/ml final concentration, and 100 μl for 50 mg/ml final concentration) is then added using a 200 μl positive displacement pipette and the solution is stirred for a further 30 minutes on ice. Solutions of 1.6 mM and 1.8 mM BAK are prepared in PBS, and 739 μl of 1.6 mM and 675 μl of 1.8 mM are then added dropwise, slowly, to the stirring poloxamer solutions with concentrations of 34 mg/ml or 50 mg/ml mixtures, respectively, over 1 min using a 1 ml pipette. The solutions at this point are clear since they are below the cloud point of the poloxamer and are stirred on ice for 30 min. The ice baths are then removed; the solutions stirred at ambient temperature for 15 minutes to produce cloudy solutions as the poloxamer passes through the cloud point.

The flasks are then placed back into the ice baths and stirred for a further 15 minutes to produce clear solutions as the mixtures cooled below the poloxamer cloud point. The ice baths are again removed and the solutions stirred for a further 15 minutes. Stirring for 15 minutes above and below the cloud point (total of 30 minutes), is defined as one thermal cycle. The mixtures are cycled two more times.

In the meantime, two Steriflip® 50 ml disposable vacuum filtration devices, each with a 0.22 μm Millipore Express® membrane (available from Millipore, cat # SCGP00525) are placed in an ice bucket, with a vacuum line attached and left for 1 hour to allow the devices to equilibrate to the temperature of the ice. The poloxamer formulations are then diluted to 2.5 mg/ml DNA with PBS and filtered under vacuum.

The resulting formulations may be used immediately, or may be transferred to glass vials, cooled below the cloud point, and frozen at −80° C. for use at a later time.

A Simplified Method Without Thermal Cycling

This example describes a simplified preparation of a formulation comprising 0.3 mM BAK, 7.5 mg/ml CRL 1005, and 5 mg/ml of DNA in a total volume of 2.0 ml. The ingredients are combined together at a temperature below the cloud point and then the formulation is simply filtered and then used or stored, according to the protocol outlined in FIG. 4.

A 0.77 mM solution of BAK is prepared in PBS, and 780 μl of the solution is placed into a 15 ml round bottom flask fitted with a magnetic stirring bar, and the solution is stirred with moderate speed, in an ice bath on top of a stirrer/hotplate (hotplate off) for 15 minutes. CRL 1005 (15 μl) is then added using a 100 μl positive displacement pipette and the solution is stirred for a further 60 minutes on ice. Plasmids comprising coding regions or codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, and or other proteins, e.g., cytokines, are mixed together at desired proportions in PBS to achieve a final concentration of about 8.3 mg/ml total DNA. This plasmid cocktail is added dropwise, slowly, to the stirring solution over 1 min using a 5 ml pipette. The solution at this point (on ice) is clear since it is below the cloud point of the poloxamer and is further stirred on ice for 15 min.

In the meantime, one Steriflip® 50 ml disposable vacuum filtration device, with a 0.22 μm Millipore Express® membrane (available from Millipore, cat # SCGP00525) is placed in an ice bucket, with a vacuum line attached and left for 1 hour to allow the device to equilibrate to the temperature of the ice. The poloxamer formulation is then filtered under vacuum, below the cloud point and then allowed to warm above the cloud point. The resulting formulations may be used immediately, or may be transferred to glass vials, cooled below the cloud point and then frozen at −80° C. for use at a later time.

Example 5

Animal Immunizations

The immunogenicity of the various SARS-CoV expression products encoded polynucleotides and codon-optimized polynucleotides described herein are initially evaluated based on each plasmid's ability to mount an immune response in vivo. Plasmids are tested individually and in combinations by injecting single constructs as well as multiple constructs. Immunizations are initially carried out in animals, such as mice, rabbits, goats, sheep, domestic cats, non-human primates, or other suitable animal, by intramuscular (IM) injections. Serum is collected from immunized animals, and the antigen specific antibody response is quantified by ELISA assay using purified immobilized antigen proteins in a protein—immunized subject antibody—anti-species antibody type assay, according to standard protocols. The tests of immunogenicity further include measuring antibody titer, neutralizing antibody titer, T-cell proliferation, T-cell secretion of cytokines, and cytolytic T cell responses. Correlation to protective levels of the immune responses in humans are made according to methods well known by those of ordinary skill in the art. See above.

A. DNA Formulations

Plasmid DNA is formulated with a poloxamer by any of the methods described in Example 3. Alternatively, plasmid DNA is prepared as described above and dissolved at a concentration of about 0.1 mg/ml to about 10 mg/ml, preferably about 1 mg/ml, in PBS with or without transfection-facilitating cationic lipids, e.g., DMRIE/DOPE at a 4:1 DNA:lipid mass ratio. Alternative DNA formulations include 150 mM sodium phosphate instead of PBS, adjuvants, e.g., Vaxfectin™ at a 4:1 DNA: Vaxfectin™ mass ratio, mono-phosphoryl lipid A (detoxified endotoxin) from *S. minnesota* (MPL) and trehalosedicorynomycolateAF (TDM), in 2% oil (squalene)-Tween 80-water (MPL+TDM, available from Sigma/Aldrich, St. Louis, Mo., (catalog # M6536)), a solubilized mono-phosphoryl lipid A formulation (AF, available from Corixa), or (±)-N-(3-Acetoxypropyl)-N,N-dimethyl-2,3-bis(octyloxy)-1-propanaminium chloride (compound # VC1240) (see Shriver, J. W. et al., *Nature* 415:331-335 (2002), and P.C.T. Publication No. WO 02/00844 A2, each of which is incorporated herein by reference in its entirety).

B. Animal Immunizations

Plasmid constructs comprising codon-optimized or non-codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, as well as various controls, e.g., empty vector, are injected into BALB/c mice as single plasmids or as cocktails of two or more plasmids, as either DNA in PBS or formulated with the poloxamer-based delivery system: 2 mg/ml DNA, 3 mg/ml CRL 1005, and 0.1 mM BAK. Groups of 10 mice are immunized three times, at biweekly intervals, and serum is obtained to determine antibody titers to each of the antigens. Groups are also included in which mice are immunized with a trivalent preparation, containing each of three plasmid constructs expressing any of the SARS Co-V polypeptides, e.g., soluble, extracellular S1, M, and N polypeptides, in equal mass.

An example of an immunization schedule is as follows:

| | |
|---|---|
| Day −3 | Pre-bleed |
| Day 0 | Plasmid injections, intramuscular, bilateral in rectus femoris, 5-50 μg/leg |
| Day 20 | Serum Collection |
| Day 21 | Plasmid injections, intramuscular, bilateral in rectus femoris, 5-50 μg/leg |
| Day 48 | Serum Collection |
| Day 49 | Plasmid injections, intramuscular, bilateral in rectus femoris, 5-50 μg/leg |
| Day 59 | Serum collection |

Serum antibody titers, at the various time points are determined by ELISA, using as the antigen SARS-CoV protein preparations including, but not limited to, purified recombinant proteins, transfection supernatants and lysates from mammalian or insect cells transfected with the various plasmids described herein, or live, inactivated, or lysed SARS-CoV virus.

C. Immunization of Mice with Vaccine Formulations Using a VAXFECTIN™ Adjuvant

VAXFECTIN™ (a 1:1 molar ratio of the cationic lipid VC1052 and the neutral co-lipid DPyPE) is a synthetic cationic lipid formulation which has shown promise for its ability to enhance antibody titers against an antigen when administered with DNA encoding the antigen intramuscularly to mice. See Hartikka et al. "Vaxfectin Enhances the Humoral Response to Plasmid DNA-encoded Antigens." *Vaccine* 19: 1911-1923 (2001).

In mice, intramuscular injection of VAXFECTIN™ formulated with, for example, DNA encoding the IAV NP protein increased antibody titers to NP up to 20-fold to levels that could not be reached with DNA alone. In rabbits, complexing DNA with VAXFECTIN™ enhanced antibody titers up to 50-fold. Thus, VAXFECTIN™ shows promise as a delivery system and as an adjuvant in a DNA vaccine.

Vaxfectin™mixtures are prepared by mixing chloroform solutions of VC1052 cationic lipid with chloroform solutions of DpyPE neutral co-lipid. Dried films are prepared in 2 ml sterile glass vials by evaporating the chloroform under a stream of nitrogen, and placing the vials under vacuum overnight to remove solvent traces. Each vial contains 1.5 μmole each of VC1052 and DPyPE. Liposomes are prepared by adding sterile water followed by vortexing. The resulting liposome solution is mixed with DNA at a phosphate mole: cationic lipid mole ratio of 4:1.

Plasmid constructs comprising codon-optimized and non-codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, as well as various controls, e.g., empty vector, are mixed together at desired proportions in PBS to achieve a final concentration of at 1.0 mg/ml. The plasmid cocktail, as well as the controls, are formulated with VAXFECTIN™. Groups of 5 Balb/c female mice are injected bilaterally in the rectus femoris muscle with 50 μl of DNA solution (100 μl total/mouse), on days 1 and 21 and 49 with each formulation. Mice are bled for serum on days 0 (prebleed), 20 (bleed 1), and 41 (bleed 2), and 62 (bleed 3), and up to 40 weeks post-injection. Antibody titers to the various SARS CoV proteins encoded by the plasmid DNAs are measured by ELISA as described elsewhere herein.

Cytolytic T-cell responses are measured as described in Hartikka et al. "Vaxfectin Enhances the Humoral Response to Plasmid DNA-encoded Antigens." *Vaccine* 19: 1911-1923 (2001) and is incorporated herein in its entirety by reference. Standard ELISPOT technology is used for the CD4+ and CD8+ T-cell assays as described in Example 6, part A.

D. Production of SARS-CoV Antisera in Animals

Plasmid constructs comprising codon-optimized and non-codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, as well as various controls, e.g., empty vector, are prepared according to the immunization scheme described above and injected into a suitable animal for generating polyclonal antibodies. Serum is collected and the antibody titered as above.

Monoclonal antibodies are also produced using hybridoma technology. Kohler, et al., *Nature* 256:495 (1975); Kohler, et al., *Eur. J. Immunol.* 6:511 (1976); Kohler, et al., *Eur. J. Immunol.* 6:292 (1976); Hammerling, et al., in *Monoclonal Antibodies and T-Cell Hybridomas*, Elsevier, N.Y., (1981), pp. 563-681, each of which is incorporated herein by reference in its entirety. In general, such procedures involve immunizing an animal (preferably a mouse) as described above. The splenocytes of such mice are extracted and fused with a suitable myeloma cell line. Any suitable myeloma cell line may be employed in accordance with the present invention; however, it is preferable to employ the parent myeloma cell line (Sp2/0), available from the American Type Culture Collection, Rockville, Md. After fusion, the resulting hybridoma cells are selectively maintained in HAT medium, and then cloned by limiting dilution as described by Wands et al., *Gastroenterology* 80:225-232 (1981), incorporated herein by reference in its entirety. The hybridoma cells obtained through such a selection are then assayed to identify clones which secrete antibodies capable of binding the various SARS-CoV proteins.

Alternatively, additional antibodies capable of binding to SARS-CoV proteins described herein may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, various SARS-CoV-specific antibodies are used to immunize an animal, preferably a mouse. The splenocytes of such an animal are then used to produce hybridoma cells, and the hybridoma cells are screened to identify clones which produce an antibody whose ability to bind to the SARS-CoV protein-specific antibody can be blocked by the cognate SARS-CoV protein. Such antibodies comprise anti-idiotypic antibodies to the SARS-CoV protein-specific antibody and can be used to immunize an animal to induce formation of further SARS-CoV-specific antibodies.

It will be appreciated that Fab and $F(ab')_2$ and other fragments of the antibodies of the present invention may be used according to the methods disclosed herein. Such fragments are typically produced by proteolytic cleavage, using enzymes such as papain (to produce Fab fragments) or pepsin (to produce $F(ab')_2$ fragments). Alternatively, SARS-CoV polypeptide binding fragments can be produced through the application of recombinant DNA technology or through synthetic chemistry.

It may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi, et al., *BioTechniques* 4:214 (1986); Cabilly, et al., U.S. Pat. No. 4,816,567; Taniguchi, et al., EP 171496; Morrison, et al., EP 173494; Neuberger, et al., WO 8601533; Robinson, et al., WO 8702671; Boulianne, et al., *Nature* 312:643 (1984); Neuberger, et al., *Nature* 314:268 (1985).

These antibodies are used, for example, in diagnostic assays, as a research reagent, or to further immunize animals to generate SARS-CoV-specific anti-idiotypic antibodies. Non-limiting examples of uses for anti-SARS-CoV antibodies include use in Western blots, ELISA (competitive, sandwich, and direct), immunofluorescence, immunoelectron microscopy, radioimmunoassay, immunoprecipitation, agglutination assays, immunodiffision, immunoelectrophoresis, and epitope mapping. Weir, D. *Ed. Handbook of Experimental Immunology,* 4th ed. Vols. I and II, Blackwell Scientific Publications (1986).

Example 6

Mouse and Rabbit Immunogenicity Studies to SARS-CoV Antigens

Balb/c mice were injected intramuscularly bilaterally with 100 μg of SARS-CoV antigen expressing plasmid. VR9204, VR9208, VR9209, VR9210, VR9219 plasmids were formulated in PBS and DMRIE:DOPE at a 4:1 DNA:lipid mass ratio.

New Zealand white rabbits were injected intramuscularly bilaterally with 1 mg of SARS-CoV antigen expressing plasmid (VR9219 (N antigen) or VR9204 (S1 fragment antigen), formulated with DMRIE:DOPE, on days 1, 28 and 56. Rabbit sera anti-antigen titers were determined by ELISA assay. The ELISA assay was performed according to standard protocols. ELISA plates used in the assay were coated with cell culture supernatants, from cells transfected with the a SARS-CoV antigen plasmid. Sera from rabbits which had been injected with the corresponding plasmid was then applied to the plates. Bound rabbit antibodies were detected using an alkaline phosphatase-modified donkey anti-rabbit IgG monoclonal antibody (Jackson Immuno Research; Cat No. 711-055-152). Bound antibodies were detected by standard colorimetric method after 2.5 hours of incubation with chromogenic substrates. Optical Density was determined at a wavelength of 405 nm. The results of the ELISA assay are summarized below.

Data shown in Table 20 demonstrate the presence of anti-nucleocapsid antibodies at day 21 in rabbits injected with plasmid VR9219 expressing full-length SARS-CoV nucleocapsid antigen. The antibody titers reach a plateau at day 42 (1:400 dilution).

In another experiment, rabbits were injected with plasmid VR9204, which expresses a fragment of the SARS-CoV Spike S1 domain. ELISA plates were coated with in vitro-produced full length-secreted Spike protein from cells transfected with plasmid VR9210. Antibodies IMG-542 and IMG-557, which recognize amino acids 288-303 and 1124-1140 of the SARS-CoV spike protein respectively (available from lmgenex, San Diego, Calif.), were used as positive controls in the ELISA assay. An ELISA plate coated with supernatant from VR1012-transfected VM92 cells was used as a negative control in the ELISA assay. The data shown in Table 20 demonstrate the presence of anti-Spike antibodies at days 42 and 50 after injection.

TABLE 20

Anti-SARS CoV Antigen Titers (Rabbits)

| | Nucleocapsid Plamsid - VR9219 1/400 sera dilution | S1 fragment Plasmid - VR9204 1/200 sera dilution |
|---|---|---|
| Day 21 | 0.92 | 0.22 |
| Day 42 | 3.9 | 0.74 |
| Day 50 | NA | 0.51 |
| Day 80 | 4 | NA |
| Pre-bleed | 0.13 | 0.19 |
| IMG-542 | NA | 0.44 |
| IMG-557 | NA | 2.41 |
| VR1012 | 0.15 | 0.21 |

Example 7

Mucosal Vaccination and Electrically Assisted Plasmid Delivery

A. Mucosal DNA Vaccination

Plasmid constructs comprising codon-optimized and non-codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, as well as various controls, e.g., empty vector, (100 μg/50 μl total DNA) are delivered to BALB/c mice at 0, 2 and 4 weeks via i.m., intranasal (i.n.), intravenous (i.v.), intravaginal (i.vag.), intrarectal (i.r.) or oral routes. The DNA is delivered unformulated, formulated with the cationic lipids DMRIE/DOPE (DD) or GAP-DLRIE/DOPE (GD), or formulatated with a poloxamer as described in Example 3. As endpoints, serum IgG titers against the various SARS-CoV antigens are measured by ELISA and splenic T-cell responses are measured by antigen-specific production of IFN-gamma and IL-4 in ELISPOT assays. Standard chromium release assays are used to measure specific cytotoxic T lymphocyte (CTL) activity against the various SARS-CoV antigens. In addition, IgG and IgA responses against the various SARS-CoV antigens are analyzed by ELISA of vaginal washes.

B. Electrically-Assisted Plasmid Delivery

In vivo gene delivery may be enhanced through the application of brief electrical pulses to injected tissues, a procedure referred to herein as electrically-assisted plasmid delivery. See, e.g., Aihara, H. & Miyazaki, J. *Nat. Biotechnol.* 16:867-70 (1998); Mir, L. M. et al., *Proc. Natl Acad. Sci. USA* 96:4262-67 (1999); Hartikka, J. et al., *Mol. Ther.* 4:407-15 (2001); and Mir, L. M. et al.; Rizzuto, G. et al., *Hum Gene Ther* 11:1891-900 (2000); Widera, G. et al, *J. of Immuno.* 164: 4635-4640 (2000). The use of electrical pulses for cell electropermeabilization has been used to introduce foreign DNA into prokaryotic and eukaryotic cells in vitro. Cell permeabilization can also be achieved locally, in vivo, using electrodes and optimal electrical parameters that are compatible with cell survival.

The electroporation procedure can be performed with various electroporation devices. These devices include external plate type electrodes or invasive needle/rod electrodes and can possess two electrodes or multiple electrodes placed in an array. Distances between the plate or needle electrodes can vary depending upon the number of electrodes, size of target area and treatment subject.

The TriGrid needle array, used in examples described herein, is a three electrode array comprising three elongate electrodes in the approximate shape of a geometric triangle. Needle arrays may include single, double, three, four, five, six or more needles arranged in various array formations. The electrodes are connected through conductive cables to a high voltage switching device that is connected to a power supply.

The electrode array is placed into the muscle tissue, around the site of nucleic acid injection, to a depth of approximately 3 mm to 3 cm. The depth of insertion varies depending upon the target tissue and the size of the patient receiving electroporation. After injection of foreign nucleic acid, such as plasmid DNA, and a period of time sufficient for distribution of the nucleic acid, square wave electrical pulses are applied to the tissue. The amplitude of each pulse ranges from about 100 volts to about 1500 volts, e.g., about 100 volts, about 200 volts, about 300 volts, about 400 volts, about 500 volts, about 600 volts, about 700 volts, about 800 volts, about 900 volts, about 1000 volts, about 1100 volts, about 1200 volts, about 1300 volts, about 1400 volts, or about 1500 volts or about 1-1.5 kV/cm, based on the spacing between electrodes. Each pulse has a duration of about 1 μs to about 1000 μs, e.g., about 1 μs, about 10 μs, about 50 μs, about 100 μs, about 200 μs, about 300 μs, about 400 μs, about 500 μs, about 600 μs, about 700 μs, about 800 μs, about 900 μs, or about 1000 μs, and a pulse frequency on the order of about 1-10 Hz. The polarity of the pulses may be reversed during the electroporation procedure by switching the connectors to the pulse generator. Pulses are repeated multiple times. The electroporation parameters (e.g., voltage amplitude, duration of pulse, number of pulses, depth of electrode insertion and frequency) will vary based on target tissue type, number of electrodes used and distance of electrode spacing, as would be understood by one of ordinary skill in the art.

Immediately after completion of the pulse regimen, subjects receiving electroporation can be optionally treated with membrane stabilizing agents to prolong cell membrane permeability as a result of the electroporation.

Examples of membrane stabilizing agents include, but are not limited to, steroids (e.g., dexamethasone, methylprednisone and progesterone), angiotensin II and vitamin E. A single dose of dexamethasone, approximately 0.1 mg per kilogram of body weight, should be sufficient to achieve a beneficial affect.

EAPD techniques such as electroporation can also be used for plasmids contained in liposome formulations. The liposome—plasmid suspension is administered to the animal or patient and the site of injection is treated with a safe but effective electrical field generated, for example, by a TriGrid needle array. The electroporation may aid in plasmid delivery to the cell by destabilizing the liposome bilayer so that membrane fusion between the liposome and the target cellular structure occurs. Electroporation may also aid in plasmid delivery to the cell by triggering the release of the plasmid, in high concentrations, from the liposome at the surface of the target cell so that the plasmid is driven across the cell membrane by a concentration gradient via the pores created in the cell membrane as a result of the electroporation.

Female BALB/c mice aged 8-10 weeks are anesthetized with inhalant isoflurane and maintained under anesthesia for the duration of the electroporation procedure. The legs are shaved prior to treatment. Plasmid constructs comprising codon-optimized and non-codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, as well as various controls, e.g., empty vector, are administered to BALB/c mice (n=10) via unilateral injection in the quadriceps with 25 μg total of a plasmid DNA per mouse using an 0.3 cc insulin syringe and a 26 gauge, ½ length needle fitted with a plastic collar to regulate injection depth. Approximately one minute after injection, electrodes are applied. Modified caliper electrodes are used to apply the electrical pulse. See Hartikka J. et al. *Mol Ther* 188:407-415 (2001). The caliper electrode plates are coated with conductivity gel and applied to the sides of the injected muscle before closing to a gap of 3 mm for administration of pulses. EAPD is applied using a square pulse type at 1-10 Hz with a field strength of 100-500 V/cm, 1-10 pulses, of 10-100 ms each.

Mice are vaccinated±EAPD at 0, 2 and 4 weeks. As endpoints, serum IgG titers against the various SARS-CoV antigens are measured by ELISA and splenic T-cell responses are measured by antigen-specific production of IFN-gamma and IL-4 in ELISPOT assays. Standard chromium release assays are used to measure specific cytotoxic T lymphocyte (CTL) activity against the various SARS-CoV antigens.

Rabbits (n=3) are given bilateral injections in the quadriceps muscle with plasmid constructs comprising codon-optimized and non-codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, as well as various controls, e.g., empty vector. The implantation area is shaved and the TriGrid electrode array is implanted into the target region of the muscle. 3.0 mg of plasmid DNA is administered per dose through the injection port of the electrode array. An injection collar is used to control the depth of injection. Electroporation begins approximately one minute after injection of the plasmid DNA is complete. Electroporation is administered with a TriGrid needle array, with eletrodes evenly spaced 7 mm apart, using an Ichor TGP-2 pulse generator. The array is inserted into the target muscle to a depth of about 1 to 2 cm. 4-8 pulses are administered. Each pulse has a duration of about 50-100 μs, an amplitude of about 1-1.2 kV/cm and a pulse frequency of 1 Hz. The injection and electroporation may be repeated.

Sera are collected from vaccinated rabbits at various time points. As endpoints, serum IgG titers against the various SARS-CoV antigens are measured by ELISA and PBMC T-cell proliferative responses are measured by antigen-specific production of IFN-gamma and IL-4 in ELISPOT assays or by quantification of intracellular cytokine staining. Standard chromium release assays are used to measure specific cytotoxic T lymphocyte (CTL) activity against the various SARS-CoV antigens.

To test the effect of electroporation on therapeutic protein expression in non-human primates, male or female rhesus monkeys are given either 2 or 6 EAPD-assisted i.m. injections of plasmid constructs comprising codon-optimized and/or non-codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, as well as various controls, e.g., empty vector, (0.1 to 10 mg DNA total per animal). Target muscle groups include, but are not limited to, bilateral rectus fermoris, cranial tibialis, biceps, gastrocenemius or deltoid muscles. The target area is shaved and a needle array, comprising between 4 and 10 electrodes, spaced between 0.5-1.5 cm apart, is implanted into the target muscle. Once injections are complete, a sequence of brief electrical pulses is applied to the electrodes implanted in the target muscle using an Ichor TGP-2 pulse generator. The pulses have an amplitude of approximately 120-200V. The pulse sequence is completed within one second. During this time, the target muscle may make brief contractions or twitches. The injection and electroporation may be repeated.

Sera are collected from vaccinated monkeys at various time points. As endpoints, serum IgG titers against the various SARS-CoV antigens are measured by ELISA and PBMC T-cell proliferative responses are measured by antigen-specific production of IFN-gamma and IL-4 in ELISPOT assays or by quantification of intracellular cytokine staining Standard chromium release assays are used to measure specific cytotoxic T lymphocyte (CTL) activity against the various SARS-CoV antigens.

Example 8

Combinatorial DNA Vaccine Using Heterologous Prime-Boost Vaccination

This Example describes vaccination with a combinatorial formulation including one or more polynucleotides comprising at least one codon-optimized or non-codon optimized coding regions encoding a SARS-CoV protein or fragment, variant, or derivative thereof prepared with an adjuvant and/or transfection facilitating agent; and also an isolated SARS-CoV protein or fragment, variant, or derivative thereof. Thus, antigen is provided in two forms. The exogenous isolated protein stimulates antigen specific antibody and CD4+ T-cell responses, while the polynucleotide-encoded protein, produced as a result of cellular uptake and expression of the coding region, stimulates a CD8+ T-cell response. Unlike conventional "prime-boost" vaccination strategies, this approach provides different forms of antigen in the same formulation. Because antigen expression from the DNA vaccine doesn't peak until 7-10 days after injection, the DNA vaccine provides a boost for the protein component. Furthermore, the formulation takes advantage of the immunostimulatory properties of the bacterial plasmid DNA.

A. Formulation Determinations for SARS-CoV proteins

This example mainly describes this procedure using an S2 subunit protein; however, the methods described herein are applicable to any SARS-CoV subunit protein combined with any polynucleotide vaccine formulation. For example any polynucleotide comprising a codon-optimized or non-codon-optimized coding region encoding any SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg may be combined with any subunit SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg. Because only a small amount of protein is needed in this method, it is conceivable that the approach could be used to reduce the dose of other types of protein or antibody based vaccines, not described herein, when administered in combination with the polynucleotides and polypeptides of the present invention. The decreased dosing of other vaccines would allow for the increased availability of scarce or expensive vaccines. This feature would be particularly important for vaccines against pandemic SARS or biological warfare agents.

In this example, an injection dose of 10 μg SARS-CoV S protein, subunit 2 (S2) DNA per mouse, prepared essentially as described in Example 2 and in Ulmer, J. B., et al., *Science* 259:1745-49 (1993) and Ulmer, J. B. et al., *J Virol.* 72:5648-53 (1998) is pre-determined in dose response studies to induce T cell and antibody responses in the linear range of the dose response and results in a response rate of greater than 95% of mice injected. Each formulation, either a plasmid comprising a codon-optimized or non-codon-optimized coding region encoding S2 alone ("S2 DNA"), or S2 DNA+/−S2 protein formulated with Ribi I or the cationic lipids, DMRIE:DOPE or Vaxfectin ™is prepared in the recommended buffer for that vaccine modality. For injections with S2 DNA formulated with cationic lipid, the DNA is diluted in 2×PBS to 0.2 mg/ml+/−purified recombinant S2 protein (produced in baculovirus as described in Example 2) at 0.08 mg/ml. Each cationic lipid is reconstituted from a dried film by adding 1 ml of sterile water for injection (SWFI) to each vial and vortexing continuously for 2 min., then diluted with SWFI to a final concentration of 0.15 mM. Equal volumes of S2 DNA (+/−S2 protein) and cationic lipid are mixed to obtain a DNA to cationic lipid molar ratio of 4:1. For injections with DNA containing Ribi I adjuvant (Sigma), Ribi I is reconstituted with saline to twice the final concentration. Ribi I (2×) is mixed with an equal volume of S2 DNA at 0.2 mg/ml in saline+/−S2 protein at 0.08 mg/ml. For immunizations without cationic lipid or Ribi, S2 DNA is prepared in 150 mM sodium phosphate buffer, pH 7.2. For each experiment, groups of 9 BALB/c female mice at 7-9 weeks of age are injected with 50 μl of S2 DNA+/−S2 protein, cationic lipid or Ribi I. Injections are given bilaterally in each rectus femoris at day 0 and day 21. The mice are bled by OSP on day 20 and day 33 and serum titers of individual mice are measured.

S2 specific serum antibody titers are determined by indirect binding ELISA using 96 well ELISA plates coated overnight at 4° C. with purified recombinant S2 protein at 0.5 μg per well in BBS buffer pH 8.3. S2-coated wells are blocked with 1% bovine serum albumin in BBS for 1 h at room temperature. Two-fold serial dilutions of sera in blocking buffer are incubated for 2 h at room temperature and detected by incubating with alkaline phosphatase conjugated (AP) goat anti-mouse IgG-Fc (Jackson Immunoresearch, West Grove, Pa.) at 1:5000 for 2 h at room temperature. Color is developed with 1 mg/ml para-nitrophenyl phosphate (Calbiochem, La Jolla, Calif.) in 50 mM sodium bicarbonate buffer, pH 9.8 and 1 MM $MgCl_2$ and the absorbance read at 405 nm. The titer is the reciprocal of the last dilution exhibiting an absorbance value 2 times that of pre-bleed samples.

Standard ELISPOT technology, used to identify the number of interferon gamma (IFN-γ) secreting cells after stimulation with specific antigen (spot forming cells per million splenocytes, expressed as SFU/million), is used for the CD4+ and CD8+ T-cell assays. For the screening assays, 3 mice from each group are sacrificed on day 34, 35, and 36. At the time of collection, spleens from each group are pooled, and single cell suspensions made in cell culture media using a dounce homogenizer. Red blood cells are lysed, and cells washed and counted. For the CD4+ and CD8+ assays, cells are serially diluted 3-fold, starting at $10^6$ cells per well and transferred to 96 well ELISPOT plates pre-coated with anti-murine IFN-γ monoclonal antibody. Spleen cells are stimulated with the H-$2K^d$ binding peptide, TYQRTRALV (SEQ ID NO: 55) at 1 μg/ml and recombinant murine IL-2 at 1 U/ml for the CD8+ assay and with purified recombinant S2 protein at 20 μg/ml for the CD4+ assay. Cells are stimulated for 20-24 hours at 37° C. in 5% $CO_2$, then the cells are washed out and biotin labeled anti-IFN-γ monoclonal antibody added for a 2 hour incubation at room temperature. Plates are washed and horseradish peroxidase-labeled avidin is added. After a 1-hour incubation at room temperature, AEC substrate is added and "spots" developed for 15 min. Spots are counted using the Immunospot automated spot counter (C.T.L. Inc., Cleveland Ohio.). Thus, CD4+ and CD8+ responses are measured in three separate assays, using spleens collected on each of three consecutive days.

B. Determining Combinatorial Formulations with SARS-CoV Polynucleotide Constructs Plasmid constructs comprising codon-optimized or non-codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, as well as various controls, e.g., empty vector, are used in the prime-boost compositions described herein. For the prime-boost modalities, the same protein may be used for the boost, e.g., DNA encoding S2 with S2 protein, or a heterologous boost may be used, e.g., DNA encoding S2 with an M protein boost. Each formulation, the plasmid comprising a coding region for the SARS-CoV protein alone, or the plasmid comprising a coding region for the SARS-CoV protein plus the isolated protein, is formulated with Ribi I or the cationic lipids, DMRIE:DOPE or Vaxfectin™. The formulations are prepared in the recommended buffer for that vaccine modality. Exemplary formulations, using S2 as an example, are described herein. Other plasmid/protein formulations, including multivalent formulations, can be easily prepared by one of ordinary skill in the art by following this example. For injections with DNA formulated with cationic lipid, the DNA is diluted in 2×PBS to 0.2 mg/ml+/−purified recombinant SARS-CoV protein at 0.08 mg/ml. Each cationic lipid is reconstituted from a dried film by adding 1 ml of sterile water for injection (SWFI) to each vial and vortexing continuously for 2 min., then diluted with SWFI to a final concentration of 0.15 mM. Equal volumes of S2 DNA (+/−S2 protein) and cationic lipid are mixed to obtain a DNA to cationic lipid molar ratio of 4:1. For injections with DNA containing Ribi I adjuvant (Sigma), Ribi I is reconstituted with saline to twice the final concentration. Ribi I (2×) is mixed with an equal volume of S2 DNA at 0.2 mg/ml in saline+/−S2 protein at 0.08 mg/ml. For immunizations without cationic lipid or Ribi, S2 DNA is prepared in 150 mM sodium phosphate buffer, pH 7.2. For each experiment, groups of 9 BALB/c female mice at 7-9 weeks of age are injected with 50 .mu.l of S2 DNA+/−S2 protein, cationic lipid or Ribi I. The formulations are administered to BALB/c mice (n=10) via bilateral injection in each rectus femoris at day 0 and day 21.

The mice are bled on day 20 and day 33, and serum titers of individual mice to the various SARS-CoV antigens are measured. Serum antibody titers specific for the various SARS-CoV antigens are determined by ELISA. Standard ELISPOT technology, used to identify the number of interferon gamma (IFN-γ) secreting cells after stimulation with specific antigen (spot forming cells per million splenocytes, expressed as SFU/million), is used for the CD4+ and CD8+ T-cell assays using 3 mice from each group vaccinated as above, sacrificed on day 34, 35, and 36, post vaccination.

Example 9

Challenge in Non-Human Primates

The purpose of these studies is to evaluate three or more of the optimal plasmid DNA vaccine formulations for immunogenicity in non-human primates. Prelmimary challenge experiments may be carried out in toher suitable animal modes, for example birds as described below, or in domestic cats. Rhesus or cynomologus monkeys (6/group) are vaccinated with plasmid constructs comprising codon-optimized and non-codon-optimized coding regions encoding SARS-CoV proteins, for example, SARS-CoV S, S1, S2, N, M, E, soluble S, soluble S1, soluble S2, soluble TPA-S, soluble TPA-S1, and soluble TPA-S2 proteins, fusions thereof, or fragments, variants or derivatives of such proteins either alone or as fusions with a carrier protein, e.g., HBcAg, as well as various controls, e.g., empty vector, intramuscularly 0.1 to 2 mg DNA combined with cationic lipid, and/or poloxamer and/or aluminum phosphate based or other adjuvants at 0, 1 and 4 months.

Blood is drawn twice at baseline and then again at the time of and two weeks following each vaccination, and then again 4 months following the last vaccination. At 2 weeks post-vaccination, plasma is analyzed for humoral response and PBMCs are monitored for cellular responses, by standard methods described herein. Animals are monitored for 4 months following the final vaccination to determine the durability of the immune response.

Animals are challenged within 2-4 weeks following the final vaccination. Animals are challenged intratracheally with the suitable dose of virus based on preliminary challege studies. Nasal swabs, pharyngeal swabs and lung lavages are collected at days 0, 2, 4, 6, 8 and 11 post-challenge and will be assayed for cell-free virus titers on monkey kidney cells. After challenge, animals are monitored for clinical symptoms, e.g., rectal temperature, body weight, leukocyte counts, and in addition, hematocrit and respiratory rate. Oropharyngeal swab samples are taken to allow determination of the length of viral shedding. Illness is scored using a variety of conventional illness scoring methods such as the system developed by Berendt & Hall (*Infect Immun* 16:476-479 (1977)), and will be analyzed by analysis of variance and the method of least significant difference.

Example 10

Challenge in Birds

In this example, various vaccine formulations of the present invention are tested in a chicken SARS-CoV model. For these studies a SARS-CoV is used for the challenge. Plasmid constructs comprising codon-optimized and non-codon-optimized coding regions encoding S, S1, S2, N, M, E, soluble S, soluble S1, soluble S2, soluble TPA-S, soluble TPA-S1, and soluble TPA-S2, as described herein, fusions; or alternatively, coding regions (either codon-optimized or non-codon optimized) encoding various SARS-CoV proteins or fragments, variants or derivatives, either alone or as fusions with a carrier protein, e.g., HBcAg, as well as various controls, e.g., empty vector, are formulated with cationic lipid, and/or poloxamer and/or aluminum phosphate based or other adjuvants. The vaccine formulations are delivered at a dose of about 1-10 μg, delivered IM into the defeathered breast area, at 0 and 1 month. The animals are bled for antibody results 3 weeks following the second vaccine. Antibody titers against the various SARS-CoV antigens are determined using techniques described in the literature. See, e.g., Kodihalli S. et al., *Vaccine* 18:2592-9 (2000). The birds are challenged intranasally with 0.1 mL containing 100 $LD_{50}$ 3 weeks post second vaccination. The birds are monitored daily for 10 days for disease symptoms, which include gasping, coughing and nasal discharge, wet eyes and swollen sinuses, reduced food consumption and weight loss. Tracheal and cloacal swabs are taken 4 days following challenge for virus titration.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. A composition comprising an isolated polynucleotide comprising a nucleic acid fragment which encodes amino acids 1-417 of a SARS-CoV-S1 polypeptide, and a carrier, wherein said nucleic acid fragment is selected from the group consisting of SEQ ID NO: 26, SEQ ID NO: 27, SEQ ID NO: 45, SEQ ID NO: 50 and SEQ ID NO: 68 wherein said composition, when administered to a vertebrate in a sufficient amount, elicits a detectable immune response against SARS CoV; and wherein said composition further comprises a component of SARS-CoV selected from the group consisting of inactivated virus, attenuated virus, a viral vector expressing an isolated SARS-CoV virus polypeptide, and an isolated polypeptide from a SARS-CoV virus protein, fragment, variant or derivative thereof and/or one or more additional polynucleotides comprising at least one coding region encoding a SARS-CoV polypeptide, or a fragment, variant, or derivative thereof.

2. The composition of claim 1 wherein the isolated polynucleotide further comprises a heterologous nucleic acid.

3. The composition of claim 2, wherein said heterologous nucleic acid encodes polypeptide fused to said amino acids encoded by said nucleic acid fragment.

4. The composition of claim 3, wherein said heterologous polypeptide comprises a small self assembly polypeptide, and wherein said heterologous polypeptide self assembles into multimers.

5. The composition of claim 3, wherein said heterologous polypeptide is a secretory signal peptide.

6. The composition of claim 1, wherein the isolated polynucleotide is DNA, and wherein said nucleic acid fragment is operably associated with a promoter.

7. The composition of claim 1, wherein the isolated polynucleotide is messenger RNA (mRNA).

8. The composition of claim 1 comprising a vector comprising the isolated polynucleotide.

9. The composition of claim 8 wherein the vector is a plasmid.

10. The composition of claim 9, wherein said vector is VR9208.

11. The composition of claim 9, wherein said vector is VR9204.

12. The composition of claim 1, further comprising a component selected from the group consisting of an adjuvant and a transfection facilitating compound.

13. The composition of claim 12, wherein said adjuvant is selected from the group consisting of:

(±)-N-(3-aminopropyl)-N,N-dimethyl-2,3-bis(syn-9-tetradeceneyloxy)-1-propanaminium bromide (GAP-DMORIE) and a neutral lipid;

a cytokine;

mono-phosphoryl lipid A and trehalosedicorynomycolateAF (MPL+TDM);

a solubilized mono-phosphoryl lipid A formulation; and CRL1005/BAK.

14. The composition of claim 12, comprising the transfection facilitating compound (±)-N-(2-hydroxyethyl)-N,N-dimethyl-2,3-bis(tetradecyloxy)-1-propanaminium bromide) (DMRIE).

15. A method for raising a detectable immune response to a SARS-CoV polypeptide, comprising administering to a vertebrate the composition of claim 12 in an amount sufficient to elicit a detectable immune response to the encoded polypeptide.

16. A method for raising a detectable immune response to a SARS-CoV polypeptide, comprising administering to a vertebrate the composition of claim 1 in an amount sufficient to elicit a detectable immune response to the encoded polypeptide.

* * * * *

SEQUENCE LISTING

```
<160> NUMBER OF SEQ ID NOS: 69

<210> SEQ ID NO 1
<211> LENGTH: 3588
<212> TYPE: DNA
<213> ORGANISM: SARS-CoV Urbani strain

<400> SEQUENCE: 1

atgtttattt tcttattatt tcttactctc actagtggta gtgaccttga ccggtgcacc     60
```

-continued

```
acttttgatg atgttcaagc tcctaattac actcaacata cttcatctat gaggggggtt    120
tactatcctg atgaaatttt tagatcagac actctttatt taactcagga tttatttctt    180
ccattttatt ctaatgttac agggtttcat actattaatc atacgtttgg caaccctgtc    240
ataccttta aggatggtat ttattttgct gccacagaga aatcaaatgt tgtccgtggt    300
tgggtttttg gttctaccat gaacaacaag tcacagtcgg tgattattat taacaattct    360
actaatgttg ttatacgagc atgtaacttt gaattgtgtg acaacccttt ctttgctgtt    420
tctaaaccca tgggtacaca gacacatact atgatattcg ataatgcatt taattgcact    480
ttcgagtaca tatctgatgc cttttcgctt gatgtttcag aaaagtcagg taattttaaa    540
cacttacgag agtttgtgtt taaaaataaa gatgggtttc tctatgttta taagggctat    600
caacctatag atgtagttcg tgatctacct tctggtttta acactttgaa acctattttt    660
aagttgcctc ttggtattaa cattacaaat tttagagcca ttcttacagc cttttcacct    720
gctcaagaca tttggggcac gtcagctgca gcctattttg ttggctattt aaagccaact    780
acatttatgc tcaagtatga tgaaaatggt acaatcacag atgctgttga ttgttctcaa    840
aatccacttg ctgaactcaa atgctctgtt aagagctttg agattgacaa aggaatttac    900
cagacctcta atttcagggt tgttccctca ggagatgttg tgagattccc taatattaca    960
aacttgtgtc cttttggaga ggtttttaat gctactaaat tcccttctgt ctatgcatgg   1020
gagagaaaaa aaatttctaa ttgtgttgct gattactctg tgctctacaa ctcaacattt   1080
ttttcaacct ttaagtgcta tggcgtttct gccactaagt tgaatgatct ttgcttctcc   1140
aatgtctatg cagattcttt tgtagtcaag ggagatgatg taagacaaat agcgccagga   1200
caaactggtg ttattgctga ttataattat aaattgccag atgatttcat gggttgtgtc   1260
cttgcttgga atactaggaa cattgatgct acttcaactg gtaattataa ttataaatat   1320
aggtatctta gacatggcaa gcttaggccc tttgagagag acatatctaa tgtgcctttc   1380
tcccctgatg gcaaaccttg caccccacct gctcttaatt gttattggcc attaaatgat   1440
tatggttttt acaccactac tggcattggc taccaacctt acagagttgt agtactttct   1500
tttgaacttt taaatgcacc ggccacggtt tgtggaccaa aattatccac tgaccttatt   1560
aagaaccagt gtgtcaattt taattttaat ggactcactg gtactggtgt gttaactcct   1620
tcttcaaaga gatttcaacc atttcaacaa tttggccgtg atgtttctga tttcactgat   1680
tccgttcgag atcctaaaac atctgaaata ttagacattt caccttgctc ttttgggggt   1740
gtaagtgtaa ttacacctgg aacaaatgct tcatctgaag ttgctgttct atatcaagat   1800
gttaactgca ctgatgtttc tacagcaatt catgcagatc aactcacacc agcttggcgc   1860
atatattcta ctggaaacaa tgtattccag actcaagcag gctgtcttat aggagctgag   1920
catgtcgaca cttcttatga gtgcgacatt cctattggag ctggcatttg tgctagttac   1980
catacagttt ctttattacg tagtactagc caaaaatcta ttgtggctta tactatgtct   2040
ttaggtgctg atagttcaat tgcttactct aataacacca ttgctatacc tactaacttt   2100
tcaattagca ttactacaga agtaatgcct gtttctatgg ctaaaacctc cgtagattgt   2160
aatatgtaca tctgcggaga ttctactgaa tgtgctaatt tgcttctcca atatggtagc   2220
ttttgcacac aactaaatcg tgcactctca ggtattgctg ctgaacagga tcgcaacaca   2280
cgtgaagtgt tcgctcaagt caaacaaatg tacaaaaccc caactttgaa atattttggt   2340
ggttttaatt tttcacaaat attacctgac cctctaaagc caactaagag gtcttttatt   2400
gaggacttgc tctttaataa ggtgacactc gctgatgctg gcttcatgaa gcaatatggc   2460
```

```
gaatgcctag gtgatattaa tgctagagat ctcatttgtg cgcagaagtt caatggactt   2520

acagtgttgc cacctctgct cactgatgat atgattgctg cctacactgc tgctctagtt   2580

agtggtactg ccactgctgg atggacattt ggtgctggcg ctgctcttca aataccttt   2640

gctatgcaaa tggcatatag gttcaatggc attggagtta cccaaaatgt tctctatgag   2700

aaccaaaaac aaatcgccaa ccaatttaac aaggcgatta gtcaaattca agaatcactt   2760

acaacaacat caactgcatt gggcaagctg caagacgttg ttaaccagaa tgctcaagca   2820

ttaaacacac ttgttaaaca acttagctct aattttggtg caatttcaag tgtgctaaat   2880

gatatccttt cgcgacttga taaagtcgag gcggaggtac aaattgacag gttaattaca   2940

ggcagacttc aaagccttca aacctatgta acacaacaac taatcagggc tgctgaaatc   3000

agggcttctg ctaatcttgc tgctactaaa atgtctgagt gtgttcttgg acaatcaaaa   3060

agagttgact tttgtggaaa gggctaccac cttatgtcct tcccacaagc agccccgcat   3120

ggtgttgtct tcctacatgt cacgtatgtg ccatcccagg agaggaactt caccacagcg   3180

ccagcaattt gtcatgaagg caaagcatac ttccctcgtg aaggtgtttt tgtgtttaat   3240

ggcacttctt ggtttattac acagaggaac ttcttttctc cacaaataat tactacagac   3300

aatacatttg tctcaggaaa ttgtgatgtc gttattggca tcattaacaa cacagtttat   3360

gatcctctgc aacctgagct cgactcattc aaagaagagc tggacaagta cttcaaaaat   3420

catacatcac cagatgttga tcttggcgac atttcaggca ttaacgcttc tgtcgtcaac   3480

attcaaaaag aaattgaccg cctcaatgag gtcgctaaaa atttaaatga atcactcatt   3540

gaccttcaag aattgggaaa atatgagcaa tatattaaat ggccttgg               3588
```

<210> SEQ ID NO 2
<211> LENGTH: 1196
<212> TYPE: PRT
<213> ORGANISM: SARS-CoV Urbani strain

<400> SEQUENCE: 2

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175
```

-continued

```
Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605
```

```
Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
```

-continued

```
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080

Trp Phe  Ile Thr Gln Arg Asn  Phe Phe Ser Pro Gln  Ile Ile Thr
    1085                1090                1095

Thr Asp  Asn Thr Phe Val Ser  Gly Asn Cys Asp Val  Val Ile Gly
    1100                1105                1110

Ile Ile  Asn Asn Thr Val Tyr  Asp Pro Leu Gln Pro  Glu Leu Asp
    1115                1120                1125

Ser Phe  Lys Glu Glu Leu Asp  Lys Tyr Phe Lys Asn  His Thr Ser
    1130                1135                1140

Pro Asp  Val Asp Leu Gly Asp  Ile Ser Gly Ile Asn  Ala Ser Val
    1145                1150                1155

Val Asn  Ile Gln Lys Glu Ile  Asp Arg Leu Asn Glu  Val Ala Lys
    1160                1165                1170

Asn Leu  Asn Glu Ser Leu Ile  Asp Leu Gln Glu Leu  Gly Lys Tyr
    1175                1180                1185

Glu Gln  Tyr Ile Lys Trp Pro  Trp
    1190                1195
```

<210> SEQ ID NO 3
<211> LENGTH: 2049
<212> TYPE: DNA
<213> ORGANISM: SARS-CoV Urbani strain

<400> SEQUENCE: 3

```
atgtttattt tcttattatt tcttactctc actagtggta gtgaccttga ccggtgcacc     60

acttttgatg atgttcaagc tcctaattac actcaacata cttcatctat gaggggggtt    120

tactatcctg atgaaatttt tagatcagac actctttatt taactcagga tttatttctt    180

ccattttatt ctaatgttac agggtttcat actattaatc atacgtttgg caaccctgtc    240

atacctttta aggatggtat ttattttgct gccacagaga aatcaaatgt tgtccgtggt    300

tgggtttttg gttctaccat gaacaacaag tcacagtcgg tgattattat taacaattct    360

actaatgttg ttatacgagc atgtaacttt gaattgtgtg acaacccttt ctttgctgtt    420

tctaaaccca tgggtacaca gacacatact atgatattcg ataatgcatt taattgcact    480

ttcgagtaca tatctgatgc cttttcgctt gatgtttcag aaaagtcagg taattttaaa    540

cacttacgag agtttgtgtt taaaaataaa gatgggtttc tctatgttta taagggctat    600

caacctatag atgtagttcg tgatctacct tctggtttta acactttgaa acctattttt    660

aagttgcctc ttggtattaa cattacaaat tttagagcca ttcttacagc cttttcacct    720

gctcaagaca tttggggcac gtcagctgca gcctattttg ttggctattt aaagccaact    780

acatttatgc tcaagtatga tgaaaatggt acaatcacag atgctgttga ttgttctcaa    840

aatccacttg ctgaactcaa atgctctgtt aagagctttg agattgacaa aggaatttac    900

cagacctcta atttcagggt tgttccctca ggagatgttg tgagattccc taatattaca    960

aacttgtgtc cttttggaga ggtttttaat gctactaaat tcccttctgt ctatgcatgg   1020

gagagaaaaa aaatttctaa ttgtgttgct gattactctg tgctctacaa ctcaacattt   1080

ttttcaacct ttaagtgcta tggcgtttct gccactaagt tgaatgatct ttgcttctcc   1140
```

```
aatgtctatg cagattcttt tgtagtcaag ggagatgatg taagacaaat agcgccagga   1200

caaactggtg ttattgctga ttataattat aaattgccag atgatttcat gggttgtgtc   1260

cttgcttgga atactaggaa cattgatgct acttcaactg gtaattataa ttataaatat   1320

aggtatctta gacatggcaa gcttaggccc tttgagagag acatatctaa tgtgcctttc   1380

tcccctgatg gcaaaccttg caccccacct gctcttaatt gttattggcc attaaatgat   1440

tatggttttt acaccactac tggcattggc taccaacctt acagagttgt agtactttct   1500

tttgaacttt taaatgcacc ggccacggtt tgtggaccaa aattatccac tgaccttatt   1560

aagaaccagt gtgtcaattt taattttaat ggactcactg gtactggtgt gttaactcct   1620

tcttcaaaga gatttcaacc atttcaacaa tttggccgtg atgtttctga tttcactgat   1680

tccgttcgag atcctaaaac atctgaaata ttagacattt caccttgctc ttttgggggt   1740

gtaagtgtaa ttacacctgg aacaaatgct tcatctgaag ttgctgttct atatcaagat   1800

gttaactgca ctgatgtttc tacagcaatt catgcagatc aactcacacc agcttggcgc   1860

atatattcta ctggaaacaa tgtattccag actcaagcag gctgtcttat aggagctgag   1920

catgtcgaca cttcttatga gtgcgacatt cctattggag ctggcatttg tgctagttac   1980

catacagttt ctttattacg tagtactagc caaaaatcta ttgtggctta tactatgtct   2040

ttaggtgct                                                           2049
```

```
<210> SEQ ID NO 4
<211> LENGTH: 683
<212> TYPE: PRT
<213> ORGANISM: SARS-CoV Urbani strain

<400> SEQUENCE: 4

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205
```

-continued

```
Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640
```

```
His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala
        675                 680


<210> SEQ ID NO 5
<211> LENGTH: 1539
<212> TYPE: DNA
<213> ORGANISM: SARS-CoV Urbani strain

<400> SEQUENCE: 5

gatagttcaa ttgcttactc taataacacc attgctatac ctactaactt ttcaattagc      60

attactacag aagtaatgcc tgtttctatg gctaaaacct ccgtagattg taatatgtac     120

atctgcggag attctactga atgtgctaat ttgcttctcc aatatggtag cttttgcaca     180

caactaaatc gtgcactctc aggtattgct gctgaacagg atcgcaacac acgtgaagtg     240

ttcgctcaag tcaaacaaat gtacaaaacc ccaactttga aatattttgg tggttttaat     300

ttttcacaaa tattacctga ccctctaaag ccaactaaga ggtcttttat tgaggacttg     360

ctctttaata aggtgacact cgctgatgct ggcttcatga agcaatatgg cgaatgccta     420

ggtgatatta atgctagaga tctcatttgt gcgcagaagt tcaatggact tacagtgttg     480

ccacctctgc tcactgatga tatgattgct gcctacactg ctgctctagt tagtggtact     540

gccactgctg gatggacatt tggtgctggc gctgctcttc aaataccttt tgctatgcaa     600

atggcatata ggttcaatgg cattggagtt acccaaaatg ttctctatga gaaccaaaaa     660

caaatcgcca accaatttaa caaggcgatt agtcaaattc aagaatcact tacaacaaca     720

tcaactgcat tgggcaagct gcaagacgtt gttaaccaga atgctcaagc attaaacaca     780

cttgttaaac aacttagctc taattttggt gcaatttcaa gtgtgctaaa tgatatcctt     840

tcgcgacttg ataaagtcga ggcggaggta caaattgaca ggttaattac aggcagactt     900

caaagccttc aaacctatgt aacacaacaa ctaatcaggg ctgctgaaat cagggcttct     960

gctaatcttg ctgctactaa aatgtctgag tgtgttcttg gacaatcaaa aagagttgac    1020

ttttgtggaa agggctacca ccttatgtcc ttcccacaag cagccccgca tggtgttgtc    1080

ttcctacatg tcacgtatgt gccatcccag gagaggaact tcaccacagc gccagcaatt    1140

tgtcatgaag gcaaagcata cttccctcgt gaaggtgttt ttgtgtttaa tggcacttct    1200

tggtttatta cacagaggaa cttcttttct ccacaaataa ttactacaga caatacattt    1260

gtctcaggaa attgtgatgt cgttattggc atcattaaca acacagttta tgatcctctg    1320

caacctgagc tcgactcatt caaagaagag ctggacaagt acttcaaaaa tcatacatca    1380

ccagatgttg atcttggcga catttcaggc attaacgctt ctgtcgtcaa cattcaaaaa    1440

gaaattgacc gcctcaatga ggtcgctaaa aatttaaatg aatcactcat tgaccttcaa    1500

gaattgggaa aatatgagca atatattaaa tggccttgg                           1539


<210> SEQ ID NO 6
<211> LENGTH: 513
<212> TYPE: PRT
<213> ORGANISM: SARS-CoV Urbani strain

<400> SEQUENCE: 6

Asp Ser Ser Ile Ala Tyr Ser Asn Asn Thr Ile Ala Ile Pro Thr Asn
1               5                   10                  15
```

```
Phe Ser Ile Ser Ile Thr Thr Glu Val Met Pro Val Ser Met Ala Lys
            20                  25                  30

Thr Ser Val Asp Cys Asn Met Tyr Ile Cys Gly Asp Ser Thr Glu Cys
        35                  40                  45

Ala Asn Leu Leu Leu Gln Tyr Gly Ser Phe Cys Thr Gln Leu Asn Arg
    50                  55                  60

Ala Leu Ser Gly Ile Ala Ala Glu Gln Asp Arg Asn Thr Arg Glu Val
65                  70                  75                  80

Phe Ala Gln Val Lys Gln Met Tyr Lys Thr Pro Thr Leu Lys Tyr Phe
                85                  90                  95

Gly Gly Phe Asn Phe Ser Gln Ile Leu Pro Asp Pro Leu Lys Pro Thr
            100                 105                 110

Lys Arg Ser Phe Ile Glu Asp Leu Leu Phe Asn Lys Val Thr Leu Ala
        115                 120                 125

Asp Ala Gly Phe Met Lys Gln Tyr Gly Glu Cys Leu Gly Asp Ile Asn
    130                 135                 140

Ala Arg Asp Leu Ile Cys Ala Gln Lys Phe Asn Gly Leu Thr Val Leu
145                 150                 155                 160

Pro Pro Leu Leu Thr Asp Asp Met Ile Ala Ala Tyr Thr Ala Ala Leu
                165                 170                 175

Val Ser Gly Thr Ala Thr Ala Gly Trp Thr Phe Gly Ala Gly Ala Ala
            180                 185                 190

Leu Gln Ile Pro Phe Ala Met Gln Met Ala Tyr Arg Phe Asn Gly Ile
        195                 200                 205

Gly Val Thr Gln Asn Val Leu Tyr Glu Asn Gln Lys Gln Ile Ala Asn
    210                 215                 220

Gln Phe Asn Lys Ala Ile Ser Gln Ile Gln Glu Ser Leu Thr Thr Thr
225                 230                 235                 240

Ser Thr Ala Leu Gly Lys Leu Gln Asp Val Val Asn Gln Asn Ala Gln
                245                 250                 255

Ala Leu Asn Thr Leu Val Lys Gln Leu Ser Ser Asn Phe Gly Ala Ile
            260                 265                 270

Ser Ser Val Leu Asn Asp Ile Leu Ser Arg Leu Asp Lys Val Glu Ala
        275                 280                 285

Glu Val Gln Ile Asp Arg Leu Ile Thr Gly Arg Leu Gln Ser Leu Gln
    290                 295                 300

Thr Tyr Val Thr Gln Gln Leu Ile Arg Ala Ala Glu Ile Arg Ala Ser
305                 310                 315                 320

Ala Asn Leu Ala Ala Thr Lys Met Ser Glu Cys Val Leu Gly Gln Ser
                325                 330                 335

Lys Arg Val Asp Phe Cys Gly Lys Gly Tyr His Leu Met Ser Phe Pro
            340                 345                 350

Gln Ala Ala Pro His Gly Val Val Phe Leu His Val Thr Tyr Val Pro
        355                 360                 365

Ser Gln Glu Arg Asn Phe Thr Thr Ala Pro Ala Ile Cys His Glu Gly
    370                 375                 380

Lys Ala Tyr Phe Pro Arg Glu Gly Val Phe Val Phe Asn Gly Thr Ser
385                 390                 395                 400

Trp Phe Ile Thr Gln Arg Asn Phe Phe Ser Pro Gln Ile Ile Thr Thr
                405                 410                 415

Asp Asn Thr Phe Val Ser Gly Asn Cys Asp Val Val Ile Gly Ile Ile
            420                 425                 430

Asn Asn Thr Val Tyr Asp Pro Leu Gln Pro Glu Leu Asp Ser Phe Lys
```

-continued

```
        435                 440                 445

Glu Glu Leu Asp Lys Tyr Phe Lys Asn His Thr Ser Pro Asp Val Asp
    450                 455                 460

Leu Gly Asp Ile Ser Gly Ile Asn Ala Ser Val Val Asn Ile Gln Lys
465                 470                 475                 480

Glu Ile Asp Arg Leu Asn Glu Val Ala Lys Asn Leu Asn Glu Ser Leu
                485                 490                 495

Ile Asp Leu Gln Glu Leu Gly Lys Tyr Glu Gln Tyr Ile Lys Trp Pro
            500                 505                 510

Trp


<210> SEQ ID NO 7
<211> LENGTH: 3633
<212> TYPE: DNA
<213> ORGANISM: SARS-CoV Urbani strain

<400> SEQUENCE: 7

atggatgcaa tgaagagagg gctctgctgt gtgctgctgc tgtgtggagc agtcttcgtt     60

tcgcccagcg ctagaggatc gggaagtgac cttgaccggt gcaccacttt tgatgatgtt    120

caagctccta attacactca acatacttca tctatgaggg ggtttacta tcctgatgaa    180

atttttagat cagacactct ttatttaact caggatttat ttcttccatt ttattctaat    240

gttacagggt ttcatactat taatcatacg tttggcaacc ctgtcatacc ttttaaggat    300

ggtatttatt ttgctgccac agagaaatca aatgttgtcc gtggttgggt tttggttct    360

accatgaaca acaagtcaca gtcggtgatt attattaaca attctactaa tgttgttata    420

cgagcatgta actttgaatt gtgtgacaac cctttctttg ctgtttctaa acccatgggt    480

acacagacac atactatgat attcgataat gcatttaatt gcactttcga gtacatatct    540

gatgcctttt cgcttgatgt ttcagaaaag tcaggtaatt ttaaacactt acgagagttt    600

gtgtttaaaa ataaagatgg gtttctctat gtttataagg gctatcaacc tatagatgta    660

gttcgtgatc taccttctgg ttttaacact ttgaaaccta tttttaagtt gcctcttggt    720

attaacatta caaattttag agccattctt acagcctttt cacctgctca agacatttgg    780

ggcacgtcag ctgcagccta ttttgttggc tatttaaagc caactacatt tatgctcaag    840

tatgatgaaa atggtacaat cacagatgct gttgattgtt ctcaaaatcc acttgctgaa    900

ctcaaatgct ctgttaagag ctttgagatt gacaaaggaa tttaccagac ctctaatttc    960

agggttgttc cctcaggaga tgttgtgaga ttccctaata ttacaaactt gtgtcctttt   1020

ggagaggttt ttaatgctac taaattccct tctgtctatg catgggagag aaaaaaaatt   1080

tctaattgtg ttgctgatta ctctgtgctc tacaactcaa cattttttc aacctttaag   1140

tgctatggcg tttctgccac taagttgaat gatctttgct tctccaatgt ctatgcagat   1200

tcttttgtag tcaagggaga tgatgtaaga caaatagcgc caggacaaac tggtgttatt   1260

gctgattata attataaatt gccagatgat ttcatgggtt gtgtccttgc ttggaatact   1320

aggaacattg atgctacttc aactggtaat tataattata aatataggta tcttagacat   1380

ggcaagctta ggccctttga gagagacata tctaatgtgc ctttctcccc tgatggcaaa   1440

ccttgcaccc cacctgctct taattgttat tggccattaa atgattatgg tttttacacc   1500

actactggca ttggctacca accttacaga gttgtagtac tttcttttga acttttaaat   1560

gcaccggcca cggtttgtgg accaaaatta tccactgacc ttattaagaa ccagtgtgtc   1620

aattttaatt ttaatggact cactggtact ggtgtgttaa ctccttcttc aaagagattt   1680
```

```
caaccatttc aacaatttgg ccgtgatgtt tctgatttca ctgattccgt tcgagatcct   1740

aaaacatctg aaatattaga catttcacct tgctcttttg ggggtgtaag tgtaattaca   1800

cctggaacaa atgcttcatc tgaagttgct gttctatatc aagatgttaa ctgcactgat   1860

gtttctacag caattcatgc agatcaactc acaccagctt ggcgcatata ttctactgga   1920

aacaatgtat tccagactca agcaggctgt cttataggag ctgagcatgt cgacacttct   1980

tatgagtgcg acattcctat tggagctggc atttgtgcta gttaccatac agtttcttta   2040

ttacgtagta ctagccaaaa atctattgtg gcttatacta tgtctttagg tgctgatagt   2100

tcaattgctt actctaataa caccattgct atacctacta acttttcaat tagcattact   2160

acagaagtaa tgcctgtttc tatggctaaa acctccgtag attgtaatat gtacatctgc   2220

ggagattcta ctgaatgtgc taatttgctt ctccaatatg gtagcttttg cacacaacta   2280

aatcgtgcac tctcaggtat tgctgctgaa caggatcgca acacacgtga agtgttcgct   2340

caagtcaaac aaatgtacaa aaccccaact ttgaaatatt ttggtggttt taatttttca   2400

caaatattac ctgaccctct aaagccaact aagaggtctt ttattgagga cttgctcttt   2460

aataaggtga cactcgctga tgctggcttc atgaagcaat atggcgaatg cctaggtgat   2520

attaatgcta gagatctcat ttgtgcgcag aagttcaatg gacttacagt gttgccacct   2580

ctgctcactg atgatatgat tgctgcctac actgctgctc tagttagtgg tactgccact   2640

gctggatgga catttggtgc tggcgctgct cttcaaatac cttttgctat gcaaatggca   2700

tataggttca atggcattgg agttacccaa aatgttctct atgagaacca aaaacaaatc   2760

gccaaccaat ttaacaaggc gattagtcaa attcaagaat cacttacaac aacatcaact   2820

gcattgggca agctgcaaga cgttgttaac cagaatgctc aagcattaaa cacacttgtt   2880

aaacaactta gctctaattt tggtgcaatt tcaagtgtgc taaatgatat cctttcgcga   2940

cttgataaag tcgaggcgga ggtacaaatt gacaggttaa ttacaggcag acttcaaagc   3000

cttcaaacct atgtaacaca acaactaatc agggctgctg aaatcagggc ttctgctaat   3060

cttgctgcta ctaaaatgtc tgagtgtgtt cttggacaat caaaaagagt tgacttttgt   3120

ggaaagggct accaccttat gtccttccca caagcagccc cgcatggtgt tgtcttccta   3180

catgtcacgt atgtgccatc ccaggagagg aacttcacca cagcgccagc aatttgtcat   3240

gaaggcaaag catacttccc tcgtgaaggt gtttttgtgt ttaatggcac ttcttggttt   3300

attacacaga ggaacttctt ttctccacaa ataattacta cagacaatac atttgtctca   3360

ggaaattgtg atgtcgttat tggcatcatt aacaacacag tttatgatcc tctgcaacct   3420

gagctcgact cattcaaaga agagctggac aagtacttca aaaatcatac atcaccagat   3480

gttgatcttg gcgacatttc aggcattaac gcttctgtcg tcaacattca aaaagaaatt   3540

gaccgcctca atgaggtcgc taaaaattta aatgaatcac tcattgacct tcaagaattg   3600

ggaaaatatg agcaatatat taaatggcct tgg                                 3633
```

<210> SEQ ID NO 8
<211> LENGTH: 1211
<212> TYPE: PRT
<213> ORGANISM: SARS-CoV Urbani strain

<400> SEQUENCE: 8

```
Met Asp Ala Met Lys Arg Gly Leu Cys Cys Val Leu Leu Leu Cys Gly
1               5                   10                  15

Ala Val Phe Val Ser Pro Ser Ala Arg Gly Ser Gly Ser Asp Leu Asp
            20                  25                  30
```

```
Arg Cys Thr Thr Phe Asp Asp Val Gln Ala Pro Asn Tyr Thr Gln His
        35                  40                  45

Thr Ser Ser Met Arg Gly Val Tyr Tyr Pro Asp Glu Ile Phe Arg Ser
    50                  55                  60

Asp Thr Leu Tyr Leu Thr Gln Asp Leu Phe Leu Pro Phe Tyr Ser Asn
65                  70                  75                  80

Val Thr Gly Phe His Thr Ile Asn His Thr Phe Gly Asn Pro Val Ile
                85                  90                  95

Pro Phe Lys Asp Gly Ile Tyr Phe Ala Ala Thr Glu Lys Ser Asn Val
            100                 105                 110

Val Arg Gly Trp Val Phe Gly Ser Thr Met Asn Asn Lys Ser Gln Ser
        115                 120                 125

Val Ile Ile Ile Asn Asn Ser Thr Asn Val Val Ile Arg Ala Cys Asn
    130                 135                 140

Phe Glu Leu Cys Asp Asn Pro Phe Phe Ala Val Ser Lys Pro Met Gly
145                 150                 155                 160

Thr Gln Thr His Thr Met Ile Phe Asp Asn Ala Phe Asn Cys Thr Phe
                165                 170                 175

Glu Tyr Ile Ser Asp Ala Phe Ser Leu Asp Val Ser Glu Lys Ser Gly
            180                 185                 190

Asn Phe Lys His Leu Arg Glu Phe Val Phe Lys Asn Lys Asp Gly Phe
        195                 200                 205

Leu Tyr Val Tyr Lys Gly Tyr Gln Pro Ile Asp Val Val Arg Asp Leu
    210                 215                 220

Pro Ser Gly Phe Asn Thr Leu Lys Pro Ile Phe Lys Leu Pro Leu Gly
225                 230                 235                 240

Ile Asn Ile Thr Asn Phe Arg Ala Ile Leu Thr Ala Phe Ser Pro Ala
                245                 250                 255

Gln Asp Ile Trp Gly Thr Ser Ala Ala Ala Tyr Phe Val Gly Tyr Leu
            260                 265                 270

Lys Pro Thr Thr Phe Met Leu Lys Tyr Asp Glu Asn Gly Thr Ile Thr
        275                 280                 285

Asp Ala Val Asp Cys Ser Gln Asn Pro Leu Ala Glu Leu Lys Cys Ser
    290                 295                 300

Val Lys Ser Phe Glu Ile Asp Lys Gly Ile Tyr Gln Thr Ser Asn Phe
305                 310                 315                 320

Arg Val Val Pro Ser Gly Asp Val Val Arg Phe Pro Asn Ile Thr Asn
                325                 330                 335

Leu Cys Pro Phe Gly Glu Val Phe Asn Ala Thr Lys Phe Pro Ser Val
            340                 345                 350

Tyr Ala Trp Glu Arg Lys Lys Ile Ser Asn Cys Val Ala Asp Tyr Ser
        355                 360                 365

Val Leu Tyr Asn Ser Thr Phe Phe Ser Thr Phe Lys Cys Tyr Gly Val
    370                 375                 380

Ser Ala Thr Lys Leu Asn Asp Leu Cys Phe Ser Asn Val Tyr Ala Asp
385                 390                 395                 400

Ser Phe Val Val Lys Gly Asp Asp Val Arg Gln Ile Ala Pro Gly Gln
                405                 410                 415

Thr Gly Val Ile Ala Asp Tyr Asn Tyr Lys Leu Pro Asp Asp Phe Met
            420                 425                 430

Gly Cys Val Leu Ala Trp Asn Thr Arg Asn Ile Asp Ala Thr Ser Thr
        435                 440                 445

Gly Asn Tyr Asn Tyr Lys Tyr Arg Tyr Leu Arg His Gly Lys Leu Arg
    450                 455                 460
```

```
Pro Phe Glu Arg Asp Ile Ser Asn Val Pro Phe Ser Pro Asp Gly Lys
465                 470                 475                 480

Pro Cys Thr Pro Pro Ala Leu Asn Cys Tyr Trp Pro Leu Asn Asp Tyr
                485                 490                 495

Gly Phe Tyr Thr Thr Thr Gly Ile Gly Tyr Gln Pro Tyr Arg Val Val
            500                 505                 510

Val Leu Ser Phe Glu Leu Leu Asn Ala Pro Ala Thr Val Cys Gly Pro
        515                 520                 525

Lys Leu Ser Thr Asp Leu Ile Lys Asn Gln Cys Val Asn Phe Asn Phe
    530                 535                 540

Asn Gly Leu Thr Gly Thr Gly Val Leu Thr Pro Ser Ser Lys Arg Phe
545                 550                 555                 560

Gln Pro Phe Gln Gln Phe Gly Arg Asp Val Ser Asp Phe Thr Asp Ser
                565                 570                 575

Val Arg Asp Pro Lys Thr Ser Glu Ile Leu Asp Ile Ser Pro Cys Ser
            580                 585                 590

Phe Gly Gly Val Ser Val Ile Thr Pro Gly Thr Asn Ala Ser Ser Glu
        595                 600                 605

Val Ala Val Leu Tyr Gln Asp Val Asn Cys Thr Asp Val Ser Thr Ala
    610                 615                 620

Ile His Ala Asp Gln Leu Thr Pro Ala Trp Arg Ile Tyr Ser Thr Gly
625                 630                 635                 640

Asn Asn Val Phe Gln Thr Gln Ala Gly Cys Leu Ile Gly Ala Glu His
                645                 650                 655

Val Asp Thr Ser Tyr Glu Cys Asp Ile Pro Ile Gly Ala Gly Ile Cys
            660                 665                 670

Ala Ser Tyr His Thr Val Ser Leu Leu Arg Ser Thr Ser Gln Lys Ser
        675                 680                 685

Ile Val Ala Tyr Thr Met Ser Leu Gly Ala Asp Ser Ser Ile Ala Tyr
    690                 695                 700

Ser Asn Asn Thr Ile Ala Ile Pro Thr Asn Phe Ser Ile Ser Ile Thr
705                 710                 715                 720

Thr Glu Val Met Pro Val Ser Met Ala Lys Thr Ser Val Asp Cys Asn
                725                 730                 735

Met Tyr Ile Cys Gly Asp Ser Thr Glu Cys Ala Asn Leu Leu Leu Gln
            740                 745                 750

Tyr Gly Ser Phe Cys Thr Gln Leu Asn Arg Ala Leu Ser Gly Ile Ala
        755                 760                 765

Ala Glu Gln Asp Arg Asn Thr Arg Glu Val Phe Ala Gln Val Lys Gln
    770                 775                 780

Met Tyr Lys Thr Pro Thr Leu Lys Tyr Phe Gly Gly Phe Asn Phe Ser
785                 790                 795                 800

Gln Ile Leu Pro Asp Pro Leu Lys Pro Thr Lys Arg Ser Phe Ile Glu
                805                 810                 815

Asp Leu Leu Phe Asn Lys Val Thr Leu Ala Asp Ala Gly Phe Met Lys
            820                 825                 830

Gln Tyr Gly Glu Cys Leu Gly Asp Ile Asn Ala Arg Asp Leu Ile Cys
        835                 840                 845

Ala Gln Lys Phe Asn Gly Leu Thr Val Leu Pro Pro Leu Leu Thr Asp
    850                 855                 860

Asp Met Ile Ala Ala Tyr Thr Ala Ala Leu Val Ser Gly Thr Ala Thr
865                 870                 875                 880

Ala Gly Trp Thr Phe Gly Ala Gly Ala Ala Leu Gln Ile Pro Phe Ala
```

-continued 885 890 895

Met Gln Met Ala Tyr Arg Phe Asn Gly Ile Gly Val Thr Gln Asn Val
900 905 910

Leu Tyr Glu Asn Gln Lys Gln Ile Ala Asn Gln Phe Asn Lys Ala Ile
915 920 925

Ser Gln Ile Gln Glu Ser Leu Thr Thr Thr Ser Thr Ala Leu Gly Lys
930 935 940

Leu Gln Asp Val Val Asn Gln Asn Ala Gln Ala Leu Asn Thr Leu Val
945 950 955 960

Lys Gln Leu Ser Ser Asn Phe Gly Ala Ile Ser Ser Val Leu Asn Asp
965 970 975

Ile Leu Ser Arg Leu Asp Lys Val Glu Ala Glu Val Gln Ile Asp Arg
980 985 990

Leu Ile Thr Gly Arg Leu Gln Ser Leu Gln Thr Tyr Val Thr Gln Gln
995 1000 1005

Leu Ile Arg Ala Ala Glu Ile Arg Ala Ser Ala Asn Leu Ala Ala
1010 1015 1020

Thr Lys Met Ser Glu Cys Val Leu Gly Gln Ser Lys Arg Val Asp
1025 1030 1035

Phe Cys Gly Lys Gly Tyr His Leu Met Ser Phe Pro Gln Ala Ala
1040 1045 1050

Pro His Gly Val Val Phe Leu His Val Thr Tyr Val Pro Ser Gln
1055 1060 1065

Glu Arg Asn Phe Thr Thr Ala Pro Ala Ile Cys His Glu Gly Lys
1070 1075 1080

Ala Tyr Phe Pro Arg Glu Gly Val Phe Val Phe Asn Gly Thr Ser
1085 1090 1095

Trp Phe Ile Thr Gln Arg Asn Phe Phe Ser Pro Gln Ile Ile Thr
1100 1105 1110

Thr Asp Asn Thr Phe Val Ser Gly Asn Cys Asp Val Val Ile Gly
1115 1120 1125

Ile Ile Asn Asn Thr Val Tyr Asp Pro Leu Gln Pro Glu Leu Asp
1130 1135 1140

Ser Phe Lys Glu Glu Leu Asp Lys Tyr Phe Lys Asn His Thr Ser
1145 1150 1155

Pro Asp Val Asp Leu Gly Asp Ile Ser Gly Ile Asn Ala Ser Val
1160 1165 1170

Val Asn Ile Gln Lys Glu Ile Asp Arg Leu Asn Glu Val Ala Lys
1175 1180 1185

Asn Leu Asn Glu Ser Leu Ile Asp Leu Gln Glu Leu Gly Lys Tyr
1190 1195 1200

Glu Gln Tyr Ile Lys Trp Pro Trp
1205 1210

<210> SEQ ID NO 9
<211> LENGTH: 2093
<212> TYPE: DNA
<213> ORGANISM: SARS-CoV Urbani strain

<400> SEQUENCE: 9
atggatgcaa tgaagagagg gctctgctgt gtgctgctgc tgtgtggagc agtcttcgtt 60
tcgcccagcg ctagaggatc gggaagtgac cttgaccggt gcaccacttt tgatgatgtt 120
caagctccta attacactca acatacttca tctatgaggg gggtttacta tcctgatgaa 180
atttttagat cagacactct ttatttaact caggatttat ttcttccatt ttattctaat 240

-continued

```
gttacagggt ttcatactat taatcatacg tttggcaacc ctgtcatacc ttttaaggat    300

ggtatttatt ttgctgccac agagaaatca aatgttgtcc gtggttgggt ttttggttct    360

accatgaaca acaagtcaca gtcggtgatt attattaaca attctactaa tgttgttata    420

cgagcatgta actttgaatt gtgtgacaac cctttctttg ctgtttctaa acccatgggt    480

acacagacac atactatgat attcgataat gcatttaatt gcactttcga gtacatatct    540

gatgcctttt cgcttgatgt ttcagaaaag tcaggtaatt ttaaacactt acgagagttt    600

gtgtttaaaa ataaagatgg gtttctctat gtttataagg gctatcaacc tatagatgta    660

gttcgtgatc taccttctgg ttttaacact ttgaaaccta tttttaagtt gcctcttggt    720

attaacatta caaattttag agccattctt acagcctttt cacctgctca agacatttgg    780

ggcacgtcag ctgcagccta ttttgttggc tatttaaagc caactacatt tatgctcaag    840

tatgatgaaa atggtacaat cacagatgct gttgattgtt ctcaaaatcc acttgctgaa    900

ctcaaatgct ctgttaagag ctttgagatt gacaaaggaa tttaccagac ctctaatttc    960

agggttgttc cctcaggaga tgttgtgaga ttccctaata ttacaaactt gtgtcctttt   1020

ggagaggttt ttaatgctac taaattccct tctgtctatg catgggagag aaaaaaaatt   1080

tctaattgtg ttgctgatta ctctgtgctc tacaactcaa cattttttc aacctttaag    1140

tgctatggcg tttctgccac taagttgaat gatctttgct tctccaatgt ctatgcagat   1200

tcttttgtag tcaagggaga tgatgtaaga caaatagcgc caggacaaac tggtgttatt   1260

gctgattata attataaatt gccagatgat ttcatgggtt gtgtccttgc ttggaatact   1320

aggaacattg atgctacttc aactggtaat tataattata aatataggta tcttagacat   1380

ggcaagctta ggccctttga gagagacata tctaatgtgc ctttctcccc tgatggcaaa   1440

ccttgcaccc cacctgctct taattgttat tggccattaa atgattatgg tttttacacc   1500

actactggca ttggctacca accttacaga gttgtagtac tttcttttga acttttaaat   1560

gcaccggcca cggtttgtgg accaaaatta tccactgacc ttattaagaa ccagtgtgtc   1620

aattttaatt ttaatggact cactggtact ggtgtgttaa ctccttcttc aaagagattt   1680

caaccatttc aacaatttgg ccgtgatgtt tctgatttca ctgattccgt tcgagatcct   1740

aaaacatctg aaatattaga catttcacct tgctcttttg gggtgtaag tgtaattaca    1800

cctggaacaa atgcttcatc tgaagttgct gttctatatc aagatgttaa ctgcactgat   1860

gtttctacag caattcatgc agatcaactc acaccagctt ggcgcatata ttctactgga   1920

aacaatgtat tccagactca agcaggctgt cttataggag ctgagcatgt cgacacttct   1980

tatgagtgcg acattcctat tggagctggc atttgtgcta gttaccatac agtttcttta   2040

ttacgtagta ctagccaaaa atctattgtg gcttatacta tgtctttagg tgc           2093
```

<210> SEQ ID NO 10
<211> LENGTH: 698
<212> TYPE: PRT
<213> ORGANISM: SARS-CoV Urbani strain

<400> SEQUENCE: 10

```
Met Asp Ala Met Lys Arg Gly Leu Cys Cys Val Leu Leu Leu Cys Gly
1               5                   10                  15

Ala Val Phe Val Ser Pro Ser Ala Arg Gly Ser Gly Ser Asp Leu Asp
            20                  25                  30

Arg Cys Thr Thr Phe Asp Asp Val Gln Ala Pro Asn Tyr Thr Gln His
        35                  40                  45
```

-continued

```
Thr Ser Ser Met Arg Gly Val Tyr Tyr Pro Asp Glu Ile Phe Arg Ser
    50                  55                  60

Asp Thr Leu Tyr Leu Thr Gln Asp Leu Phe Leu Pro Phe Tyr Ser Asn
65                  70                  75                  80

Val Thr Gly Phe His Thr Ile Asn His Thr Phe Gly Asn Pro Val Ile
                85                  90                  95

Pro Phe Lys Asp Gly Ile Tyr Phe Ala Ala Thr Glu Lys Ser Asn Val
            100                 105                 110

Val Arg Gly Trp Val Phe Gly Ser Thr Met Asn Asn Lys Ser Gln Ser
        115                 120                 125

Val Ile Ile Ile Asn Asn Ser Thr Asn Val Val Ile Arg Ala Cys Asn
    130                 135                 140

Phe Glu Leu Cys Asp Asn Pro Phe Phe Ala Val Ser Lys Pro Met Gly
145                 150                 155                 160

Thr Gln Thr His Thr Met Ile Phe Asp Asn Ala Phe Asn Cys Thr Phe
                165                 170                 175

Glu Tyr Ile Ser Asp Ala Phe Ser Leu Asp Val Ser Glu Lys Ser Gly
            180                 185                 190

Asn Phe Lys His Leu Arg Glu Phe Val Phe Lys Asn Lys Asp Gly Phe
        195                 200                 205

Leu Tyr Val Tyr Lys Gly Tyr Gln Pro Ile Asp Val Val Arg Asp Leu
    210                 215                 220

Pro Ser Gly Phe Asn Thr Leu Lys Pro Ile Phe Lys Leu Pro Leu Gly
225                 230                 235                 240

Ile Asn Ile Thr Asn Phe Arg Ala Ile Leu Thr Ala Phe Ser Pro Ala
                245                 250                 255

Gln Asp Ile Trp Gly Thr Ser Ala Ala Ala Tyr Phe Val Gly Tyr Leu
            260                 265                 270

Lys Pro Thr Thr Phe Met Leu Lys Tyr Asp Glu Asn Gly Thr Ile Thr
        275                 280                 285

Asp Ala Val Asp Cys Ser Gln Asn Pro Leu Ala Glu Leu Lys Cys Ser
    290                 295                 300

Val Lys Ser Phe Glu Ile Asp Lys Gly Ile Tyr Gln Thr Ser Asn Phe
305                 310                 315                 320

Arg Val Val Pro Ser Gly Asp Val Val Arg Phe Pro Asn Ile Thr Asn
                325                 330                 335

Leu Cys Pro Phe Gly Glu Val Phe Asn Ala Thr Lys Phe Pro Ser Val
            340                 345                 350

Tyr Ala Trp Glu Arg Lys Lys Ile Ser Asn Cys Val Ala Asp Tyr Ser
        355                 360                 365

Val Leu Tyr Asn Ser Thr Phe Phe Ser Thr Phe Lys Cys Tyr Gly Val
    370                 375                 380

Ser Ala Thr Lys Leu Asn Asp Leu Cys Phe Ser Asn Val Tyr Ala Asp
385                 390                 395                 400

Ser Phe Val Val Lys Gly Asp Asp Val Arg Gln Ile Ala Pro Gly Gln
                405                 410                 415

Thr Gly Val Ile Ala Asp Tyr Asn Tyr Lys Leu Pro Asp Asp Phe Met
            420                 425                 430

Gly Cys Val Leu Ala Trp Asn Thr Arg Asn Ile Asp Ala Thr Ser Thr
        435                 440                 445

Gly Asn Tyr Asn Tyr Lys Tyr Arg Tyr Leu Arg His Gly Lys Leu Arg
    450                 455                 460

Pro Phe Glu Arg Asp Ile Ser Asn Val Pro Phe Ser Pro Asp Gly Lys
465                 470                 475                 480
```

```
Pro Cys Thr Pro Pro Ala Leu Asn Cys Tyr Trp Pro Leu Asn Asp Tyr
                485                 490                 495

Gly Phe Tyr Thr Thr Thr Gly Ile Gly Tyr Gln Pro Tyr Arg Val Val
            500                 505                 510

Val Leu Ser Phe Glu Leu Leu Asn Ala Pro Ala Thr Val Cys Gly Pro
        515                 520                 525

Lys Leu Ser Thr Asp Leu Ile Lys Asn Gln Cys Val Asn Phe Asn Phe
    530                 535                 540

Asn Gly Leu Thr Gly Thr Gly Val Leu Thr Pro Ser Ser Lys Arg Phe
545                 550                 555                 560

Gln Pro Phe Gln Gln Phe Gly Arg Asp Val Ser Asp Phe Thr Asp Ser
                565                 570                 575

Val Arg Asp Pro Lys Thr Ser Glu Ile Leu Asp Ile Ser Pro Cys Ser
            580                 585                 590

Phe Gly Gly Val Ser Val Ile Thr Pro Gly Thr Asn Ala Ser Ser Glu
        595                 600                 605

Val Ala Val Leu Tyr Gln Asp Val Asn Cys Thr Asp Val Ser Thr Ala
    610                 615                 620

Ile His Ala Asp Gln Leu Thr Pro Ala Trp Arg Ile Tyr Ser Thr Gly
625                 630                 635                 640

Asn Asn Val Phe Gln Thr Gln Ala Gly Cys Leu Ile Gly Ala Glu His
                645                 650                 655

Val Asp Thr Ser Tyr Glu Cys Asp Ile Pro Ile Gly Ala Gly Ile Cys
            660                 665                 670

Ala Ser Tyr His Thr Val Ser Leu Leu Arg Ser Thr Ser Gln Lys Ser
        675                 680                 685

Ile Val Ala Tyr Thr Met Ser Leu Gly Ala
    690                 695
```

<210> SEQ ID NO 11
<211> LENGTH: 1623
<212> TYPE: DNA
<213> ORGANISM: SARS-CoV Urbani strain

<400> SEQUENCE: 11

```
atggatgcaa tgaagagagg gctctgctgt gtgctgctgc tgtgtggagc agtcttcgtt     60

tcgcccagcg ctagaggatc gggagatagt tcaattgctt actctaataa caccattgct    120

atacctacta acttttcaat tagcattact acagaagtaa tgcctgtttc tatggctaaa    180

acctccgtag attgtaatat gtacatctgc ggagattcta ctgaatgtgc taatttgctt    240

ctccaatatg gtagcttttg cacacaacta aatcgtgcac tctcaggtat tgctgctgaa    300

caggatcgca acacacgtga agtgttcgct caagtcaaac aaatgtacaa aaccccaact    360

ttgaaatatt ttggtggttt taatttttca caaatattac ctgaccctct aaagccaact    420

aagaggtctt ttattgagga cttgctcttt aataaggtga cactcgctga tgctggcttc    480

atgaagcaat atggcgaatg cctaggtgat attaatgcta gagatctcat ttgtgcgcag    540

aagttcaatg gacttacagt gttgccacct ctgctcactg atgatatgat tgctgcctac    600

actgctgctc tagttagtgg tactgccact gctggatgga catttggtgc tggcgctgct    660

cttcaaatac cttttgctat gcaaatggca tataggttca atggcattgg agttacccaa    720

aatgttctct atgagaacca aaaacaaatc gccaaccaat ttaacaaggc gattagtcaa    780

attcaagaat cacttacaac aacatcaact gcattgggca agctgcaaga cgttgttaac    840

cagaatgctc aagcattaaa cacacttgtt aaacaactta gctctaattt tggtgcaatt    900
```

-continued tcaagtgtgc taaatgatat cctttcgcga cttgataaag tcgaggcgga ggtacaaatt 960
gacaggttaa ttacaggcag acttcaaagc cttcaaacct atgtaacaca acaactaatc 1020
agggctgctg aaatcagggc ttctgctaat cttgctgcta ctaaaatgtc tgagtgtgtt 1080
cttggacaat caaaaagagt tgacttttgt ggaaagggct accaccttat gtccttccca 1140
caagcagccc cgcatggtgt tgtcttccta catgtcacgt atgtgccatc ccaggagagg 1200
aacttcacca cagcgccagc aatttgtcat gaaggcaaag catacttccc tcgtgaaggt 1260
gtttttgtgt ttaatggcac ttcttggttt attacacaga ggaacttctt ttctccacaa 1320
ataattacta cagacaatac atttgtctca ggaaattgtg atgtcgttat tggcatcatt 1380
aacaacacag tttatgatcc tctgcaacct gagctcgact cattcaaaga agagctggac 1440
aagtacttca aaaatcatac atcaccagat gttgatcttg gcgacatttc aggcattaac 1500
gcttctgtcg tcaacattca aaaagaaatt gaccgcctca atgaggtcgc taaaaattta 1560
aatgaatcac tcattgacct tcaagaattg ggaaaatatg agcaatatat taaatggcct 1620
tgg 1623

<210> SEQ ID NO 12
<211> LENGTH: 541
<212> TYPE: PRT
<213> ORGANISM: SARS-CoV Urbani strain

<400> SEQUENCE: 12

Met Asp Ala Met Lys Arg Gly Leu Cys Cys Val Leu Leu Leu Cys Gly
1 5 10 15

Ala Val Phe Val Ser Pro Ser Ala Arg Gly Ser Gly Asp Ser Ser Ile
20 25 30

Ala Tyr Ser Asn Asn Thr Ile Ala Ile Pro Thr Asn Phe Ser Ile Ser
35 40 45

Ile Thr Thr Glu Val Met Pro Val Ser Met Ala Lys Thr Ser Val Asp
50 55 60

Cys Asn Met Tyr Ile Cys Gly Asp Ser Thr Glu Cys Ala Asn Leu Leu
65 70 75 80

Leu Gln Tyr Gly Ser Phe Cys Thr Gln Leu Asn Arg Ala Leu Ser Gly
85 90 95

Ile Ala Ala Glu Gln Asp Arg Asn Thr Arg Glu Val Phe Ala Gln Val
100 105 110

Lys Gln Met Tyr Lys Thr Pro Thr Leu Lys Tyr Phe Gly Gly Phe Asn
115 120 125

Phe Ser Gln Ile Leu Pro Asp Pro Leu Lys Pro Thr Lys Arg Ser Phe
130 135 140

Ile Glu Asp Leu Leu Phe Asn Lys Val Thr Leu Ala Asp Ala Gly Phe
145 150 155 160

Met Lys Gln Tyr Gly Glu Cys Leu Gly Asp Ile Asn Ala Arg Asp Leu
165 170 175

Ile Cys Ala Gln Lys Phe Asn Gly Leu Thr Val Leu Pro Pro Leu Leu
180 185 190

Thr Asp Asp Met Ile Ala Ala Tyr Thr Ala Ala Leu Val Ser Gly Thr
195 200 205

Ala Thr Ala Gly Trp Thr Phe Gly Ala Gly Ala Ala Leu Gln Ile Pro
210 215 220

Phe Ala Met Gln Met Ala Tyr Arg Phe Asn Gly Ile Gly Val Thr Gln
225 230 235 240

```
Asn Val Leu Tyr Glu Asn Gln Lys Gln Ile Ala Asn Gln Phe Asn Lys
                245                 250                 255

Ala Ile Ser Gln Ile Gln Glu Ser Leu Thr Thr Thr Ser Thr Ala Leu
            260                 265                 270

Gly Lys Leu Gln Asp Val Val Asn Gln Asn Ala Gln Ala Leu Asn Thr
        275                 280                 285

Leu Val Lys Gln Leu Ser Ser Asn Phe Gly Ala Ile Ser Ser Val Leu
    290                 295                 300

Asn Asp Ile Leu Ser Arg Leu Asp Lys Val Glu Ala Glu Val Gln Ile
305                 310                 315                 320

Asp Arg Leu Ile Thr Gly Arg Leu Gln Ser Leu Gln Thr Tyr Val Thr
                325                 330                 335

Gln Gln Leu Ile Arg Ala Ala Glu Ile Arg Ala Ser Ala Asn Leu Ala
            340                 345                 350

Ala Thr Lys Met Ser Glu Cys Val Leu Gly Gln Ser Lys Arg Val Asp
        355                 360                 365

Phe Cys Gly Lys Gly Tyr His Leu Met Ser Phe Pro Gln Ala Ala Pro
    370                 375                 380

His Gly Val Val Phe Leu His Val Thr Tyr Val Pro Ser Gln Glu Arg
385                 390                 395                 400

Asn Phe Thr Thr Ala Pro Ala Ile Cys His Glu Gly Lys Ala Tyr Phe
                405                 410                 415

Pro Arg Glu Gly Val Phe Val Phe Asn Gly Thr Ser Trp Phe Ile Thr
            420                 425                 430

Gln Arg Asn Phe Phe Ser Pro Gln Ile Ile Thr Thr Asp Asn Thr Phe
        435                 440                 445

Val Ser Gly Asn Cys Asp Val Val Ile Gly Ile Ile Asn Asn Thr Val
    450                 455                 460

Tyr Asp Pro Leu Gln Pro Glu Leu Asp Ser Phe Lys Glu Glu Leu Asp
465                 470                 475                 480

Lys Tyr Phe Lys Asn His Thr Ser Pro Asp Val Asp Leu Gly Asp Ile
                485                 490                 495

Ser Gly Ile Asn Ala Ser Val Val Asn Ile Gln Lys Glu Ile Asp Arg
            500                 505                 510

Leu Asn Glu Val Ala Lys Asn Leu Asn Glu Ser Leu Ile Asp Leu Gln
        515                 520                 525

Glu Leu Gly Lys Tyr Glu Gln Tyr Ile Lys Trp Pro Trp
    530                 535                 540
```

```
<210> SEQ ID NO 13
<211> LENGTH: 1269
<212> TYPE: DNA
<213> ORGANISM: SARS-CoV Urbani strain

<400> SEQUENCE: 13

atgtctgata atggacccca atcaaaccaa cgtagtgccc cccgcattac atttggtgga      60

cccacagatt caactgacaa taaccagaat ggaggacgca atggggcaag gccaaaacag     120

cgccgacccc aaggtttacc caataatact gcgtcttggt tcacagctct cactcagcat     180

ggcaaggagg aacttagatt ccctcgaggc cagggcgttc caatcaacac caatagtggt     240

ccagatgacc aaattggcta ctaccgaaga gctacccgac gagttcgtgg tggtgacggc     300

aaaatgaaag agctcagccc cagatggtac ttctattacc taggaactgg cccagaagct     360

tcacttccct acggcgctaa caaagaaggc atcgtatggg ttgcaactga gggagccttg     420

aatacaccca aagaccacat tggcacccgc aatcctaata acaatgctgc caccgtgcta     480
```

```
caacttcctc aaggaacaac attgccaaaa ggcttctacg cagagggaag cagaggcggc    540

agtcaagcct cttctcgctc ctcatcacgt agtcgcggta attcaagaaa ttcaactcct    600

ggcagcagta ggggaaattc tcctgctcga atggctagcg gaggtggtga aactgccctc    660

gcgctattgc tgctagacag attgaaccag cttgagagca aagtttctgg taaaggccaa    720

caacaacaag gccaaactgt cactaagaaa tctgctgctg aggcatctaa aaagcctcgc    780

caaaaacgta ctgccacaaa acagtacaac gtcactcaag catttgggag acgtggtcca    840

gaacaaaccc aaggaaattt cggggaccaa gacctaatca gacaaggaac tgattacaaa    900

cattggccgc aaattgcaca atttgctcca agtgcctctg cattctttgg aatgtcacgc    960

attggcatgg aagtcacacc ttcgggaaca tggctgactt atcatggagc cattaaattg   1020

gatgacaaag atccacaatt caaagacaac gtcatactgc tgaacaagca cattgacgca   1080

tacaaaacat tcccaccaac agagcctaaa aaggacaaaa agaaaaagac tgatgaagct   1140

cagcctttgc cgcagagaca aaagaagcag cccactgtga ctcttcttcc tgcggctgac   1200

atggatgatt tctccagaca acttcaaaat tccatgagtg gagcttctgc tgattcaact   1260

caggcataa                                                           1269
```

```
<210> SEQ ID NO 14
<211> LENGTH: 422
<212> TYPE: PRT
<213> ORGANISM: SARS-CoV Urbani strain

<400> SEQUENCE: 14

Met Ser Asp Asn Gly Pro Gln Ser Asn Gln Arg Ser Ala Pro Arg Ile
1               5                   10                  15

Thr Phe Gly Gly Pro Thr Asp Ser Thr Asp Asn Asn Gln Asn Gly Gly
            20                  25                  30

Arg Asn Gly Ala Arg Pro Lys Gln Arg Arg Pro Gln Gly Leu Pro Asn
        35                  40                  45

Asn Thr Ala Ser Trp Phe Thr Ala Leu Thr Gln His Gly Lys Glu Glu
    50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95

Gly Gly Asp Gly Lys Met Lys Glu Leu Ser Pro Arg Trp Tyr Phe Tyr
            100                 105                 110

Tyr Leu Gly Thr Gly Pro Glu Ala Ser Leu Pro Tyr Gly Ala Asn Lys
        115                 120                 125

Glu Gly Ile Val Trp Val Ala Thr Glu Gly Ala Leu Asn Thr Pro Lys
    130                 135                 140

Asp His Ile Gly Thr Arg Asn Pro Asn Asn Asn Ala Ala Thr Val Leu
145                 150                 155                 160

Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Ser Arg Ser Arg
            180                 185                 190

Gly Asn Ser Arg Asn Ser Thr Pro Gly Ser Ser Arg Gly Asn Ser Pro
        195                 200                 205

Ala Arg Met Ala Ser Gly Gly Gly Glu Thr Ala Leu Ala Leu Leu Leu
    210                 215                 220

Leu Asp Arg Leu Asn Gln Leu Glu Ser Lys Val Ser Gly Lys Gly Gln
```

-continued

```
225                 230                 235                 240

Gln Gln Gln Gly Gln Thr Val Thr Lys Lys Ser Ala Ala Glu Ala Ser
                245                 250                 255

Lys Lys Pro Arg Gln Lys Arg Thr Ala Thr Lys Gln Tyr Asn Val Thr
            260                 265                 270

Gln Ala Phe Gly Arg Arg Gly Pro Glu Gln Thr Gln Gly Asn Phe Gly
        275                 280                 285

Asp Gln Asp Leu Ile Arg Gln Gly Thr Asp Tyr Lys His Trp Pro Gln
    290                 295                 300

Ile Ala Gln Phe Ala Pro Ser Ala Ser Ala Phe Phe Gly Met Ser Arg
305                 310                 315                 320

Ile Gly Met Glu Val Thr Pro Ser Gly Thr Trp Leu Thr Tyr His Gly
                325                 330                 335

Ala Ile Lys Leu Asp Asp Lys Asp Pro Gln Phe Lys Asp Asn Val Ile
            340                 345                 350

Leu Leu Asn Lys His Ile Asp Ala Tyr Lys Thr Phe Pro Pro Thr Glu
        355                 360                 365

Pro Lys Lys Asp Lys Lys Lys Lys Thr Asp Glu Ala Gln Pro Leu Pro
    370                 375                 380

Gln Arg Gln Lys Lys Gln Pro Thr Val Thr Leu Leu Pro Ala Ala Asp
385                 390                 395                 400

Met Asp Asp Phe Ser Arg Gln Leu Gln Asn Ser Met Ser Gly Ala Ser
                405                 410                 415

Ala Asp Ser Thr Gln Ala
            420


<210> SEQ ID NO 15
<211> LENGTH: 1209
<212> TYPE: DNA
<213> ORGANISM: SARS-CoV Urbani strain

<400> SEQUENCE: 15

atgtctgata atggacccca atcaaaccaa cgtagtgccc cccgcattac atttggtgga      60

cccacagatt caactgacaa taaccagaat ggaggacgca atggggcaag gccaaaacag     120

cgccgacccc aaggtttacc caataatact gcgtcttggt tcacagctct cactcagcat     180

ggcaaggagg aacttagatt ccctcgaggc cagggcgttc caatcaacac caatagtggt     240

ccagatgacc aaattggcta ctaccgaaga gctacccgac gagttcgtgg tggtgacggc     300

aaaatgaaag agctcagccc cagatggtac ttctattacc taggaactgg cccagaagct     360

tcacttccct acggcgctaa caaagaaggc atcgtatggg ttgcaactga gggagccttg     420

aatacaccca aagaccacat tggcacccgc aatcctaata acaatgctgc caccgtgcta     480

caacttcctc aaggaacaac attgccaaaa ggcttctacg cagagggaag cagaggcggc     540

agtcaagcct cttctcgctc ctcatcacgt agtcgcggta attcaagaaa ttcaactcct     600

ggcagcagta ggggaaattc tcctgctcga atggctagcg gaggtggtga aactgccctc     660

gcgctattgc tgctagacag attgaaccag cttgagagca aagtttctgg taaaggccaa     720

caacaacaag gccaaactgt cactaagaaa tctgctgctg aggcatctaa aaagcctcgc     780

caaaaacgta ctgccacaaa acagtacaac gtcactcaag catttgggag acgtggtcca     840

gaacaaaccc aaggaaattt cggggaccaa gacctaatca gacaaggaac tgattacaaa     900

cattggccgc aaattgcaca atttgctcca agtgcctctg cattctttgg aatgtcacgc     960

attggcatgg aagtcacacc ttcgggaaca tggctgactt atcatggagc cattaaattg    1020
```

gatgacaaag atccacaatt caaagacaac gtcatactgc tgaacaagca cattgacgca 1080
taccctttgc cgcagagaca aaagaagcag cccactgtga ctcttcttcc tgcggctgac 1140
atggatgatt tctccagaca acttcaaaat tccatgagtg gagcttctgc tgattcaact 1200
caggcataa 1209

<210> SEQ ID NO 16
<211> LENGTH: 402
<212> TYPE: PRT
<213> ORGANISM: SARS-CoV Urbani strain

<400> SEQUENCE: 16

Met Ser Asp Asn Gly Pro Gln Ser Asn Gln Arg Ser Ala Pro Arg Ile
1 5 10 15

Thr Phe Gly Gly Pro Thr Asp Ser Thr Asp Asn Asn Gln Asn Gly Gly
20 25 30

Arg Asn Gly Ala Arg Pro Lys Gln Arg Arg Pro Gln Gly Leu Pro Asn
35 40 45

Asn Thr Ala Ser Trp Phe Thr Ala Leu Thr Gln His Gly Lys Glu Glu
50 55 60

Leu Arg Phe Pro Arg Gly Gln Gly Val Pro Ile Asn Thr Asn Ser Gly
65 70 75 80

Pro Asp Asp Gln Ile Gly Tyr Tyr Arg Arg Ala Thr Arg Arg Val Arg
85 90 95

Gly Gly Asp Gly Lys Met Lys Glu Leu Ser Pro Arg Trp Tyr Phe Tyr
100 105 110

Tyr Leu Gly Thr Gly Pro Glu Ala Ser Leu Pro Tyr Gly Ala Asn Lys
115 120 125

Glu Gly Ile Val Trp Val Ala Thr Glu Gly Ala Leu Asn Thr Pro Lys
130 135 140

Asp His Ile Gly Thr Arg Asn Pro Asn Asn Asn Ala Ala Thr Val Leu
145 150 155 160

Gln Leu Pro Gln Gly Thr Thr Leu Pro Lys Gly Phe Tyr Ala Glu Gly
165 170 175

Ser Arg Gly Gly Ser Gln Ala Ser Ser Arg Ser Ser Ser Arg Ser Arg
180 185 190

Gly Asn Ser Arg Asn Ser Thr Pro Gly Ser Ser Arg Gly Asn Ser Pro
195 200 205

Ala Arg Met Ala Ser Gly Gly Gly Glu Thr Ala Leu Ala Leu Leu Leu
210 215 220

Leu Asp Arg Leu Asn Gln Leu Glu Ser Lys Val Ser Gly Lys Gly Gln
225 230 235 240

Gln Gln Gln Gly Gln Thr Val Thr Lys Lys Ser Ala Ala Glu Ala Ser
245 250 255

Lys Lys Pro Arg Gln Lys Arg Thr Ala Thr Lys Gln Tyr Asn Val Thr
260 265 270

Gln Ala Phe Gly Arg Arg Gly Pro Glu Gln Thr Gln Gly Asn Phe Gly
275 280 285

Asp Gln Asp Leu Ile Arg Gln Gly Thr Asp Tyr Lys His Trp Pro Gln
290 295 300

Ile Ala Gln Phe Ala Pro Ser Ala Ser Ala Phe Phe Gly Met Ser Arg
305 310 315 320

Ile Gly Met Glu Val Thr Pro Ser Gly Thr Trp Leu Thr Tyr His Gly
325 330 335

Ala Ile Lys Leu Asp Asp Lys Asp Pro Gln Phe Lys Asp Asn Val Ile

-continued 340 345 350

Leu Leu Asn Lys His Ile Asp Ala Tyr Pro Leu Pro Gln Arg Gln Lys
355 360 365

Lys Gln Pro Thr Val Thr Leu Leu Pro Ala Ala Asp Met Asp Asp Phe
370 375 380

Ser Arg Gln Leu Gln Asn Ser Met Ser Gly Ala Ser Ala Asp Ser Thr
385 390 395 400

Gln Ala

<210> SEQ ID NO 17
<211> LENGTH: 20
<212> TYPE: PRT
<213> ORGANISM: SARS-CoV Urbani strain

<400> SEQUENCE: 17

Lys Thr Phe Pro Pro Thr Glu Pro Lys Lys Asp Lys Lys Lys Lys Thr
1 5 10 15

Asp Glu Ala Gln
20

<210> SEQ ID NO 18
<211> LENGTH: 666
<212> TYPE: DNA
<213> ORGANISM: SARS-CoV Urbani strain

<400> SEQUENCE: 18
atggcagaca acggtactat taccgttgag gagcttaaac aactcctgga acaatggaac 60
ctagtaatag gtttcctatt cctagcctgg attatgttac tacaatttgc ctattctaat 120
cggaacaggt tttgtacat aataaagctt gttttcctct ggctcttgtg gccagtaaca 180
cttgcttgtt ttgtgcttgc tgctgtctac agaattaatt gggtgactgg cgggattgcg 240
attgcaatgg cttgtattgt aggcttgatg tggcttagct acttcgttgc ttccttcagg 300
ctgtttgctc gtacccgctc aatgtggtca ttcaacccag aaacaaacat tcttctcaat 360
gtgcctctcc gggggacaat tgtgaccaga ccgctcatgg aaagtgaact tgtcattggt 420
gctgtgatca ttcgtggtca cttgcgaatg gccggacacc ccctagggcg ctgtgacatt 480
aaggacctgc caaaagagat cactgtggct acatcacgaa cgctttctta ttacaaatta 540
ggagcgtcgc agcgtgtagg cactgattca ggttttgctg catacaaccg ctaccgtatt 600
ggaaactata aattaaatac agaccacgcc ggtagcaacg acaatattgc tttgctagta 660
cagtaa 666

<210> SEQ ID NO 19
<211> LENGTH: 221
<212> TYPE: PRT
<213> ORGANISM: SARS-CoV Urbani strain

<400> SEQUENCE: 19

Met Ala Asp Asn Gly Thr Ile Thr Val Glu Glu Leu Lys Gln Leu Leu
1 5 10 15

Glu Gln Trp Asn Leu Val Ile Gly Phe Leu Phe Leu Ala Trp Ile Met
20 25 30

Leu Leu Gln Phe Ala Tyr Ser Asn Arg Asn Arg Phe Leu Tyr Ile Ile
35 40 45

Lys Leu Val Phe Leu Trp Leu Leu Trp Pro Val Thr Leu Ala Cys Phe
50 55 60

Val Leu Ala Ala Val Tyr Arg Ile Asn Trp Val Thr Gly Gly Ile Ala

```
65                  70                  75                  80

Ile Ala Met Ala Cys Ile Val Gly Leu Met Trp Leu Ser Tyr Phe Val
                85                  90                  95

Ala Ser Phe Arg Leu Phe Ala Arg Thr Arg Ser Met Trp Ser Phe Asn
            100                 105                 110

Pro Glu Thr Asn Ile Leu Leu Asn Val Pro Leu Arg Gly Thr Ile Val
        115                 120                 125

Thr Arg Pro Leu Met Glu Ser Glu Leu Val Ile Gly Ala Val Ile Ile
    130                 135                 140

Arg Gly His Leu Arg Met Ala Gly His Pro Leu Gly Arg Cys Asp Ile
145                 150                 155                 160

Lys Asp Leu Pro Lys Glu Ile Thr Val Ala Thr Ser Arg Thr Leu Ser
                165                 170                 175

Tyr Tyr Lys Leu Gly Ala Ser Gln Arg Val Gly Thr Asp Ser Gly Phe
            180                 185                 190

Ala Ala Tyr Asn Arg Tyr Arg Ile Gly Asn Tyr Lys Leu Asn Thr Asp
        195                 200                 205

His Ala Gly Ser Asn Asp Asn Ile Ala Leu Leu Val Gln
    210                 215                 220


<210> SEQ ID NO 20
<211> LENGTH: 231
<212> TYPE: DNA
<213> ORGANISM: SARS-CoV Urbani strain

<400> SEQUENCE: 20

atgtactcat tcgtttcgga agaaacaggt acgttaatag ttaatagcgt acttcttttt      60

cttgctttcg tggtattctt gctagtcaca ctagccatcc ttactgcgct tcgattgtgt     120

gcgtactgct gcaatattgt taacgtgagt ttagtaaaac caacggttta cgtctactcg     180

cgtgttaaaa atctgaactc ttctgaagga gttcctgatc ttctggtcta a              231


<210> SEQ ID NO 21
<211> LENGTH: 76
<212> TYPE: PRT
<213> ORGANISM: SARS-CoV Urbani strain

<400> SEQUENCE: 21

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Thr Val Tyr Val Tyr Ser Arg Val Lys Asn
    50                  55                  60

Leu Asn Ser Ser Glu Gly Val Pro Asp Leu Leu Val
65                  70                  75


<210> SEQ ID NO 22
<211> LENGTH: 3768
<212> TYPE: DNA
<213> ORGANISM: SARS-CoV Urbani strain

<400> SEQUENCE: 22

atgtttattt tcttattatt tcttactctc actagtggta gtgaccttga ccggtgcacc      60

acttttgatg atgttcaagc tcctaattac actcaacata cttcatctat gaggggggtt     120
```

-continued

```
tactatcctg atgaaatttt tagatcagac actctttatt taactcagga tttatttctt    180
ccattttatt ctaatgttac agggtttcat actattaatc atacgtttgg caaccctgtc    240
ataccttta aggatggtat ttattttgct gccacagaga aatcaaatgt tgtccgtggt     300
tgggtttttg gttctaccat gaacaacaag tcacagtcgg tgattattat taacaattct    360
actaatgttg ttatacgagc atgtaacttt gaattgtgtg acaacccttt ctttgctgtt    420
tctaaaccca tgggtacaca gacacatact atgatattcg ataatgcatt taattgcact    480
ttcgagtaca tatctgatgc cttttcgctt gatgtttcag aaaagtcagg taattttaaa    540
cacttacgag agtttgtgtt taaaaataaa gatgggtttc tctatgttta taagggctat    600
caacctatag atgtagttcg tgatctacct tctggtttta acactttgaa acctattttt    660
aagttgcctc ttggtattaa cattacaaat tttagagcca ttcttacagc cttttcacct    720
gctcaagaca tttggggcac gtcagctgca gcctattttg ttggctattt aaagccaact    780
acatttatgc tcaagtatga tgaaaatggt acaatcacag atgctgttga ttgttctcaa    840
aatccacttg ctgaactcaa atgctctgtt aagagctttg agattgacaa aggaatttac    900
cagacctcta atttcagggt tgttccctca ggagatgttg tgagattccc taatattaca    960
aacttgtgtc cttttggaga ggtttttaat gctactaaat tcccttctgt ctatgcatgg   1020
gagagaaaaa aaatttctaa ttgtgttgct gattactctg tgctctacaa ctcaacattt   1080
ttttcaacct ttaagtgcta tggcgtttct gccactaagt tgaatgatct ttgcttctcc   1140
aatgtctatg cagattcttt tgtagtcaag ggagatgatg taagacaaat agcgccagga   1200
caaactggtg ttattgctga ttataattat aaattgccag atgatttcat gggttgtgtc   1260
cttgcttgga atactaggaa cattgatgct acttcaactg gtaattataa ttataaatat   1320
aggtatctta gacatggcaa gcttaggccc tttgagagag acatatctaa tgtgcctttc   1380
tcccctgatg gcaaaccttg caccccacct gctcttaatt gttattggcc attaaatgat   1440
tatggttttt acaccactac tggcattggc taccaacctt acagagttgt agtactttct   1500
tttgaacttt taaatgcacc ggccacggtt tgtggaccaa aattatccac tgaccttatt   1560
aagaaccagt gtgtcaattt taattttaat ggactcactg gtactggtgt gttaactcct   1620
tcttcaaaga gatttcaacc atttcaacaa tttggccgtg atgtttctga tttcactgat   1680
tccgttcgag atcctaaaac atctgaaata ttagacattt caccttgctc ttttgggggt   1740
gtaagtgtaa ttacacctgg aacaaatgct tcatctgaag ttgctgttct atatcaagat   1800
gttaactgca ctgatgtttc tacagcaatt catgcagatc aactcacacc agcttggcgc   1860
atatattcta ctggaaacaa tgtattccag actcaagcag gctgtcttat aggagctgag   1920
catgtcgaca cttcttatga gtgcgacatt cctattggag ctggcatttg tgctagttac   1980
catacagttt ctttattacg tagtactagc caaaaatcta ttgtggctta tactatgtct   2040
ttaggtgctg atagttcaat tgcttactct aataacacca ttgctatacc tactaacttt   2100
tcaattagca ttactacaga agtaatgcct gtttctatgg ctaaaacctc cgtagattgt   2160
aatatgtaca tctgcggaga ttctactgaa tgtgctaatt tgcttctcca atatggtagc   2220
ttttgcacac aactaaatcg tgcactctca ggtattgctg ctgaacagga tcgcaacaca   2280
cgtgaagtgt tcgctcaagt caaacaaatg tacaaaaccc caactttgaa atattttggt   2340
ggttttaatt tttcacaaat attacctgac cctctaaagc caactaagag gtcttttatt   2400
gaggacttgc tctttaataa ggtgacactc gctgatgctg gcttcatgaa gcaatatggc   2460
gaatgcctag gtgatattaa tgctagagat ctcatttgtg cgcagaagtt caatggactt   2520
```

-continued

```
acagtgttgc cacctctgct cactgatgat atgattgctg cctacactgc tgctctagtt   2580

agtggtactg ccactgctgg atggacattt ggtgctggcg ctgctcttca aatacctttt   2640

gctatgcaaa tggcatatag gttcaatggc attggagtta cccaaaatgt tctctatgag   2700

aaccaaaaac aaatcgccaa ccaatttaac aaggcgatta gtcaaattca agaatcactt   2760

acaacaacat caactgcatt gggcaagctg caagacgttg ttaaccagaa tgctcaagca   2820

ttaaacacac ttgttaaaca acttagctct aattttggtg caatttcaag tgtgctaaat   2880

gatatccttt cgcgacttga taaagtcgag gcggaggtac aaattgacag gttaattaca   2940

ggcagacttc aaagccttca aacctatgta acacaacaac taatcagggc tgctgaaatc   3000

agggcttctg ctaatcttgc tgctactaaa atgtctgagt gtgttcttgg acaatcaaaa   3060

agagttgact tttgtggaaa gggctaccac cttatgtcct tcccacaagc agccccgcat   3120

ggtgttgtct tcctacatgt cacgtatgtg ccatcccagg agaggaactt caccacagcg   3180

ccagcaattt gtcatgaagg caaagcatac ttccctcgtg aaggtgtttt tgtgtttaat   3240

ggcacttctt ggtttattac acagaggaac ttcttttctc cacaaataat tactacagac   3300

aatacatttg tctcaggaaa ttgtgatgtc gttattggca tcattaacaa cacagtttat   3360

gatcctctgc aacctgagct cgactcattc aaagaagagc tggacaagta cttcaaaaat   3420

catacatcac cagatgttga tcttggcgac atttcaggca ttaacgcttc tgtcgtcaac   3480

attcaaaaag aaattgaccg cctcaatgag gtcgctaaaa atttaaatga atcactcatt   3540

gaccttcaag aattgggaaa atatgagcaa tatattaaat ggccttggta tgtttggctc   3600

ggcttcattg ctggactaat tgccatcgtc atggttacaa tcttgctttg ttgcatgact   3660

agttgttgca gttgcctcaa gggtgcatgc tcttgtggtt cttgctgcaa gtttgatgag   3720

gatgactctg agccagttct caagggtgtc aaattacatt acacataa               3768
```

<210> SEQ ID NO 23
<211> LENGTH: 1255
<212> TYPE: PRT
<213> ORGANISM: SARS-CoV Urbani strain

<400> SEQUENCE: 23

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160
```

```
Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590
```

```
Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                 1005

Thr Lys  Met Ser Glu Cys Val  Leu Gly Gln Ser Lys  Arg Val Asp
```

-continued

```
    1010                1015                1020

Phe Cys  Gly Lys Gly Tyr His  Leu Met Ser Phe Pro  Gln Ala Ala
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080

Trp Phe  Ile Thr Gln Arg Asn  Phe Phe Ser Pro Gln  Ile Ile Thr
    1085                1090                1095

Thr Asp  Asn Thr Phe Val Ser  Gly Asn Cys Asp Val  Val Ile Gly
    1100                1105                1110

Ile Ile  Asn Asn Thr Val Tyr  Asp Pro Leu Gln Pro  Glu Leu Asp
    1115                1120                1125

Ser Phe  Lys Glu Glu Leu Asp  Lys Tyr Phe Lys Asn  His Thr Ser
    1130                1135                1140

Pro Asp  Val Asp Leu Gly Asp  Ile Ser Gly Ile Asn  Ala Ser Val
    1145                1150                1155

Val Asn  Ile Gln Lys Glu Ile  Asp Arg Leu Asn Glu  Val Ala Lys
    1160                1165                1170

Asn Leu  Asn Glu Ser Leu Ile  Asp Leu Gln Glu Leu  Gly Lys Tyr
    1175                1180                1185

Glu Gln  Tyr Ile Lys Trp Pro  Trp Tyr Val Trp Leu  Gly Phe Ile
    1190                1195                1200

Ala Gly  Leu Ile Ala Ile Val  Met Val Thr Ile Leu  Leu Cys Cys
    1205                1210                1215

Met Thr  Ser Cys Cys Ser Cys  Leu Lys Gly Ala Cys  Ser Cys Gly
    1220                1225                1230

Ser Cys  Cys Lys Phe Asp Glu  Asp Asp Ser Glu Pro  Val Leu Lys
    1235                1240                1245

Gly Val  Lys Leu His Tyr Thr
    1250                1255
```

<210> SEQ ID NO 24
<211> LENGTH: 3588
<212> TYPE: DNA
<213> ORGANISM: Artificial Sequence
<220> FEATURE:
<223> OTHER INFORMATION: Fully optimized soluble S protein

<400> SEQUENCE: 24

```
atgtttatct tcctcctctt cctgacgctc actagcggat ccgacttaga tcggtgtacc     60

actttcgacg acgtccaggc ccctaactat actcaacata cctccagtat gcgcggggtg    120

tactatccag atgagatttt tcggagcgac actctgtact taacacagga cctgtttcta    180

ccgttttatt caaatgtaac cggcttccac accattaacc atacatttgg caatcccgtg    240

ataccattca aagacggcat ttacttcgcc gcaacagaaa agagcaatgt tgtgaggggg    300

tgggtcttcg gctccacaat gaacaataaa tctcagtctg tcatcatcat caataacagc    360

actaacgtgg taatccgtgc ctgcaatttc gagctttgtg acaacccatt cttcgccgtg    420

tctaagccta tgggcaccca gactcacaca atgatctttg acaatgcttt caactgcacc    480

ttcgaataca tatcagatgc attctctttg gatgtcagtg aaaagtctgg aaactttaaa    540

catctgagag agtttgtctt caaaaacaag gacggctttc tctacgttta caagggttat    600
```

-continued

```
cagcccattg atgtggtgcg ggacctccct tcagggttta acacattgaa accaatattc    660
aaactgcccc tgggtatcaa tattactaac tttcgagcca tcttgaccgc cttttccccc    720
gcgcaagaca tatggggaac cagcgcggca gcctatttcg tcggttatct gaagcccact    780
acatttatgc tgaagtacga cgagaacgga accattaccg atgctgtcga ttgttcacag    840
aatccactgg ctgaattgaa atgctccgtg aagagctttg agatcgataa ggggatttac    900
cagacgtcta attttcgagt ggttccctca ggagatgtgg ttagattccc caatatcaca    960
aatttgtgcc ccttcggtga agtgttcaat gccacaaagt tcccgtctgt ctacgcttgg   1020
gagcggaaaa agataagcaa ctgtgtcgcg gattacagtg tcctatataa ctcgaccttt   1080
tttagcacgt tcaagtgtta cggggtgagt gctactaaac tgaatgattt atgttttagt   1140
aacgtttatg cagactcctt tgttgtaaag ggtgatgacg tgcgccaaat tgcacctggg   1200
cagaccggag tgatcgcaga ttataactac aaacttccag acgactttat gggatgcgtg   1260
ctcgcctgga acactcgcaa catcgacgca accagcaccg ggaactataa ttacaaatac   1320
agatacctca ggcacggcaa gctgcggcct tttgagcggg atatctcaaa cgtcccattt   1380
agcccggacg gcaagccctg tactcctccc gcacttaact gttactggcc actgaacgat   1440
tatggctttt ataccacaac cggcatcggc taccagccct accgggtggt ggtgctatct   1500
ttcgagctgc tgaacgcgcc tgccaccgta tgtgggccca agctttcgac agatctcatc   1560
aagaaccaat gcgtaaattt caatttcaat ggccttacag gaaccggtgt gctgacaccc   1620
tcctccaaga ggtttcaacc tttccagcag tttggacgtg acgtctcaga ctttactgac   1680
agtgtgaggg atcctaagac ctctgaaatc ctggatatat ctccctgttc cttcggtggg   1740
gttagtgtga taacccctgg gacaaatgct agttccgaag tggccgtact ctatcaagac   1800
gtgaactgca cagacgtgtc aaccgccatc cacgctgatc aactcacacc ggcttggcgg   1860
atctatagca ctggcaataa cgtgttccaa acgcaggccg gctgccttat aggggcagag   1920
catgtcgaca cttcttacga gtgtgatata ccaatcggag ccggcatctg cgcctcatac   1980
cacacggtga gcttgctgcg ctccaccagt cagaagagta ttgtcgcata caccatgtca   2040
ctcggcgcag attcaagtat cgcctacagc aataacacta tcgctattcc taccaacttt   2100
tccatttcca tcacaactga ggttatgcct gtctccatgg ctaagacttc cgtggactgc   2160
aatatgtaca tttgtgggga ctctaccgag tgcgctaacc ttttactgca gtatggctcc   2220
ttctgcacac agctgaatag agccctgagc ggaattgccg ctgagcagga tagaaatacg   2280
agagaagtgt ttgcccaggt gaaacagatg tataagactc caaccttgaa gtatttcgga   2340
gggttcaatt ttagccagat ccttcctgac cccttgaagc cgaccaaaag gagcttcatc   2400
gaagatcttc tgttcaacaa agttacttta gcggacgccg ggttcatgaa acagtatggc   2460
gagtgtctcg ggatattaa tgcccgcgat ctcatctgtg ctcagaaatt caacggcctc   2520
acagtgctcc ccccacttct gacggatgat atgatcgccg cttacacagc cgcactcgtg   2580
agcggcaccg ccacagccgg ttggacattc ggagctggag ccgcattaca gattccattc   2640
gctatgcaga tggcgtacag gttcaacgga ataggcgtga cccagaacgt gttgtatgaa   2700
aatcagaagc agattgcgaa ccagttcaac aaagccattt ctcaaatcca ggagtccctg   2760
accaccacaa gcacggcact gggaaagctg caagacgtgg tcaaccagaa cgcccaagcc   2820
ctaaataccc tggttaagca gctgtctagc aattttggag cgatttcatc tgtccttaac   2880
gatatactat caagactgga caaagtggag gcagaggtcc aaatcgaccg cctgattacg   2940
ggccgcctcc agagccttca gacgtatgtg acacagcagc tgataagagc tgctgaaata   3000
```

```
cgagcctcgg ctaatctggc cgcaaccaaa atgtccgaat gcgtcctggg gcagtccaaa   3060

cgtgtcgatt tctgcggcaa aggttaccat ttgatgtcat ttccacaggc ggctcctcac   3120

ggcgtagtgt ttctgcacgt gacttatgta ccttcgcagg aaaggaactt cacaactgcc   3180

ccagccatct gccatgaggg aaaagcatat ttcccccgag aaggtgtttt cgttttcaac   3240

gggacaagct ggttcattac tcaaaggaat ttttttcgc cacagatcat taccactgat   3300

aacacatttg tatctggtaa ctgcgacgta gttatcggga ttatcaataa tacggtctat   3360

gacccccttgc aacctgagct ggatagcttt aaggaagagc tggacaagta ctttaagaat   3420

cacacctctc cagacgtgga cctgggagac atctccggca ttaatgcaag tgttgtgaat   3480

attcagaaag agattgatag actaaacgaa gttgctaaga acttgaatga gagtttaatt   3540

gacctacagg agctcggtaa gtacgaacag tacatcaaat ggccgtgg                3588
```

<210> SEQ ID NO 25
<211> LENGTH: 3588
<212> TYPE: DNA
<213> ORGANISM: Artificial Sequence
<220> FEATURE:
<223> OTHER INFORMATION: Uniform optimization of S protein

<400> SEQUENCE: 25

```
atgttcatct tcctgctgtt cctgaccctg accagcggca gcgacctgga ccggtgcacc     60

accttcgacg acgtgcaggc ccccaactac acccagcaca ccagcagcat gcggggcgtg    120

tactaccccg acgagatctt ccggagcgac accctgtacc tgacccagga cctgttcctg    180

cccttctaca gcaacgtgac cggcttccac accatcaacc acaccttcgg caaccccgtg    240

atccccttca aggacggcat ctacttcgcc gccaccgaga agagcaacgt ggtgcggggc    300

tgggtgttcg gcagcaccat gaacaacaag agccagagcg tgatcatcat caacaacagc    360

accaacgtgg tgatccgggc ctgcaacttc gagctgtgcg acaacccctt cttcgccgtg    420

agcaagccca tgggcaccca gacccacacc atgatcttcg acaacgcctt caactgcacc    480

ttcgagtaca tcagcgacgc cttcagcctg gacgtgagcg agaagagcgg caacttcaag    540

cacctgcggg agttcgtgtt caagaacaag gacggcttcc tgtacgtgta caagggctac    600

cagcccatcg acgtggtgcg ggacctgccc agcggcttca acaccctgaa gcccatcttc    660

aagctgcccc tgggcatcaa catcaccaac ttccgggcca tcctgaccgc cttcagcccc    720

gcccaggaca tctggggcac cagcgccgcc gcctacttcg tgggctacct gaagcccacc    780

accttcatgc tgaagtacga cgagaacggc accatcaccg acgccgtgga ctgcagccag    840

aacccccctgg ccgagctgaa gtgcagcgtg aagagcttcg agatcgacaa gggcatctac    900

cagaccagca acttccgggt ggtgcccagc ggcgacgtgg tgcggttccc caacatcacc    960

aacctgtgcc ccttcggcga ggtgttcaac gccaccaagt tccccagcgt gtacgcctgg   1020

gagcggaaga agatcagcaa ctgcgtggcc gactacagcg tgctgtacaa cagcaccttc   1080

ttcagcacct tcaagtgcta cggcgtgagc gccaccaagc tgaacgacct gtgcttcagc   1140

aacgtgtacg ccgacagctt cgtggtgaag ggcgacgacg tgcggcagat cgcccccggc   1200

cagaccggcg tgatcgccga ctacaactac aagctgcccg acgacttcat gggctgcgtg   1260

ctggcctgga acacccggaa catcgacgcc accagcaccg gcaactacaa ctacaagtac   1320

cggtacctgc ggcacggcaa gctgcggccc ttcgagcggg acatcagcaa cgtgcccttc   1380

agccccgacg gcaagccctg cacccccccc gccctgaact gctactggcc cctgaacgac   1440

tacggcttct acaccaccac cggcatcggc taccagccct accgggtggt ggtgctgagc   1500
```

```
ttcgagctgc tgaacgcccc cgccaccgtg tgcggcccca agctgagcac cgacctgatc   1560

aagaaccagt gcgtgaactt caacttcaac ggcctgaccg gcaccggcgt gctgaccccc   1620

agcagcaagc ggttccagcc cttccagcag ttcggccggg acgtgagcga cttcaccgac   1680

agcgtgcggg accccaagac cagcgagatc ctggacatca gcccctgcag cttcggcggc   1740

gtgagcgtga tcacccccgg caccaacgcc agcagcgagg tggccgtgct gtaccaggac   1800

gtgaactgca ccgacgtgag caccgccatc cacgccgacc agctgacccc cgcctggcgg   1860

atctacagca ccggcaacaa cgtgttccag acccaggccg gctgcctgat cggcgccgag   1920

cacgtggaca ccagctacga gtgcgacatc cccatcggcg ccggcatctg cgccagctac   1980

cacaccgtga gcctgctgcg gagcaccagc cagaagagca tcgtggccta caccatgagc   2040

ctgggcgccg acagcagcat cgcctacagc aacaacacca tcgccatccc caccaacttc   2100

agcatcagca tcaccaccga ggtgatgccc gtgagcatgg ccaagaccag cgtggactgc   2160

aacatgtaca tctgcggcga cagcaccgag tgcgccaacc tgctgctgca gtacggcagc   2220

ttctgcaccc agctgaaccg ggccctgagc ggcatcgccg ccgagcagga ccggaacacc   2280

cgggaggtgt tcgcccaggt gaagcagatg tacaagaccc ccaccctgaa gtacttcggc   2340

ggcttcaact tcagccagat cctgcccgac cccctgaagc ccaccaagcg gagcttcatc   2400

gaggacctgc tgttcaacaa ggtgaccctg gccgacgccg gcttcatgaa gcagtacggc   2460

gagtgcctgg gcgacatcaa cgcccgggac ctgatctgcg cccagaagtt caacggcctg   2520

accgtgctgc ccccctgct gaccgacgac atgatcgccg cctacaccgc cgccctggtg   2580

agcggcaccg ccaccgccgg ctggaccttc ggcgccggcg ccgccctgca gatccccttc   2640

gccatgcaga tggcctaccg gttcaacggc atcggcgtga cccagaacgt gctgtacgag   2700

aaccagaagc agatcgccaa ccagttcaac aaggccatca gccagatcca ggagagcctg   2760

accaccacca gcaccgccct gggcaagctg caggacgtgg tgaaccagaa cgcccaggcc   2820

ctgaacaccc tggtgaagca gctgagcagc aacttcggcg ccatcagcag cgtgctgaac   2880

gacatcctga gccggctgga caaggtggag gccgaggtgc agatcgaccg gctgatcacc   2940

ggccggctgc agagcctgca gacctacgtg acccagcagc tgatccgggc cgccgagatc   3000

cgggccagcg ccaacctggc cgccaccaag atgagcgagt gcgtgctggg ccagagcaag   3060

cgggtggact tctgcggcaa gggctaccac ctgatgagct tcccccaggc cgccccccac   3120

ggcgtggtgt tcctgcacgt gacctacgtg cccagccagg agcggaactt caccaccgcc   3180

cccgccatct gccacgaggg caaggcctac ttcccccggg agggcgtgtt cgtgttcaac   3240

ggcaccagct ggttcatcac ccagcggaac ttcttcagcc cccagatcat caccaccgac   3300

aacaccttcg tgagcggcaa ctgcgacgtg gtgatcggca tcatcaacaa caccgtgtac   3360

gacccccctgc agcccgagct ggacagcttc aaggaggagc tggacaagta cttcaagaac   3420

cacaccagcc ccgacgtgga cctgggcgac atcagcggca tcaacgccag cgtggtgaac   3480

atccagaagg agatcgaccg gctgaacgag gtggccaaga acctgaacga gagcctgatc   3540

gacctgcagg agctgggcaa gtacgagcag tacatcaagt ggccctgg                3588
```

```
<210> SEQ ID NO 26
<211> LENGTH: 2049
<212> TYPE: DNA
<213> ORGANISM: Artificial Sequence
<220> FEATURE:
<223> OTHER INFORMATION: Fully Optimized soluble S1 protein

<400> SEQUENCE: 26
```

-continued

```
atgtttatct ttttgctgtt tctcacatta acttcggggt ctgacctgga ccggtgcacc     60

acattcgatg acgtccaagc ccccaactac actcagcata catctagcat gcgcggcgtg    120

tactacccag atgagatctt taggtccgac accctttatc tgacccagga cctttttctt    180

cctttctact ctaatgtaac tgggttccat accatcaacc atacctttgg caacccagtg    240

attccattta aggatggtat ttacttcgcc gcgaccgaga aatcaaatgt tgtgcgcggc    300

tgggttttcg gctccaccat gaacaataag agtcagtccg taattatcat taacaatagt    360

acaaacgtgg tgatcagggc atgtaatttt gaattgtgcg acaacccttt cttcgctgta    420

agcaaaccca tggggacgca gactcacacg atgatcttcg ataacgcttt caattgcacg    480

tttgagtaca tatccgatgc cttttctcta gatgtgtccg aaaaatcagg gaattttaag    540

cacctgagag agttcgtctt taagaacaag gacggtttct tgtacgtgta caagggatac    600

cagccgatcg acgtggtgcg ggacctaccc agcggattca acaccctcaa gcccattttt    660

aagctcccac tgggtatcaa tataactaac ttcagagcca ttctcacagc tttctctcca    720

gctcaggata tttgggggac tagtgcggca gcttatttcg tgggatacct taagcccaca    780

accttcatgt tgaaatacga tgagaacgga accataactg acgcagttga ctgctcacag    840

aaccccctcg cagagttgaa atgctcagtt aaatcctttg agatcgacaa gggtatttac    900

cagaccagta actttagagt cgtgccgtca ggcgacgtcg tgaggtttcc taacatcaca    960

aatctatgtc ctttcggaga agtgttcaat gccacaaagt tccccagcgt gtacgcctgg   1020

gagcgaaaaa agatatctaa ctgcgtcgca gactacagcg tactgtataa cagcactttt   1080

ttcagcacct ttaagtgtta tggggtgtca gcaacaaaac tgaacgatct ctgcttttca   1140

aacgtttatg ccgattcctt cgttgtcaag ggagacgatg tccgtcaaat tgctcccggg   1200

caaactggcg ttatcgctga ctataactat aaactgccag acgattttat ggggtgtgtc   1260

ctcgcatgga atacgcgcaa catcgatgcg acctctaccg gaaactacaa ctataaatat   1320

aggtatcttc ggcacgggaa attacggccg ttcgagcgag atatttcgaa cgtgcctttc   1380

agtcccgatg gaaaaccatg tactcctcca gccctcaatt gttactggcc attgaatgac   1440

tacgggttct acacgacaac tggaataggc tatcagcctt atcgtgtcgt cgttctttct   1500

ttcgaactgc tgaatgctcc cgccacggtg tgcggtccaa aactcagcac cgacctgatc   1560

aagaatcagt gcgtgaattt caatttcaac ggcctgacag gcacaggcgt tctgacccca   1620

agctccaagc gcttccagcc cttccagcaa tttggcaggg atgtgtccga ctttaccgat   1680

tcagtgcgag atcccaagac cagtgaaata ctagacattt ctccgtgtag ctttggcggc   1740

gtgtctgtca ttactcctgg gacgaatgcc tcgagcgagg tggcggtgtt atatcaggac   1800

gttaattgta cagacgtcag taccgccata catgctgatc agctgactcc tgcatggaga   1860

atctactcca caggaaataa tgtgtttcag acacaagcag gttgcctgat cggagccgaa   1920

cacgtcgaca ccagctacga atgtgatatc cctatcggtg ccggcatctg cgctagttat   1980

cacacagtaa gcctgctgcg gagcaccagt cagaagtcca ttgtggccta tactatgtcc   2040

ctgggcgcc                                                            2049
```

```
<210> SEQ ID NO 27
<211> LENGTH: 2049
<212> TYPE: DNA
<213> ORGANISM: Artificial Sequence
<220> FEATURE:
<223> OTHER INFORMATION: Uniform optimization of soluble S1 protein

<400> SEQUENCE: 27
```

-continued

```
atgttcatct tcctgctgtt cctgaccctg accagcggca gcgacctgga cagatgcacc     60

accttcgacg acgtgcaggc ccccaactac acccagcaca ccagcagcat gagaggcgtg    120

tactaccccg acgagatctt cagaagcgac accctgtacc tgacccagga cctgttcctg    180

cccttctaca gcaacgtgac cggcttccac accatcaacc acaccttcgg caaccccgtg    240

atccccttca aggacggcat ctacttcgcc gccaccgaga agagcaacgt ggtgagaggc    300

tgggtgttcg gcagcaccat gaacaacaag agccagagcg tgatcatcat caacaacagc    360

accaacgtgg tgatcagagc ctgcaacttc gagctgtgcg acaacccctt cttcgccgtg    420

agcaagccca tgggcaccca gacccacacc atgatcttcg acaacgcctt caactgcacc    480

ttcgagtaca tcagcgacgc cttcagcctg gacgtgagcg agaagagcgg caacttcaag    540

cacctgagag agttcgtgtt caagaacaag gacggcttcc tgtacgtgta caagggctac    600

cagcccatcg acgtggtgag agacctgccc agcggcttca acaccctgaa gcccatcttc    660

aagctgcccc tgggcatcaa catcaccaac ttcagagcca tcctgaccgc cttcagcccc    720

gcccaggaca tctggggcac cagcgccgcc gcctacttcg tgggctacct gaagcccacc    780

accttcatgc tgaagtacga cgagaacggc accatcaccg acgccgtgga ctgcagccag    840

aaccccctgg ccgagctgaa gtgcagcgtg aagagcttcg agatcgacaa gggcatctac    900

cagaccagca acttcagagt ggtgcccagc ggcgacgtgg tgagattccc caacatcacc    960

aacctgtgcc ccttcggcga ggtgttcaac gccaccaagt tccccagcgt gtacgcctgg   1020

gagagaaaga agatcagcaa ctgcgtggcc gactacagcg tgctgtacaa cagcaccttc   1080

ttcagcacct tcaagtgcta cggcgtgagc gccaccaagc tgaacgacct gtgcttcagc   1140

aacgtgtacg ccgacagctt cgtggtgaag ggcgacgacg tgagacagat cgcccccggc   1200

cagaccggcg tgatcgccga ctacaactac aagctgcccg acgacttcat gggctgcgtg   1260

ctggcctgga acaccagaaa catcgacgcc accagcaccg gcaactacaa ctacaagtac   1320

agatacctga gacacggcaa gctgagaccc ttcgagagag acatcagcaa cgtgcccttc   1380

agccccgacg gcaagccctg cacccccccc gccctgaact gctactggcc cctgaacgac   1440

tacggcttct acaccaccac cggcatcggc taccagccct acagagtggt ggtgctgagc   1500

ttcgagctgc tgaacgcccc cgccaccgtg tgcggcccca agctgagcac cgacctgatc   1560

aagaaccagt gcgtgaactt caacttcaac ggcctgaccg gcaccggcgt gctgaccccc   1620

agcagcaaga gattccagcc cttccagcag ttcggcagag acgtgagcga cttcaccgac   1680

agcgtgagag accccaagac cagcgagatc ctggacatca gcccctgcag cttcggcggc   1740

gtgagcgtga tcacccccgg caccaacgcc agcagcgagg tggccgtgct gtaccaggac   1800

gtgaactgca ccgacgtgag caccgccatc cacgccgacc agctgacccc cgcctggaga   1860

atctacagca ccggcaacaa cgtgttccag acccaggccg gctgcctgat cggcgccgag   1920

cacgtggaca ccagctacga gtgcgacatc cccatcggcg ccggcatctg cgccagctac   1980

cacaccgtga gcctgctgag aagcaccagc cagaagagca tcgtggccta caccatgagc   2040

ctgggcgcc                                                           2049
```

<210> SEQ ID NO 28
<211> LENGTH: 1539
<212> TYPE: DNA
<213> ORGANISM: Artificial Sequence
<220> FEATURE:
<223> OTHER INFORMATION: Fully optimized S2 protein

<400> SEQUENCE: 28
gacagttcaa tcgcctattc gaacaacact atagcaatcc caacaaattt ttcaatttct 60
ataacaacag aggtgatgcc agtgtccatg gcaaagacta gcgtagactg caatatgtac 120
atctgcggag attctacaga atgtgcaaac ttgctgctac agtatggatc gttctgtacc 180
cagctcaacc gggcgctgag cggcattgct gccgaacagg atcgcaatac gagagaggtg 240
tttgctcaag tgaaacaaat gtataagacc ccaacattga aatacttcgg tggattcaat 300
ttcagtcaga ttctgccaga cccactcaaa cccaccaaga ggagctttat tgaagatctt 360
ctgttcaaca aagttacctt ggccgacgct gggtttatga agcaatacgg tgagtgcctg 420
ggcgacatta acgcacgaga cctgatctgc gcccagaagt ttaacgggct cacggtttta 480
ccgccactgc tgactgatga tatgattgcc gcttacactg cggcccttgt gagtggtacc 540
gcaactgctg gctggacgtt tggcgctggg gcggccttac agatcccttt tgccatgcag 600
atggcctaca ggttcaatgg aattggtgtc actcagaatg tcctgtacga gaaccagaaa 660
cagatcgcca accagttcaa taaagctatt tcacagattc aggaatcact taccacaact 720
tccacggcac tcggtaaact gcaggacgtg gtgaatcaga acgctcaggc actaaataca 780
ctcgtcaagc aactgagttc caatttcggg gccatatcta gcgtattgaa cgacatcctc 840
agtcggctcg acaaagtgga ggccgaagtc caaatagacc gtcttatcac aggcagacta 900
cagtcattgc agacctacgt tacccagcag ttgatccgcg ccgctgagat acgagcctcc 960
gccaatctgg ccgctaccaa aatgtctgag tgtgtgctcg gacaaagtaa gcgggtggat 1020
ttttgcggca agggctatca cctcatgtcc ttccctcaag cagcacccca cggagtcgtt 1080
tttctgcatg tgacatacgt gcctagccag gagagaaact ttaccactgc gcctgccatt 1140
tgtcatgaag gcaaagctta ttttccccgc gagggggtgt tcgttttcaa cggaactagc 1200
tggtttatca cacaaaggaa tttcttctcc ccccagatca tcaccaccga caacaccttt 1260
gtctctggaa actgtgacgt cgttataggc atcatcaata atacagtata cgatcccctg 1320
cagcccgaac ttgactcttt caaggaggaa ctagataagt acttcaagaa tcacaccagc 1380
ccggatgtag atttagggga tattagcggg attaacgcat ccgtggtcaa catccaaaaa 1440
gagattgaca gactgaacga agtggcgaag aacctgaatg agtccctgat cgatcttcag 1500
gagctgggca agtatgaaca gtatatcaag tggccttgg 1539

<210> SEQ ID NO 29
<211> LENGTH: 1539
<212> TYPE: DNA
<213> ORGANISM: Artificial Sequence
<220> FEATURE:
<223> OTHER INFORMATION: Uniform Optimization of S2 protein
<400> SEQUENCE: 29
gacagcagca tcgcctacag caacaacacc atcgccatcc ccaccaactt cagcatcagc 60
atcaccaccg aggtgatgcc cgtgagcatg gccaagacca gcgtggactg caacatgtac 120
atctgcggcg acagcaccga gtgcgccaac ctgctgctgc agtacggcag cttctgcacc 180
cagctgaacc gggccctgag cggcatcgcc gccgagcagg accggaacac ccgggaggtg 240
ttcgcccagg tgaagcagat gtacaagacc cccaccctga agtacttcgg cggcttcaac 300
ttcagccaga tcctgcccga ccccctgaag cccaccaagc ggagcttcat cgaggacctg 360
ctgttcaaca aggtgaccct ggccgacgcc ggcttcatga agcagtacgg cgagtgcctg 420
ggcgacatca acgcccggga cctgatctgc gcccagaagt tcaacggcct gaccgtgctg 480
ccccccctgc tgaccgacga catgatcgcc gcctacaccg ccgccctggt gagcggcacc 540

-continued gccaccgccg gctggacctt cggcgccggc gccgccctgc agatcccctt cgccatgcag 600
atggcctacc ggttcaacgg catcggcgtg acccagaacg tgctgtacga gaaccagaag 660
cagatcgcca accagttcaa caaggccatc agccagatcc aggagagcct gaccaccacc 720
agcaccgccc tgggcaagct gcaggacgtg gtgaaccaga acgcccaggc cctgaacacc 780
ctggtgaagc agctgagcag caacttcggc gccatcagca gcgtgctgaa cgacatcctg 840
agccggctgg acaaggtgga ggccgaggtg cagatcgacc ggctgatcac cggccggctg 900
cagagcctgc agacctacgt gacccagcag ctgatccggg ccgccgagat ccgggccagc 960
gccaacctgg ccgccaccaa gatgagcgag tgcgtgctgg gccagagcaa gcgggtggac 1020
ttctgcggca agggctacca cctgatgagc ttcccccagg ccgcccccca cggcgtggtg 1080
ttcctgcacg tgacctacgt gcccagccag gagcggaact tcaccaccgc cccccgccatc 1140 tgccacgagg gcaaggccta cttcccccgg gagggcgtgt tcgtgttcaa cggcaccagc 1200
tggttcatca cccagcggaa cttcttcagc ccccagatca tcaccaccga caacaccttc 1260
gtgagcggca actgcgacgt ggtgatcggc atcatcaaca acaccgtgta cgacccccctg 1320 cagcccgagc tggacagctt caaggaggag ctggacaagt acttcaagaa ccacaccagc 1380
cccgacgtgg acctgggcga catcagcggc atcaacgcca gcgtggtgaa catccagaag 1440
gagatcgacc ggctgaacga ggtggccaag aacctgaacg agagcctgat cgacctgcag 1500
gagctgggca agtacgagca gtacatcaag tggccctgg 1539

<210> SEQ ID NO 30
<211> LENGTH: 3633
<212> TYPE: DNA
<213> ORGANISM: Artificial Sequence
<220> FEATURE:
<223> OTHER INFORMATION: Fully optimized TPA-S protein

<400> SEQUENCE: 30
atggatgcaa tgaagcgggg cctgtgctgc gtgctcctgc tctgcggggc ggtgtttgtg 60
agccccagtg ccagaggtag cggcagcgat ttggataggt gcaccacatt tgatgacgtg 120
caggctccca attacaccca gcacaccagt tctatgagag gagtatacta ccctgacgag 180
atcttccgca gtgataccct atatttaaca caagatttat tcttaccctt ctactccaac 240
gtcacagggt ttcacaccat caaccacacc ttcggcaacc ccgtgatccc gtttaaagat 300
ggcatttatt tcgcagccac agagaagtcg aatgtagtgc ggggttgggt gtttggatca 360
acaatgaata ataaatctca gtccgtgatc attattaaca actctacgaa tgtggttata 420
cgagcctgta atttcgagtt atgcgataat ccatttttcg cggtcagtaa accaatgggc 480
actcagaccc atacgatgat tttcgataac gcattcaatt gtacgtttga atacatttct 540
gatgcttttt cactcgacgt ttcagaaaag tctgggaact tcaagcattt aagagagttc 600
gtctttaaaa ataaagacgg gttcctgtac gtgtataaag gataccagcc tatcgacgtg 660
gtgcgggacc tgccaagcgg ttttaatacc ctgaagccca tctttaagct gcccctggga 720
atcaatatta caaacttcag ggctatcctc accgctttta gcccagctca ggacatatgg 780
ggaacctccg ccgccgccta cttcgtcgga tatttgaaac caaccacatt catgctgaag 840
tatgacgaaa atgggacgat taccgacgcc gtagactgta gtcagaaccc tttggcggag 900
ttgaagtgct cagtcaagag ctttgagatc gacaagggaa tttatcaaac tagcaacttc 960
agggtggtgc cctccggaga tgtagttcgc ttccccaaca tcaccaacct gtgcccgttc 1020
ggtgaggtgt ttaatgcaac taaattcccc tcagtgtatg cctgggaaag aaagaaaatt 1080

-continued agcaactgtg ttgccgatta cagcgtcctt tataactcaa cattcttctc tacctttaag 1140
tgctatggtg tgtccgccac taagttgaac gacctctgct ttagtaacgt gtacgctgat 1200
tccttcgtgg tgaaagggga tgacgtgcgt cagattgcac cgggccagac cggagtaatc 1260
gccgattaca attacaagtt gcctgacgac ttcatgggct gcgttctagc atggaatacc 1320
cgcaacatag atgccacctc aacggggaac tacaactaca agtacagata tctgagacac 1380
ggtaagctgc ggccttttga gcgggatatc tccaatgtgc cttttagccc cgatggcaaa 1440
ccatgcaccc cacctgccct gaattgttat tggcctttga acgattatgg attctacact 1500
accactggga tcggttatca accctaccgg gtcgtcgtcc tgagttttga actcttgaac 1560
gcgcctgcaa cagtctgcgg acccaagctg tcgacagacc ttatcaagaa tcagtgtgtg 1620
aactttaact tcaatgggct caccggtacc ggtgttctga ctccatctag taagcgattt 1680
caaccattcc aacagttcgg ccgtgacgtt tccgatttta cggattcggt gcgtgatcca 1740
aaaacatcag agatccttga catatcgccg tgttcttttg gaggcgtgtc tgtgattaca 1800
ccaggcacta atgctagtag cgaagtcgct gtactatacc aggacgtgaa ctgcaccgac 1860
gtgagcacgg caatccacgc tgaccagctg acccccgcct ggcgcatcta cagtacaggc 1920
aataacgtct ttcagaccca ggccggctgt ctgattgggg ctgagcacgt cgacacttcc 1980
tatgaatgtg atattcccat cggcgctgga atttgtgcta gctatcacac agtctccctt 2040
ttaagatcaa ccagccagaa atctattgtg gcttacacaa tgtctctcgg cgcagactca 2100
tcaattgcct atagcaacaa taccattgca atccctacca attttagtat atccataacc 2160
accgaggtga tgcccgtgtc tatggcgaaa acttccgtcg attgcaacat gtatatctgc 2220
ggggactcca cagaatgcgc caacctgctt ctgcagtatg gaagcttctg tactcaactc 2280
aaccgcgcat tgtctgggat tgccgccgag caggatagga atactagaga ggtgttcgct 2340
caggttaaac aaatgtacaa gacaccgaca cttaagtact tcggaggttt taacttttcc 2400
cagatactcc ctgaccctct aaagcctact aaacgcagtt tcatcgagga tctcctgttt 2460
aataaggtga cactcgccga tgctggcttc atgaaacaat acggagaatg cctgggagac 2520
attaacgcca gagacctgat ctgtgcccag aagttcaacg gtctgacagt acttcctccc 2580
cttctgacgg acgacatgat tgctgcatac acagccgccc tagttagcgg cacagccaca 2640
gctgggtgga cctttggcgc tggcgcagcg ttgcagattc cattcgcgat gcagatggct 2700
taccgattta acgggatcgg cgtgactcag aatgttttgt atgagaacca gaaacagatc 2760
gctaatcagt ttaacaaggc aatcagccag atacaagaat ctctgactac cacaagcacc 2820
gctctgggaa aactgcagga cgtggtgaat cagaatgcac aggccctcaa cacgctcgtg 2880
aagcagctta gttccaattt cggggccatc tcctccgttt taaatgatat cctgagtcgc 2940
ctggacaagg tcgaggccga agttcagatc gaccgcctga tcacagggag gctacaatca 3000
ttgcagactt acgtgactca gcagctcata agggctgcag agattagggc ctctgcaaac 3060
cttgccgcga ccaagatgtc cgagtgtgtt ctcggtcagt ccaaacgggt tgacttttgt 3120
ggcaaaggct accatctgat gagcttcccc caggccgcac cccatggcgt agtctttctg 3180
cacgtaactt atgtgccatc ccaagaaagg aacttcacta cggcgccagc catatgccat 3240
gaaggtaaag catatttccc tcgagaaggg gtatttgttt tcaacgggac tagctggttt 3300
attacgcagc ggaatttctt ctcaccacaa atcatcacta ctgataacac attcgtcagc 3360
ggcaattgtg acgtcgtcat tggaattata aacaacactg tgtacgatcc tctgcagccg 3420
gaactggatt cttttaagga ggagctcgac aagtacttca aaaaccatac ctcgcccgac 3480
gtggacctag gcgatatctc tgggattaat gcctcagtag tcaacatcca gaaggagata 3540
gaccgactta atgaggttgc caagaatctg aatgagagtc tcatcgatct gcaagaactt 3600
ggcaagtatg aacaatatat caaatggcca tgg 3633

<210> SEQ ID NO 31
<211> LENGTH: 3633
<212> TYPE: DNA
<213> ORGANISM: Artificial Sequence
<220> FEATURE:
<223> OTHER INFORMATION: Uniform optimization of TPA-S protein

<400> SEQUENCE: 31
atggacgcca tgaagcgggg cctgtgctgc gtgctgctgc tgtgcggcgc cgtgttcgtg 60
agccccagcg cccggggcag cggcagcgac ctggaccggt gcaccacctt cgacgacgtg 120
caggccccca actacaccca gcacaccagc agcatgcggg gcgtgtacta ccccgacgag 180
atcttccgga gcgacaccct gtacctgacc caggacctgt tcctgccctt ctacagcaac 240
gtgaccggct tccacaccat caaccacacc ttcggcaacc ccgtgatccc cttcaaggac 300
ggcatctact tcgccgccac cgagaagagc aacgtggtgc ggggctgggt gttcggcagc 360
accatgaaca acaagagcca gagcgtgatc atcatcaaca acagcaccaa cgtggtgatc 420
cgggcctgca acttcgagct gtgcgacaac cccttcttcg ccgtgagcaa gcccatgggc 480
acccagaccc acaccatgat cttcgacaac gccttcaact gcaccttcga gtacatcagc 540
gacgccttca gcctggacgt gagcgagaag agcggcaact tcaagcacct gcgggagttc 600
gtgttcaaga acaaggacgg cttcctgtac gtgtacaagg gctaccagcc catcgacgtg 660
gtgcgggacc tgcccagcgg cttcaacacc ctgaagccca tcttcaagct gcccctgggc 720
atcaacatca ccaacttccg ggccatcctg accgccttca gccccgccca ggacatctgg 780
ggcaccagcg ccgccgccta cttcgtgggc tacctgaagc ccaccacctt catgctgaag 840
tacgacgaga acggcaccat caccgacgcc gtggactgca gccagaaccc cctggccgag 900
ctgaagtgca gcgtgaagag cttcgagatc gacaagggca tctaccagac cagcaacttc 960
cgggtggtgc ccagcggcga cgtggtgcgg ttccccaaca tcaccaacct gtgccccttc 1020
ggcgaggtgt tcaacgccac caagttcccc agcgtgtacg cctgggagcg gaagaagatc 1080
agcaactgcg tggccgacta cagcgtgctg tacaacagca ccttcttcag caccttcaag 1140
tgctacggcg tgagcgccac caagctgaac gacctgtgct tcagcaacgt gtacgccgac 1200
agcttcgtgg tgaagggcga cgacgtgcgg cagatcgccc ccggccagac cggcgtgatc 1260
gccgactaca actacaagct gcccgacgac ttcatgggct gcgtgctggc ctggaacacc 1320
cggaacatcg acgccaccag caccggcaac tacaactaca agtaccggta cctgcggcac 1380
ggcaagctgc ggcccttcga gcgggacatc agcaacgtgc ccttcagccc cgacggcaag 1440
ccctgcaccc cccccgccct gaactgctac tggcccctga acgactacgg cttctacacc 1500
accaccggca tcggctacca gccctaccgg gtggtggtgc tgagcttcga gctgctgaac 1560
gcccccgcca ccgtgtgcgg ccccaagctg agcaccgacc tgatcaagaa ccagtgcgtg 1620
aacttcaact tcaacggcct gaccggcacc ggcgtgctga cccccagcag caagcggttc 1680
cagcccttcc agcagttcgg ccgggacgtg agcgacttca ccgacagcgt gcgggacccc 1740
aagaccagcg agatcctgga catcagcccc tgcagcttcg gcggcgtgag cgtgatcacc 1800
cccggcacca acgccagcag cgaggtggcc gtgctgtacc aggacgtgaa ctgcaccgac 1860
gtgagcaccg ccatccacgc cgaccagctg acccccgcct ggcggatcta cagcaccggc 1920

-continued aacaacgtgt tccagaccca ggccggctgc ctgatcggcg ccgagcacgt ggacaccagc 1980
tacgagtgcg acatccccat cggcgccggc atctgcgcca gctaccacac cgtgagcctg 2040
ctgcggagca ccagccagaa gagcatcgtg gcctacacca tgagcctggg cgccgacagc 2100
agcatcgcct acagcaacaa caccatcgcc atccccacca acttcagcat cagcatcacc 2160
accgaggtga tgcccgtgag catggccaag accagcgtgg actgcaacat gtacatctgc 2220
ggcgacagca ccgagtgcgc caacctgctg ctgcagtacg gcagcttctg cacccagctg 2280
aaccgggccc tgagcggcat cgccgccgag caggaccgga acacccggga ggtgttcgcc 2340
caggtgaagc agatgtacaa gacccccacc ctgaagtact tcggcggctt caacttcagc 2400
cagatcctgc ccgaccccct gaagcccacc aagcggagct tcatcgagga cctgctgttc 2460
aacaaggtga ccctggccga cgccggcttc atgaagcagt acggcgagtg cctgggcgac 2520
atcaacgccc gggacctgat ctgcgcccag aagttcaacg gcctgaccgt gctgcccccc 2580
ctgctgaccg acgacatgat cgccgcctac accgccgccc tggtgagcgg caccgccacc 2640
gccggctgga ccttcggcgc cggcgccgcc ctgcagatcc ccttcgccat gcagatggcc 2700
taccggttca acggcatcgg cgtgacccag aacgtgctgt acgagaacca gaagcagatc 2760
gccaaccagt tcaacaaggc catcagccag atccaggaga gcctgaccac caccagcacc 2820
gccctgggca agctgcagga cgtggtgaac cagaacgccc aggccctgaa caccctggtg 2880
aagcagctga gcagcaactt cggcgccatc agcagcgtgc tgaacgacat cctgagccgg 2940
ctggacaagg tggaggccga ggtgcagatc gaccggctga tcaccggccg gctgcagagc 3000
ctgcagacct acgtgaccca gcagctgatc cgggccgccg agatccgggc cagcgccaac 3060
ctggccgcca ccaagatgag cgagtgcgtg ctgggccaga gcaagcgggt ggacttctgc 3120
ggcaagggct accacctgat gagcttcccc caggccgccc cccacggcgt ggtgttcctg 3180
cacgtgacct acgtgcccag ccaggagcgg aacttcacca ccgcccccgc catctgccac 3240
gagggcaagg cctacttccc ccgggagggc gtgttcgtgt tcaacggcac cagctggttc 3300
atcacccagc ggaacttctt cagcccccag atcatcacca ccgacaacac cttcgtgagc 3360
ggcaactgcg acgtggtgat cggcatcatc aacaacaccg tgtacgaccc cctgcagccc 3420
gagctggaca gcttcaagga ggagctggac aagtacttca agaaccacac cagccccgac 3480
gtggacctgg gcgacatcag cggcatcaac gccagcgtgg tgaacatcca gaaggagatc 3540
gaccggctga acgaggtggc caagaacctg aacgagagcc tgatcgacct gcaggagctg 3600
ggcaagtacg agcagtacat caagtggccc tgg 3633

<210> SEQ ID NO 32
<211> LENGTH: 2094
<212> TYPE: DNA
<213> ORGANISM: Artificial Sequence
<220> FEATURE:
<223> OTHER INFORMATION: Fully optimized soluble TPA-S1 protein

<400> SEQUENCE: 32
atggacgcca tgaagcgagg actgtgctgc gttttgttgc tgtgcggcgc agtttttgtc 60
agtccatccg cccgggggtc gggatctgac ctagatagat gcacgacctt cgatgacgtg 120
caggcaccaa attacaccca acatacttca tccatgcgcg gcgtttacta tcccgacgaa 180
atcttccgga gtgacaccct gtatctgact caggacctgt ttctgccctt ctacagcaat 240
gtgacaggct ttcacaccat taaccatacc ttcgggaatc cagtaatccc ttttaaggat 300
gggatttact ttgctgctac tgagaaaagt aatgttgtca gggggtgggt ttttggctca 360

-continued acaatgaaca ataagtctca gagtgtcatc atcattaaca attctaccaa tgtagtcatc 420
agagcatgca acttcgagct ctgtgataac cctttctttg ctgtgtctaa gcccatgggc 480
actcaaacac ataccatgat cttcgacaat gcgttcaatt gtacctttga gtatatatca 540
gacgccttca gcctagacgt ctcggaaaag tccggaaact ttaaacacct gcgggaattc 600
gtgtttaaga acaaagatgg atttttgtac gtatacaagg gttatcagcc tatcgatgtc 660
gtgcgtgatc tgccctccgg cttcaacacc ctgaagccta tattcaaact acccctaggg 720
atcaacatca ccaattttag ggcaatactt acggcatttt ccccagccca ggacatctgg 780
ggaacttccg ccgctgccta ctttgtgggc tatctcaagc ctactacttt catgcttaag 840
tatgatgaga atggcacaat cacggatgca gtggattgct cgcagaatcc acttgctgag 900
ctgaaatgct ccgtaaagag cttcgaaatt gataaaggaa tctatcagac cagcaacttc 960
cgggtcgtgc cctctggcga cgttgtccgg ttccccaaca tcaccaacct ctgcccattc 1020
ggcgaggtgt tcaacgctac aaaattccca agtgtctacg cctgggagag gaaaaagatc 1080
tctaattgtg tggcagatta ttccgtgtta tacaacagca cattcttctc aacgttcaag 1140
tgttatggcg tgagcgccac caagcttaac gacctctgct tctccaatgt atacgctgac 1200
tcttttgtgg ttaagggaga cgatgtgcga cagatcgccc cggggcaaac cggagtgatt 1260
gcggactaca actataaact gcccgacgat ttcatgggtt gtgtgcttgc ttggaatacg 1320
aggaacattg acgcaacgag caccgggaac tataattaca aatatcgtta cctgcgccat 1380
gggaaactca gaccttttga acgagatatt agcaacgtcc ctttctcacc ggatgggaag 1440
ccctgtaccc cacctgccct gaactgctat tggcctctca acgactacgg cttctacact 1500
accacaggga tcgggtacca gccctatcgc gtggtggttc tctcctttga actccttaat 1560
gctcccgcga ctgtgtgtgg gccgaagttg agtactgact taataaaaaa tcaatgcgta 1620
aactttaact ttaatggctt gacaggtaca ggtgtgctca caccgagtag caaaaggttc 1680
cagccatttc agcaatttgg cagagatgtg tctgacttta cagacagcgt gcgcgatcct 1740
aagacttctg agattttaga catctcacct tgttcctttg gaggagtgag cgtgataact 1800
cccggtacca acgcctcatc cgaagtggct gtcctgtatc aggacgttaa ttgcaccgat 1860
gtctctacag ccattcacgc cgatcagctg acaccagctt ggcgcatcta cagtaccggt 1920
aacaatgttt tccagactca ggccggttgt ctgattggcg ccgagcacgt cgacacatct 1980
tacgagtgcg atattcccat aggtgccggc atttgtgcga gctaccacac tgtatcactg 2040
ctgagaagca caagccagaa atcaattgtg gcatacacaa tgtccttggg agca 2094

<210> SEQ ID NO 33
<211> LENGTH: 2091
<212> TYPE: DNA
<213> ORGANISM: Artificial Sequence
<220> FEATURE:
<223> OTHER INFORMATION: Uniform optimization of soluble TPA-S1 protein

<400> SEQUENCE: 33
atggacgcca tgaagcgggg cctgtgctgc gtgctgctgc tgtgcggcgc cgtgttcgtg 60
agccccagcg cccggggcag cggcagcgac ctggaccggt gcaccacctt cgacgacgtg 120
caggccccca actacaccca gcacaccagc agcatgcggg gcgtgtacta ccccgacgag 180
atcttccgga gcgacaccct gtacctgacc caggacctgt tcctgccctt ctacagcaac 240
gtgaccggct tccacaccat caaccacacc ttcggcaacc ccgtgatccc cttcaaggac 300
ggcatctact tcgccgccac cgagaagagc aacgtggtgc ggggctgggt gttcggcagc 360

-continued

```
accatgaaca acaagagcca gagcgtgatc atcatcaaca acagcaccaa cgtggtgatc    420

cgggcctgca acttcgagct gtgcgacaac cccttcttcg ccgtgagcaa gcccatgggc    480

acccagaccc acaccatgat cttcgacaac gccttcaact gcaccttcga gtacatcagc    540

gacgccttca gcctggacgt gagcgagaag agcggcaact tcaagcacct gcgggagttc    600

gtgttcaaga acaaggacgg cttcctgtac gtgtacaagg gctaccagcc catcgacgtg    660

gtgcgggacc tgcccagcgg cttcaacacc ctgaagccca tcttcaagct gcccctgggc    720

atcaacatca ccaacttccg ggccatcctg accgccttca gccccgccca ggacatctgg    780

ggcaccagcg ccgccgccta cttcgtgggc tacctgaagc ccaccacctt catgctgaag    840

tacgacgaga acggcaccat caccgacgcc gtggactgca gccagaaccc cctggccgag    900

ctgaagtgca gcgtgaagag cttcgagatc gacaagggca tctaccagac cagcaacttc    960

cgggtggtgc ccagcggcga cgtggtgcgg ttccccaaca tcaccaacct gtgccccttc   1020

ggcgaggtgt tcaacgccac caagttcccc agcgtgtacg cctgggagcg gaagaagatc   1080

agcaactgcg tggccgacta cagcgtgctg tacaacagca ccttcttcag caccttcaag   1140

tgctacggcg tgagcgccac caagctgaac gacctgtgct tcagcaacgt gtacgccgac   1200

agcttcgtgg tgaagggcga cgacgtgcgg cagatcgccc ccggccagac cggcgtgatc   1260

gccgactaca actacaagct gcccgacgac ttcatgggct gcgtgctggc ctggaacacc   1320

cggaacatcg acgccaccag caccggcaac tacaactaca agtaccggta cctgcggcac   1380

ggcaagctgc ggcccttcga gcgggacatc agcaacgtgc ccttcagccc cgacggcaag   1440

ccctgcaccc cccccgccct gaactgctac tggcccctga acgactacgg cttctacacc   1500

accaccggca tcggctacca gccctaccgg gtggtggtgc tgagcttcga gctgctgaac   1560

gcccccgcca ccgtgtgcgg ccccaagctg agcaccgacc tgatcaagaa ccagtgcgtg   1620

aacttcaact tcaacggcct gaccggcacc ggcgtgctga cccccagcag caagcggttc   1680

cagcccttcc agcagttcgg ccgggacgtg agcgacttca ccgacagcgt gcgggacccc   1740

aagaccagcg agatcctgga catcagcccc tgcagcttcg gcggcgtgag cgtgatcacc   1800

cccggcacca acgccagcag cgaggtggcc gtgctgtacc aggacgtgaa ctgcaccgac   1860

gtgagcaccg ccatccacgc cgaccagctg acccccgcct ggcggatcta cagcaccggc   1920

aacaacgtgt tccagaccca ggccggctgc ctgatcggcg ccgagcacgt ggacaccagc   1980

tacgagtgcg acatccccat cggcgccggc atctgcgcca gctaccacac cgtgagcctg   2040

ctgcggagca ccagccagaa gagcatcgtg gcctacacca tgagcctggg c            2091
```

```
<210> SEQ ID NO 34
<211> LENGTH: 1623
<212> TYPE: DNA
<213> ORGANISM: Artificial Sequence
<220> FEATURE:
<223> OTHER INFORMATION: Fully optimized soluble TPA-S2

<400> SEQUENCE: 34

atggatgcaa tgaaaagagg cctgtgttgt gttctgctgc tgtgtggggc ggtatttgtg     60

agtccctctg ccaggggaag cggcgacagc agtatagcct actcaaacaa taccatcgcc    120

attcctacaa atttttccat ctcaatcacg acggaagtca tgccagttag catggccaaa    180

acctctgtcg actgcaacat gtacatctgc ggagactcta ctgagtgcgc aaacctgctc    240

ttgcagtatg gctcgttttg cacccagttg aatcgggccc tcagtggcat tgccgcagaa    300

caagatcgga ataccaggga ggtcttcgcg caagtcaagc agatgtacaa aaccccctaca    360
```

ctcaaatact tcgggggttt caactttagc caaatcctgc cagacccccct caagcctact 420 aagcgcagtt ttatcgaaga cttactcttt aataaggtga cattagctga tgccggattc 480
atgaagcagt acggagagtg cctgggggat atcaacgcgc gggacctaat ctgtgcccag 540
aagttcaacg gtctgacagt gcttccgcct ctcctgaccg atgatatgat cgcagcttac 600
accgccgcac tggttagtgg tacggccaca gcaggctgga ccttcggtgc cggtgctgcc 660
ctgcaaatcc cattcgcgat gcagatggca tacagattta acggcattgg agtcacccag 720
aatgtcctat acgagaacca gaagcaaatc gctaaccagt tcaacaaagc catatcccag 780
attcaggagt cccttactac aaccagtact gctttaggta aactgcaaga tgtagtgaac 840
cagaacgctc aggccttaaa tacccttgtt aaacagctat cctcaaactt tggggctatc 900
tcctccgtgc tcaacgatat cctgagccgc ctcgataagg tggaagcgga ggtccagatc 960
gatagactta ttacaggcag gcttcagtct ctccagacct atgtcacaca acagctcatt 1020
cgtgctgcag agatccgcgc ttccgccaac ttggctgcaa caaagatgtc tgaatgtgtg 1080
ctgggacaga gcaagagagt ggacttttgt gggaaaggct atcacttgat gagcttcccc 1140
caggccgccc cccatggagt ggtattccta cacgtgacgt acgttccatc tcaagaacga 1200
aatttcacca ccgcacctgc catttgccac gaagggaagg cttatttccc tcgagagggc 1260
gtgttcgttt ttaacgggac ttcatggttt ataactcaaa ggaatttctt ctcgccccag 1320
ataattacaa cagacaacac ttttgtgagc ggcaattgcg acgtggtcat aggtattatt 1380
aataatactg tgtatgaccc gctgcagccc gaactggaca gctttaaaga ggagctggac 1440
aaatacttca agaatcatac ttcacccgac gtggatctgg gcgacatatc cggaatcaat 1500
gcctctgtgg taaacattca gaaggagatc gatcggctga acgaagtggc taagaatctg 1560
aatgaatcat tgattgacct tcaggagttg ggcaagtatg agcagtatat taaatggcca 1620
tgg 1623

<210> SEQ ID NO 35
<211> LENGTH: 1623
<212> TYPE: DNA
<213> ORGANISM: Artificial Sequence
<220> FEATURE:
<223> OTHER INFORMATION: Uniform optimization of TPA-S2 protein

<400> SEQUENCE: 35
atggacgcca tgaagcgggg cctgtgctgc gtgctgctgc tgtgcggcgc cgtgttcgtg 60
agccccagcg cccggggcag cggcgacagc agcatcgcct acagcaacaa caccatcgcc 120
atccccacca acttcagcat cagcatcacc accgaggtga tgcccgtgag catggccaag 180
accagcgtgg actgcaacat gtacatctgc ggcgacagca ccgagtgcgc caacctgctg 240
ctgcagtacg gcagcttctg cacccagctg aaccgggccc tgagcggcat cgccgccgag 300
caggaccgga acacccggga ggtgttcgcc caggtgaagc agatgtacaa gacccccacc 360
ctgaagtact tcggcggctt caacttcagc cagatcctgc ccgacccccct gaagcccacc 420 aagcggagct tcatcgagga cctgctgttc aacaaggtga ccctggccga cgccggcttc 480
atgaagcagt acggcgagtg cctgggcgac atcaacgccc gggacctgat ctgcgcccag 540
aagttcaacg gcctgaccgt gctgcccccc ctgctgaccg acgacatgat cgccgcctac 600
accgccgccc tggtgagcgg caccgccacc gccggctgga ccttcggcgc cggcgccgcc 660
ctgcagatcc ccttcgccat gcagatggcc taccggttca acggcatcgg cgtgacccag 720
aacgtgctgt acgagaacca gaagcagatc gccaaccagt tcaacaaggc catcagccag 780

-continued atccaggaga gcctgaccac caccagcacc gccctgggca agctgcagga cgtggtgaac 840
cagaacgccc aggccctgaa caccctggtg aagcagctga gcagcaactt cggcgccatc 900
agcagcgtgc tgaacgacat cctgagccgg ctggacaagg tggaggccga ggtgcagatc 960
gaccggctga tcaccggccg gctgcagagc ctgcagacct acgtgaccca gcagctgatc 1020
cgggccgccg agatccgggc cagcgccaac ctggccgcca ccaagatgag cgagtgcgtg 1080
ctgggccaga gcaagcgggt ggacttctgc ggcaagggct accacctgat gagcttcccc 1140
caggccgccc cccacggcgt ggtgttcctg cacgtgacct acgtgcccag ccaggagcgg 1200
aacttcacca ccgcccccgc catctgccac gagggcaagg cctacttccc ccgggagggc 1260
gtgttcgtgt tcaacggcac cagctggttc atcacccagc ggaacttctt cagcccccag 1320
atcatcacca ccgacaacac cttcgtgagc ggcaactgcg acgtggtgat cggcatcatc 1380
aacaacaccg tgtacgaccc cctgcagccc gagctggaca gcttcaagga ggagctggac 1440
aagtacttca agaaccacac cagccccgac gtggacctgg gcgacatcag cggcatcaac 1500
gccagcgtgg tgaacatcca gaaggagatc gaccggctga acgaggtggc caagaacctg 1560
aacgagagcc tgatcgacct gcaggagctg ggcaagtacg agcagtacat caagtggccc 1620
tgg 1623

<210> SEQ ID NO 36
<211> LENGTH: 1269
<212> TYPE: DNA
<213> ORGANISM: Artificial Sequence
<220> FEATURE:
<223> OTHER INFORMATION: Fully optimized N protein

<400> SEQUENCE: 36
atgtccgata atggtcccca gtctaaccag aggtcggcgc caagaatcac attcgggggc 60
ccaacagaca gtaccgataa caaccagaac ggcggaagaa acggggccag gcccaagcag 120
cggagacctc agggattacc aaataatacc gcaagctggt tcacagccct gacccagcat 180
ggaaaagagg aactgagatt ccctagagga caaggggtgc ctattaatac taatagcggg 240
cctgacgatc aaattggcta ttatcgacgt gcgactcgcc gtgttagagg gggggacggg 300
aagatgaagg agcttagccc acgctggtac ttttactatc tgggaaccgg acctgaagct 360
agtctgccct acggcgctaa caaggaggga atagtatggg tcgccacgga aggtgcgttg 420
aatactccga aagatcacat cggcaccaga aatcctaaca ataacgccgc aaccgtgcta 480
caattacccc agggaactac tctgccgaag ggttctatg cggagggaag ccgcggcggc 540
tcacaagcca gttcacgctc cagctcccgg tcgaggggta attcccgaaa cagcaccccg 600
ggatcatcta ggggaaactc tcccgcccgg atggcctcag gcggcggcga aacagctctg 660
gctctgctat tgctggaccg gctcaaccag ctcgagtcca aagtctctgg taaaggtcag 720
cagcagcagg gtcaaacagt gaccaaaaaa agtgcagccg aggccagcaa gaaaccacgc 780
cagaaacgta cggccacaaa gcaatacaat gtgacccaag cctttggaag gcgggggccc 840
gaacagacac agggcaattt cggcgatcaa gatttgatac gacagggcac tgactacaaa 900
cactggccgc agatcgctca gtttgcacct agcgcctccg ctttctttgg catgagtcgg 960
attggcatgg aggtgacacc atcaggtact tggttaacgt accacggggc aatcaaactt 1020
gatgataaag atccccagtt taaggacaac gttatcctcc tgaataagca tattgacgcc 1080
tataagacct tccccccaac cgaaccaaag aaggacaaga agaagaagac agacgaggca 1140
cagcctctcc cccagaggca gaaaaagcag cctactgtca cccttctgcc cgctgcagac 1200
atggatgact tttcccgcca actccagaac tctatgagtg gggcttccgc tgactctacg 1260
caggcctga 1269

<210> SEQ ID NO 37
<211> LENGTH: 1266
<212> TYPE: DNA
<213> ORGANISM: Artificial Sequence
<220> FEATURE:
<223> OTHER INFORMATION: Uniform optimization of N protein

<400> SEQUENCE: 37
atgagcgaca acggccccca gagcaaccag agaagcgccc ccagaatcac cttcggcggc 60
cccaccgaca gcaccgacaa caaccagaac ggcggcagaa acggcgccag acccaagcag 120
agaagacccc agggcctgcc caacaacacc gccagctggt tcaccgccct gacccagcac 180
ggcaaggagg agctgagatt ccccagaggc cagggcgtgc ccatcaacac caacagcggc 240
cccgacgacc agatcggcta ctacagaaga gccaccagaa gagtgagagg cggcgacggc 300
aagatgaagg agctgagccc cagatggtac ttctactacc tgggcaccgg ccccgaggcc 360
agcctgccct acggcgccaa caaggagggc atcgtgtggg tggccaccga gggcgccctg 420
aacaccccca aggaccacat cggcaccaga aaccccaaca acaacgccgc caccgtgctg 480
cagctgcccc agggcaccac cctgcccaag ggcttctacg ccgagggcag cagaggcggc 540
agccaggcca gcagcagaag cagcagcaga agcagaggca acagcagaaa cagcaccccc 600
ggcagcagca gaggcaacag ccccgccaga atggccagcg gcggcggcga gaccgccctg 660
gccctgctgc tgctggacag actgaaccag ctggagagca aggtgagcgg caagggccag 720
cagcagcagg gccagaccgt gaccaagaag agcgccgccg aggccagcaa gaagcccaga 780
cagaagagaa ccgccaccaa gcagtacaac gtgacccagg ccttcggcag aagaggcccc 840
gagcagaccc agggcaactt cggcgaccag gacctgatca gacagggcac cgactacaag 900
cactggcccc agatcgccca gttcgccccc agcgccagcg ccttcttcgg catgagcaga 960
atcggcatgg aggtgacccc cagcggcacc tggctgacct accacggcgc catcaagctg 1020
gacgacaagg acccccagtt caaggacaac gtgatcctgc tgaacaagca catcgacgcc 1080
tacaagacct tcccccccac cgagcccaag aaggacaaga agaagaagac cgacgaggcc 1140
cagcccctgc cccagagaca gaagaagcag cccaccgtga ccctgctgcc cgccgccgac 1200
atggacgact tcagcagaca gctgcagaac agcatgagcg gcgccagcgc cgacagcacc 1260
caggcc 1266

<210> SEQ ID NO 38
<211> LENGTH: 1209
<212> TYPE: DNA
<213> ORGANISM: Artificial Sequence
<220> FEATURE:
<223> OTHER INFORMATION: Fully optimized N protein lacking NLS

<400> SEQUENCE: 38
atgagtgata atggccccca gtctaaccag aggagcgcac cgcggatcac gttcggtggc 60
ccaaccgact caacagacaa taatcagaac ggaggacgca atggtgcacg tcctaagcag 120
agacgccccc aagggctgcc taataataca gcaagttggt ttaccgcact cacacaacat 180
ggaaaggaag agttgcggtt cccccgcggc cagggcgtgc ccatcaacac aaatagcgga 240
cccgacgatc agatcggata ttaccgaaga gctacaagga gagttcgcgg cggggatggc 300
aagatgaagg agctatcacc acgatggtac ttctattacc tcgggacagg cccagaggcc 360

-continued

```
tcgctaccat acggggccaa caaggagggt attgtctggg tcgctaccga aggggccctg    420

aatacaccta aagaccacat aggtaccaga aatcccaaca ataacgccgc gaccgtgtta    480

cagcttcctc agggaacgac ccttccaaaa gggttttacg ccgaaggatc tcggggaggg    540

tcacaggcta gctcccgtag ctcctcaagg tccaggggga attctagaaa cagtacaccc    600

ggctctagcc gtggtaactc cccagctcgc atggcatccg gcggaggggga aaccgctctg    660

gctctgctcc tgttagatcg gttgaaccaa ctggaatcga aggtatccgg aaagggacag    720

cagcagcaag gccagactgt gactaagaag tccgcggccg aggccagtaa gaaaccccgc    780

cagaaacgaa ctgccaccaa acagtataat gtgacacagg ccttcggcag acggggtcca    840

gagcagaccc aaggcaactt cggggatcag gacctgattc ggcagggtac cgactataag    900

cactggccgc aaattgctca gtttgctccc agtgcgagtg ccttcttcgg catgtctagg    960

atcgggatgg aggttactcc tagcggcact tggcttactt atcacggagc catcaaactc   1020

gatgataagg acccacagtt taaggataac gtgattctgc tgaacaaaca tatagacgcg   1080

taccctctcc cgcaaaggca gaaaaaacag cctaccgtca cgttactgcc tgccgcagac   1140

atggacgact tttctagaca gttgcaaaac agcatgtcag gcgcatccgc cgatagcact   1200

caagcttga                                                           1209


<210> SEQ ID NO 39
<211> LENGTH: 1206
<212> TYPE: DNA
<213> ORGANISM: Artificial Sequence
<220> FEATURE:
<223> OTHER INFORMATION: Uniform optimization of N protein lacking NLS

<400> SEQUENCE: 39

atgagcgaca acggccccca gagcaaccag agaagcgccc ccagaatcac cttcggcggc     60

cccaccgaca gcaccgacaa caaccagaac ggcggcagaa acggcgccag acccaagcag    120

agaagacccc agggcctgcc caacaacacc gccagctggt tcaccgccct gacccagcac    180

ggcaaggagg agctgagatt ccccagaggc cagggcgtgc ccatcaacac caacagcggc    240

cccgacgacc agatcggcta ctacagaaga gccaccagaa gagtgagagg cggcgacggc    300

aagatgaagg agctgagccc cagatggtac ttctactacc tgggcaccgg ccccgaggcc    360

agcctgccct acggcgccaa caaggagggc atcgtgtggg tggccaccga gggcgccctg    420

aacaccccca aggaccacat cggcaccaga aaccccaaca acaacgccgc caccgtgctg    480

cagctgcccc agggcaccac cctgcccaag ggcttctacg ccgagggcag cagaggcggc    540

agccaggcca gcagcagaag cagcagcaga agcagaggca acagcagaaa cagcaccccc    600

ggcagcagca gaggcaacag ccccgccaga atggccagcg gcggcggcga gaccgccctg    660

gccctgctgc tgctggacag actgaaccag ctggagagca aggtgagcgg caagggccag    720

cagcagcagg gccagaccgt gaccaagaag agcgccgccg aggccagcaa gaagcccaga    780

cagaagagaa ccgccaccaa gcagtacaac gtgacccagg ccttcggcag aagaggcccc    840

gagcagaccc agggcaactt cggcgaccag gacctgatca gacagggcac cgactacaag    900

cactggcccc agatcgccca gttcgccccc agcgccagcg ccttcttcgg catgagcaga    960

atcggcatgg aggtgacccc cagcggcacc tggctgacct accacggcgc catcaagctg   1020

gacgacaagg acccccagtt caaggacaac gtgatcctgc tgaacaagca catcgacgcc   1080

taccccctgc ccagagaca gaagaagcag cccaccgtga ccctgctgcc cgccgccgac   1140

atggacgact tcagcagaca gctgcagaac agcatgagcg gcgccagcgc cgacagcacc   1200
```

caggcc 1206

<210> SEQ ID NO 40
<211> LENGTH: 666
<212> TYPE: DNA
<213> ORGANISM: Artificial Sequence
<220> FEATURE:
<223> OTHER INFORMATION: Fully optimized M protein

<400> SEQUENCE: 40
atggctgaca acggcaccat aaccgtcgag gagcttaaac agttattaga acaatggaac 60
ttggtgatag gattcctctt tctggcatgg atcatgttgc ttcagttcgc ctattctaac 120
cgcaataggt ttttgtacat tatcaagctg gtcttccttt ggctgctctg gcccgtaaca 180
ctagcctgtt ttgttttggc ggccgtgtat cggatcaatt gggtgacagg tggcattgct 240
attgcgatgg cttgcatcgt ggggctgatg tggctgtcgt atttcgttgc ctcattccgg 300
ctgtttgccc gaacaaggag tatgtggtct tttaaccccg agaccaatat tctgctcaat 360
gtgcctttac gcggcactat cgtgacccgg cctctaatgg aatccgagct ggtaattggc 420
gcagtcatca taagggggca cctcagaatg gccgggcacc cacttgggag atgcgacatc 480
aaggatctgc cgaaggaaat tactgttgca acttcacgaa cgctgagcta ttacaaactg 540
ggagctagcc agagagtggg taccgactcc ggcttcgctg cctacaaccg ctaccgtatc 600
ggaaattaca aactcaacac agatcatgca ggaagcaatg ataacatcgc cctcctggtc 660
cagtga 666

<210> SEQ ID NO 41
<211> LENGTH: 663
<212> TYPE: DNA
<213> ORGANISM: Artificial Sequence
<220> FEATURE:
<223> OTHER INFORMATION: Uniform optimization of M protein

<400> SEQUENCE: 41
atggccgaca acggcaccat caccgtggag gagctgaagc agctgctgga gcagtggaac 60
ctggtgatcg gcttcctgtt cctggcctgg atcatgctgc tgcagttcgc ctacagcaac 120
agaaacagat tcctgtacat catcaagctg gtgttcctgt ggctgctgtg gcccgtgacc 180
ctggcctgct tcgtgctggc cgccgtgtac agaatcaact gggtgaccgg cggcatcgcc 240
atcgccatgg cctgcatcgt gggcctgatg tggctgagct acttcgtggc cagcttcaga 300
ctgttcgcca gaaccagaag catgtggagc ttcaaccccg agaccaacat cctgctgaac 360
gtgcccctga gaggcaccat cgtgaccaga cccctgatgg agagcgagct ggtgatcggc 420
gccgtgatca tcagaggcca cctgagaatg gccggccacc ccctgggcag atgcgacatc 480
aaggacctgc ccaaggagat caccgtggcc accagcagaa ccctgagcta ctacaagctg 540
ggcgccagcc agagagtggg caccgacagc ggcttcgccg cctacaacag atacagaatc 600
ggcaactaca agctgaacac cgaccacgcc ggcagcaacg acaacatcgc cctgctggtg 660
cag 663

<210> SEQ ID NO 42
<211> LENGTH: 231
<212> TYPE: DNA
<213> ORGANISM: Artificial Sequence
<220> FEATURE:
<223> OTHER INFORMATION: Fully optimized E protein

<400> SEQUENCE: 42

-continued

```
atgtacagct ttgtgtctga agaaacagga acgttgatag ttaatagtgt tttgcttttc     60

ttagcgttcg tagtcttcct tcttgtcaca cttgccattt taactgcgct tcgtctatgc    120

gcttactgtt gcaatatcgt aaacgtgtcg cttgttaaac caacggttta cgtatactcg    180

cgagttaaaa acctgaattc ttcagaaggt gttcctgatc tgctagtcta a             231
```

```
<210> SEQ ID NO 43
<211> LENGTH: 231
<212> TYPE: DNA
<213> ORGANISM: Artificial Sequence
<220> FEATURE:
<223> OTHER INFORMATION: Uniform optimization of E protein

<400> SEQUENCE: 43

atgtacagct tcgtgagcga ggagaccggc accctgatcg tgaacagcgt gctgctgttc     60

ctggccttcg tggtgttcct gctggtgacc ctggccatcc tgaccgccct gcggctgtgc    120

gcctactgct gcaacatcgt gaacgtgagc ctggtgaagc ccaccgtgta cgtgtacagc    180

cgggtgaaga acctgaacag cagcgagggc gtgcccgacc tgctggtgtg a             231
```

```
<210> SEQ ID NO 44
<211> LENGTH: 3588
<212> TYPE: DNA
<213> ORGANISM: Artificial Sequence
<220> FEATURE:
<223> OTHER INFORMATION: Minimal optimization of soluble S protein

<400> SEQUENCE: 44

atgtttatct tcctgctgtt tctgacactg acaagcggca gtgacctgga tagatgcaca     60

acgtttgacg acgtgcaggc ccccaactac acccagcata catccagcat gaggggcgtt    120

tactaccccg atgagatctt tagaagtgat actctgtatc tgactcagga cctgtttctg    180

cccttctatt ctaacgttac tggcttccat acaatcaacc acaccttcgg caaccccgta    240

ataccottta aggatggcat ctactttgcc gccaccgaga agtctaacgt agtgagaggc    300

tgggtgttcg gcagtactat gaacaacaag tctcagtctg tgataataat caacaactcc    360

actaacgtcg tcatcagagc ctgtaacttc gagctgtgcg ataacccctt cttcgccgtt    420

tcgaagccca tgggcactca gacccataca atgatctttg ataacgcctt caactgcacc    480

tttgagtata tctctgatgc cttcagtctg gatgtgtccg agaagtcagg caacttcaag    540

catctgagag agtttgtgtt caagaacaag gatggctttc tgtacgtcta caagggctac    600

cagcccatag atgtggtacg tgacctgccc agcggcttca acactctgaa gcccatattc    660

aagctgcccc tgggcataaa cattaccaac tttagagcca ttctgacggc cttctccccc    720

gcccaggata tctggggcac aagtgccgcc gcctacttcg tgggctacct gaagcccaca    780

acttttatgc tgaagtacga cgagaacggc accataacag atgccgtgga ctgttctcag    840

aacccccctgg ccgagctgaa gtgctcagtt aagagttttg agatagataa gggcatctat    900

cagacaagca acttccgcgt ggtccccagc ggcgatgtgg tgaggtttcc caacattacc    960

aacctgtgcc ccttcggcga ggtattcaac gccacaaagt tcccctccgt ttacgcctgg   1020

gagaggaaga agatttcaaa ctgcgtggcc gactactcgg tgctgtataa ctctactttc   1080

ttcagtacct ttaagtgcta cggcgtgtct gccacaaagc tgaacgatct gtgctttagc   1140

aacgtgtatg ccgatagctt cgtcgtcaag ggcgacgacg tcagacagat cgcccccggc   1200

cagacaggcg tcatcgccga ctacaactac aagctgcccg acgatttcat gggctgcgtg   1260

ctggcctgga acacgaggaa catagatgcc accagcactg gcaactacaa ctacaagtac   1320
```

```
agatatctgc ggcacggcaa gctgaggccc ttcgagagag acatctctaa cgttcccttt   1380
tcccccgatg gcaagccctg cactcccccc gccctgaact gctactggcc cctgaacgac   1440
tatggcttct acaccacaac tggcatcggc tatcagccct accgcgtagt cgtgctgtcg   1500
ttcgagctgc tgaacgcccc cgccacagtc tgcggcccca agctgtccac tgacctgatt   1560
aagaaccagt gtgtgaactt caactttaac ggcctgactg gcaccggcgt gctgacaccc   1620
agcagcaagc ggttccagcc cttccagcag tttggcagag acgtgtctga tttcacagat   1680
tccgtgagag atcccaagac ttccgagata ctggatatca gtccctgctc cttcggcggc   1740
gtgtcagtta ttacacccgg cactaacgcc tcgtccgagg tagccgttct gtatcaggac   1800
gtgaactgca ctgatgtgag tacagccatc cacgccgacc agctgacccc cgcctggcgg   1860
atttatagta cgggcaacaa cgtctttcag actcaggccg gctgcctgat cggcgccgag   1920
catgtagata cgtcttatga gtgcgacatc cccatcggcg ccggcatctg cgccagctat   1980
cacaccgttt ctctgctgcg aagtacttct cagaagtcta tagtggccta caccatgtct   2040
ctgggcgccg atagctctat cgcctatagc aacaacacta tagccatccc cacaaacttc   2100
tctatttcta tcactacaga ggtgatgccc gtctccatgg ccaagaccag cgttgattgc   2160
aacatgtaca tctgcggcga tagtacagag tgcgccaacc tgctgctgca gtatggcagc   2220
ttctgcaccc agctgaacag agccctgtct ggcatcgccg ccgagcagga taggaacaca   2280
agagaggttt tcgcccaggt taagcagatg tacaagactc ccactctgaa gtactttggc   2340
ggctttaact tttctcagat tctgcccgat cccctgaagc ccactaagag gagtttcata   2400
gaggacctgc tgttcaacaa ggtgactctg gccgacgccg gctttatgaa gcagtacggc   2460
gagtgcctgg gcgatatcaa cgccagagac ctgatctgtg cccagaagtt taacggcctg   2520
acagtactgc ccccccctgct gactgatgac atgattgccg cctatacggc cgccctggtg   2580
tctggcactg ccaccgccgg ctggaccttt ggcgccggcg ccgccctgca gatacccttt   2640
gccatgcaga tggcctaccg attcaacggc ataggcgtaa cccagaacgt tctgtatgag   2700
aaccagaagc agatagccaa ccagttcaac aaggccatct ctcagattca ggagtctctg   2760
accactacat ctactgccct gggcaagctg caggacgtag tgaaccagaa cgcccaggcc   2820
ctgaacaccc tggttaagca gctgtcaagt aacttcggcg ccatctctag cgttctgaac   2880
gatatactga gtcggctgga taaggtggag gccgaggtgc agattgacag actgatcaca   2940
ggcagactgc agtctctgca gacatatgtt actcagcagc tgataagggc cgccgagatt   3000
agagccagtg ccaacctggc cgccactaag atgtccgagt gcgtcctggg ccagagtaag   3060
agggtagact tttgtggcaa gggctatcac ctgatgtcct tcccccaggc cgccccccac   3120
ggcgtcgtgt ttctgcatgt cacttatgtt ccctcacagg agaggaactt cacgaccgcc   3180
cccgccatct gccacgaggg caaggcctat ttccccaggg agggcgtctt cgtattcaac   3240
ggcacgagtt ggttcatcac ccagcgaaac ttcttttcgc cccagataat tacaacggac   3300
aacacttttg taagtggcaa ctgcgatgtc gtcatcggca taatcaacaa cacggtttac   3360
gacccccctgc agcccgagct ggattcattc aaggaggagc tggacaagta cttcaagaac   3420
catactagcc ccgacgttga tctgggcgac ataagcggca tcaacgccag tgtagtcaac   3480
atacagaagg agatcgatag actgaacgag gtggccaaga acctgaacga gtctctgata   3540
gacctgcagg agctgggcaa gtacgagcag tacatcaagt ggccctgg                3588
```

<210> SEQ ID NO 45
<211> LENGTH: 2049
<212> TYPE: DNA

<213> ORGANISM: Artificial Sequence
<220> FEATURE:
<223> OTHER INFORMATION: Minimal optimization of soluble S1 protein

<400> SEQUENCE: 45
atgttcatct tcctgctgtt tctgacactg acttctggct cagatctgga tagatgcact 60
acctttgacg atgtacaggc ccccaactac actcagcaca catcgtccat gcgaggcgtg 120
tattaccccg acgagatctt cagaagtgac actctgtacc tgacacagga cctgttcctg 180 ccctttact ctaacgtgac tggctttcac actatcaacc ataccttcgg caaccccgta 240
atccccttca aggatggcat ctattttgcc gccaccgaga agtccaacgt ggtgaggggc 300
tgggtcttcg gcagtacgat gaacaacaag tctcagtccg tgataatcat aaacaacagt 360
actaacgtgg ttataagagc ctgcaacttc gagctgtgcg acaacccctt cttcgccgtg 420
tccaagccca tgggcacaca gacccacacc atgatattcg acaacgcctt taactgtact 480
ttcgagtata taagcgatgc cttcagtctg gatgtttctg agaagtcagg caactttaag 540
catctgagag agttcgtatt caagaacaag gacggctttc tgtatgttta taagggctac 600
cagcccatag atgtcgtgcg ggatctgccc agcggcttca acacactgaa gcccattttt 660
aagctgcccc tgggcatcaa cataaccaac tttagagcca tcctgactgc ctttagcccc 720
gcccaggata tatggggcac tagcgccgcc gcctatttcg tcggctacct gaagcccacc 780
acattcatgc tgaagtacga tgagaacggc acaattacgg atgccgtaga ttgcagtcag 840
aaccccctgg ccgagctgaa gtgcagtgtg aagtctttcg agatcgacaa gggcatatac 900
cagacttcta actttcgggt ggttcccagc ggcgacgttg ttaggtttcc caacatcacc 960
aacctgtgcc ccttcggcga ggtgtttaac gccacaaagt tcccctccgt atatgcctgg 1020
gagaggaaga agatttcgaa ctgcgtggcc gactatagcg tcctgtacaa ctctacattc 1080
ttttctacat tcaagtgcta cggcgtcagt gccactaagc tgaacgacct gtgcttcagc 1140
aacgtgtatg ccgactcatt tgtagttaag ggcgatgatg tgagacagat tgcccccggc 1200
cagacaggcg tgatcgccga ttataactat aagctgcccg acgatttcat gggctgcgtt 1260
ctggcctgga acacaaggaa catcgatgcc actagcactg gcaactacaa ctacaagtac 1320
aggtatctga gacacggcaa gctgaggccc ttcgagcgag atatcagtaa cgtacccttc 1380
agtcccgacg gcaagccctg cactcccccc gccctgaact gctattggcc cctgaacgac 1440
tacggctttt ataccactac aggcatcggc taccagccct acagggttgt ggtgctgagc 1500
ttcgagctgc tgaacgcccc cgccactgtt tgcggcccca agctgtcaac ggatctgatc 1560
aagaaccagt gcgtaaactt taactttaac ggcctgacag gcacaggcgt cctgactccc 1620
tctagtaaga gattccagcc ctttcagcag ttcggccgcg acgtcagcga ttttacggat 1680
agtgtgagag atcccaagac cagcgagatc ctggacatta gtccctgttc tttcggcggc 1740
gtgtctgtca taacgcccgg cacgaacgcc tcttctgagg tcgccgttct gtaccaggac 1800
gtcaactgta cagacgtctc cacagccata cacgccgatc agctgactcc cgcctggaga 1860
atttactcta ccggcaacaa cgtcttccag acccaggccg gctgcctgat cggcgccgag 1920
catgtggata cttcctacga gtgcgacata cccatcggcg ccggcatttg cgcctcgtac 1980
cataccgtgt ctctgctgag atctacctct cagaagagta tcgttgccta cactatgtcc 2040
ctgggcgcc 2049

<210> SEQ ID NO 46
<211> LENGTH: 1539
<212> TYPE: DNA

-continued

<213> ORGANISM: Artificial Sequence
<220> FEATURE:
<223> OTHER INFORMATION: Minimal optimization of soluble S2 protein

<400> SEQUENCE: 46
gatagcagca tagcctactc aaacaacacg atcgccatcc ccacaaactt ttccatttcc 60
ataactaccg aggtgatgcc cgtgagcatg gccaagacat cggtagattg caacatgtac 120
atctgtggcg attctacaga gtgtgccaac ctgctgctgc agtacggctc tttctgcacg 180
cagctgaaca gggccctgtc tggcatcgcc gccgagcagg atcggaacac acgggaggtt 240
ttcgcccagg taaagcagat gtataagacg cccactctga agtacttcgg cggcttcaac 300
ttctctcaga tactgcccga ccccctgaag cccactaaga ggtcttttat cgaggatctg 360
ctgttcaaca aggttaccct ggccgatgcc ggctttatga agcagtatgg cgagtgcctg 420
ggcgacatca acgccagaga tctgatatgc gcccagaagt tcaacggcct gactgtgctg 480 cccccccctgc tgactgacga catgatcgcc gcctataccg ccgccctggt gagtggcaca 540
gccactgccg gctggacatt cggcgccggc gccgccctgc agatcccctt cgccatgcag 600
atggcctaca gatttaacgg cattggcgtc actcagaacg tcctgtatga gaaccagaag 660
cagatcgcca accagtttaa caaggccata agccagatcc aggagtcact gacaacgaca 720
agtaccgccc tgggcaagct gcaggatgta gtgaaccaga acgcccaggc cctgaacact 780
ctggttaagc agctgtctag caacttcggc gccatcagta gtgttctgaa cgatattctg 840
tctaggctgg acaaggtcga ggccgaggtg cagattgatc gcctgattac cggcagactg 900
cagagtctgc agacttatgt aactcagcag ctgatcagag ccgccgagat tcgagcctcc 960
gccaacctgg ccgccacaaa gatgtctgag tgcgtcctgg gccagagtaa gagggttgac 1020
ttctgcggca agggctatca tctgatgtct tttccccagg ccgcccccca cggcgtcgtg 1080
ttcctgcacg taacttacgt gcccagtcag gagagaaact ttaccactgc ccccgccatc 1140
tgccacgagg gcaaggccta cttccccaga gagggcgtgt ttgtgttcaa cggcacatct 1200
tggttcatca cccagaggaa ctttttcagc ccccagatca taacaactga caacactttc 1260
gtttcgggca actgcgacgt agtgatcggc ataataaaca acaccgtgta cgatcccctg 1320
cagcccgagc tggacagctt taaggaggag ctggacaagt actttaagaa ccatacctca 1380
cccgatgtgg acctgggcga catttctggc ataaacgcct ccgtcgtcaa catccagaag 1440
gagatagata gactgaacga ggttgccaag aacctgaacg agtccctgat cgatctgcag 1500
gagctgggca agtacgagca gtatataaag tggccctgg 1539

<210> SEQ ID NO 47
<211> LENGTH: 1620
<212> TYPE: DNA
<213> ORGANISM: Artificial Sequence
<220> FEATURE:
<223> OTHER INFORMATION: Minimal optimization of TPA-S protein

<400> SEQUENCE: 47
atggatgcca tgaagcgagg cctgtgttgc gtactgctgc tgtgcggcgc cgtgtttgtg 60
agccccagcg cccggggcag tggcgacagc agcatcgcct attcgaacaa cactattgcc 120
atacccacaa acttctctat atctataact acggaggtga tgcccgtgtc tatggccaag 180
actagtgtag actgcaacat gtacatctgc ggcgactcta ctgagtgcgc caacctgctg 240
ctgcagtatg gctctttctg cacccagctg aacagagccc tgagtggcat cgccgccgag 300
caggaccgga acacaagaga ggttttcgcc caggtaaagc agatgtacaa gacccccact 360

-continued ctgaagtatt ttggcggctt caacttctct cagatcctgc ccgatcccct gaagcccacc 420
aagaggtctt tcatcgagga cctgctgttc aacaaggtca ctctggccga tgccggcttc 480
atgaagcagt acggcgagtg cctgggcgac attaacgccc gcgacctgat ctgtgcccag 540
aagtttaacg gcctgacggt cctgcccccc ctgctgacag atgatatgat cgccgcctac 600
actgccgccc tggtctctgg caccgccacc gccggctgga ctttcggcgc cggcgccgcc 660
ctgcagatcc ccttcgccat gcagatggcc tatagattta acggcatagg cgtaactcag 720
aacgtcctgt acgagaacca gaagcagatc gccaaccagt ttaacaaggc catctcccag 780
attcaggaga gcctgacaac cactagcact gccctgggca agctgcagga cgtggtgaac 840
cagaacgccc aggccctgaa cacactggtt aagcagctga gttctaactt tggcgccata 900
tcctcggtgc tgaacgacat actgtcaagg ctggacaagg tcgaggccga ggttcagata 960
gatagactga tcacaggcag actgcagagc ctgcagacct acgttacaca gcagctgatc 1020
agagccgccg agatcagagc ctcagccaac ctggccgcca cgaagatgtc tgagtgcgtc 1080
ctgggccagt ctaagagagt cgatttctgc ggcaagggct accacctgat gagtttcccc 1140
caggccgccc cccatggcgt tgtattcctg catgtgacat atgttccctc ccaggagagg 1200
aactttacca cggcccccgc catctgccac gagggcaagg cctacttccc cagagagggc 1260
gtgttcgttt ttaacggcac tagctggttt attacccaga ggaacttctt ctcccccag 1320 attataacaa cagataacac tttcgtgtcc ggcaactgcg atgttgtgat aggcatcatt 1380
aacaacacag tgtacgatcc cctgcagccc gagctggata gttttaagga ggagctggac 1440
aagtatttta agaaccacac ttcccccgat gtagacctgg gcgatatcag tggcataaac 1500
gccagtgtcg tgaacataca gaaggagatc gataggctga acgaggtggc caagaacctg 1560
aacgagtcac tgatcgatct gcaggagctg ggcaagtacg agcagtatat taagtggccc 1620

<210> SEQ ID NO 48
<211> LENGTH: 231
<212> TYPE: DNA
<213> ORGANISM: Artificial Sequence
<220> FEATURE:
<223> OTHER INFORMATION: Minimal optimization of E protein

<400> SEQUENCE: 48
atgtatagtt ttgtgagtga ggagacgggc accctgattg tcaactcagt gctgctgttc 60
ctggcctttg ttgtcttcct gctggtaact ctggccatcc tgactgccct gagactgtgc 120
gcctactgct gcaacatcgt gaacgtctct ctggtaaagc ccacagttta cgtgtattct 180
agggtgaaga acctgaactc cagcgagggc gttcccgatc tgctggtatg a 231

<210> SEQ ID NO 49
<211> LENGTH: 1620
<212> TYPE: DNA
<213> ORGANISM: Artificial Sequence
<220> FEATURE:
<223> OTHER INFORMATION: Minimal optimization of TPA-S2 protein

<400> SEQUENCE: 49
atggatgcca tgaagcgagg cctgtgttgc gtactgctgc tgtgcggcgc cgtgtttgtg 60
agccccagcg cccggggcag tggcgacagc agcatcgcct attcgaacaa cactattgcc 120
atacccacaa acttctctat atctataact acggaggtga tgcccgtgtc tatggccaag 180
actagtgtag actgcaacat gtacatctgc ggcgactcta ctgagtgcgc caacctgctg 240
ctgcagtatg gctctttctg cacccagctg aacagagccc tgagtggcat cgccgccgag 300

```
caggaccgga acacaagaga ggttttcgcc caggtaaagc agatgtacaa gacccccact    360
ctgaagtatt ttggcggctt caacttctct cagatcctgc ccgatcccct gaagcccacc    420
aagaggtctt tcatcgagga cctgctgttc aacaaggtca ctctggccga tgccggcttc    480
atgaagcagt acggcgagtg cctgggcgac attaacgccc gcgacctgat ctgtgcccag    540
aagtttaacg gcctgacggt cctgcccccc ctgctgacag atgatatgat cgccgcctac    600
actgccgccc tggtctctgg caccgccacc gccggctgga ctttcggcgc cggcgccgcc    660
ctgcagatcc ccttcgccat gcagatggcc tatagattta acggcatagg cgtaactcag    720
aacgtcctgt acgagaacca gaagcagatc gccaaccagt ttaacaaggc catctcccag    780
attcaggaga gcctgacaac cactagcact gccctgggca agctgcagga cgtggtgaac    840
cagaacgccc aggccctgaa cacactggtt aagcagctga gttctaactt tggcgccata    900
tcctcggtgc tgaacgacat actgtcaagg ctggacaagg tcgaggccga ggttcagata    960
gatagactga tcacaggcag actgcagagc ctgcagacct acgttacaca gcagctgatc   1020
agagccgccg agatcagagc ctcagccaac ctggccgcca cgaagatgtc tgagtgcgtc   1080
ctgggccagt ctaagagagt cgatttctgc ggcaagggct accacctgat gagtttcccc   1140
caggccgccc cccatggcgt tgtattcctg catgtgacat atgttccctc ccaggagagg   1200
aactttacca cggcccccgc catctgccac gagggcaagg cctacttccc cagagagggc   1260
gtgttcgttt ttaacggcac tagctggttt attacccaga ggaacttctt ctcccccccag  1320
attataacaa cagataacac tttcgtgtcc ggcaactgcg atgttgtgat aggcatcatt   1380
aacaacacag tgtacgatcc cctgcagccc gagctggata gttttaagga ggagctggac   1440
aagtatttta agaaccacac ttcccccgat gtagacctgg gcgatatcag tggcataaac   1500
gccagtgtcg tgaacataca gaaggagatc gataggctga acgaggtggc caagaacctg   1560
aacgagtcac tgatcgatct gcaggagctg ggcaagtacg agcagtatat taagtggccc   1620
```

<210> SEQ ID NO 50
<211> LENGTH: 2052
<212> TYPE: DNA
<213> ORGANISM: Artificial Sequence
<220> FEATURE:
<223> OTHER INFORMATION: Sequence contain in VR9208

<400> SEQUENCE: 50

```
atggttatct ttctgctgtt cctcaccctc accagcggca gcgatctgga taggtgcacc     60
accttcgacg acgtgcaggc ccccaactac acccagcaca ccagcagcat gaggggcgtg    120
tactaccccg acgagatttt cagaagcgac accctgtacc tcacccagga cctgttcctg    180
cccttctaca gcaacgtgac cggcttccac accatcaacc acaccttcgg caaccccgtg    240
atccctttca aggacggcat ctacttcgcc gccaccgaga agagcaatgt ggtgcggggc    300
tgggtgttcg gcagcaccat gaacaacaag agccagagcg tgatcatcat caacaacagc    360
accaacgtgg tgatccgggc ctgcaatttc gagctgtgcg acaacccttt cttcgccgtg    420
tccaaaccta tgggcaccca gacccacacc atgatcttcg acaacgcctt caactgcacc    480
ttcgagtaca tcagcgacgc cttcagcctg gatgtgagcg agaagagcgg caacttcaag    540
cacctgcggg agttcgtgtt caagaacaag gacggcttcc tgtacgtgta caagggctac    600
cagcccatcg acgtggtgag agacctgccc agcggcttca acaccctgaa gcccatcttc    660
aagctgcccc tgggcatcaa catcaccaac ttccgggcca tcctcaccgc ctttagccct    720
gcccaggata tctggggcac cagcgccgct gcctacttcg tgggctacct gaagcctacc    780
```

accttcatgc tgaagtacga cgagaacggc accatcaccg atgccgtgga ctgcagccag 840
aaccccctgg ccgagctgaa gtgcagcgtg aagagcttcg agatcgacaa gggcatctac 900
cagaccagca acttcagagt ggtgcctagc ggcgatgtgg tgaggttccc caatatcacc 960
aacctgtgcc ccttcggcga ggtgttcaac gccaccaagt tccctagcgt gtacgcctgg 1020
gagcggaaga agatcagcaa ctgcgtggcc gattacagcg tgctgtacaa ctccaccttc 1080
ttcagcacct tcaagtgcta cggcgtgagc gccaccaagc tgaacgacct gtgcttcagc 1140
aacgtgtacg ccgactcatt cgtggtgaag ggcgacgacg tgagacagat cgcccctggc 1200
cagaccggcg tgatcgccga ctacaactac aagcttcccg acgacttcat gggctgcgtg 1260
ctggcctgga acaccagaaa catcgacgcc acctccaccg gcaactacaa ttacaagtac 1320
cgctacctga ggcacggcaa gctgagaccc ttcgagcggg acatctccaa cgtgcccttc 1380
agccccgacg gcaagccctg cacccccccct gccctgaact gctactggcc cctgaacgac 1440
tacggcttct acaccaccac cggcatcggc tatcagccct acagagtggt ggtgctgagc 1500
ttcgagctgc tgaacgcccc tgccaccgtg tgcggcccca agctgagcac cgacctcatc 1560
aagaaccagt gcgtgaactt caacttcaac ggcctcaccg gcaccggcgt gctcaccccc 1620
agcagcaaga gattccagcc cttccagcag ttcggcaggg acgtgagcga tttcaccgac 1680
agcgtgaggg atcctaagac cagcgagatc ctggacatca gcccttgcag cttcggcggc 1740
gtgtccgtga tcacccccgg caccaacgcc agcagcgagg tggccgtgct gtaccaggac 1800
gtgaactgca ccgacgtgag caccgccatc cacgccgacc agctcacccc cgcctggaga 1860
atctacagca ccggcaacaa cgtgttccag acccaggccg gctgcctcat cggcgccgag 1920
cacgtggaca ccagctacga gtgcgacatc cccatcggag ccggcatctg cgccagctac 1980
cacaccgtga gcctgctgag aagcaccagc cagaagagca tcgtggccta caccatgagc 2040
ctgggcgcct ga 2052

<210> SEQ ID NO 51

<400> SEQUENCE: 51

000

<210> SEQ ID NO 52

<400> SEQUENCE: 52

000

<210> SEQ ID NO 53
<211> LENGTH: 231
<212> TYPE: DNA
<213> ORGANISM: Artificial Sequence
<220> FEATURE:
<223> OTHER INFORMATION: Minimal optimization of E protein

<400> SEQUENCE: 53
atgtatagtt ttgtgagtga ggagacgggc accctgattg tcaactcagt gctgctgttc 60
ctggcctttg ttgtcttcct gctggtaact ctggccatcc tgactgccct gagactgtgc 120
gcctactgct gcaacatcgt gaacgtctct ctggtaaagc ccacagttta cgtgtattct 180
agggtgaaga acctgaactc cagcgagggc gttcccgatc tgctggtatg a 231

<210> SEQ ID NO 54
<211> LENGTH: 1542
<212> TYPE: DNA

<213> ORGANISM: Artificial Sequence
<220> FEATURE:
<223> OTHER INFORMATION: Optimized soluble S2 protein with MET

<400> SEQUENCE: 54

```
atggatagtt caattgctta ctctaataac accattgcta tacctactaa cttttcaatt      60

agcattacta cagaagtaat gcctgtttct atggctaaaa cctccgtaga ttgtaatatg     120

tacatctgcg gagattctac tgaatgtgct aatttgcttc tccaatatgg tagcttttgc     180

acacaactaa atcgtgcact ctcaggtatt gctgctgaac aggatcgcaa cacacgtgaa     240

gtgttcgctc aagtcaaaca aatgtacaaa accccaactt tgaaatattt tggtggtttt     300

aatttttcac aaatattacc tgaccctcta aagccaacta agaggtcttt tattgaggac     360

ttgctcttta ataaggtgac actcgctgat gctggcttca tgaagcaata tggcgaatgc     420

ctaggtgata ttaatgctag agatctcatt tgtgcgcaga agttcaatgg acttacagtg     480

ttgccacctc tgctcactga tgatatgatt gctgcctaca ctgctgctct agttagtggt     540

actgccactg ctggatggac atttggtgct ggcgctgctc ttcaaatacc ttttgctatg     600

caaatggcat ataggttcaa tggcattgga gttacccaaa atgttctcta tgagaaccaa     660

aaacaaatcg ccaaccaatt taacaaggcg attagtcaaa ttcaagaatc acttacaaca     720

acatcaactg cattgggcaa gctgcaagac gttgttaacc agaatgctca agcattaaac     780

acacttgtta aacaacttag ctctaatttt ggtgcaattt caagtgtgct aaatgatatc     840

ctttcgcgac ttgataaagt cgaggcggag gtacaaattg acaggttaat tacaggcaga     900

cttcaaagcc ttcaaaccta tgtaacacaa caactaatca gggctgctga aatcagggct     960

tctgctaatc ttgctgctac taaaatgtct gagtgtgttc ttggacaatc aaaaagagtt    1020

gacttttgtg gaaagggcta ccaccttatg tccttcccac aagcagcccc gcatggtgtt    1080

gtcttcctac atgtcacgta tgtgccatcc caggagagga acttcaccac agcgccagca    1140

atttgtcatg aaggcaaagc atacttccct cgtgaaggtg tttttgtgtt taatggcact    1200

tcttggttta ttacacagag gaacttcttt tctccacaaa taattactac agacaataca    1260

tttgtctcag gaaattgtga tgtcgttatt ggcatcatta acaacacagt ttatgatcct    1320

ctgcaacctg agctcgactc attcaaagaa gagctggaca agtacttcaa aaatcataca    1380

tcaccagatg ttgatcttgg cgacatttca ggcattaacg cttctgtcgt caacattcaa    1440

aaagaaattg accgcctcaa tgaggtcgct aaaaatttaa atgaatcact cattgacctt    1500

caagaattgg gaaaatatga gcaatatatt aaatggcctt gg                       1542
```

<210> SEQ ID NO 55
<211> LENGTH: 9
<212> TYPE: PRT
<213> ORGANISM: Artificial Sequence
<220> FEATURE:
<223> OTHER INFORMATION: H-2Kd binding pepride

<400> SEQUENCE: 55

```
Thr Tyr Gln Arg Thr Arg Ala Leu Val
1               5
```

<210> SEQ ID NO 56
<211> LENGTH: 514
<212> TYPE: PRT
<213> ORGANISM: Artificial Sequence
<220> FEATURE:
<223> OTHER INFORMATION: Optimized S2 protein with MET

<400> SEQUENCE: 56

```
Met Asp Ser Ser Ile Ala Tyr Ser Asn Asn Thr Ile Ala Ile Pro Thr
1               5                   10                  15

Asn Phe Ser Ile Ser Ile Thr Thr Glu Val Met Pro Val Ser Met Ala
            20                  25                  30

Lys Thr Ser Val Asp Cys Asn Met Tyr Ile Cys Gly Asp Ser Thr Glu
        35                  40                  45

Cys Ala Asn Leu Leu Leu Gln Tyr Gly Ser Phe Cys Thr Gln Leu Asn
    50                  55                  60

Arg Ala Leu Ser Gly Ile Ala Ala Glu Gln Asp Arg Asn Thr Arg Glu
65                  70                  75                  80

Val Phe Ala Gln Val Lys Gln Met Tyr Lys Thr Pro Thr Leu Lys Tyr
                85                  90                  95

Phe Gly Gly Phe Asn Phe Ser Gln Ile Leu Pro Asp Pro Leu Lys Pro
            100                 105                 110

Thr Lys Arg Ser Phe Ile Glu Asp Leu Leu Phe Asn Lys Val Thr Leu
        115                 120                 125

Ala Asp Ala Gly Phe Met Lys Gln Tyr Gly Glu Cys Leu Gly Asp Ile
    130                 135                 140

Asn Ala Arg Asp Leu Ile Cys Ala Gln Lys Phe Asn Gly Leu Thr Val
145                 150                 155                 160

Leu Pro Pro Leu Leu Thr Asp Asp Met Ile Ala Ala Tyr Thr Ala Ala
                165                 170                 175

Leu Val Ser Gly Thr Ala Thr Ala Gly Trp Thr Phe Gly Ala Gly Ala
            180                 185                 190

Ala Leu Gln Ile Pro Phe Ala Met Gln Met Ala Tyr Arg Phe Asn Gly
        195                 200                 205

Ile Gly Val Thr Gln Asn Val Leu Tyr Glu Asn Gln Lys Gln Ile Ala
    210                 215                 220

Asn Gln Phe Asn Lys Ala Ile Ser Gln Ile Gln Glu Ser Leu Thr Thr
225                 230                 235                 240

Thr Ser Thr Ala Leu Gly Lys Leu Gln Asp Val Val Asn Gln Asn Ala
                245                 250                 255

Gln Ala Leu Asn Thr Leu Val Lys Gln Leu Ser Ser Asn Phe Gly Ala
            260                 265                 270

Ile Ser Ser Val Leu Asn Asp Ile Leu Ser Arg Leu Asp Lys Val Glu
        275                 280                 285

Ala Glu Val Gln Ile Asp Arg Leu Ile Thr Gly Arg Leu Gln Ser Leu
    290                 295                 300

Gln Thr Tyr Val Thr Gln Gln Leu Ile Arg Ala Ala Glu Ile Arg Ala
305                 310                 315                 320

Ser Ala Asn Leu Ala Ala Thr Lys Met Ser Glu Cys Val Leu Gly Gln
                325                 330                 335

Ser Lys Arg Val Asp Phe Cys Gly Lys Gly Tyr His Leu Met Ser Phe
            340                 345                 350

Pro Gln Ala Ala Pro His Gly Val Val Phe Leu His Val Thr Tyr Val
        355                 360                 365

Pro Ser Gln Glu Arg Asn Phe Thr Thr Ala Pro Ala Ile Cys His Glu
    370                 375                 380

Gly Lys Ala Tyr Phe Pro Arg Glu Gly Val Phe Val Phe Asn Gly Thr
385                 390                 395                 400

Ser Trp Phe Ile Thr Gln Arg Asn Phe Phe Ser Pro Gln Ile Ile Thr
                405                 410                 415

Thr Asp Asn Thr Phe Val Ser Gly Asn Cys Asp Val Val Ile Gly Ile
```

```
            420                 425                 430

Ile Asn Asn Thr Val Tyr Asp Pro Leu Gln Pro Glu Leu Asp Ser Phe
        435                 440                 445

Lys Glu Glu Leu Asp Lys Tyr Phe Lys Asn His Thr Ser Pro Asp Val
    450                 455                 460

Asp Leu Gly Asp Ile Ser Gly Ile Asn Ala Ser Val Val Asn Ile Gln
465                 470                 475                 480

Lys Glu Ile Asp Arg Leu Asn Glu Val Ala Lys Asn Leu Asn Glu Ser
                485                 490                 495

Leu Ile Asp Leu Gln Glu Leu Gly Lys Tyr Glu Gln Tyr Ile Lys Trp
            500                 505                 510

Pro Trp


<210> SEQ ID NO 57
<211> LENGTH: 1242
<212> TYPE: DNA
<213> ORGANISM: Artificial Sequence
<220> FEATURE:
<223> OTHER INFORMATION: Fragment of S protein

<400> SEQUENCE: 57

gtcgacatgg ttatctttct gctgttcctc accctcacca gcggcagcga tctggatagg     60

tgcaccacct tcgacgacgt gcaggccccc aactacaccc agcacaccag cagcatgagg    120

ggcgtgtact accccgacga gattttcaga agcgacaccc tgtacctcac ccaggacctg    180

ttcctgccct tctacagcaa cgtgaccggc ttccacacca tcaaccacac cttcggcaac    240

cccgtgatcc ctttcaagga cggcatctac ttcgccgcca ccgagaagag caatgtggtg    300

cggggctggg tgttcggcag caccatgaac aacaagagcc agagcgtgat catcatcaac    360

aacagcacca acgtggtgat ccgggcctgc aatttcgagc tgtgcgacaa ccctttcttc    420

gccgtgtcca aacctatggg cacccagacc cacaccatga tcttcgacaa cgccttcaac    480

tgcaccttcg agtacatcag cgacgccttc agcctggatg tgagcgagaa gagcggcaac    540

ttcaagcacc tgcgggagtt cgtgttcaag aacaaggacg gcttcctgta cgtgtacaag    600

ggctaccagc ccatcgacgt ggtgagagac ctgcccagcg gcttcaacac cctgaagccc    660

atcttcaagc tgcccctggg catcaacatc accaacttcc gggccatcct caccgccttt    720

agccctgccc aggatatctg ggcaccagc gccgctgcct acttcgtggg ctacctgaag     780

cctaccacct tcatgctgaa gtacgacgag aacggcacca tcaccgatgc cgtggactgc    840

agccagaacc ccctggccga gctgaagtgc agcgtgaaga gcttcgagat cgacaagggc    900

atctaccaga ccagcaactt cagagtggtg cctagcggcg atgtggtgag gttccccaat    960

atcaccaacc tgtgcccctt cggcgaggtg ttcaacgcca ccaagttccc tagcgtgtac   1020

gcctgggagc ggaagaagat cagcaactgc gtggccgatt acagcgtgct gtacaactcc   1080

accttcttca gcaccttcaa gtgctacggc gtgagcgcca ccaagctgaa cgacctgtgc   1140

ttcagcaacg tgtacgccga ctcattcgtg gtgaagggcg acgacgtgag acagatcgcc   1200

cctggccaga ccggcgtgat cgccgactac aactacaagc tt                      1242


<210> SEQ ID NO 58
<211> LENGTH: 412
<212> TYPE: PRT
<213> ORGANISM: Artificial Sequence
<220> FEATURE:
<223> OTHER INFORMATION: Fragment of S protein

<400> SEQUENCE: 58
```

```
Met Val Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu
                405                 410
```

<210> SEQ ID NO 59
<211> LENGTH: 1432
<212> TYPE: DNA
<213> ORGANISM: Artificial Sequence
<220> FEATURE:
<223> OTHER INFORMATION: Fragment of S protein

<400> SEQUENCE: 59

```
aagcttcccg acgacttcat gggctgcgtg ctggcctgga acaccagaaa catcgacgcc     60

acctccaccg gcaactacaa ttacaagtac cgctacctga ggcacggcaa gctgagaccc    120

ttcgagcggg acatctccaa cgtgcccttc agccccgacg gcaagccctg cacccccccct   180

gccctgaact gctactggcc cctgaacgac tacggcttct acaccaccac cggcatcggc    240

tatcagccct acagagtggt ggtgctgagc ttcgagctgc tgaacgcccc tgccaccgtg    300

tgcggcccca agctgagcac cgacctcatc aagaaccagt gcgtgaactt caacttcaac    360

ggcctcaccg gcaccggcgt gctcaccccc agcagcaaga gattccagcc cttccagcag    420

ttcggcaggg acgtgagcga tttcaccgac agcgtgaggg atcctaagac cagcgagatc    480

ctggacatca gcccttgcag cttcggcggc gtgtccgtga tcacccccgg caccaacgcc    540

agcagcgagg tggccgtgct gtaccaggac gtgaactgca ccgacgtgag caccgccatc    600

cacgccgacc agctcacccc cgcctggaga atctacagca ccggcaacaa cgtgttccag    660

acccaggccg gctgcctcat cggcgccgag cacgtggaca ccagctacga gtgcgacatc    720

cccatcggag ccggcatctg cgccagctac cacaccgtga gcctgctgag aagcaccagc    780

cagaagagca tcgtggccta caccatgagc ctgggcgccg acagcagcat cgcctacagc    840

aacaacacca tcgccatccc caccaacttc agcatctcca tcaccaccga ggtgatgccc    900

gtgagcatgg ccaagaccag cgtggattgc aacatgtaca tctgcggcga cagcaccgag    960

tgcgccaacc tgctgctgca gtacggcagc ttctgcaccc agctgaacag agccctgagc   1020

ggcattgccg ccgagcagga cagaaacacc agggaggtgt tcgcccaggt gaagcagatg   1080

tataagaccc ccaccctgaa gtacttcggc gggttcaact tcagccagat cctgcccgat   1140

cctctgaagc ccaccaagcg gagcttcatc gaggacctgc tgttcaacaa ggtgaccctg   1200

gccgacgccg gctttatgaa gcagtacggc gagtgcctgg gcgatatcaa cgccagggac   1260

ctcatctgcg cccagaagtt caacggcttg accgtgctgc cccctctgct caccgatgat   1320

atgatcgccg cctatacagc cgccctggtg tcaggcaccg ccaccgccgg ctggaccttt   1380

ggcgccggag ccgccctgca gatccccttc gccatgcaga tggcctaccg gt           1432
```

<210> SEQ ID NO 60
<211> LENGTH: 1118
<212> TYPE: DNA
<213> ORGANISM: Artificial Sequence
<220> FEATURE:
<223> OTHER INFORMATION: Fragment of S protein

<400> SEQUENCE: 60

```
accggttcaa tggcatcggc gtgacccaga acgtgctgta cgagaaccag aagcagatcg     60

ccaaccagtt caataaggcc atctcccaga tccaggagag cctcaccacc acaagcaccg    120

ccctgggcaa gctgcaggac gtggtgaacc agaacgccca ggccctgaat accctggtga    180

agcagctgag cagcaacttc ggcgccatca gcagcgtgct gaacgacatc ctgagcaggc    240

tggataaggt ggaggccgag gtgcagatcg acagactcat caccggcaga ctgcagagcc    300

tgcagaccta cgtgacccag cagctcatca gagccgccga gatcagagcc agcgccaatc    360

tggccgccac caagatgagc gagtgcgtgc tgggccagag caagagagtg gacttctgcg    420
```

gcaagggcta tcacctcatg agcttccctc aggccgctcc ccacggcgtg gtgttcctgc 480
acgtgaccta cgtgcctagc caggagagga atttcaccac cgccccagcc atctgccacg 540
agggcaaggc ctacttcccc agagagggcg tgttcgtgtt taacggcacc agctggttca 600
tcacccagcg gaacttcttc agcccccaga tcatcaccac agacaacacc ttcgtgtccg 660
gcaattgcga cgtggtcatc ggcatcatca ataacaccgt gtacgacccc ctgcagcccg 720
agctggatag cttcaaggag gagctggaca agtacttcaa gaaccacacc tcccccgacg 780
tggacctggg cgacatcagc ggcatcaatg ccagcgtggt gaacatccag aaggagatcg 840
accggctgaa cgaggtggcc aagaacctga acgagagcct catcgacctg caggagctgg 900
gaaagtacga gcagtacatc aagtggccct ggtacgtgtg gctgggcttc atcgccggcc 960
tcatcgccat cgtgatggtg accatcctgc tgtgctgcat gaccagctgc tgctcctgcc 1020
tgaagggcgc ctgcagctgt ggcagctgct gcaagttcga cgaggacgac tcagagcccg 1080
tgctgaaggg cgtgaagctg cactacacct gaagatct 1118

<210> SEQ ID NO 61
<211> LENGTH: 3780
<212> TYPE: DNA
<213> ORGANISM: Artificial Sequence
<220> FEATURE:
<223> OTHER INFORMATION: Mutated S protein

<400> SEQUENCE: 61
gtcgacatgg ttatctttct gctgttcctc accctcacca gcggcagcga tctggatagg 60
tgcaccacct tcgacgacgt gcaggccccc aactacaccc agcacaccag cagcatgagg 120
ggcgtgtact accccgacga gattttcaga agcgacaccc tgtacctcac ccaggacctg 180
ttcctgccct tctacagcaa cgtgaccggc ttccacacca tcaaccacac cttcggcaac 240
cccgtgatcc ctttcaagga cggcatctac ttcgccgcca ccgagaagag caatgtggtg 300
cggggctggg tgttcggcag caccatgaac aacaagagcc agagcgtgat catcatcaac 360
aacagcacca acgtggtgat ccgggcctgc aatttcgagc tgtgcgacaa ccctttcttc 420
gccgtgtcca aacctatggg cacccagacc cacaccatga tcttcgacaa cgccttcaac 480
tgcaccttcg agtacatcag cgacgccttc agcctggatg tgagcgagaa gagcggcaac 540
ttcaagcacc tgcgggagtt cgtgttcaag aacaaggacg gcttcctgta cgtgtacaag 600
ggctaccagc ccatcgacgt ggtgagagac ctgcccagcg gcttcaacac cctgaagccc 660
atcttcaagc tgcccctggg catcaacatc accaacttcc gggccatcct caccgccttt 720
agccctgccc aggatatctg ggcaccagc gccgctgcct acttcgtggg ctacctgaag 780
cctaccacct tcatgctgaa gtacgacgag aacggcacca tcaccgatgc cgtggactgc 840
agccagaacc ccctggccga gctgaagtgc agcgtgaaga gcttcgagat cgacaagggc 900
atctaccaga ccagcaactt cagagtggtg cctagcggcg atgtggtgag gttccccaat 960
atcaccaacc tgtgcccctt cggcgaggtg ttcaacgcca ccaagttccc tagcgtgtac 1020
gcctgggagc ggaagaagat cagcaactgc gtggccgatt acagcgtgct gtacaactcc 1080
accttcttca gcaccttcaa gtgctacggc gtgagcgcca ccaagctgaa cgacctgtgc 1140
ttcagcaacg tgtacgccga ctcattcgtg gtgaagggcg acgacgtgag acagatcgcc 1200
cctggccaga ccggcgtgat cgccgactac aactacaagc ttcccgacga cttcatgggc 1260
tgcgtgctgg cctggaacac cagaaacatc gacgccacct ccaccggcaa ctacaattac 1320
aagtaccgct acctgaggca cggcaagctg agacccttcg agcgggacat ctccaacgtg 1380

-continued cccttcagcc ccgacggcaa gccctgcacc ccccctgccc tgaactgcta ctggcccctg 1440
aacgactacg gcttctacac caccaccggc atcggctatc agccctacag agtggtggtg 1500
ctgagcttcg agctgctgaa cgcccctgcc accgtgtgcg gccccaagct gagcaccgac 1560
ctcatcaaga accagtgcgt gaacttcaac ttcaacggcc tcaccggcac cggcgtgctc 1620
acccccagca gcaagagatt ccagcccttc cagcagttcg gcagggacgt gagcgatttc 1680
accgacagcg tgagggatcc taagaccagc gagatcctgg acatcagccc ttgcagcttc 1740
ggcggcgtgt ccgtgatcac ccccggcacc aacgccagca gcgaggtggc cgtgctgtac 1800
caggacgtga actgcaccga cgtgagcacc gccatccacg ccgaccagct cacccccgcc 1860
tggagaatct acagcaccgg caacaacgtg ttccagaccc aggccggctg cctcatcggc 1920
gccgagcacg tggacaccag ctacgagtgc gacatcccca tcggagccgg catctgcgcc 1980
agctaccaca ccgtgagcct gctgagaagc accagccaga agagcatcgt ggcctacacc 2040
atgagcctgg gcgccgacag cagcatcgcc tacagcaaca acaccatcgc catcccccacc 2100 aacttcagca tctccatcac caccgaggtg atgcccgtga gcatggccaa gaccagcgtg 2160
gattgcaaca tgtacatctg cggcgacagc accgagtgcg ccaacctgct gctgcagtac 2220
ggcagcttct gcacccagct gaacagagcc ctgagcggca ttgccgccga gcaggacaga 2280
aacaccaggg aggtgttcgc ccaggtgaag cagatgtata agacccccac cctgaagtac 2340
ttcggcgggt tcaacttcag ccagatcctg cccgatcctc tgaagcccac caagcggagc 2400
ttcatcgagg acctgctgtt caacaaggtg accctggccg acgccggctt tatgaagcag 2460
tacggcgagt gcctgggcga tatcaacgcc agggacctca tctgcgccca gaagttcaac 2520
ggcttgaccg tgctgccccc tctgctcacc gatgatatga tcgccgccta tacagccgcc 2580
ctggtgtcag gcaccgccac cgccggctgg acctttggcg ccggagccgc cctgcagatc 2640
cccttcgcca tgcagatggc ctaccggttc aatggcatcg gcgtgaccca gaacgtgctg 2700
tacgagaacc agaagcagat cgccaaccag ttcaataagg ccatctccca gatccaggag 2760
agcctcacca ccacaagcac cgccctgggc aagctgcagg acgtggtgaa ccagaacgcc 2820
caggccctga ataccctggt gaagcagctg agcagcaact tcggcgccat cagcagcgtg 2880
ctgaacgaca tcctgagcag gctggataag gtggaggccg aggtgcagat cgacagactc 2940
atcaccggca gactgcagag cctgcagacc tacgtgaccc agcagctcat cagagccgcc 3000
gagatcagag ccagcgccaa tctggccgcc accaagatga gcgagtgcgt gctgggccag 3060
agcaagagag tggacttctg cggcaagggc tatcacctca tgagcttccc tcaggccgct 3120
ccccacggcg tggtgttcct gcacgtgacc tacgtgccta gccaggagag gaatttcacc 3180
accgccccag ccatctgcca cgagggcaag gcctacttcc ccagagaggg cgtgttcgtg 3240
tttaacggca ccagctggtt catcacccag cggaacttct tcagccccca gatcatcacc 3300
acagacaaca ccttcgtgtc cggcaattgc gacgtggtca tcggcatcat caataacacc 3360
gtgtacgacc ccctgcagcc cgagctggat agcttcaagg aggagctgga caagtacttc 3420
aagaaccaca cctcccccga cgtggacctg ggcgacatca gcggcatcaa tgccagcgtg 3480
gtgaacatcc agaaggagat cgaccggctg aacgaggtgg ccaagaacct gaacgagagc 3540
ctcatcgacc tgcaggagct gggaaagtac gagcagtaca tcaagtggcc ctggtacgtg 3600
tggctgggct tcatcgccgg cctcatcgcc atcgtgatgg tgaccatcct gctgtgctgc 3660
atgaccagct gctgctcctg cctgaagggc gcctgcagct gtggcagctg ctgcaagttc 3720
gacgaggacg actcagagcc cgtgctgaag ggcgtgaagc tgcactacac ctgaagatct 3780

<210> SEQ ID NO 62
<211> LENGTH: 1255
<212> TYPE: PRT
<213> ORGANISM: Artificial Sequence
<220> FEATURE:
<223> OTHER INFORMATION: Mutated S protein

<400> SEQUENCE: 62

Met Val Ile Phe Leu Leu Phe Leu Thr Leu Thr Ser Gly Ser Asp Leu
1 5 10 15

Asp Arg Cys Thr Thr Phe Asp Asp Val Gln Ala Pro Asn Tyr Thr Gln
20 25 30

His Thr Ser Ser Met Arg Gly Val Tyr Tyr Pro Asp Glu Ile Phe Arg
35 40 45

Ser Asp Thr Leu Tyr Leu Thr Gln Asp Leu Phe Leu Pro Phe Tyr Ser
50 55 60

Asn Val Thr Gly Phe His Thr Ile Asn His Thr Phe Gly Asn Pro Val
65 70 75 80

Ile Pro Phe Lys Asp Gly Ile Tyr Phe Ala Ala Thr Glu Lys Ser Asn
85 90 95

Val Val Arg Gly Trp Val Phe Gly Ser Thr Met Asn Asn Lys Ser Gln
100 105 110

Ser Val Ile Ile Ile Asn Asn Ser Thr Asn Val Val Ile Arg Ala Cys
115 120 125

Asn Phe Glu Leu Cys Asp Asn Pro Phe Phe Ala Val Ser Lys Pro Met
130 135 140

Gly Thr Gln Thr His Thr Met Ile Phe Asp Asn Ala Phe Asn Cys Thr
145 150 155 160

Phe Glu Tyr Ile Ser Asp Ala Phe Ser Leu Asp Val Ser Glu Lys Ser
165 170 175

Gly Asn Phe Lys His Leu Arg Glu Phe Val Phe Lys Asn Lys Asp Gly
180 185 190

Phe Leu Tyr Val Tyr Lys Gly Tyr Gln Pro Ile Asp Val Val Arg Asp
195 200 205

Leu Pro Ser Gly Phe Asn Thr Leu Lys Pro Ile Phe Lys Leu Pro Leu
210 215 220

Gly Ile Asn Ile Thr Asn Phe Arg Ala Ile Leu Thr Ala Phe Ser Pro
225 230 235 240

Ala Gln Asp Ile Trp Gly Thr Ser Ala Ala Ala Tyr Phe Val Gly Tyr
245 250 255

Leu Lys Pro Thr Thr Phe Met Leu Lys Tyr Asp Glu Asn Gly Thr Ile
260 265 270

Thr Asp Ala Val Asp Cys Ser Gln Asn Pro Leu Ala Glu Leu Lys Cys
275 280 285

Ser Val Lys Ser Phe Glu Ile Asp Lys Gly Ile Tyr Gln Thr Ser Asn
290 295 300

Phe Arg Val Val Pro Ser Gly Asp Val Val Arg Phe Pro Asn Ile Thr
305 310 315 320

Asn Leu Cys Pro Phe Gly Glu Val Phe Asn Ala Thr Lys Phe Pro Ser
325 330 335

Val Tyr Ala Trp Glu Arg Lys Lys Ile Ser Asn Cys Val Ala Asp Tyr
340 345 350

Ser Val Leu Tyr Asn Ser Thr Phe Phe Ser Thr Phe Lys Cys Tyr Gly
355 360 365

-continued

```
Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800
```

```
Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080

Trp Phe  Ile Thr Gln Arg Asn  Phe Phe Ser Pro Gln  Ile Ile Thr
    1085                1090                1095

Thr Asp  Asn Thr Phe Val Ser  Gly Asn Cys Asp Val  Val Ile Gly
    1100                1105                1110

Ile Ile  Asn Asn Thr Val Tyr  Asp Pro Leu Gln Pro  Glu Leu Asp
    1115                1120                1125

Ser Phe  Lys Glu Glu Leu Asp  Lys Tyr Phe Lys Asn  His Thr Ser
    1130                1135                1140

Pro Asp  Val Asp Leu Gly Asp  Ile Ser Gly Ile Asn  Ala Ser Val
    1145                1150                1155

Val Asn  Ile Gln Lys Glu Ile  Asp Arg Leu Asn Glu  Val Ala Lys
    1160                1165                1170

Asn Leu  Asn Glu Ser Leu Ile  Asp Leu Gln Glu Leu  Gly Lys Tyr
    1175                1180                1185

Glu Gln  Tyr Ile Lys Trp Pro  Trp Tyr Val Trp Leu  Gly Phe Ile
    1190                1195                1200

Ala Gly  Leu Ile Ala Ile Val  Met Val Thr Ile Leu  Leu Cys Cys
```

```
    1205                1210                1215

Met Thr  Ser Cys Cys Ser Cys  Leu Lys Gly Ala Cys  Ser Cys Gly
    1220                1225                1230

Ser Cys  Cys Lys Phe Asp Glu  Asp Asp Ser Glu Pro  Val Leu Lys
    1235                1240                1245

Gly Val  Lys Leu His Tyr Thr
    1250                1255
```

```
<210> SEQ ID NO 63
<211> LENGTH: 1281
<212> TYPE: DNA
<213> ORGANISM: Artificial Sequence
<220> FEATURE:
<223> OTHER INFORMATION: Mutated N protein

<400> SEQUENCE: 63

gtcgacatga gcgacaacgg cccccagagc aaccagagaa gcgcccccag aatcaccttt     60

ggcggcccta ccgacagcac cgacaacaac cagaacggcg gcagaaacgg cgccagaccc    120

aagcagagga gaccccaggg cctgcccaac aacaccgcca gctggttcac cgccctcacc    180

cagcacggca aggaggagct gagattcccc agaggccagg gcgtgcccat caataccaac    240

agcggcccag acgatcagat cggctactac cggagggcca ccagaagagt gagaggcggc    300

gacggcaaga tgaaggagct gagcccccgg tggtacttct actacctggg caccggccct    360

gaggccagcc tgccctacgg cgccaacaag gagggcatcg tgtgggtggc caccgagggc    420

gccctgaata cccccaagga ccacatcggc accaggaacc ccaacaacaa tgccgccacc    480

gtgctgcagc tgccccaggg caccaccctg cccaagggct tctacgccga gggcagcaga    540

ggcggcagcc aggccagcag cagaagcagc agcaggagca ggggcaacag cagaaatagc    600

acccccggca gcagcagagg aaattcaccc gccagaatgg ccagcggcgg aggcgagacc    660

gccctggccc tgctgctcct ggacaggctg aatcagctgg agagcaaggt gagcggcaag    720

ggccagcaac agcagggaca gaccgtgacc aagaagtctg ccgccgaggc cagcaagaag    780

cccaggcaga agagaaccgc caccaagcag tacaatgtga cccaggcctt cggcagaaga    840

ggcccccgagc agacccaggg caatttcggc gaccaggacc tcatcagaca gggcaccgac    900

tacaagcact ggcctcagat cgcccagttc gcccccagcg ccagcgcctt cttcggcatg    960

agccggatcg gcatggaggt gacccccagc ggcacctggc tcacctacca cggcgccatc   1020

aagctggacg acaaggaccc ccagttcaag gacaacgtga tcctgctgaa caagcacatc   1080

gacgcctaca agaccttccc acccaccgag cccaagaagg acaagaagaa gaaaaccgac   1140

gaggcccagc ccctgcccca gagacagaag aagcagccca ccgtgaccct gctgcctgcc   1200

gccgacatgg acgacttcag ccgccagctg cagaatagca tgagcggcgc ctctgccgat   1260

tcaacccagg cctgaagatc t                                             1281
```

```
<210> SEQ ID NO 64
<211> LENGTH: 1542
<212> TYPE: DNA
<213> ORGANISM: Artificial Sequence
<220> FEATURE:
<223> OTHER INFORMATION: Uniform optimization of S2 protein with MET

<400> SEQUENCE: 64

atggacagca gcatcgccta cagcaacaac accatcgcca tccccaccaa cttcagcatc     60

agcatcacca ccgaggtgat gcccgtgagc atggccaaga ccagcgtgga ctgcaacatg    120

tacatctgcg gcgacagcac cgagtgcgcc aacctgctgc tgcagtacgg cagcttctgc    180
```

acccagctga accgggccct gagcggcatc gccgccgagc aggaccggaa cacccgggag 240
gtgttcgccc aggtgaagca gatgtacaag acccccaccc tgaagtactt cggcggcttc 300
aacttcagcc agatcctgcc cgacccccctg aagcccacca agcggagctt catcgaggac 360
ctgctgttca acaaggtgac cctggccgac gccggcttca tgaagcagta cggcgagtgc 420
ctgggcgaca tcaacgcccg ggacctgatc tgcgcccaga agttcaacgg cctgaccgtg 480
ctgccccccc tgctgaccga cgacatgatc gccgcctaca ccgccgccct ggtgagcggc 540
accgccaccg ccggctggac cttcggcgcc ggcgccgccc tgcagatccc cttcgccatg 600
cagatggcct accggttcaa cggcatcggc gtgacccaga acgtgctgta cgagaaccag 660
aagcagatcg ccaaccagtt caacaaggcc atcagccaga tccaggagag cctgaccacc 720
accagcaccg ccctgggcaa gctgcaggac gtggtgaacc agaacgccca ggccctgaac 780
accctggtga agcagctgag cagcaacttc ggcgccatca gcagcgtgct gaacgacatc 840
ctgagccggc tggacaaggt ggaggccgag gtgcagatcg accggctgat caccggccgg 900
ctgcagagcc tgcagaccta cgtgacccag cagctgatcc gggccgccga gatccgggcc 960
agcgccaacc tggccgccac caagatgagc gagtgcgtgc tgggccagag caagcgggtg 1020
gacttctgcg gcaagggcta ccacctgatg agcttccccc aggccgcccc ccacggcgtg 1080
gtgttcctgc acgtgaccta cgtgcccagc caggagcgga acttcaccac cgcccccgcc 1140
atctgccacg agggcaaggc ctacttcccc cgggagggcg tgttcgtgtt caacggcacc 1200
agctggttca tcacccagcg gaacttcttc agcccccaga tcatcaccac cgacaacacc 1260
ttcgtgagcg gcaactgcga cgtggtgatc ggcatcatca acaacaccgt gtacgacccc 1320
ctgcagcccg agctggacag cttcaaggag gagctggaca agtacttcaa gaaccacacc 1380
agccccgacg tggacctggg cgacatcagc ggcatcaacg ccagcgtggt gaacatccag 1440
aaggagatcg accggctgaa cgaggtggcc aagaacctga acgagagcct gatcgacctg 1500
caggagctgg gcaagtacga gcagtacatc aagtggccct gg 1542

<210> SEQ ID NO 65
<211> LENGTH: 1542
<212> TYPE: DNA
<213> ORGANISM: Artificial Sequence
<220> FEATURE:
<223> OTHER INFORMATION: Fully optimized S2 protein with MET

<400> SEQUENCE: 65
atggacagtt caatcgccta ttcgaacaac actatagcaa tcccaacaaa tttttcaatt 60
tctataacaa cagaggtgat gccagtgtcc atggcaaaga ctagcgtaga ctgcaatatg 120
tacatctgcg gagattctac agaatgtgca aacttgctgc tacagtatgg atcgttctgt 180
acccagctca accgggcgct gagcggcatt gctgccgaac aggatcgcaa tacgagagag 240
gtgtttgctc aagtgaaaca aatgtataag accccaacat tgaaatactt cggtggattc 300
aatttcagtc agattctgcc agacccactc aaacccacca agaggagctt tattgaagat 360
cttctgttca acaaagttac cttggccgac gctgggttta tgaagcaata cggtgagtgc 420
ctgggcgaca ttaacgcacg agacctgatc tgcgcccaga agtttaacgg gctcacggtt 480
ttaccgccac tgctgactga tgatatgatt gccgcttaca ctgcggccct tgtgagtggt 540
accgcaactg ctggctggac gtttggcgct ggggcggcct tacagatccc ttttgccatg 600
cagatggcct acaggttcaa tggaattggt gtcactcaga atgtcctgta cgagaaccag 660
aaacagatcg ccaaccagtt caataaagct atttcacaga ttcaggaatc acttaccaca 720
acttccacgg cactcggtaa actgcaggac gtggtgaatc agaacgctca ggcactaaat 780
acactcgtca agcaactgag ttccaatttc ggggccatat ctagcgtatt gaacgacatc 840
ctcagtcggc tcgacaaagt ggaggccgaa gtccaaatag accgtcttat cacaggcaga 900
ctacagtcat tgcagaccta cgttacccag cagttgatcc gcgccgctga gatacgagcc 960
tccgccaatc tggccgctac caaaatgtct gagtgtgtgc tcggacaaag taagcgggtg 1020
gatttttgcg gcaagggcta tcacctcatg tccttccctc aagcagcacc ccacggagtc 1080
gtttttctgc atgtgacata cgtgcctagc caggagagaa actttaccac tgcgcctgcc 1140
atttgtcatg aaggcaaagc ttattttccc cgcgaggggg tgttcgtttt caacggaact 1200
agctggttta tcacacaaag gaatttcttc tccccccaga tcatcaccac cgacaacacc 1260
tttgtctctg gaaactgtga cgtcgttata ggcatcatca ataatacagt atacgatccc 1320
ctgcagcccg aacttgactc tttcaaggag gaactagata agtacttcaa gaatcacacc 1380
agcccggatg tagatttagg ggatattagc gggattaacg catccgtggt caacatccaa 1440
aaagagattg acagactgaa cgaagtggcg aagaacctga atgagtccct gatcgatctt 1500
caggagctgg gcaagtatga acagtatatc aagtggcctt gg 1542

<210> SEQ ID NO 66
<211> LENGTH: 1542
<212> TYPE: DNA
<213> ORGANISM: Artificial Sequence
<220> FEATURE:
<223> OTHER INFORMATION: Minimal optimization of S2 protein with MET

<400> SEQUENCE: 66
atggatagca gcatagccta ctcaaacaac acgatcgcca tccccacaaa cttttccatt 60
tccataacta ccgaggtgat gcccgtgagc atggccaaga catcggtaga ttgcaacatg 120
tacatctgtg gcgattctac agagtgtgcc aacctgctgc tgcagtacgg ctctttctgc 180
acgcagctga acagggccct gtctggcatc gccgccgagc aggatcggaa cacacgggag 240
gttttcgccc aggtaaagca gatgtataag acgcccactc tgaagtactt cggcggcttc 300
aacttctctc agatactgcc cgaccccctg aagcccacta agaggtcttt tatcgaggat 360
ctgctgttca acaaggttac cctggccgat gccggcttta tgaagcagta tggcgagtgc 420
ctgggcgaca tcaacgccag agatctgata tgcgcccaga agttcaacgg cctgactgtg 480
ctgccccccc tgctgactga cgacatgatc gccgcctata ccgccgccct ggtgagtggc 540
acagccactg ccggctggac attcggcgcc ggcgccgccc tgcagatccc cttcgccatg 600
cagatggcct acagatttaa cggcattggc gtcactcaga acgtcctgta tgagaaccag 660
aagcagatcg ccaaccagtt taacaaggcc ataagccaga tccaggagtc actgacaacg 720
acaagtaccg ccctgggcaa gctgcaggat gtagtgaacc agaacgccca ggccctgaac 780
actctggtta agcagctgtc tagcaacttc ggcgccatca gtagtgttct gaacgatatt 840
ctgtctaggc tggacaaggt cgaggccgag gtgcagattg atcgcctgat taccggcaga 900
ctgcagagtc tgcagactta tgtaactcag cagctgatca gagccgccga gattcgagcc 960
tccgccaacc tggccgccac aaagatgtct gagtgcgtcc tgggccagag taagagggtt 1020
gacttctgcg gcaagggcta tcatctgatg tcttttcccc aggccgcccc ccacggcgtc 1080
gtgttcctgc acgtaactta cgtgcccagt caggagagaa actttaccac tgccccgcc 1140 atctgccacg agggcaaggc ctacttcccc agagagggcg tgtttgtgtt caacggcaca 1200
tcttggttca tcacccagag gaactttttc agcccccaga tcataacaac tgacaacact 1260
ttcgtttcgg gcaactgcga cgtagtgatc ggcataataa acaacaccgt gtacgatccc 1320
ctgcagcccg agctggacag ctttaaggag gagctggaca agtactttaa gaaccatacc 1380
tcacccgatg tggacctggg cgacatttct ggcataaacg cctccgtcgt caacatccag 1440
aaggagatag atagactgaa cgaggttgcc aagaacctga acgagtccct gatcgatctg 1500
caggagctgg gcaagtacga gcagtatata aagtggccct gg 1542

<210> SEQ ID NO 67
<211> LENGTH: 3588
<212> TYPE: DNA
<213> ORGANISM: Artificial Sequence
<220> FEATURE:
<223> OTHER INFORMATION: Standardized optimization of soluble S protein

<400> SEQUENCE: 67
atgttcatct tcctgctgtt cctgaccctg accagcggca gcgacctgga tcgctgcacc 60
accttcgatg acgtgcaggc ccccaactac acccagcata ccagcagcat gcgcggcgtg 120
tactaccccg atgagatctt ccgcagcgac accctgtacc tgacccagga cctgttcctg 180
cccttctaca gcaacgtgac cggcttccac accatcaacc ataccttcgg caaccccgtg 240
atccccttca aggacggcat ctacttcgcc gccaccgaga agagcaacgt ggtgcgcggc 300
tgggtgttcg gcagcaccat gaacaacaag agccagagcg tgatcatcat caacaacagc 360
accaacgtgg tgatccgcgc ctgcaacttc gagctgtgcg acaacccctt cttcgccgtg 420
agcaagccca tgggcaccca gacccatacc atgatcttcg ataacgcctt caactgcacc 480
ttcgagtaca tcagcgacgc cttcagcctg gacgtgagcg agaagagcgg caacttcaag 540
catctgcgcg agttcgtgtt caagaacaag gatggcttcc tgtacgtgta caagggctac 600
cagcccatcg acgtggtgcg cgatctgccc agcggcttca acaccctgaa gcccatcttc 660
aagctgcccc tgggcatcaa catcaccaac ttccgcgcca tcctgaccgc cttcagcccc 720
gcccaggaca tctggggcac cagcgccgcc gcctacttcg tgggctacct gaagcccacc 780
accttcatgc tgaagtacga tgagaacggc accatcaccg acgccgtgga ctgcagccag 840 aacccccctgg ccgagctgaa gtgcagcgtg aagagcttcg agatcgataa gggcatctac 900
cagaccagca acttccgcgt ggtgcccagc ggcgacgtgg tgcgcttccc caacatcacc 960
aacctgtgtc ccttcggcga ggtgttcaac gccaccaagt tccccagcgt gtacgcctgg 1020
gagcgcaaga agatcagcaa ctgcgtggcc gactacagcg tgctgtacaa cagcaccttc 1080
ttcagcacct tcaagtgcta cggcgtgagc gccaccaagc tgaacgatct gtgcttcagc 1140
aacgtgtacg ccgacagctt cgtggtgaag ggcgatgatg tgcgccagat cgcccccggc 1200
cagaccggcg tgatcgccga ttacaactac aagctgcccg acgacttcat gggctgcgtg 1260
ctggcctgga acacccgcaa catcgacgcc accagcaccg gcaactacaa ctacaagtac 1320
cgctacctgc gccatggcaa gctgcgcccc ttcgagcgcg atatcagcaa cgtgcccttc 1380
agccccgatg gcaagccctg cacccccccc gccctgaact gttactggcc cctgaacgac 1440
tacggcttct acaccaccac cggcatcggc taccagccct accgcgtggt ggtgctgagc 1500
ttcgagctgc tgaacgcccc cgccaccgtg tgcggcccca agctgagcac cgacctgatc 1560
aagaaccagt gcgtgaactt caacttcaac ggcctgaccg gcaccggcgt gctgaccccc 1620
agcagcaagc gcttccagcc cttccagcag ttcggccgcg atgtgagcga cttcaccgat 1680
agcgtgcgcg accccaagac cagcgagatc ctggatatca gcccctgcag cttcggcggc 1740
gtgagcgtga tcacccccgg caccaacgcc agcagcgagg tggccgtgct gtaccaggat 1800
gtgaactgta ccgatgtgag caccgccatc cacgccgatc agctgacccc cgcctggcgc 1860
atctacagca ccggcaacaa cgtgttccag acccaggccg gctgcctgat cggcgccgag 1920
catgtggaca ccagctacga gtgtgacatc cccatcggcg ccggcatctg tgccagctac 1980
cacaccgtga gcctgctgcg cagcaccagc cagaagagca tcgtggccta caccatgagc 2040
ctgggcgccg atagcagcat cgcctacagc aacaacacca tcgccatccc caccaacttc 2100
agcatcagca tcaccaccga ggtgatgccc gtgagcatgg ccaagaccag cgtggactgc 2160
aacatgtaca tctgcggcga tagcaccgag tgcgccaacc tgctgctgca gtacggcagc 2220
ttctgcaccc agctgaaccg cgccctgagc ggcatcgccg ccgagcagga tcgcaacacc 2280
cgcgaggtgt tcgcccaggt gaagcagatg tacaagaccc ccaccctgaa gtacttcggc 2340
ggcttcaact tcagccagat cctgcccgat cccctgaagc ccaccaagcg cagcttcatc 2400
gaggatctgc tgttcaacaa ggtgaccctg gccgatgccg gcttcatgaa gcagtacggc 2460
gagtgcctgg gcgatatcaa cgcccgcgat ctgatctgcg cccagaagtt caacggcctg 2520
accgtgctgc ccccctgct gaccgacgac atgatcgccg cctacaccgc cgccctggtg 2580
agcggcaccg ccaccgccgg ctggaccttc ggcgccggcg ccgccctgca gatccccttc 2640
gccatgcaga tggcctaccg cttcaacggc atcggcgtga cccagaacgt gctgtacgag 2700
aaccagaagc agatcgccaa ccagttcaac aaggccatca gccagatcca ggagagcctg 2760
accaccacca gcaccgccct gggcaagctg caggacgtgg tgaaccagaa cgcccaggcc 2820
ctgaacaccc tggtgaagca gctgagcagc aacttcggcg ccatcagcag cgtgctgaac 2880
gacatcctga gccgcctgga taaggtggag gccgaggtgc agatcgatcg cctgatcacc 2940
ggccgcctgc agagcctgca gacctacgtg acccagcagc tgatccgcgc cgccgagatc 3000
cgcgccagcg ccaacctggc cgccaccaag atgagcgagt gcgtgctggg ccagagcaag 3060
cgcgtggatt tctgcggcaa gggctaccac ctgatgagct tcccccaggc cgccccccat 3120
ggcgtggtgt tcctgcacgt gacctacgtg cccagccagg agcgcaactt caccaccgcc 3180
cccgccatct gccacgaggg caaggcctac ttcccccgcg agggcgtgtt cgtgttcaac 3240
ggcaccagct ggttcatcac ccagcgcaac ttcttcagcc cccagatcat caccaccgat 3300
aacaccttcg tgagcggcaa ctgcgatgtg gtgatcggca tcatcaacaa caccgtgtac 3360
gatcccctgc agcccgagct ggacagcttc aaggaggagc tggataagta cttcaagaac 3420
cacaccagcc ccgacgtgga tctgggcgat atcagcggca tcaacgccag cgtggtgaac 3480
atccagaagg agatcgatcg cctgaacgag gtggccaaga acctgaacga gagcctgatc 3540
gacctgcagg agctgggcaa gtacgagcag tacatcaagt ggccctgg 3588

<210> SEQ ID NO 68
<211> LENGTH: 2049
<212> TYPE: DNA
<213> ORGANISM: Artificial Sequence
<220> FEATURE:
<223> OTHER INFORMATION: Standardized optimization of soluble S1 protein

<400> SEQUENCE: 68
atgttcatct tcctgctgtt cctgaccctg accagcggca gcgatctgga ccgctgcacc 60
accttcgacg atgtgcaggc ccccaactac acccagcaca ccagcagcat gcgcggcgtg 120
tactaccccg atgagatctt ccgcagcgat accctgtacc tgacccagga tctgttcctg 180
cccttctaca gcaacgtgac cggcttccat accatcaacc acaccttcgg caaccccgtg 240
atccccttca aggatggcat ctacttcgcc gccaccgaga agagcaacgt ggtgcgcggc 300

-continued

```
tgggtgttcg gcagcaccat gaacaacaag agccagagcg tgatcatcat caacaacagc    360
accaacgtgg tgatccgcgc ctgcaacttc gagctgtgcg acaacccctt cttcgccgtg    420
agcaagccca tgggcaccca gacccacacc atgatcttcg acaacgcctt caactgcacc    480
ttcgagtaca tcagcgatgc cttcagcctg gacgtgagcg agaagagcgg caacttcaag    540
catctgcgcg agttcgtgtt caagaacaag gatggcttcc tgtacgtgta caagggctac    600
cagcccatcg acgtggtgcg cgacctgccc agcggcttca acaccctgaa gcccatcttc    660
aagctgcccc tgggcatcaa catcaccaac ttccgcgcca tcctgaccgc cttcagcccc    720
gcccaggata tctggggcac cagcgccgcc gcctacttcg tgggctacct gaagcccacc    780
accttcatgc tgaagtacga cgagaacggc accatcaccg atgccgtgga ttgcagccag    840
aacccctgg ccgagctgaa gtgcagcgtg aagagcttcg agatcgataa gggcatctac    900
cagaccagca acttccgcgt ggtgcccagc ggcgacgtgg tgcgcttccc caacatcacc    960
aacctgtgcc ccttcggcga ggtgttcaac gccaccaagt tccccagcgt gtacgcctgg   1020
gagcgcaaga agatcagcaa ctgcgtggcc gattacagcg tgctgtacaa cagcaccttc   1080
ttcagcacct tcaagtgcta cggcgtgagc gccaccaagc tgaacgacct gtgcttcagc   1140
aacgtgtacg ccgacagctt cgtggtgaag ggcgacgacg tgcgccagat cgcccccggc   1200
cagaccggcg tgatcgccga ttacaactac aagctgcccg atgacttcat gggctgcgtg   1260
ctggcctgga acacccgcaa catcgatgcc accagcaccg gcaactacaa ctacaagtac   1320
cgctacctgc gccacggcaa gctgcgcccc ttcgagcgcg atatcagcaa cgtgcccttc   1380
agccccgatg gcaagccctg cacccccccc gccctgaact gttactggcc cctgaacgat   1440
tacggcttct acaccaccac cggcatcggc taccagccct accgcgtggt ggtgctgagc   1500
ttcgagctgc tgaacgcccc cgccaccgtg tgcggcccca agctgagcac cgacctgatc   1560
aagaaccagt gcgtgaactt caacttcaac ggcctgaccg gcaccggcgt gctgaccccc   1620
agcagcaagc gcttccagcc cttccagcag ttcggccgcg acgtgagcga cttcaccgac   1680
agcgtgcgcg atcccaagac cagcgagatc ctggatatca gcccctgcag cttcggcggc   1740
gtgagcgtga tcacccccgg caccaacgcc agcagcgagg tggccgtgct gtaccaggac   1800
gtgaactgca ccgatgtgag caccgccatc cacgccgatc agctgacccc cgcctggcgc   1860
atctacagca ccggcaacaa cgtgttccag acccaggccg gctgtctgat cggcgccgag   1920
catgtggaca ccagctacga gtgtgatatc cccatcggcg ccggcatctg cgccagctac   1980
cataccgtga gcctgctgcg cagcaccagc cagaagagca tcgtggccta caccatgagc   2040
ctgggcgcc                                                           2049
```

<210> SEQ ID NO 69
<211> LENGTH: 1623
<212> TYPE: DNA
<213> ORGANISM: Artificial Sequence
<220> FEATURE:
<223> OTHER INFORMATION: Standardized optimization of TPA-S2 protein

<400> SEQUENCE: 69

```
atggatgcca tgaagcgcgg cctgtgctgt gtgctgctgc tgtgtggcgc cgtgttcgtg     60
agccccagcg cccgcggcag cggcgatagc agcatcgcct acagcaacaa caccatcgcc    120
atccccacca acttcagcat cagcatcacc accgaggtga tgcccgtgag catggccaag    180
accagcgtgg attgcaacat gtacatctgc ggcgacagca ccgagtgcgc caacctgctg    240
ctgcagtacg gcagcttctg cacccagctg aaccgcgccc tgagcggcat cgccgccgag    300
```

-continued

| | |
|---|---|
| caggaccgca acacccgcga ggtgttcgcc caggtgaagc agatgtacaa gacccccacc | 360 |
| ctgaagtact tcggcggctt caacttcagc cagatcctgc ccgacccccct gaagcccacc | 420 |
| aagcgcagct tcatcgagga tctgctgttc aacaaggtga ccctggccga cgccggcttc | 480 |
| atgaagcagt acggcgagtg cctgggcgac atcaacgccc gcgacctgat ctgcgcccag | 540 |
| aagttcaacg gcctgaccgt gctgcccccc ctgctgaccg atgacatgat cgccgcctac | 600 |
| accgccgccc tggtgagcgg caccgccacc gccggctgga ccttcggcgc cggcgccgcc | 660 |
| ctgcagatcc ccttcgccat gcagatggcc taccgcttca acggcatcgg cgtgacccag | 720 |
| aacgtgctgt acgagaacca gaagcagatc gccaaccagt tcaacaaggc catcagccag | 780 |
| atccaggaga gcctgaccac caccagcacc gccctgggca agctgcagga tgtggtgaac | 840 |
| cagaacgccc aggccctgaa caccctggtg aagcagctga gcagcaactt cggcgccatc | 900 |
| agcagcgtgc tgaacgatat cctgagccgc ctggataagg tggaggccga ggtgcagatc | 960 |
| gaccgcctga tcaccggccg cctgcagagc ctgcagacct acgtgaccca gcagctgatc | 1020 |
| cgcgccgccg agatccgcgc cagcgccaac ctggccgcca ccaagatgag cgagtgcgtg | 1080 |
| ctgggccaga gcaagcgcgt ggatttctgc ggcaagggct accacctgat gagcttcccc | 1140 |
| caggccgccc cccacggcgt ggtgttcctg catgtgacct acgtgcccag ccaggagcgc | 1200 |
| aacttcacca ccgcccccgc catctgccac gagggcaagg cctacttccc ccgcgagggc | 1260 |
| gtgttcgtgt tcaacggcac cagctggttc atcacccagc gcaacttctt cagcccccag | 1320 |
| atcatcacca ccgacaacac cttcgtgagc ggcaactgcg acgtggtgat cggcatcatc | 1380 |
| aacaacaccg tgtacgatcc cctgcagccc gagctggata gcttcaagga ggagctggac | 1440 |
| aagtacttca agaaccatac cagccccgat gtggatctgg gcgacatcag cggcatcaac | 1500 |
| gccagcgtgg tgaacatcca gaaggagatc gatcgcctga acgaggtggc caagaacctg | 1560 |
| aacgagagcc tgatcgatct gcaggagctg ggcaagtacg agcagtacat caagtggccc | 1620 |
| tgg | 1623 |